| 
US011090355B2

(12) United States Patent
Barnea

(10) Patent No.: US 11,090,355 B2
(45) Date of Patent: Aug. 17, 2021

(54) COMPOSITIONS AND METHODS FOR THE TREATMENT OF NEURODAMAGE

(71) Applicant: BIOINCEPT, LLC, Cherry Hill, NJ (US)

(72) Inventor: Eytan R. Barnea, Cherry Hill, NJ (US)

(73) Assignee: BIOINCEPT, LLC, New York, NY (US)

( * ) Notice: Subject to any disclaimer, the term of this patent is extended or adjusted under 35 U.S.C. 154(b) by 0 days.

(21) Appl. No.: 15/756,386

(22) PCT Filed: Aug. 25, 2016

(86) PCT No.: PCT/US2016/048601
§ 371 (c)(1),
(2) Date: Feb. 28, 2018

(87) PCT Pub. No.: WO2017/040186
PCT Pub. Date: Sep. 3, 2017

(65) Prior Publication Data
US 2019/0201477 A1 Jul. 4, 2019

Related U.S. Application Data

(60) Provisional application No. 62/211,660, filed on Aug. 28, 2015, provisional application No. 62/361,334, filed on Jul. 12, 2016.

(51) Int. Cl.
| | |
|---|---|
| *A61K 38/10* | (2006.01) |
| *C07K 7/08* | (2006.01) |
| *A61K 38/08* | (2019.01) |
| *A61P 25/28* | (2006.01) |
| *G01N 33/567* | (2006.01) |
| *G01N 33/68* | (2006.01) |
| *G01N 33/564* | (2006.01) |
| *A61K 35/28* | (2015.01) |
| *A61P 37/00* | (2006.01) |

(52) U.S. Cl.
CPC .............. *A61K 38/10* (2013.01); *A61K 35/28* (2013.01); *A61K 38/08* (2013.01); *A61P 25/28* (2018.01); *A61P 37/00* (2018.01); *C07K 7/08* (2013.01); *G01N 33/564* (2013.01); *G01N 33/567* (2013.01); *G01N 33/68* (2013.01); *G01N 33/6896* (2013.01)

(58) Field of Classification Search
CPC ........ A61K 38/10; A61K 38/08; A61K 35/28; G01N 33/567; G01N 33/68; G01N 33/564; G01N 33/6896; C07K 7/08; A61P 37/00; A61P 25/28
See application file for complete search history.

(56) References Cited

U.S. PATENT DOCUMENTS

| | | |
|---|---|---|
| 4,629,722 A | 12/1986 | Ribi |
| 5,279,941 A | 1/1994 | Lessey |
| 5,393,534 A | 2/1995 | Cavanaugh et al. |
| 5,658,792 A | 6/1997 | Nuell et al. |
| 5,645,829 A | 7/1997 | Shockley et al. |
| 5,646,003 A | 7/1997 | Barnea et al. |
| 5,648,340 A | 7/1997 | Barnea |
| 5,665,355 A | 9/1997 | Primi |
| 5,981,198 A | 11/1999 | Barnea et al. |
| 6,171,591 B1 | 1/2001 | Hall |
| 6,225,097 B1 | 5/2001 | Obata et al. |
| 6,365,727 B1 | 4/2002 | Yoon et al. |
| 6,585,979 B1 | 7/2003 | Berman |
| 7,273,708 B2 | 9/2007 | Barnea et al. |
| 7,670,652 B2 | 3/2010 | Barnea et al. |
| 7,670,850 B2 | 3/2010 | Barnea et al. |
| 7,670,851 B2 | 3/2010 | Barnea et al. |
| 7,678,582 B2 | 3/2010 | Barnea et al. |
| 7,695,977 B2 | 4/2010 | Barnea et al. |
| 7,723,289 B2 | 5/2010 | Barnea |
| 7,723,290 B2 | 5/2010 | Barnea |
| 8,222,211 B2 | 7/2012 | Barnea |
| 8,454,967 B2 | 6/2013 | Barnes |
| 9,097,725 B2 | 8/2015 | Barnea |
| 9,737,585 B2 | 8/2017 | Barnea |
| 10,071,131 B2 | 9/2018 | Barnea |
| 2002/0004205 A1 | 1/2002 | Consler et al. |
| 2003/0099643 A1 | 5/2003 | June et al. |
| 2003/0109690 A1 | 6/2003 | Ruben et al. |
| 2003/0203410 A1 | 10/2003 | Barnea et al. |
| 2003/0228256 A1 | 12/2003 | Inverardi et al. |
| 2005/0003397 A1 | 1/2005 | Hardy et al. |
| 2005/0064520 A1 | 3/2005 | Barnea et al. |
| 2007/0136003 A1 | 6/2007 | Choi et al. |
| 2007/0231310 A1 | 10/2007 | Friedlander et al. |

(Continued)

FOREIGN PATENT DOCUMENTS

| | | |
|---|---|---|
| CA | 2490538 A1 | 1/2003 |
| DE | 4400640 A1 | 7/1995 |
| EP | 1404877 A2 | 4/2004 |
| JP | 4593106 B2 | 12/2010 |
| JP | 2014-508164 A | 4/2014 |

(Continued)

OTHER PUBLICATIONS

Constantinescu etal., British J Pharmacology (2011), 164:1079-1106. (Year: 2011)*

(Continued)

*Primary Examiner* — Kimberly Ballard
*Assistant Examiner* — Stacey N MacFarlane
(74) *Attorney, Agent, or Firm* — Ballard Spahr LLP

(57) ABSTRACT

The disclosure relates to a pharmaceutical composition comprising any one or combination of PIF peptides or analogs or pharmaceutically acceptable salts thereof. Methods of treating cellular neurodamage or neurotrauma to the peripheral or central nervous system using the one or a combination of PIF peptide or analogs thereof or pharmaceutically acceptable salts thereof is also disclosed.

10 Claims, 41 Drawing Sheets

Specification includes a Sequence Listing.

(56) References Cited

U.S. PATENT DOCUMENTS

| | | |
|---|---|---|
| 2008/0003178 A1 | 1/2008 | Barnea |
| 2008/0227778 A1 | 9/2008 | Dinsmore et al. |
| 2008/0269137 A1 | 10/2008 | Barnea |
| 2008/0293149 A1 | 11/2008 | Barnea et al. |
| 2008/0299677 A1 | 12/2008 | Barnea et al. |
| 2008/0305468 A1 | 12/2008 | Barnea et al. |
| 2008/0305552 A1 | 12/2008 | Barnea et al. |
| 2009/0011427 A1 | 1/2009 | Barnea et al. |
| 2009/0081225 A1 | 3/2009 | Barnea |
| 2010/0004430 A1 | 1/2010 | Nilsson et al. |
| 2010/0197040 A1 | 6/2010 | Barnea et al. |
| 2011/0033539 A1 | 2/2011 | Quart et al. |
| 2011/0070184 A1 | 3/2011 | Bernhagen et al. |
| 2011/0112016 A1 | 5/2011 | Barnea |
| 2012/0107318 A9 | 5/2012 | Barnea |
| 2012/0301921 A1 | 11/2012 | Williams et al. |
| 2013/0058943 A1 | 3/2013 | Fox et al. |
| 2014/0004545 A1 | 1/2014 | Barnea |
| 2014/0147414 A1 | 5/2014 | Barnea |
| 2014/0271652 A1 | 9/2014 | Scoville |
| 2015/0125886 A9 | 5/2015 | Barnea |
| 2015/0232418 A1 | 8/2015 | Schlechtingen et al. |
| 2016/0263186 A1 | 9/2016 | Barnea |
| 2017/0080047 A1 | 3/2017 | Barnea |
| 2017/0319645 A1 | 11/2017 | Barnea |
| 2018/0021401 A1 | 1/2018 | Barnea |
| 2019/0022181 A1 | 1/2019 | Barnea |
| 2019/0054139 A1 | 2/2019 | Barnes |
| 2020/0000874 A1 | 1/2020 | Barnea |

FOREIGN PATENT DOCUMENTS

| | | |
|---|---|---|
| MX | 277034 | 7/2010 |
| WO | WO-92/09294 A1 | 6/1992 |
| WO | WO-94/06464 A1 | 3/1994 |
| WO | WO-95/26982 A2 | 10/1995 |
| WO | WO-97/09418 A1 | 3/1997 |
| WO | WO-98/52550 A1 | 11/1998 |
| WO | WO 00/01402 A1 | 1/2000 |
| WO | WO-00/43789 A1 | 7/2000 |
| WO | WO-00/063675 A1 | 10/2000 |
| WO | WO-02/40717 A2 | 5/2002 |
| WO | WO-02/053092 A2 | 7/2002 |
| WO | WO-03/004601 A2 | 1/2003 |
| WO | WO-03/033644 A2 | 4/2003 |
| WO | WO-2004/053086 A2 | 6/2004 |
| WO | WO-2005/030791 A2 | 4/2005 |
| WO | WO-2005/040196 A2 | 5/2005 |
| WO | WO-2006/113898 A2 | 10/2006 |
| WO | WO-2007/131218 A2 | 11/2007 |
| WO | WO-2012/119072 A2 | 9/2012 |
| WO | WO-2014/201118 A2 | 12/2014 |
| WO | WO-2015/040196 A2 | 3/2015 |
| WO | WO-2015/061483 A2 | 4/2015 |
| WO | WO-2016/030901 A1 | 3/2016 |
| WO | WO-2016/073513 A1 | 5/2016 |
| WO | WO-2017/040186 A1 | 3/2017 |
| WO | WO-2017/079430 A1 | 5/2017 |

OTHER PUBLICATIONS

Miyamoto etal., Brain (2006), 129, 1984-1992. (Year: 2006)*

Dasgupta et al.: "Neuronopathic Gaucher disease: dysregulated mRNAs and miRNAs in brain pathogenesis and effects of pharmacologic chaperone treatment in a mouse model", Human Molecular Genetics, vol. 24, (2015), pp. 7031-7048.

Duzy J et al.: "Preimplantation factor (PIF*) promotes embryotrophic and neuroprotective decidual genes: effect negated by epidermal growth factor", Journal of Neurodevelopmental Disorders 2014, 6:36.

Mueller et al.: "Preimplantation factor promotes neuroprotection by targeting microRNA let-7", Proc Natl Acad Sci U S A. (2014); 111(38): 13882-13887.

Mueller et al.: "Preimplantation Factor bolsters neuroprotection via modulating Protein Kinase A and Protein Kinase C signaling", Cell Death Differ. (2015); 22(12): 2078-2086.

Mueller et al.: "Synthetic Preimplantation Factor (sPIF) neuroprotective role in intracranial stem cell transplantation: Encephalopathy of prematurity rat model", Zeitschrift für Geburtshilfe and Neonatologie, DGPM: 26th German Congress for Perinatal Medicine, (2013).

Mueller et al: "106: Synthetic preimplantation factor (sPIF*) promotes neuroprotection by modulating PKA/PKC kinases", American Journal of Obstetrics & Gynecology, vol. 212, No. 1, (2015), pp. S70-S71.

Paidas et al: "Pregnancy and Multiple Sclerosis (MS): A Beneficial Association. Possible therapeutic application of embryo-specific Pre-implantation Factor (PIF*)", Am J Reprod Immunol. (2012), 68(6):456-64.

Weiss et al.: "Preimplantation Factor (PIF*) reverses neuroinflammation while promoting neural repair in EAE model", Journal of Neurological Sciences, Elsevier Scientific Publishing Co, vol. 312, No. 1, Jul. 28, 2011 (Jul. 28, 2011),pp. 146-157.

Zhang et al.: "MicroRNA Expression Profile in Hyperoxia-Exposed Newborn Mice During the Development of Bronchopulmonary Dysplasia", Respiratory Care, vol. 56, No. 7, (2011), pp. 1009-1015.

International Search Report and Written Opinion were dated Feb. 6, 2017 by the International Searching Authority for International Application No. PCT/US2016/048601, filed on Aug. 25, 2016 and published as WO 2017/040186 dated Mar. 9, 2017(Applicant-Bioincept, LLC) (10 Pages).

International Preliminary Report on Patentability dated Mar. 6, 2018 by the International Searching Authority for International Application No. PCT/US2016/048601, filed on Aug. 25, 2016 and published as WO 2017/040186 on Mar. 9, 2017(Applicant-Bioincept, LLC) (7 Pages).

European Search Report dated Feb. 13, 2019 by the European Patent Office for EP Application No. 16842635.1, filed on Aug. 25, 2016 and published as EP 3341006 on Jul. 4, 2018(Applicant-Bioincept, LLC) (9 Pages).

Abbas, A. K., et al., Functional diversity of helper T lymphocytes, Nature, 1996, 383(6603):787-793.

Ancsin, J. B., et al., A binding site for highly sulfated heparan sulfate is identified in the N terminus of the circumsporozoite protein: significance for malarial sporozoite attachment to hepatocytes, J. Biol. Chem., 2004, 279(21):21824-21832.

Aplin, J. D., et al., Trophoblast-uterine interactions at implantation, Reprod. Biol. And Endocrinol., 2004, 2:48, 12 pages.

Asai, K., et al., Dexamthasone-induced suppression of aortic atherosclerosis in cholesterol fed rabbits—possible mechanisms, Arterosclerol. Thrombos., 1993, 13:892-899.

Asano, M., et al., Autoimmune Disease as a Consequence of Developmental Abnormality of a T Cell Subpopulation, J. Exp. Med., 1996, 184(2):387-396.

Atkinson, M. A., et al., The NOD mouse model of type 1 diabetes. As good as it gets?, Nat. Med., 1999, 5(6):601-604.

Azar, Y., et al., Preimplantation Factor Reduces Graft-Versus-Host Disease by Regulating Immune Response and Lowering Oxidative Stress (Murine Model), Biol. Blood Marrow Transplant, 2013, 19(4):519-528.

Bainbridge, D., et al., HLA-G remains a mystery, Trends Immunol., 2001, 22(10):548-552.

Banker, G. S., et al., Eds., Modern Pharmaceutics, Marcel Dekker, Inc., New York, 1979, TOC only.

Barnea, E. R., et al., Human embryo regulates placental function in first trimester, International Congress of Endocrinology, Kyoto, Japan, 1988, (Abstract).

Barnea, E. R., et al., Human embryonal extracts modulate placental function in the first trimester: effects of visceral tissues upon chorionic gonadotropin and progesterone secretion, Placenta, 1989, 10(4):331-344.

Barnea, E. R., et al., Endocrinology of the placental and embryoplacental interaction, in Barnea, E R., et al., Eds., The First Twelve Weeks of Gestation, Berlin: Springer-Verlag, 1992, pp. 128-153.

Barnea, E. R., et al., Epilogue, in Barnea, E. R., et al., Eds., The First Twelve Weeks of Gestation, Berlin: Springer-Verlag, 1992, pp. pp. 542-548.

(56) References Cited

OTHER PUBLICATIONS

Barnea, E R., et al., Eds., The First Twelve Weeks of Gestation, Berlin: Springer-Verlag, 1992, Forward and TOC only.

Barnea, E. R., et al., Use of lymphocyte platelet binding assay for detecting a preimplantation factor: A quantitative assay, Am. J. Reprod. Immunol., 1994, 32:133-138.

Barnea, E. R., Dual effects of embryo-derived factors on hCG secretion by placental explants, in Barnea, E. R., et al., Eds., Implantation and Early Pregnancy in Humans, Camforth: Parthenon Publishing, 1994, pp. 271-282.

Barnea, E R., et al., Identification and validation of an assay for preimplantation (PIF), The Second World Conference on Implantation and Early Pregnancy in Humans, May 12-14, 1994, (Abstract).

Barnea, E. R., New Frontiers in Early Pregnancy Investigation, Early Pregnancy, Biol. & Med., 1995, 1:1-3.

Barnea, E. A., EnVision the Field of Early Pregnancy Investigation, Early Pregnancy, Biol. & Med., 1995, 1:169-170.

Barnea, E R., et al., Reflections on early pregnancy: organizing chaos or organized chaos?, (Editorial) Early Pregnancy: Biol. & Med., 1996, 2:77-79.

Barnea, E. R., et al., Control of cell proliferation by embryonal-origin factors, Am. J. Reprod. Immunol., 1996, 35(4):318-324.

Barnea, E. R., et al., New perspectives on prevention of environmentally-induced damage to the embryo, Reproduction—Humaines et Hormones, 1996, 7:423-428.

Barnea, E. R., et al., Preimplantation factor (PIF): current developments, Third World Conference on Early Pregnancy—An Interdisciplinary Approach, Atlantic City, NJ, Oct. 3-6, 1996, (Abstract).

Barnea, E. R., et al., Preimplantation signalling by the embryo, The 3$^{rd}$ World Conference on Early Pregnancy, Oct. 3-6, 1996, (Abstract).

Barnea, E. R., et al., Partial characterization of embryo-derived preimplantation factor (PIF), IXth World Congress on Human Reproduction, Philadelphia, PA, May 28-Jun. 2, 1996, (Abstract).

Barnea, E. R., et al., Embryonic signals, in Embryonic Medicine and Therapy, Jauniaux, E., et al., Eds., 1997, Oxford: Oxford University Press, pp. 63-75.

Barnea, E. R., The Embryo: a privileged entity in a privileged site: Lessons learnt from embryonal development, (Editorial) Early Pregnancy: Biol. & Med., 1997, 3:77-80.

Barnea, E. R., et al., The Embryo-Trophoblast Paradox, Embryonic Medicine and Therapy, Oxford University Press, 1997, 15:256-279.

Barnea, E. R., et al., Partial characterization of mammalian preimplantation factor (PIF) in culture and in vivo, Fourth International Meeting of Alps Adria Society for Immunology of Reproduction (AASIR), Sep. 1998, Opatija, Croatia (abstract).

Barnea, E. R., et al., Progress in characterization of pre-implantation factor in embryo cultures and in vivo, Am. J. Reprod. Immunol., 1999, 42(2):95-99.

Barnea, E. R., et al., Maternal Immune Response to Trophoblast, GTD, and Cancer, in the Decade of Autoimmunity, Shoenfeld Y., Ed., Elsevier Science B.V. Publishers, 1999, pp. 309-316.

Barnea, E. R., Preimplantation Factor: A specific embryo viability factor, The First National Congress on Human Assisted Reproduction with International Participation under the patronage of the Romanian Academy, Timisoara, Romania, May 27-29, 1999, (Abstract).

Barnea, E. R., Current progress in Early Pregnancy investigation and the steps ahead, (Editorial) Early Pregnancy Biology & Medicine, 2000, IV(1):1-4.

Barnea, E. R., et al., Pregnancy derived compounds that control proliferation, Cancer and Pregnancy, 2000, 22:275-284.

Barnea, E. R., et al., Maternal Immune Response to Trophoblast, GTD and Cancer, In: Cancer and Autoimmunity, Shoenfeld, Y. and Gerhwin, M.E ,eds., Elsevier Science BV Publishers, 2000, pp. 343-350.

Barnea, E. R., Embryo-Maternal dialogue: Linking pregnancy recognition and proliferation control, 4th World Conference on Early Pregnancy, under the auspices of the Hungarian Society of Obstetrics and Gynecology and SIEP, The Society for the Investigation of Early Pregnancy, Pecs, Hungary, Jun. 1-3, 2000, (Abstract).

Barnea, E. R., Embryo-maternal dialogue: from pregnancy recognition to proliferation control, 14th Rochester Trophoblast Conference, by Trophoblast Conference and SIEP, Rochester, NY, Oct. 4-8, 2000, (Abstract).

Barnea, E., Embryo Maternal Dialogue: From Pregnancy Recognition to Proliferation Control, Early Pregnancy, 2001, V(1):65-68.

Barnea, E. R., et al., Immune System (IS) and Proliferation Control (PC) from Embryo to Adulthood: Roles of Preimplantation Factor (PIE) and of Developmental Proteins (DPs), from Renaissance Congress of 21.sup.st Century: The Woman and Child Before, During and After Pregnancy, Cosmi ed., Monduzzi Editore, Rome, Italy, May 22-26, 2001, pp. 93-102.

Barnea, E. R., et al., Embryo-maternal signaling prior to implantation, Textbook of Obstetrics & Gynecology, SIEP, BBRI, 2001, 2:112-117.

Barnea, E. R., et al., From embryo-trophoblastic to feto-placental unit, Implantation in Obstetrics and Gynecology, Section 2 Human Reproduction-Anatomy, Physiology, Embryology, Munteanu, I., Ed., Romanian Academy of Science Publishers, 2001, TOC and pp. 117-123.

Barnea, E. R., et al., Evolution of Feto-Placental Unit, Textbook of Obstetrics & Gynecology, SIEP, BBRI, 2001, 2:170-175.

Barnea, E R., Safeguards established at conception influence pen and postnatal life: Roles of Preimplantation Factor (PIF) and Developmental Proteins (DPs), World Congress of Perinatal Medicine, Parallel Scientific SIEP Meeting, Barcelona, Spain, Sep. 23-27, 2001, (Abstract).

Barnea, E R., Underlying mechanisms and treatment of early pregnancy failure, Ferti Magazine (Ferti.Net <http://Ferti.Net> Worldwide Fertility Network), 2001, 4 pp.

Barnea, E. R., Novel Preimplantation Factors (PIF) and Developmental Peptides (DPs) are involved in safeguarding pregnancy, The Fetus as a Patient, Budapest, Hungary, 2002, (Abstract).

Barnea, E R., Critical Elements for Early Development and Beyond: Immune Tolerance (PIE) and Proliferation Control (DPs), Sixth World Conference of Early Pregnancy: Workshop on Embryology Early Pregnancy Investigation, Organized by SIEP, supported by Rotunda the Center for Human Reproduction and Mangeshikar Center for Gynaelogical Endoscopic Surgery, Jodphur, India, 2002, (Abstract).

Barnea, E. R., et al., Immune Modulation, by Embryo-Specific Peptides, Allow for Embryo Tolerance whilst Preserving the Maternal Host's Ability to Fight Pathogens: Preimplantation Factor (PIF), First Brown-Linkoping Meeting on Basic and clinical Aspects of Reproductive Immunology, Providence, RI, Nov. 15, 2002, (Abstract).

Barnea, E. R., Maternal Immune Recognition of Pregnancy is Initiated by Novel Embryo-Derived Preimplantation Factor (PIF). Invited Speaker. Hippokration Congress on Reproductive Immunology (4$^{th}$ ESRADI C) European Society for Reproductive and Developmental Immunology, Rhodes, Greece, 2003, pp. 123-124 (Abstract 1.32); also pub. in J. Reprod. Immun. pp. 23-24, (Abstract).

Barnea, E. R., et al., Prediction of Implantation in ART using Molecular Biology, Assisted Reproductive Technology, 2004, pp. 183-194.

Barnea, E. R., Insight into early pregnancy events: the emerging role of the embryo, Am. J. Reprod. Immunol., 2004, 51:319-322.

Barnea, E. R., et al., Embryo-derived Preimplantation Factor (PIF*): Methods to assess embryo viability towards successful pregnancy, 5$^{th}$ Indian Congress of Gynecologic Endoscopy and ART and SIEP, Khajuraho, India, Nov. 2004, (Abstract).

Barnea, E. R., et al., Preimplantation Factor (PIF): Relevance for Human Pregnancy, 24$^{th}$ Ann. Mtg. of the American Society for Reproductive Immunology, St. Louis, MO, 2004, (Abstract).

Barnea, E. R., et al., Expression of Novel Immunomodulators (PIF*) and Proliferation Controllers (DPs) by the Embryo and by the Placenta, Invited Speaker at the 32nd Conference of the European Teratology Society, Thessaloniki, Greece, Sep. 19-22, 2004, Reproductive Toxicology, 2004, 18:707-756 (Abstract at p. 715).

Barnea, E. R., et al., Preimplantation Factor (PIF): Novel Immunomodulatory Peptide and Expression by Gestational Tissues, The 12$^{th}$ International Federation of Placenta Association (IFPA), Kobe, Japan, Sep. 6-9, 2006, (Abstract).

(56) References Cited

OTHER PUBLICATIONS

Barnea, E. R., et al., Novel Embryo-Derived Preimplantation Factor (PIF): An Immune-Modulatory Therapy Approach for Immune Disorders, 5th International Congress on Autoimmunity, Sorrento, Italy, 2006, (Abstract).

Barnea, E. R., et al., Preimplantation Factor PIF: From Embryo Tolerance to Embryo Viability Detection and Treatment of Autoimmune Diseases, Eleventh International Symposium for Immunology of Reproduction. (ISIR) International House of Scientists, Varna, Bulgaria, 2006, (Abstract).

Barnea, E. R., Signaling Between Embryo and Mother in Early Pregnancy: Basis for Development of Tolerance, in Recurrent Pregnancy Loss Causes, Controversies and Treatment. CARP, H. J. A., Ed., Series in Maternal-Fetal Medicine, Informs Healthcare, Taylor and Francis Group publ., 2007, 2:15-22.

Barnea, E. R., Applying embryo-derived immune tolerance to the treatment of immune disorders, Ann. N. Y. Acad. Sci., 2007, 1110: 602-618.

Barnea, E. R., Apply Embryo Derived Tolerance for Managing Reproductive and Immune Disorders: Preimplantation Factor (PIF), 27th Annual Meeting of the American Society for Reproductive Immunology, Toronto, Canada, 2007, (Abstract).

Barnea, E. R., From PIF identification to clinical applications: Immunemodulatory Embryo-Derived Novel Peptide: True BioMarker Dx and Nontoxic Rx Application, Mining the Plasma Proteone Meeting, Success Stories Session, PepTalk Conf., CHI Cambridge Healthtech Institute, Coronado, San Diego CA, Jan. 7-9, 2008, (Abstract).

Barnea, E. R. et al., Preimplantation Factor (PIF) Orchestrates Systemic Antiinflammatory Response by Immune Cells: Effect on Peripheral Blood Mononuclear Cells, Am. J. Obstet. Gynecol., 2012; 207(4):313.e1-11.

Basu, U., et al., Translational Regulation of Utrophin by miRNAs, PLOS ONE, 2011, 6(12): e29376, 9 pages.

Bates, M. D., et al., Aberrant cytokine production by peripheral blood mononuclear cells in recurrent pregnancy loss?, Hum. Reprod., 2002, 17(9):2439-2444.

Battye, K. M., et al., Production of platelet-activating factor by the pre-implantation sheep embryo, J. Reprod. Fertil., 1991, 93::507-514.

Beausoleil, S. A., et al., Large-scale characterization of HeLa cell nuclear phosphoproteins, Proc. Natl. Acad. Sci. USA, 2004, 101(33):12130-12135.

Bell, J. J., et al., In Trans T Cell Tolerance Diminishes Autoantibody Responses and Exacerbates Experimental Allergic Encephalomyelitis, J. Immunology, 2008, 180:1508-1516.

Bhattacharya, R., et al., Impact of Genetic Variation on Three Dimensional Structure and Function of Proteins, PLOS ONE, 2017, 12(3):e0171355, 22 pages.

Bodian, D. L., et al., Crystal structure of the extracellular region of the human cell adhesion molecule CD2 at 2.5 A resolution, Structure, 1994, 2(8):755-766.

Boklage, C. E., Survival probability of human conceptions from fertilization to term, Int. J. Fertil., 1990, 35(2):75, 79-80, 81-94, Abstract only.

Bose, R., et al., Purified human early pregnancy factor from preimplantation embryo possesses immunosuppressive properties, Am. J. Obstet. Gynecol 1989, 160(4):954-960, Abstract only.

Bose, R., Properties of human pre- and post-implantation embryo-associated immunosuppressor factor(s), Immunol. Letters, 1991, 30(3):325-332.

Bresson, D., et al., Mechanisms underlying type I diabetes, Drug Discovery Today: Disease Mechanisms, 2004, 1(3):321-327.

Bringer, R., et al., PIF-1 Improves Graft vs. Host Disease (GVHD) while maintaining Graft vs. Leukemia (GVL) effect after bone marrow transplantation in mice, The 5th Annual Congress of the Federation of the Israel Societies for Experimental Biology, Eilat, Israel, Jan. 28-31, 2008, (Abstract).

Burgess, W. H., et al., Possible Dissociation of the Heparin-binding and Mitogenic Activities of Heparin-binding (Acidic Fibroblast) Growth Factor-1 from its Receptor-binding Activities by Site-directed Mutagenesis of a Single Lysine Residue, J. Cell Biol., 1990, 111(5 Pt 1):2129-2138.

Burt, R. K., et al., Hematopoietic stem cell transplantation for progressive multiple sclerosis: failure of a total body irradiation-based conditioning regimen to prevent disease progression in patients with high disability scores, Blood, 2003, 102(7):2373-2376.

Cavanagh, A. C., et al., The purification of early-pregnancy factor to homogeneity from human platelets and identification as chaperonin 10, Eur. J. Biochem., 1994, 222(2):551-560.

Chakrabarti, L., et al., Sequence of simian immunodeficiency virus from macaque and its relationship to other human and simian retroviruses, Nature, 1987, 328(6130):543-547.

Chalasani, N., et al., The Diagnosis and Management of Nonalcoholic Fatty Liver Disease: Practice Guidance From the American Association for the Study of Liver Diseases, Hepatology, 2018, 67(1):328-357.

Chaouat, G., et al., Control of fetal survival in CBA X DBA/2 mice by lymphokine therapy, J. Reprod. Fed., 1990, 89(2):447-458.

Chaouat, G., et al., IL-10 prevents naturally occurring fetal loss in the CBA X DBA/2 mating combination, and local defect in IL-10 production in this abortion-prone combination is corrected by in vivo injection of IFN-tau, J. Immunol., 1995, 154(9):4261-4268, Abstract only.

Chaouat, G., et al., Th1/Th2 Paradigm in Pregnancy: Paradigm lost? Cytokines in Pregnancy/Early Abortion Reexamining the Th1/Th2 Paradigm, Int. Arch. Allergy Immunol., 2004, 134(2):93-119.

Chard, T., et al., Early pregnancy factor, Biol. Res. Pregnancy Perinatol., 1987, 8(2 2D Half):53-56, Abstract only.

Chen, C., et al., Monitoring embryos after in vitro fertilization using early pregnancy factor, Ann. N. Y. Acad. Sci., 1985, 142:420-428.

Chen, J. D., et al., A transcriptional co-repressor that interacts with nuclear hormone receptors, Nature, 1995, 377(6548):454-457.

Choudhury, S. R., et al., Human reproductive failure I: Immunological factors, Human Reprod. Update, 2001, 7(2):113-134.

Clarke, F. M., et al., Identification of molecules involved in the 'early pregnancy factor' phenomenon, J. Reprod. Fertil., 1991,93(2):525-539.

Clarke, F. M., Identification of molecules and mechanisms involved in the 'early pregnancy factor' system, Reprod. Fertil. Day., 1992, 4(4):423-433.

Collier, M., et al., Biochemical and pharmacological characterization of human embryo-derived activating factor, Hum. Reprod., 1988, 3(8):993-998, Abstract only.

Constantinescu, C. S., et al., Experimental Autoimmune Encephalomyelitis (EAE) as a Model for Multiple Sclerosis (MS), British J. Pharmacology, 2011, 164(4):1079-1106.

Cooper, D. W., et al., Failure to detect altered rosette inhibition titres in human pregnancy serum, J. Reprod. Fertil., 1981, 61(1):241-245.

Coulam, C. B., et al., Preimplantation Factor (PIF) Predicts Subsequence Pregnancy Loss, The American Fertility Society 50th Annual Meeting, San Antonio, TX, Nov. 5-10, 1994, (Abstract).

Coulam, C. B., et al., Preimplantation Factor (PIF) Predicts Subsequent Pregnancy Loss, Am. J. Reprod. Immunol., 1995, 34(2):86-92.

Critser, E. S., et al., The Role of Platelet-Activating Factor in Reproduction, Chapter 15 in Immunological Obstetrics, W. W. Norton, New York, 1993, pp. 202-215.

Cross, K. P., et al., Single dose dexamthasone for mild to moderate asthma exacerbations, Can. Fam. Phys., 2011, 57:1134-1136.

Curti, B. D., Physical barriers to drug delivery in tumors, Crit. Rev. Oncol. Hematol., 1993, 14(1):29-39.

Dasgupta, N., et al. Neuronopathic Gaucher Disease: Dysregulated mRNAs and miRNAs in Brain Pathogenesis and Effects of Pharmacologic Chaperone Treatment in a Mouse Model, Human Molecular Genetics, 2015, 24(24):7031-7048.

Database YbuOrit [Online], Nuclear receptor corepressor 2 (N-CoR2) (Silencing mediator of retinoic acid and thyroid hormone receptor) (SMRT) (SMRTe) (Thyroid-, retinoic-acid-receptor-associated corepressor) (T3 receptor-associating factor) (TRAC) (CTG repeat protein 26) (SMAP270), retrieved from EBI accession No. UNIPROT:Q9Y618 Database accession No. Q9Y618 (Nov. 1, 1999).

(56) References Cited

OTHER PUBLICATIONS

Dermer, G. B., Another Anniversary for the War on Cancer, Bio/Technology, 1994, 12:320.
Dinh, T. A., et al., The epidemiology of cancer in pregnancy, In Cancer and Pregnancy, Barnea, E. R., et al., Eds., Springer, 2005, 1:1-5.
Diouf, I., et al., Monocyte Activation and T Cell Inhibition in *Plasmodium falciparum*-Infected Placenta, J. Infect. Dis., 2004, 189(12):2235-2242.
Dong, V. M., et al., Transplantation tolerance: the concept and its applicability, Pediatr. Transplantation, 1999, 3(3):181-192.
Dressman, H. K., et al., Gene expression profiles of multiple breast cancer phenotypes and response to neoadjuvant Chemotherapy, Clin. Cancer Res., 2006, 12(3):819-826.
Du, W. W., et al., Inhibition of dexamthasone-induced fatty liver development by reducing miR-17-5p levels, Mol. Ther., 2015, 23(7):1222-1233.
Duzyj, C. M., et al., Preimplantation Factor (PIF*) Promotes Embryotrophic and Neuroprotective Decidual Genes: Effect Negated by Epidermal Growth Factor, J. Neurodevelopmental Disorders, 2014, 6(1):36.
Dyment, D. A., et al., Genetics of multiple sclerosis, Lancet Neurol., 2004, 3(2):104-110.
Eisenbarth, G. S., et al., Anti-thymocyte globulin and prednisone immunotherapy of recent onset type 1 diabetes mellitus, Diabetes Res., 1985, 2(6):271-276.
Elad, S., et al., Budesonide: A novel treatment for oral chronic graft versus host disease, Oral Surg. Oral Med. Oral Pathol. Oral Radiol. Endod., 2003, 95(3):308-311.
Elkin, G., et al., Prevention of diabetes in nonobese diabetic mice by nonmyeloablative allogeneic bone marrow transplantation, Exp. Hematol., 2004, 32(6):579-584.
Fernandez, E., et al., Cancer and pregnancy: Clinical management and biological analogy, in Barnea, E. R., et al. (Eds), Implantation and Early Pregnancy in Humans, Carnforth: Parthenon Publishing, 1994, pp. 355-377.
Ferrara, J. L. M., et al., Acute Graft Versus Host Disease: Pathophysiology, Risk Factors, and Prevention Strategies, Clin. Adv. Hematol. Oncol., 2005, 3(5):415-419, 428.
Fiocchi, C., Intestinal Inflammation: a complex interplay of immune and nonimmune cell interactions, Am. Physiol., 1997, 273(41:G769-G775.
Fischer, D. D., et al., Isolation and Characterization of a Novel Class II Histone Deacetylase, HDAC10, J. Biol. Chem., 2002, 277(8):6656-6666.
Fortin, M., et al., TGF-β2 and PGE2 in Rabbit Blastocoelic Fluid Can Modulate GM-CSF Production by Human Lymphocytes, Am. J. Reprod. Immunol., 1997, 38(2):129-139.
Freshney, R. I., Culture of Animal Cells, A Manual of Basic Technique, Alan R. Liss, Inc., New York, NY, 1983, pp. 3-4.
Freshney, R. I., Culture of Animal Cells, A Manual of Basic Technique, Wiley-Liss, Inc., New York, NY, 1994, p. 5.
Fuzzi, B., et al., HLA-G expression in early embryos is a fundamental prerequisite for the obtainment of pregnancy, Eur. J. Immunol., 2002, 32(2):311-315.
Gardner, D., et al., Complex physiologically based serum-free culture media increase mammalian embryo development, 10th World Congress on In Vitro Fertilization and Assisted Reproduction, May 24-28, 1997, p. 187-190.
Gardner, D. K., et al., Culture of viable human blastocysts in defined sequential serum-free media, Hum. Reprod., 1998, 13(suppl 3):148-160.
Gonzales, R. R., et al., Preimplantation factors (PIF) embryo-derived immunomodulatory peptides: possible implications for maternal recognition and allograft tolerance, 2002, 22nd Annual Meeting of the American Society for Reproductive Immunology, Chicago, IL (abstract).
Gonzalez, R. R., et al., Preimplantation Factor (PIF*) May Modulate Maternal Immunity (CD2), VII International Congress of Reproductive Immunology, Organized by ISIR, The International Society for Immunology of Reproduction, 2001, Opatja, Croatia; also published in Am. J. Reproduction Immunology, 2001, 46(1):68-69 (Abstract).
Gonzales, R. R., et al., Preimplantation factor (PIE) could be a portion of CD2 or a homologue peptide, 57th Annual Meeting of the American Society for Reproductive Medicine, Orlando, FL, Oct. 20-25, 2001, (abstract).
Gonzalez, R. R., et al., Preimplantation Factors (PIF) embryo-derived immunomodulatory peptides: possible implications for maternal recognition and allograft tolerance, American Journal of Reproductive Immunology, 2002, 47(6):347.
Gonzalez, R. R., et al., Immunomodulatory features of preimplantation factors (PIF) from mouse embryos, 11th World Congress on Human Reproduction, Montreal, Canada, Jun. 1-4, 2002, (Abstract).
Goodman, et al., The Pharmacological Basis of Therapeutics, 6th Ed., MacMillan Publ. Co., New York, 1980, TOC only.
Goodnow, C. C., Pathways for self-tolerance and the treatment of autoimmune diseases, The Lancet, 2001, 357:2115-2121.
Guenther, M. G., et al., A core SMRT corepressor complex containing HDAC3 and TBL1, a WD40-repeat protein linked to deafness, Genes Dev., 2000, 14(9):1048-1057.
Guller, S., et al., The role of placental Fas ligand in maintaining immune privilege at maternal-fetal interfaces, Semin. Reprod. Endocrinol., 1999, 17(1):39-44.
Gura, T., Systems for identifying new drugs are often faulty, Science, 1997, 278(5340):1041-1042.
Hafler, D. A., Multiple sclerosis, J. Clin. Invest., 2004, 113(6):788-794.
Hardy, K., et al., Growth factor expression and function in the human and mouse preimplantation embryo, J. Endocrinol., 2002, 172(2):221-236.
Herold, K. C., et al., Anti-Cd3 Monoclonal Antibody in New-Onset Type 1 Diabetes Mellitus, N. Engl. J. Med., 2002, 346(22):1692-1698.
Heyner, S., Growth factors in preimplantation development: role of insulin and insulin-like growth factors, Early Pregnancy: Biol. & Medicine, 1997, 3(3):153-163.
Ho, H. N., et al., Distribution of Th1 and Th2 cell populations in human peripheral and decidual T cells from normal and anembryonic pregnancies, Fertil..Steril., 2001, 76(4):797-803.
Hruby, V. J., et al., Synthesis of oligopeptide and peptidomimetic libraries, Curr. Op. Chem. Biol., 1997, 1(1):114-119.
Hruby, V. J., et al., Conformational and Topographical Considerations in Designing Agonist Peptidomimetics from Peptide Leads, Curr. Med. Cham., 2000, 7(9): 945-970.
Huggett, A. C., et al., Characterization of a hepatic proliferation inhibitor (HPI): effect of HPI on the growth of normal liver cells—comparison with transforming growth factor beta, J. Cell. Biochem., 1987, 35(4):305-314; also published in Growth Regulation of Cancer, pp. 55-64.
Hughes, R.A.C., Systematic Reviews of Treatment for Inflammatory Demyelinating Neuropathy; J. Anat. 2002, 200(4):331-339.
Hunter, C., et al., Selective inhibitors of Kv11.1 regulate IL-6 expression by macrophages in response to TRL/IL-1R ligands, The Scientific World Journal, 2010, 10:1580-1596.
Irving, P. M., et al., Review article: Appropriate use of corticosteroids in Crohn's disease, Alimentary Pharmacol. Ther., 2007, 26:313-329.
Jain, R. K., Barriers to drug delivery in solid tumors, Sci. Am., 1994, 271(1):58-65.
Janeway, Jr., C. A., et al., Eds., Immunobiology, The Immune System in Health and Disease, Third Edition, Garland Publishing Inc., 1997, pp. 7:25 and 9:31.
Jauniaux, E., et al., Preface: Future Directions and Limitations, in Jauniaux, E., et al., Eds., Embryonic Medicine and Therapy, Oxford: Oxford University Press, 1997, pp. 7-8.
Jiang, S.-P., et al., Cutting Edge: Multiple Mechanisms of Peripheral T Cell Tolerance to the Fetal "Allograft", J. Immunol., 1998, 160(7):3086-3090.
Johnson, K. I., et al., Copolymer 1 reduces relapse rate and improves disability in relapsing-remitting multiple sclerosis: Results of phase III multicenter, double-blind placebo-controlled trial, Neurology, 1995, 45(7):1268-1276.

(56) References Cited

OTHER PUBLICATIONS

Johnson, O. L., et al., Peptide and Protein Drug Delivery, in: Encyclopedia of Controlled Drug Delivery, vol. 2, 1999, pp. 816-833.
Kaaja, R. J., et al., Manifestations of Chronic Disease During Pregnancy, JAMA, 2005, 294(21):2751-2757.
Karussis, D. M., et al., Inhibition of Acute, Experimental Autoimmune, Encephalomyelitis by the Synthetic Immunomodulator Linomide, Ann. Neurol., 1993, 34(5):654-660.
Kraus, T. A., et al., Oral tolerance and inflammatory bowel disease, Curr. Opin. Gastroenterol., 2005, 21(6):692-696.
Lederman, M. M., et al., Defective Suppressor Cell Generation in Juvenile Onset Diabetes, J. Immunol., 1981, 127(5):2051-2055.
Li, J., et al., Both corepressor proteins SMRT and N-CoR exist in large protein complexes containing HDAC3, EMBO J., 2000, 19(16):4342-4350.
Liu, J. Q., The Yins of T Cell Activation, Sci. STKE, 2005, 2005(265):re1, 8 pages.
Uungdahl, M., et al., Immune cell distribution in gut-associated lymphoid tissue and synthesis of IL-6 in experimental porcine peritonitis, Eur. Surg. Res., 2000, 32(6):323-330.
Loke, Y. W., et al., Immunology of implantation, Bailliere's Best Pract. Res. Clin. Obstet. Gynaecol., 2000, 14(5):827-837.
Margolis, R. L., et al., cDNAs with long CAG trinucleotide repeats from human brain, Hum. Genet., 1997, 100:114-122.
Marketletter, AutoImmune shares collapse on Colloral data in rheumatoid arthritis, Marketletter Publications Ltd., 1999, 2 pp.
Mashima, K., et al., Multiple forms of growth inhibitors secreted from cultured rat liver cells: purification and Characterization, J. Biochem., 1986, 103(6):1020-1026.
Matsuyama, K., et al., Purification of three antibacterial proteins from the culture medium of NIH-Sape-4, an embryonic cell line of *Sarcophaga peregrina*, J. Biol. Chem., 1988, 263(32):17112-17116.
Mattsson, R., et al., Placental MCH class I antigen expression is induced in mice following in vivo treatment with recombinant interferon gamma, J. Reprod. Immunol., 1991, 19(2):115-129.
McFarland, H. F., Correlation between MR and Clinical Findings of Disease Activity in Multiple Sclerosis, AJNR Am. J. Neuroradiol., 1999, 20(10):1777-1778.
McGuirk, P., et al., Pathogen-specific regulatory T cells provoke a shift in the Th1/Th2 paradigm in immunity to infectious diseases, Trends Immunol., 2002, 23(9):450-455.
Medrano, L., et al., Sequence Analysis of the Polymerase Domain of HIV-1 Reverse Transcriptase in Naive and Zidovudine-Treated Individuals Reveals a Higher Polymorphism in a-Helices as Compared with 3-strands, Virus Genes, 1999, 18(3):203-210.
Mellor, A. L., et al., Extinguishing maternal immune responses during pregnancy: implications for immunosuppression, Semin. Immunol., 2001, 13(4):213-218.
Mielcarek, M., et al., Graft-vs-host disease after non-myeloablative hematopoietic cell transplantation, Leuk. Lymphona, 2005, 46(9):1251-1260.
Miller, D. H., et al., A Controlled Trial of Natalizumab for Relapsing Multiple Sclerosis, N. Engl. J. Med., 2003, 348(1):15-23.
Minhas, B.S., et al., Platelet Activating Factor and Conception, Am. J. Reprod. Immunol., 1996, 35(3):267-271.
Mirhashemi, R., Cancer and Pregnancy, Edited by Eytan R. Barnea, Eric Jaunlaux, and Peter E. Schwartz, The New England Journal of Medicine Book Review, 2002, 346(24):1921-1922.
Miyamoto, K., et al., Selective COX-2 Inhibitor Celecoxib Prevents Experimental Autoimmune Encephalomyelitis through COX-2-Independent Pathway, Brain, 2006, 129:1984-1992.
Mocellin, S., et al., The dual role of IL-10, Trends Immunol., 2003, 24(1):36-43.
Moffett-King, A., Natural Killer Cells and Pregnancy, Nat. Rev. Immunol., 2002, 2(9):656-663.
Moindjie, H., Preimplantation factor is an anti-apoptotic effector in human trophoblasts involving p53 signaling pathway, Cell Death and Disease, 2016, 7, e2504, 12 pages.
Morgan, B. A., et al., Approaches to the Discovery of Non-Peptide Ligands for Peptide Receptors and Peptidases, Annual Reports in Medicinal Chemistry, 1989, 24(VI): 243-252.
Morton, H., et al., Studies of the rosette inhibition test in pregnant mice: evidence of immunosuppression?, Proc. R. Sac. Land. B. Biol. Sci., 1976, 193(1113):413-419.
Morton, H., et al., An early pregnancy factor detected in human serum by the rosette inhibition test, Lancet, 1977, 1(8008):394-397.
Moschen, A. R., et al., Interleukin-32: A New Proinflammatory Cytokine Involved in Hepatitis C Virus-Related Liver Inflammation and Fibrosis, Hepatology, 2011, 53(6):1819-1829.
Muley, S. A., et al., Treatment of chronic inflammatory demyelinating polyneuropathy with pulsed oral steroids, Arch. Neurol., 2008, 65(11):1460-1464.
Müller, M., et al., Synthetic PreImplantation Factor (sPIF) # Neuroprotective Role in Intracranial Stem Cell Transplantation: Encephalopathy of Prematurity Rat Model, Z. Geburtshilfe Neonatol., DGPM: 26th German Congress for Perinatal Medicine, 2013, 217-V22_3, 1 page.
Müller, M., PreImplantation factor promotes neuroprotection by targeting microRNA let-7, PNAS, 2014, 111(38):13882-13887.
Müller, M., et al., 106: Synthetic Preimplantation Factor (sPIF*) Promotes Neuroprotection by Modulating PKA/PKC Kinases, American Journal of Obstetrics & Gynecology, 2015, 212(1):S70-S71.
Müller, M., et al., PreImplantation Factor Bolsters Neuroprotection via Modulating Protein Kinase A and Protein Kinase C Signaling, Cell Death and Differentiation, 2015, 22:2078-2086.
Nahhas, F., et al., Early Pregnancy Factor (EPF) Determination in Pregnant and IVF/ET Patients, and in Human Embryo Cultures, American Fertility Society 15th Ann. Mtg., San Francisco, CA, 1989, pp. S53-S54 (Abstract).
Nahhas, et al., Human Embryonic Origin Early Pregnancy Factor Before and After Implantation, Am. J. Reprod, Immunol., 1990, 22(3-4):105-108.
Nakamura, K., et al., Delayed and acute effects of interferon-γ on activity of an inwardly rectifying K+ channel in cultured human proximal tubule cells, Am. J. Physiol. Renal. Physiol., 2009, 296(1):F46-F53.
Navot, D., et al., Poor oocyte quality rather than implantation failure as a cause of age-related decline in female fertility, Lancet, 1991, 337(8754):1375-1377.
Olsen, J. V., et al., Global, In Vivo, and Site-Specific Phosphorylation Dynamics in Signaling Networks, Cell, 2006, 127(3):635-648.
O'Neill, C., Partial characterization of the embryo-derived platelet-activating factor in mice, J. Reprod. Fertil., 1985, 75(2):375-380.
O'Neill, C., et al., Use of a bioassay for embryo-derived platelet activating factor as a means of assessing quality and pregnancy potential of human embryos, Fertil. Steril., 1967, 47(6):969-975.
O'Neill, C., Thrombocytopenia is an initial maternal response to fertilization in the mouse, J. Reprod. Fertil., 1985, 73(2):559-566.
Or, R., et al., The prophylactic potential of fludarabine monophosphate in graft-versus-host disease after bone marrow transplantation in murine models, Bone Marrow Transplantation, 2000, 25(3):263-266.
Or, R., Safety study of preimplantation factor (PIF-1) to treat acute steroid-resistant graft-versus-host disease (GVHD), last updated 2015, available at https://trialbulletin.com/lib/entry/ct-00517907.
Ordentlich, P., et al., Unique forms of human and mouse nuclear receptor corepressor SMRT, Proc. Natl. Acad. Sci. USA, 1999, 96(6):2639-2644.
Paidas, M., et al., Pregnancy Implantation Factor (PIF) Activity Is Correlated With a Pro-Inflammatory Response, 23$^{rd}$ Annual Society for Maternal-Fetal Medicine Conference, San Francisco, CA, Dec. 2002, (Abstract).
Paidas, M., et al., Preimplantation Factor (PIF) Upregulates First Trimester Toll Like Receptor-2, Supporting the Role of PIF as an Embryo Derived Factor Influencing Maternal Innate Immunity, 27th Annual Scientific Meeting of the Society for Maternal-Fetal Medicine, San Francisco, CA, Feb. 5-10, 2007, S140 (Abstract 448).
Paidas, M. J., et al., A Genomic and Proteomic Investigation of the Impact of Preimplantation Factor on Human Decidual Cells, American Journal of Obstetrics and Gynecology, 2010, 202(5):459.e1-459.e8.

(56) References Cited

OTHER PUBLICATIONS

Paidas, M. J., et al., Pregnancy and Multiple Sclerosis (MS): A Beneficial Association. Possible Therapeutic Application of Embryo-Specific Pre-Implantation Factor (PIF*), American Journal of Reproductive Immunology, 2012, 68(6):456-464.

Paidas, M. Treatment of Acute Radiation Syndrome Using PIF, a Natural Immune Modulator, BioIncept, LLC, Project No. 1R41AI120546-01, Jun. 10, 2015, Retrieved from the Internet: https://projectreporter.nih.gov/project/info_description.cfm?projectnumber=1R41AI120546-01 on Nov. 18, 2015.

Park, E.-J., et al., SMRTe, a silencing mediator for retinoid and thyroid hormone receptors-extended isoform that is more related to the nuclear receptor corepressor, Proc. Natl. Acad. Sci. USA, 1999, 96(7):3519-3524.

Pearson, W. R., An Introduction to Sequence Similarity ("Homology") Searching, Current Protocols in Bioinformatics, 2013, Chapter 3, pp. 3.1.1-3.1.8.

Pessina, P., et al., Novel and optimized strategies for inducing fibrosis in vivo: focus on Duchenne Muscular Dystrophy, Skeletal Muscle, 2014, 4(1):7, 17 pages.

Piccinni, M. P., et al., Production of IL-4 and leukemia inhibitory factor by T cells of the cumulus oophorus: a favorable microenvironment for pre-implantation embryo development, Eur. J. Immunol., 2001, 31(8):2431-2437.

Pinkas, H., et al., Immunosuppressive Activity in Culture Media Containing Oocytes Fertilized In Vitro, Arch. Androl., 1992, 28(1):53-59.

Pozzilli, P., et al., No effect of oral insulin on residual beta-cell function in recent-onset type I diabetes (the IMDIAB VII), Diabetologia, 2000, 43(8):1000-1004.

Qin, Z. H., et al., Detection of early pregnancy factor in human sera, Am. J. Reprod. Immunol. Microbial., 1987, 13(1):15-18, Abstract only.

Raghupathy, R., Th1-type immunity is incompatible with successful pregnancy, Immunol. Today, 1997, 18(10):478-482.

Raghupathy, R., Pregnancy: success and failure within the Th1/Th2/Th3 paradigm, Semin. Immunol., 2001, 13(4):219-227.

Rayburn, W. F., Embryonic Medicine and Therapy, (Jauniaux, E., Barnea, E.R., Edwards, R.G., eds.), The New England Journal of Medicine Book Review, 1999, 340(19):1519.

Raz, I., et al., β-cell function in new-onset type 1 diabetes and immunomodulation with heat-shock protein peptide (DiaPep277): a randomised, double-blind, phase II trial, Lancet, 2001, 358(9295):1749-1753.

Reeck, G. R., et al., Homology in Proteins and Nucleic Acids: A Terminology Muddle and a Way Out of It, Cell, 1987, 50(5):667.

Resnick, I. B., et al., Nonmyeloablative stem cell transplantation and cell therapy for malignant and non-malignant diseases, Transpl. Immunol., 2005, 14(3-4):207-219.

Rieger, L., et al., Th1- and Th2-like cytokine production by first trimester decidual large granular lymphocytes is influenced by HLA-G and HLA-E, Mol. Hum. Reprod., 2002, 8(3):255-261.

Ripka, A. S., et al., Peptidomimetic design, Curr. Op. Chem. Biol., 1998, 2(4):441-452.

Rogers, A. M., et al., Maternal-fetal tolerance is maintained despite transgene-driven trophoblast expression of MHC class I, and defects in Fas and its ligand, Eur. J. Immunol., 1998, 28(11):3479-3487.

Rolfe, B. E., Detection of fetal wastage, Fertil. Steril., 1982, 37(5):655-660.

Rolfe, F. G., et al., Cyclosporin A and FK506 Reduce Interleukin-5 mRNA Abundance by Inhibiting Gene Transcription, Am. J. Respir. Cell Mol. Biol., 1997, 17(2):243-250.

Romagnani, S., Lymphokine Production by Human T Cells in Disease States, Annu. Rev. Immunol., 1994, 12:227-257, Abstract only.

Rosario, G. X., et al., Morphological events in the primate endometrium in the presence of a preimplantation embryo, detected by the serum preimplantation factor bioassay, Hum. Reprod., 2005, 20(1):61-71.

Rose, N. R., et al., Manual of Clinical Laboratory Immunology, Fifth Edition, ASM Press, 1997, pp. 20-48.

Roussev, R. G., et al., Clinical Validation of Preimplantation Factor (PIF) Assay, 2nd World Conference on Preimplantation and Early Pregnancy in Humans, Atlantic City, NJ, May 1994, (Abstract).

Roussev, R. G., et al., A Novel Bioassay for Detection of Preimplantation Factor (PIF), American Society of Reproductive Immunology, XVI Annual Meeting, Jun. 1994, Philadelphia, PA, (abstract).

Roussev, R. G., et al., A Novel Bioassay for Detection of Preimplantation Factor (PIF), Am. J. Reprod. Immunol., 1995, 33(1):68-73.

Roussev, R. G., et al., Embryonic Origin of Preimplantation Factor, Society for Gynecological Investigation 42nd Meeting, Chicago, IL, 1995, (Abstract).

Roussev, R. G., et al., Embryonic origin of preimplantation factor (PIF): biological activity and partial characterization, Mol. Hum. Reprod., 1996, 2(11):883-887.

Roussev, R. G., et al., Development and Validation of an Assay for Measuring Preimplantation Factor (PIF) of Embryonal Origin, Am. J. Reprod. Immunol., 1996, 35(3):281-287.

Roussev, R. G., et al., Preimplantation Factor Inhibits Circulating Natural Killer Cell Cytotoxicity and Reduces CD69 Expression: Implications for Recurrent Pregnancy Loss Therapy, Reproductive BioMedicine Online, 2013, 26(1):79-87.

Runmarker, B., et al., Pregnancy is associated with a lower risk of onset and a better diagnosis in multiple sclerosis, Brain, 1995, 118(1):253-261.

Salomon, B., et al., B7/CD28 Costimulation Is Essential for the Homeostasis of the CD4+CD25+ Immunoregulatory T Cells that Control Autoimmune Diabetes, Immunity, 2000, 12(4):431-440.

Sande, S., et al., Identification of TRACS (T3 Receptor-Associating Cofactors), a Family of Cofactors that Associate with, and Modulate the Activity of, Nuclear Hormone Receptors, Mol. Endocrinol., 1996, 10(7):813-825.

Sanyal, M. K, et al., Immunoregulatory activity in supernatants from cultures of normal human trophoblast cells of the first trimester, Am. J. Obstet. Gynecol., 1989, 161(2):446-453.

Sbracia, M., et al., Preimplantation Factor in Endometriosis: A Potential Role in Inducing Immune Privilege for Ectopic endometrium, PLoS ONE, 2017, 12(9):e0184399, 14 pages.

Schroeder, R. A., et al., Tolerance and the "Holy Grail" of Transplantation, J. of Surg. Res., 2003, 111:109-119.

Schumacher, Jr., H. R., et al., Primer on the Rheumatic Diseases, Tenth Edition, Arthritis Foundation (1993), pp. 86-89, 100-105.

Shainer, R., et al., Immune regulation and oxidative stress reduction by preimplantation factor following syngeneic or allogeneic bone marrow transplantation, Conference Papers in Medicine, 2013, 2013:1-8.

Shainer, R., et al. PB-277: Pre-Implantation Factor (PIF) as Prophylaxis after Radiation Exposure: Immune-Regulation and iNOS Reduced Expression, Poster presented in the $7^{th}$ Congress of the Federation of the Israel Societies for Experimental Biology, Feb. 10-13, 2014.

Shainer, R., et al., PreImplantation Factor (PIF) Therapy Provides Comprehensive Protection against Radiation Induced Pathologies, Oncotarget, 2016, 7(37):58975-58994.

Sharma, S., et al., Genes regulating implantation and fetal development: a focus on mouse knockout models, Front. Biosci., 2006, 11:2123-2137.

Shi, Y., et al., Sharp, an inducible cofactor that integrates nuclear receptor repression and activation, Genes Dev., 2001, 15(9):1140-1151.

Shurtz-Swirski, R., et al., Human Embryo Modulates Placental Function in the First Trimester; Effects of Neural Tissues upon Chorionic Gonadotropin and Progesterone Secretion, Placenta, 1991, 12(5):521-531.

Shurtz-Swirski, R., et al., Patterns of secretion of human chorionic gonadotropin by superfused placental explants and the embryo-placental relationship following maternal use of medications, Hum. Reprod., 1992, 7(3):300-304.

Shurtz-Swirski, R., et al., In Vitro Effect of Anticardiolipin Autoantibodies Upon Total and Pulsatile Placental hCG Secretion During Early Pregnancy, Am. J. Reprod. Immunol., 1993, 29(4):206-210.

(56) References Cited

OTHER PUBLICATIONS

Shurtz-Swirski, R., et al., Anti-Cardiolipin Antibodies Affect Total and Pulsatile Placental Hcg Secretion During Early Pregnancy, Israel Conference of Fertility, Tel Aviv, Israel, 1993, (Abstract).
Sicotte, N. L., et al., Onset of Multiple Sclerosis Associated with Anti-TNF Therapy, Neurology, 2001, 57:1885-1888.
Singh, V. K., et al., Animal models for acute radiation syndrome drug discovery, Expert Opin. Drug Discov., 2015, 10(5):497-517.
Sipka, S., et al., Glucocorticosteroid dependent decrease in the activity of calcineurin in the peripheral blood mononuclear cells of patients with systemic lupus erythematosus, Ann. Rheum. Dis., 2001, 60(4):380-384.
Skolnick, J., et al., From genes to protein structure and function: novel applications of computational approaches in the genomic era, Trends Biotechnol., 2000, 18(1):34-39.
Skyler, J. S., et al., Use of Inhaled Insulin in a Basal/Bolus Insulin Regimen in Type 1 Diabetic Subjects, Diabetes Care, 2005, 28(7):1630-1635.
Slavin, S., et al., The graft-versus-leukemia (GVL) phenomenon: is GVL separable from GVHD?, Bone Marrow Transplant, 1990, 6(3):155-161.
Slavin, S., et al., Non-myeloablative stem cell transplantation for the treatment of cancer and life-threatening non-malignant disorders; past accomplishments and future goals, Transfusion and Apheresis Sci., 2002, 27(2):159-166.
Smart, Y. C., et al., Early pregnancy factor: its role in mammalian reproduction—research review, Fertil. Steril., 1981, 35(4):397-402.
Smart, Y. C., et al., Validation of the rosette inhibition test for the detection of early pregnancy in women, Fertil. Steril., 1962,37(6):779-765.
Somerset, D. A., et al., Normal human pregnancy is associated with an elevation in the human suppressive CD25+ CD4+ regulatory T-cell subset, Immunology, 2004, 112(1):38-43.
Sospedra, M., et al., Immunology of Multiple Sclerosis, Annu. Rev. Immunol., 2005, 23:683-747.
Stewart, C. L., et al., Preimplantation Development of the Mammalian Embryo and Its Regulation by Growth Factors, Dev. Genetics, 1997, 21:91-101.
Streifler, J., et al., Effects of dexamethasone in myotonic muscular dystrophy, J. Neruol. Neruosurg. Psychiartry, 1987, 50(7):937.
Stürzebecher, S., et al., Expression profiling identifies responder and non-responder phenotypes to interferon-β in multiple sclerosis, Brain, 2003, 126(6):1419-1429.
Szekeres-Bartho, J., Immunological Relationship Between the Mother and the Fetus, Int. Rev. Immunol., 2002, 21(6):471-495.
Tangri, S., et al., Maternal Anti-Placental Reactivity in Natural, Immunologically-Mediated Fetal Resorptions, J. Immunol., 1994, 152(10):4903-4911.
Taubes, G., Vaccines. Malaria Parasite Outwits the Immune System, Science, 2000, 290(5491):435.
Than, N. G., et al., Embryo-Placento-Maternal Interaction and Biomarkers: From Diagnosis to Therapy—A Workshop Report, Placenta, 2007, 28(Suppl. A)(21):S107-S110.
The staff at US Pharmacists, Autoimmune disease, US Pharm., 2016, 41(6):13-14.
Thwaites, G. E., et al., Dexamethasone for the treatment of tuberculosis meningitis in adolescents and adults, N. Engl. J. Med., 2004, 351:1741-1751.
TNF neutralization in MS: results of a randomized, placebo-controlled multicenter study. The Lenercept Multiple Sclerosis Study Group and the University of British Columbia MS/MRI Analysis Group, Neurology, 1999, 53:457-465.
Tokuriki, N., et al., Stability Effects of Mutations and Protein Evolvability, Current Opinion in Structural Biology, 2009, 19:596-604.
Treister, N., et al., An open label phase II randomized trial of topical dexamethasone and tacrolimus solutions for the treatment of oral chronic graft vs host disease, Biol. Blood Marrow Transplant, 2016, 22:2084-2091.
Truitt, R. L., The Mortimer M. Bortin Lecture: to destroy by the Reaction of Immunity: the Search for Separation of Graft-versus-Leukemia and Graft Host, Biol. Blood Marrow Transplant, 2004, 10(8):505-523.
U.S. Congress, Office of Technology Assessment, Infertility. Medical and Social Choices, OTA-BA-358, Washington, DC: Government Printing Office, May 1988.
Vallera, D. A., Targeting T Cells for GVHD Therapy, Semin. Cancer Biol., 1996, 7(2):57-64.
Valverde, P., et al., Potassium channel-blockers as therapeutic agents to interfere with bone resorption of periodontal Disease, J. Dental. Res, 2005, 84(6):468-499.
Verma, A. K., et al., Anti-mullerian hormone: A marker of ovarian reserve and its association with polycystic ovarian syndrome, J. Clin. Diagn. Res., 2016, 10(12):QC10-QC12.
Wegmann, T. G., et al., Bidirectional cytokine interactions in the maternal-fetal relationship: is successful pregnancy a TH2 phenomenon?, Immunol. Today, 1993, 14(7):353-356, Abstract only.
Weiss, L., et al., Induction of resistance to diabetes in non-obese diabetic mice by targeting CD44 with a specific monoclonal antibody, Proc. Natl. Acad. Sci. USA, 2000, 97(1):285-290.
Weiss. L., et al., Preimplantation Factor (PIF) Analog Prevents Type I Diabetes Mellitus (TIDM) Development by Preserving Pancreatic Function in NOD Mice, Endocrine, 2011, 40:42-54.
Weiss, L., et al., Preimplantation factor (PIF) reverses neuroinflammation while promoting neural repair in EAE model, J. Neurol. Sci., 2012, 312(1-2):146-157.
Whyte, A., et al., Reproductive immunology. Early pregnancy factor, Nature, 1983, 304(5922):121-122.
Wickramasinghe, S. N., et al., Blood and bone marrow changes in malaria, Baillieres Best Pract. Res. Clin. Haematol., 2000, 13(2):277-299.
Wu, M. Y., et al., Increase in the Production of Interleukin-10 Early After Implantation is Related to the Success of Pregnancy, Am. J. Reprod. Immunol., 2001, 46(6):386-392.
Wu, A. I., et al., Tumor necrosis factor-α regulation of CD4+C25+ T cell levels in NOD mice, Proc. Natl. Acad. Sci. USA, 2002, 99(19):12287-12292.
Yampolsky, L. Y., et al., The exchangeability of amino acids in proteins, Genetics, 2005, 170:1459-1472.
Zhang, X., et al., MicroRNA Expression Profile in Hyperoxia-Exposed Newborn Mice during the Development of Bronchopulmonary Dysplasia, Respiratory Care, 2011, 56(7):1009-1015.
Zhang, J., et al., The N-CoR-HDAC3 Nuclear Receptor Corepressor Complex Inhibits the JNK Pathway through the Integral Subunit GPS2, Mol. Cell, 2002, 9(3):611-623.
Zhou, M., et al., Expanded cohorts of maternal CD8+ T-cells specific for paternal MCH class I accumulate during pregnancy, J. Reprod. Immunol., 1998, 40(1):47-62.
Afkhami, F., et al., Investigation of antiangiogenic tumor therapy potential of microencapsulated HEK293 VEGF165b producing cells, J. Biomedicine and Biotechnology, 2010, 2010:645610, 7 pages.
Barnea, E. R., et al., Identification and validation of an assay for preimplantation factor (PIF), The Second World Conference on Implantation and Early Pregnancy in Humans, May 12-14, 1994, Atlantic City, NJ (Abstract).
Barnea, E. R., et al., The role of pre-implantation factor (PIF) in the immune recognition of pregnancy, The Second International Congress on Autoimmunity, Mar. 7-12, 1999, Tel Aviv, Israel (Abstract).
Chen, Y. C., et al., PreImplantation factor prevents atherosclerosis via its immunomodulatory effects without affecting serum lipids, Thromb. Haemost, 2016, 115(5):1010-24, Abstract only.
Gurudutta, G. U., et al., Stem cell therapy: A novel & futuristic treatment modality for disaster injuries, Indian J. Med. Res., 2012, 135:15-25.
Hayrabedyan, S. B., et al., Structural design-based preimplantation factor (PIF*) fusion peptide synthetic DNA cloning and eukaryote expression aimed for functional proteomic studies and possible chronic immune disorders therapy, J. Reproductive Immunology, 2014, 101-102:60.

(56) References Cited

OTHER PUBLICATIONS

Stamatkin, C. W., et al., Preimplantation factor negates embryo toxicity and promotes embryo development in culture, 2011, 23(4):517-524.

* cited by examiner

PIF IS A BENIGN STEROID
Regulates Immune Response / Endogenous Cortisone Competitor

VOLTAGE DEPENDENT K+ CHANNEL BETA SUBUNIT

PIF BINDS
Same Binding Site (Receptor) as Cortisone

PIF SPECIFICITY: SINGLE AA MUTATION ABOLISHES ACTIVITY
Effect on Immune and Neural Cells A  BV-2 cells B  N2a cells mPIF (mutate) effect compared to sPIF (wild type) or PIFscr (scrambled)

INTACT PIF CROSSES THE BLOOD BRAIN BARRIER
Clears Rapidly from Circulation

Mouse injected SQ and brain is harvested
after 6h – HPLC/Mass spec

PIF clearance from circulation

PIF PRESENT IN BRAIN, ABSENT IN CIRCULATION
PIF Targets Neurons and Microglia

PIF
PIF presence in the brain 12h post injection – IHC Using anti-PIF-monoclonal antibody PIF measured in the serum after 12h using mass-spectrometry is not detected

PIF PREVENTS ACUTE PARALYSIS
Prevents Access of Inflammatory Cells to the Spinal Cord Alzet pumps: SC implants RX; PIF 0.1 or 0.5 mg/kg for 28 days. Area under the curve $p<0.002$ EAE mouse model – injected
PLP / Tuberculin / Pertussis, $P<0.002$ Mann-Whitney PIF PROTECTS AGAINST VASCULAR DAMAGE
(ApoE + Murine Model + High-Fat Diet)

PIF 10uM

Control PBS

\* Quantification using OPTIMAS Pro computer software

PBS

| | | | | | | | | |
|---|---|---|---|---|---|---|---|---|
| CD4 | Vβ4-Jβ1.6 | ■ | | | | ■ | | |
| | Vβ10-Jβ1.1 | | | | | | | |
| CD8 | Vβ17-Jβ1.6 | | | | | | | ■ |
| | Vβ20-Jβ2.3 | | | | | | ■ | |
| pre-immune | Vβ18-Jβ1.2 | | ■ | | | | | |
| | Vβ19-Jβ1.2 | | ■ | | | ■ | | ■ |

PIF

| | | | | | | | | |
|---|---|---|---|---|---|---|---|---|
| CD4 | Vβ4-Jβ1.6 | | | | | | | |
| | Vβ10-Jβ1.1 | | | | | | | ▦ |
| CD8 | Vβ17-Jβ1.6 | | | | | | | |
| | Vβ20-Jβ2.3 | | | | | | | ■ |
| pre-immune | Vβ18-Jβ1.2 | | | | | | | |
| | Vβ19-Jβ1.2 | ■ | ■ | ■ | ■ | | | |

FIG. 29

SEQUENCE LISTING

<160> NUMBER OF SEQ ID NOS: 33

<210> SEQ ID NO 1
<211> LENGTH: 15
<212> TYPE: PRT
<213> ORGANISM: Artificial Sequence
<220> FEATURE:
<223> OTHER INFORMATION: nPIF-1 (15)

-continued

```
<400> SEQUENCE: 1

Met Val Arg Ile Lys Pro Gly Ser Ala Asn Lys Pro Ser Asp Asp
1               5                   10                  15

<210> SEQ ID NO 2
<211> LENGTH: 15
<212> TYPE: PRT
<213> ORGANISM: Artificial Sequence
<220> FEATURE:
<223> OTHER INFORMATION: nPIF-1 (15-alter)

<400> SEQUENCE: 2

Met Val Arg Ile Lys Tyr Gly Ser Tyr Asn Lys Pro Ser Asp
1               5                   10                  15

<210> SEQ ID NO 3
<211> LENGTH: 13
<212> TYPE: PRT
<213> ORGANISM: Artificial Sequence
<220> FEATURE:
<223> OTHER INFORMATION: nPIF-1 (13)

<400> SEQUENCE: 3

Met Val Arg Ile Lys Pro Gly Ser Ala Asn Lys Pro Ser
1               5                   10

<210> SEQ ID NO 4
<211> LENGTH: 9
<212> TYPE: PRT
<213> ORGANISM: Artificial Sequence
<220> FEATURE:
<223> OTHER INFORMATION: nPIF-1 (9)

<400> SEQUENCE: 4

Met Val Arg Ile Lys Pro Gly Ser Ala
1               5

<210> SEQ ID NO 5
<211> LENGTH: 15
<212> TYPE: PRT
<213> ORGANISM: Artificial Sequence
<220> FEATURE:
<223> OTHER INFORMATION: scrPIF-1 (15)

<400> SEQUENCE: 5

Gly Arg Val Asp Pro Ser Asn Lys Ser Met Pro Lys Asp Ile Ala
1               5                   10                  15

<210> SEQ ID NO 6
<211> LENGTH: 10
<212> TYPE: PRT
<213> ORGANISM: Artificial Sequence
<220> FEATURE:
<223> OTHER INFORMATION: nPIF-2 (10)

<400> SEQUENCE: 6

Ser Gln Ala Val Gln Glu His Ala Ser Thr
1               5                   10

<210> SEQ ID NO 7
<211> LENGTH: 13
<212> TYPE: PRT
<213> ORGANISM: Artificial Sequence
<220> FEATURE:
<223> OTHER INFORMATION: nPIF-2 (13)
```

<400> SEQUENCE: 7

Ser Gln Ala Val Gln Glu His Ala Ser Thr Asn Met Gly
1               5                   10

<210> SEQ ID NO 8
<211> LENGTH: 13
<212> TYPE: PRT
<213> ORGANISM: Artificial Sequence
<220> FEATURE:
<223> OTHER INFORMATION: scrPIF-2 (13)

<400> SEQUENCE: 8

Glu Val Ala Gln His Ser Gln Ala Ser Thr Met Asn Gly
1               5                   10

<210> SEQ ID NO 9
<211> LENGTH: 14
<212> TYPE: PRT
<213> ORGANISM: Artificial Sequence
<220> FEATURE:
<223> OTHER INFORMATION: scrPIF-2 (14)

<400> SEQUENCE: 9

Gly Gln Ala Ser Ser Ala Gln Met Asn Ser Thr Gly Val His
1               5                   10

<210> SEQ ID NO 10
<211> LENGTH: 18
<212> TYPE: PRT
<213> ORGANISM: Artificial Sequence
<220> FEATURE:
<223> OTHER INFORMATION: nPIF-3 (18)

<400> SEQUENCE: 10

Ser Gly Ile Val Ile Tyr Gln Tyr Met Asp Asp Arg Tyr Val Gly Ser
1               5                   10                  15

Asp Leu

<210> SEQ ID NO 11
<211> LENGTH: 11
<212> TYPE: PRT
<213> ORGANISM: Artificial Sequence
<220> FEATURE:
<223> OTHER INFORMATION: Neg control for negPIF-1 (15)

<400> SEQUENCE: 11

Gly Met Arg Glu Leu Gln Arg Ser Ala Asn Lys
1               5                   10

<210> SEQ ID NO 12
<211> LENGTH: 9
<212> TYPE: PRT
<213> ORGANISM: Artificial Sequence
<220> FEATURE:
<223> OTHER INFORMATION: nPIF-4 (9)

<400> SEQUENCE: 12

Val Ile Ile Ile Ala Gln Tyr Met Asp
1               5

<210> SEQ ID NO 13
<211> LENGTH: 15
<212> TYPE: PRT
<213> ORGANISM: Artificial Sequence
<220> FEATURE:
<223> OTHER INFORMATION: sPIF-1 (15)

```
<400> SEQUENCE: 13

Met Val Arg Ile Lys Pro Gly Ser Ala Asn Lys Pro Ser Asp Asp
1               5                   10                  15

<210> SEQ ID NO 14
<211> LENGTH: 13
<212> TYPE: PRT
<213> ORGANISM: Artificial Sequence
<220> FEATURE:
<223> OTHER INFORMATION: sPIF-2 (13)

<400> SEQUENCE: 14

Ser Gln Ala Val Gln Glu His Ala Ser Thr Asn Met Gly
1               5                   10

<210> SEQ ID NO 15
<211> LENGTH: 18
<212> TYPE: PRT
<213> ORGANISM: Artificial Sequence
<220> FEATURE:
<223> OTHER INFORMATION: sPIF-3 (18)

<400> SEQUENCE: 15

Ser Gly Ile Val Ile Tyr Gln Tyr Met Asp Asp Arg Tyr Val Gly Ser
1               5                   10                  15

Asp Leu

<210> SEQ ID NO 16
<211> LENGTH: 9
<212> TYPE: PRT
<213> ORGANISM: Artificial Sequence
<220> FEATURE:
<223> OTHER INFORMATION: sPIF-1 (9)

<400> SEQUENCE: 16

Met Val Arg Ile Lys Pro Gly Ser Ala
1               5

<210> SEQ ID NO 17
<211> LENGTH: 9
<212> TYPE: PRT
<213> ORGANISM: Artificial Sequence
<220> FEATURE:
<223> OTHER INFORMATION: sPIF-4 (9)

<400> SEQUENCE: 17

Val Ile Ile Ile Ala Gln Tyr Met Asp
1               5

<210> SEQ ID NO 18
<211> LENGTH: 5
<212> TYPE: PRT
<213> ORGANISM: Artificial Sequence
<220> FEATURE:
<223> OTHER INFORMATION: sPIF-1(5)

<400> SEQUENCE: 18

Met Val Arg Ile Lys
1               5

<210> SEQ ID NO 19
<211> LENGTH: 4
<212> TYPE: PRT
<213> ORGANISM: Artificial Sequence
<220> FEATURE:
<223> OTHER INFORMATION: sPIF-1 (4)
```

```
<400> SEQUENCE: 19

Pro Gly Ser Ala
1

<210> SEQ ID NO 20
<211> LENGTH: 15
<212> TYPE: PRT
<213> ORGANISM: Artificial Sequence
<220> FEATURE:
<223> OTHER INFORMATION: PIF (-3)
<220> FEATURE:
<221> NAME/KEY: misc_feature
<222> LOCATION: (3)..(3)
<223> OTHER INFORMATION: Xaa can be any naturally occurring amino acid

<400> SEQUENCE: 20

Met Val Xaa Ile Lys Pro Gly Ser Ala Asn Lys Pro Ser Asp Asp
1               5                   10                  15

<210> SEQ ID NO 21
<211> LENGTH: 14
<212> TYPE: PRT
<213> ORGANISM: Artificial Sequence
<220> FEATURE:
<223> OTHER INFORMATION: PIF mutant
<220> FEATURE:
<221> NAME/KEY: MISC_FEATURE
<222> LOCATION: (1)..(1)
<223> OTHER INFORMATION: Xaa = any natural or non-natural amino acid
<220> FEATURE:
<221> NAME/KEY: MISC_FEATURE
<222> LOCATION: (3)..(3)
<223> OTHER INFORMATION: Xaa = any natural or non-natural amino acid

<400> SEQUENCE: 21

Xaa Val Xaa Ile Lys Pro Gly Ser Ala Asn Lys Pro Ser Asp
1               5                   10

<210> SEQ ID NO 22
<211> LENGTH: 13
<212> TYPE: PRT
<213> ORGANISM: Artificial Sequence
<220> FEATURE:
<223> OTHER INFORMATION: PIF mutant
<220> FEATURE:
<221> NAME/KEY: MISC_FEATURE
<222> LOCATION: (1)..(1)
<223> OTHER INFORMATION: Xaa = any natural or non-natural amino acid
<220> FEATURE:
<221> NAME/KEY: MISC_FEATURE
<222> LOCATION: (3)..(3)
<223> OTHER INFORMATION: Xaa = any natural or non-natural amino acid

<400> SEQUENCE: 22

Xaa Val Xaa Ile Lys Pro Gly Ser Ala Asn Lys Pro Ser
1               5                   10

<210> SEQ ID NO 23
<211> LENGTH: 12
<212> TYPE: PRT
<213> ORGANISM: Artificial Sequence
<220> FEATURE:
<223> OTHER INFORMATION: PIF mutant
<220> FEATURE:
<221> NAME/KEY: MISC_FEATURE
<222> LOCATION: (1)..(1)
<223> OTHER INFORMATION: Xaa = any natural or non-natural amino acid
<220> FEATURE:
<221> NAME/KEY: MISC_FEATURE
<222> LOCATION: (3)..(3)
<223> OTHER INFORMATION: Xaa = any natural or non-natural amino acid
```

```
<400> SEQUENCE: 23

Xaa Val Xaa Ile Lys Pro Gly Ser Ala Asn Lys Pro
1               5                   10

<210> SEQ ID NO 24
<211> LENGTH: 10
<212> TYPE: PRT
<213> ORGANISM: Artificial Sequence
<220> FEATURE:
<223> OTHER INFORMATION: PIF mutant
<220> FEATURE:
<221> NAME/KEY: MISC_FEATURE
<222> LOCATION: (1)..(1)
<223> OTHER INFORMATION: Xaa = any natural or non-natural amino acid
<220> FEATURE:
<221> NAME/KEY: MISC_FEATURE
<222> LOCATION: (3)..(3)
<223> OTHER INFORMATION: Xaa = any natural or non-natural amino acid

<400> SEQUENCE: 24

Xaa Val Xaa Ile Lys Pro Gly Ser Ala Asn
1               5                   10

<210> SEQ ID NO 25
<211> LENGTH: 10
<212> TYPE: PRT
<213> ORGANISM: Artificial Sequence
<220> FEATURE:
<223> OTHER INFORMATION: PIF mutant
<220> FEATURE:
<221> NAME/KEY: MISC_FEATURE
<222> LOCATION: (1)..(1)
<223> OTHER INFORMATION: Xaa = any natural or non-natural amino acid
<220> FEATURE:
<221> NAME/KEY: MISC_FEATURE
<222> LOCATION: (3)..(3)
<223> OTHER INFORMATION: Xaa = any natural or non-natural amino acid

<400> SEQUENCE: 25

Xaa Val Xaa Ile Lys Pro Gly Ser Ala Asn
1               5                   10

<210> SEQ ID NO 26
<211> LENGTH: 9
<212> TYPE: PRT
<213> ORGANISM: Artificial Sequence
<220> FEATURE:
<223> OTHER INFORMATION: PIF mutant
<220> FEATURE:
<221> NAME/KEY: MISC_FEATURE
<222> LOCATION: (1)..(1)
<223> OTHER INFORMATION: Xaa = any natural or non-natural amino acid
<220> FEATURE:
<221> NAME/KEY: MISC_FEATURE
<222> LOCATION: (3)..(3)
<223> OTHER INFORMATION: Xaa = any natural or non-natural amino acid

<400> SEQUENCE: 26

Xaa Val Xaa Ile Lys Pro Gly Ser Ala
1               5

<210> SEQ ID NO 27
<211> LENGTH: 8
<212> TYPE: PRT
<213> ORGANISM: Artificial Sequence
<220> FEATURE:
<223> OTHER INFORMATION: PIF mutant
<220> FEATURE:
<221> NAME/KEY: MISC_FEATURE
<222> LOCATION: (1)..(1)
<223> OTHER INFORMATION: Xaa = any natural or non-natural amino acid
```

```
<220> FEATURE:
<221> NAME/KEY: MISC_FEATURE
<222> LOCATION: (3)..(3)
<223> OTHER INFORMATION: Xaa = any natural or non-natural amino acid

<400> SEQUENCE: 27

Xaa Val Xaa Ile Lys Pro Gly Ser
1               5

<210> SEQ ID NO 28
<211> LENGTH: 7
<212> TYPE: PRT
<213> ORGANISM: Artificial Sequence
<220> FEATURE:
<223> OTHER INFORMATION: PIF mutant
<220> FEATURE:
<221> NAME/KEY: MISC_FEATURE
<222> LOCATION: (1)..(1)
<223> OTHER INFORMATION: Xaa = any natural or non-natural amino acid
<220> FEATURE:
<221> NAME/KEY: MISC_FEATURE
<222> LOCATION: (3)..(3)
<223> OTHER INFORMATION: Xaa = any natural or non-natural amino acid

<400> SEQUENCE: 28

Xaa Val Xaa Ile Lys Pro Gly
1               5

<210> SEQ ID NO 29
<211> LENGTH: 6
<212> TYPE: PRT
<213> ORGANISM: Artificial Sequence
<220> FEATURE:
<223> OTHER INFORMATION: PIF mutant
<220> FEATURE:
<221> NAME/KEY: MISC_FEATURE
<222> LOCATION: (1)..(1)
<223> OTHER INFORMATION: Xaa = any natural or non-natural amino acid
<220> FEATURE:
<221> NAME/KEY: MISC_FEATURE
<222> LOCATION: (3)..(3)
<223> OTHER INFORMATION: Xaa = any natural or non-natural amino acid

<400> SEQUENCE: 29

Xaa Val Xaa Ile Lys Pro
1               5

<210> SEQ ID NO 30
<211> LENGTH: 5
<212> TYPE: PRT
<213> ORGANISM: Artificial Sequence
<220> FEATURE:
<223> OTHER INFORMATION: PIF mutant
<220> FEATURE:
<221> NAME/KEY: MISC_FEATURE
<222> LOCATION: (1)..(1)
<223> OTHER INFORMATION: Xaa = any natural or non-natural amino acid
<220> FEATURE:
<221> NAME/KEY: MISC_FEATURE
<222> LOCATION: (3)..(3)
<223> OTHER INFORMATION: Xaa = any natural or non-natural amino acid

<400> SEQUENCE: 30

Xaa Val Xaa Ile Lys
1               5

<210> SEQ ID NO 31
<211> LENGTH: 4
<212> TYPE: PRT
<213> ORGANISM: Artificial Sequence
```

```
<220> FEATURE:
<223> OTHER INFORMATION: PIF mutant
<220> FEATURE:
<221> NAME/KEY: MISC_FEATURE
<222> LOCATION: (1)..(1)
<223> OTHER INFORMATION: Xaa = any natural or non-natural amino acid
<220> FEATURE:
<221> NAME/KEY: MISC_FEATURE
<222> LOCATION: (3)..(3)
<223> OTHER INFORMATION: Xaa = any natural or non-natural amino acid

<400> SEQUENCE: 31

Xaa Val Xaa Ile
1

<210> SEQ ID NO 32
<211> LENGTH: 20
<212> TYPE: DNA
<213> ORGANISM: Artificial Sequence
<220> FEATURE:
<223> OTHER INFORMATION: S12 forward primer

<400> SEQUENCE: 32
tgctggaggt gtaatggacg                                               20

<210> SEQ ID NO 33
<211> LENGTH: 20
<212> TYPE: DNA
<213> ORGANISM: Artificial Sequence
<220> FEATURE:
<223> OTHER INFORMATION: S12 reverse primer

<400> SEQUENCE: 33
caagcacaca aagatgggct                                               20
```

COMPOSITIONS AND METHODS FOR THE TREATMENT OF NEURODAMAGE

CROSS-REFERENCE TO RELATED APPLICATIONS

This application is a U.S. National Stage entry under 35 U.S.C. § 371 of International Application No. PCT/US2016/048601, filed on Aug. 25, 2016, which claims priority to and the benefit of U.S. Provisional Application Nos. 62/211,660, filed Aug. 28, 2015 and 62/361,334, filed Jul. 12, 2016, which are each hereby incorporated by reference in their entirety.

TECHNOLOGY FIELD

The present disclosure generally relates to compositions and methods for treatment of neurological conditions, such as neurotrauma, which refers to injury to a peripheral or nerve, especially part of the central nervous system (the brain and/or spinal cord). The injury can be caused by a condition such as MS and the like. The disclosure also relates to pre-implantation factor (PIF) mutants and methods of treatment using the same, including the treatment of neurotrauma.

BACKGROUND

Neurotrauma encompasses TBI, SCI and CNS injuries as well as other nerve disorders/diseases, including peripheral trauma to the nerve. Neurotrauma can have local and/or systemic consequences, which can manifest themselves short-term (acute) or long-term (chronic). Also often the onset of symptoms coincides with the time of the trauma. In case of injury, neurotrauma can develop itself over time presenting clinical manifestations days, weeks or even years afterwards. Neurotrauma can be mild or severe, and can present devastating consequences including paralysis, brain damage, and death. Beyond penetrating wounds, neurotrauma results from inflammatory responses that can be caused by injuries or changes in the body. The central nervous system (CNS) consists of the brain and spinal cord and is an essential part of the nervous system. The CNS is so named because it integrates, coordinates and influences all information and activity from all parts of the body. The CNS is well protected in vertebrates; the brain protected by the skull and the spinal cord protected by the vertebrae, in addition to both being enclosed in meninges and cerebrospinal fluid. However, various forms of neurotrauma can either temporarily or permanently affect CNS function. For example, traumatic brain injury (TBI) and spinal cord injury (SCI) following acute or even mild events can lead to progressive inflammation and neurodegeneration even years after the initial event. Unfortunately early symptoms do not predict, or correlate with potential adverse outcome, actually they can be unrelated.

Traumatic brain injury (TBI) and spinal cord injury (SCI) collectively called neurotrauma are major causes of death and disability worldwide. For the civilian population, neurotrauma occurs especially in children and young adults and the causes include falls, vehicle accidents and trauma. The most common cause of neurotrauma in the US includes violence, accidents, construction and sports injuries. It is estimated that there are between 1.6 and 3.8 million of neurotrauma as the results of sports and recreational activities alone. The neurotrauma affects normal motor, sensory, or autonomic function, partially or permanently. Neurotrauma commonly occurs in military operations. As of June 2014, overseas operations resulted in over 52,000 U.S. military personnel wounded in action in OEF, OIF, and OND (Defense Casualty Analysis System, www.dmdc.osd.mil/dcas/). Over half traumatic injuries in recent US military conflicts are caused by explosive devices, requiring rapid soldier evacuation, inpatient hospitalizations, extensive rehabilitation, and have the highest costs associated with long-term disability. Both in civilian, a battlefield triage setting or emergency response, early treatment is vital to increase chances of recovery and manage potentially chronic complications. Regardless of the cause, it is important to begin treatment for neurotrauma as soon as possible following the injury. Prognosis differs depending on the severity and location of the lesion and access to immediate medical management. Efforts to halt or mitigate inflammation and primary or secondary nerve injury have been largely unsuccessful to date and identification of an effective medical countermeasure would be of great utility to the medical community.

In case of penetrating wounds or need for decompression, neurosurgical inventions are used. Beyond surgery, post neurotrauma mostly supporting measures (intravenous fluid, oxygen, neuroleptic agents) are utilized followed by longer-term rehabilitation techniques. Research into treatment for neurotrauma therapy has been studied thoroughly however despite very intensive research for the past 30 years very few new interventions have been implemented in standard of care. As recently reported, all clinical trials failed to improve outcome.

An element of neurotrauma is the resulting progressive inflammatory response which may perpetuate the dysfunction long-term. Current therapies are unable to counteract the inflammatory response and arrest the development of cognitive, motor and sensory dysfunction. The resulting systemic immune activation post neurotrauma further negatively impacts the recovery. Accordingly, there is still a need for improved and new treatments for neurotrauma diseases including neurodegenerative diseases such as those described herein.

SUMMARY

The present disclosure relates to a method of treating or preventing traumatic injury of the central nervous system in a subject in need thereof, the method comprising administering to the subject at least one pre-implantation factor (PIF) peptide, an analog thereof, or a pharmaceutically acceptable salt thereof.

In some embodiments, the step of administering to the subject at least one PIF peptide, an analog thereof, or a pharmaceutically acceptable salt thereof comprises administering a therapeutically effective dose of the at least one PIF molecule, an analog thereof, or a pharmaceutically acceptable salt thereof.

In some embodiments, the step of administering to the subject at least one PIF peptide, an analog thereof, or a pharmaceutically acceptable salt thereof comprises administering a therapeutically effective dose of the PIF peptide, an analog thereof, or pharmaceutically acceptable salt thereof from about 0.001 mg/kg to about 200 mg/kg.

In some embodiments, the step of administering to the subject at least one PIF peptide, an analog thereof, or a pharmaceutically acceptable salt thereof comprises administering a therapeutically effective dose of the PIF peptide, an analog thereof, or pharmaceutically acceptable salt thereof from about 0.5 mg/kg to about 5 mg/kg.

In some embodiments, the at least the PIF peptide, an analog thereof, or pharmaceutically acceptable salt thereof comprises a chemical targeting moiety and/or a radioactive moiety.

In some embodiments, the at least one inhibitor of nuclear translocation of beta-catenin or pharmaceutically acceptable salt thereof comprises at least one radioactive moiety comprising at least one or a combination of the following isotopes: $^{2}H$, $^{3}H$, $^{13}C$, $^{14}C$, $^{15}N$ $^{16}O$, $^{17}O$, $^{31}P$, $^{32}P$, $^{35}S$, $^{18}F$, and $^{36}Cl$.

In some embodiments, the method further comprises administering at least one analgesic and/or one anti-inflammatory compound.

In some embodiments, the method further comprises administering at least one analgesic and or one anti-inflammatory compound before, after, or simultaneously with the administration of a therapeutically effective dose of at least one PIF peptide, an analog thereof or pharmaceutically acceptable salt thereof.

In some embodiments, the traumatic injury to the central nervous system comprises a concussion.

In some embodiments, the therapeutically effective dose is from about 1.0 mg/kg to about 5.5 mg/kg, wherein kg is kilograms of the subject and mg is milligrams of the therapeutically effective dose.

In some embodiments, the PIF peptide comprises SEQ ID NO:1, SEQ ID NO:2, and/or SEQ ID NO:3. In some embodiments, the PIF peptide comprises SEQ ID NO:20 or a pharmaceutically acceptable salt thereof.

The present disclosure also relates to a method of treating or preventing traumatic brain injury in a subject in need thereof, the method comprising administering to the subject at least one pharmaceutical composition comprising: pre-implantation factor (PIF) peptide, an analog thereof, or a pharmaceutically acceptable salt thereof; and a pharmaceutically acceptable carrier.

In some embodiments, the pharmaceutically acceptable carrier is sterile and pyrogen-free water.

In some embodiments, the therapeutically effective dose is about 1.0 mg/kg, wherein kg is kilograms of the subject and mg is milligrams of the therapeutically effective dose. In some embodiments, the therapeutically effective dose is about 2.0 mg/kg, wherein kg is kilograms of the subject and mg is milligrams of the therapeutically effective dose. In some embodiments, the therapeutically effective dose is about 3.0 mg/kg, wherein kg is kilograms of the subject and mg is milligrams of the therapeutically effective dose. In some embodiments, the therapeutically effective dose is about 4.0 mg/kg, wherein kg is kilograms of the subject and mg is milligrams of the therapeutically effective dose. In some embodiments, the therapeutically effective dose is about 0.2 mg/kg, wherein kg is kilograms of the subject and mg is milligrams of the therapeutically effective dose. In some embodiments, the therapeutically effective dose is about 0.3 mg/kg, wherein kg is kilograms of the subject and mg is milligrams of the therapeutically effective dose. In some embodiments, the therapeutically effective dose is about 0.4 mg/kg, wherein kg is kilograms of the subject and mg is milligrams of the therapeutically effective dose. In some embodiments, the therapeutically effective dose is about 0.5 mg/kg, wherein kg is kilograms of the subject and mg is milligrams of the therapeutically effective dose. In some embodiments, the therapeutically effective dose is about 0.6 mg/kg, wherein kg is kilograms of the subject and mg is milligrams of the therapeutically effective dose. In some embodiments, the therapeutically effective dose is about 0.7 mg/kg, wherein kg is kilograms of the subject and mg is milligrams of the therapeutically effective dose. In some embodiments, the therapeutically effective dose is about 0.8 mg/kg, wherein kg is kilograms of the subject and mg is milligrams of the therapeutically effective dose.

The present disclosure also relates to a pharmaceutical composition comprising (i) a therapeutically effective dose of one or a combination of PIF peptide or analogs thereof or pharmaceutically acceptable salts thereof; and (ii) a pharmaceutically acceptable carrier.

In some embodiments, the pharmaceutically acceptable carrier is sterile and pyrogen-free water or Lactated Ringer's solution.

In some embodiments, the composition further comprises a therapeutically effective dose of one or a plurality of active agents.

In some embodiments, the one or plurality of active agents is one or a combination of compounds chosen from: an anti-inflammatory compound, alpha-adrenergic agonist, antiarrhythmic compound, analgesic compound, and an anesthetic compound.

In some embodiments, the therapeutically effective dose of one or a combination of PIF peptide or analogs thereof or pharmaceutically acceptable salts thereof is about 1.0 mg/kg, wherein kg is kilograms of the subject and mg is milligrams of the therapeutically effective dose.

In some embodiments, the therapeutically effective dose of one or a combination of PIF peptide or analogs thereof or pharmaceutically acceptable salts thereof is about 2.0 mg/kg, wherein kg is kilograms of the subject and mg is milligrams of the therapeutically effective dose.

In some embodiments, the therapeutically effective dose of one or a combination of PIF peptide or analogs thereof or pharmaceutically acceptable salts thereof is about 3.0 mg/kg, wherein kg is kilograms of the subject and mg is milligrams of the therapeutically effective dose.

In some embodiments, the therapeutically effective dose of one or a combination of PIF peptide or analogs thereof or pharmaceutically acceptable salts thereof is about 4.0 mg/kg, wherein kg is kilograms of the subject and mg is milligrams of the therapeutically effective dose.

In some embodiments, wherein the therapeutically effective dose of one or a combination of PIF peptide or analogs thereof or pharmaceutically acceptable salts thereof is about 0.2 mg/kg, wherein kg is kilograms of the subject and mg is milligrams of the therapeutically effective dose.

In some embodiments, the therapeutically effective dose of one or a combination of PIF peptide or analogs thereof or pharmaceutically acceptable salts thereof is about 0.3 mg/kg, wherein kg is kilograms of the subject and mg is milligrams of the therapeutically effective dose.

In some embodiments, the therapeutically effective dose of one or a combination of PIF peptide or analogs thereof or pharmaceutically acceptable salts thereof is about 0.4 mg/kg, wherein kg is kilograms of the subject and mg is milligrams of the therapeutically effective dose.

In some embodiments, the therapeutically effective dose of one or a combination of PIF peptide or analogs thereof or pharmaceutically acceptable salts thereof is about 0.5 mg/kg, wherein kg is kilograms of the subject and mg is milligrams of the therapeutically effective dose.

In some embodiments, the therapeutically effective dose of one or a combination of PIF peptide or analogs thereof or pharmaceutically acceptable salts thereof is about 0.6 mg/kg, wherein kg is kilograms of the subject and mg is milligrams of the therapeutically effective dose.

In some embodiments, the therapeutically effective dose of one or a combination of PIF peptide or analogs thereof or pharmaceutically acceptable salts thereof is about 0.7 mg/kg, wherein kg is kilograms of the subject and mg is milligrams of the therapeutically effective dose.

In some embodiments, wherein the therapeutically effective dose of one or a combination of PIF peptide or analogs thereof or pharmaceutically acceptable salts thereof is about 0.8 mg/kg, wherein kg is kilograms of the subject and mg is milligrams of the therapeutically effective dose.

In some embodiments, the therapeutically effective dose of one or a combination of PIF peptide or analogs thereof or pharmaceutically acceptable salts thereof is about 0.9 mg/kg, wherein kg is kilograms of the subject and mg is milligrams of the therapeutically effective dose.

In some embodiments, the composition further comprises one or a plurality of stem cells.

In some embodiments, the stem cell is an autologous stem cell.

The present disclosure also relates to a method of treating or preventing bronchopulmonary dysplasia in a subject in need thereof, the method comprising administering to the subject at least one pharmaceutical composition comprising: pre-implantation factor (PIF) peptide, an analog thereof, or a pharmaceutically acceptable salt thereof; and a pharmaceutically acceptable carrier.

The present disclosure also relates to a method of treating or preventing peripheral nerve injury in a subject in need thereof, the method comprising administering to the subject at least one pharmaceutical composition comprising: pre-implantation factor (PIF) peptide, an analog thereof, or a pharmaceutically acceptable salt thereof; and a pharmaceutically acceptable carrier.

The present disclosure also relates to method of treating or preventing Gaucher's disease in a subject in need thereof, the method comprising administering to the subject at least one pharmaceutical composition comprising: pre-implantation factor (PIF) peptide, an analog thereof, or a pharmaceutically acceptable salt thereof; and a pharmaceutically acceptable carrier.

In some embodiments, the pharmaceutical composition is administered via parenteral injection, subcutaneous injection, intravenous injection, intramuscular injection, intraperitoneal injection, transdermally, orally, buccally, ocular routes, intravaginally, by inhalation, by depot injections, or by implants.

In some embodiments, the compositions further comprise one or a combination of active agents chosen from: an anti-inflammatory compound, alpha-adrenergic agonist, antiarrhythmic compound, analgesic compound, and an anesthetic compound.

In some embodiments, the one or combination of active agents is selected from Table Y.

The present disclosure also relates to a method of preserving microglial cell function comprising administering to the subject at least one pharmaceutical composition comprising: pre-implantation factor (PIF) peptide, an analog thereof, or a pharmaceutically acceptable salt thereof; and a pharmaceutically acceptable carrier.

The present disclosure also relates to a method of treating or preventing vascular inflammation simultaneously to preserving microglial cell function comprising administering to the subject at least one pharmaceutical composition comprising: pre-implantation factor (PIF) peptide, an analog thereof, or a pharmaceutically acceptable salt thereof; and a pharmaceutically acceptable carrier.

The present disclosure also relates to a method of improving the clinical outcome in a subject suffering with, diagnosed with or suspected of having peripheral or CNS neurotrauma comprising administering to the subject at least one pharmaceutical composition comprising: pre-implantation factor (PIF) peptide, an analog thereof, or a pharmaceutically acceptable salt thereof; and a pharmaceutically acceptable carrier.

The present disclosure also relates to a method of treating or preventing pathogen induced inflammation in the brain or throughout the entire CNS comprising administering to the subject at least one pharmaceutical composition comprising: pre-implantation factor (PIF) peptide, an analog thereof, or a pharmaceutically acceptable salt thereof; and a pharmaceutically acceptable carrier.

The present disclosure also relates to a method of increasing myelination in the brain or CNS comprising administering to the subject at least one pharmaceutical composition comprising: pre-implantation factor (PIF) peptide, an analog thereof, or a pharmaceutically acceptable salt thereof; and a pharmaceutically acceptable carrier.

The present disclosure also relates to a method of treating or preventing the decrease of myelination in the brain of CNS comprising administering to the subject at least one pharmaceutical composition comprising: pre-implantation factor (PIF) peptide, an analog thereof, or a pharmaceutically acceptable salt thereof; and a pharmaceutically acceptable carrier.

BRIEF DESCRIPTION OF THE DRAWINGS

FIG. 5A depicts sPIF treatment that resulted in neuronal rescue. FIG. 5B depicts sPIF treatment that resulted in reduced microglial activation in neuronal and microglial cells. FIG. 5C depicts sPIF co-localization in neuronal and microglial cells in vivo. FIG. 5D depicts sPIF reduction of let-7 levels Akt dependent in vivo. FIG. 5E depicts sPIF reduction of let-7 levels in the brain. FIG. 5F depicts sPIF induced reduction of apoptosis and promotion of neuroprotection in vivo. FIG. 5G depicts a diagram of proposed sPIF mediated molecular pathways.

FIG. 25A shows disease course and average total score of disease in mice treated continuously until day 50 after infection with 0.75 mg/Kg of PIF (n=6) or with vehicle only (n=4) FIG. 25B shows disease course and average total score of disease in mice treated from day 3 until day 18 and then from day 51 until day 70 with 0.75 mg/Kg of PIF (n=6) or with vehicle only (n=4). FIG. 25C shows disease course and average total score of disease in mice treated from day 3 until day 25 and then from day 51 until day 65 with 1.5 mg/Kg of PIF (n=7) or with vehicle only (n=6). Disease score was monitored by two independent examiners, blind with respect to treatment, as described. *p<0.05, **p<0.01 (Mann-Whitney test).

FIG. 26A shows IHC imaging of brain comparing the three groups. FIG. 26B shows quantitative analysis of myelin positive cells. The PIF protective effect is significant. *p<0.05 and **p<0.01. Further details on staining are described in the methods section.

FIG. 27A shows FITC-PIF aligns the blood vessels confirmed by fluorescent and black images. Scale bar 100 µm. FIG. 27B shows negative control injection of PBS alone, brain, Scale bar 100 µm. FIG. 27C shows FITC-PIF stained microglia-like elements whose soma is labelled with a granular pattern confirmed by the black image as well. Scale Bar 50 µm. FIG. 27D shows PIF-FITC stains the spinal cord vasculature, confirmed by the black image as well. Scale bar 30 µm.

FIG. 29 depicts that PIF does not affect splenic T cell repertoire. Seven SJL mice per group were infected sc with rMSp139 and treated daily with 0.75 mg/Kg PIF. Thirty days later, cells from spleen were obtained and cultured in the presence or absence of p139. After 3 days of culture, mRNA was obtained and submitted to TCR BV-BJ spectratyping for the shared rearrangements characterizing the induced CD4+ T cells specific for p139 (Vb 4-Jb1.6; Vb10-Jb1.1), the T cells spontaneously responding to this epitope (Vb18-Jb1.2; Vb19-Jb1.2) and the induced CD8+ T cells specific for p139 (Vb17-Jb1.6; Vb20-Jb2.3). Each column reports data from one individual mouse, and a black square indicates the detection of T cells bearing the indicated TCR rearrangement.

FIG. 32A shows that PIF promotes BDNF expression (myelin synthesis inducer). FIG. 32B shows that PIF promotes SLC2A1 expression (glucose transporter). FIG. 32C shows that PIF reduces HSP90AB1 expression (oxidative stress). FIG. 32D shows that PIF reduces E2F5 expression (neuro-injury activated). *p<0.001.

DETAILED DESCRIPTION OF THE DISCLOSURE

Figure 1:
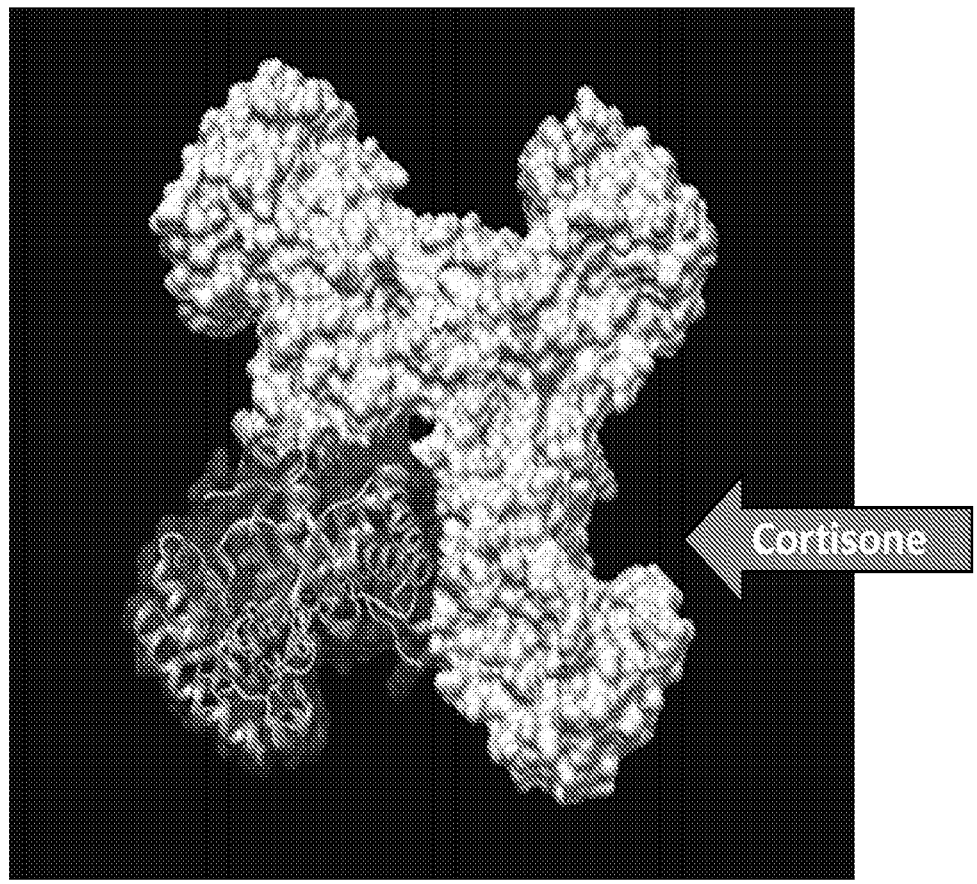
FIG. 1 depicts a crystal structure of PIF binding to the cortisone receptor at the cortisone-binding site. While PIF modulates the immune response, the protein also competes with cortisone.

Before the present compositions and methods are described, it is to be understood that this disclosure is not limited to the particular molecules, compositions, methodologies or protocols described, as these may vary. It is also to be understood that the terminology used in the description is for the purpose of describing the particular versions or embodiments only, and is not intended to limit the scope of the present disclosure and exclude equivalents. It is understood that these embodiments are not limited to the particular methodology, protocols, cell lines, vectors, and reagents described, as these may vary. It also is to be understood that the terminology used herein is for the purpose of describing particular embodiments only, and is not intended to limit the scope of the present embodiments or claims. The compositions described herein may include D amino acids, L amino acids, a racemic backbone of D and L amino acids, or any mixture thereof at each residue. That is, at each position, the residue may be a D amino acid residue or a L-amino acid residue and each position can be independently D or L of each other position, unless context dictates otherwise.

Unless defined otherwise, all technical and scientific terms used herein have the same meanings as commonly understood by one of ordinary skill in the art. Although any methods and materials similar or equivalent to those described herein can be used in the practice or testing of embodiments of the present disclosure, the preferred methods, devices, and materials are now described. All publications mentioned herein are incorporated by reference. Nothing herein is to be construed as an admission that the disclosure is not entitled to antedate such disclosure.

As used herein, the phrase "in need thereof" means that the animal or mammal has been identified or suspected as having a need for the particular method or treatment. In some embodiments, the identification can be by any means of diagnosis or observation. In any of the methods and treatments described herein, the animal or mammal can be in need thereof. In some embodiments, the animal or mammal is in an environment or will be traveling to an environment in which a particular disorder or condition is prevalent or more likely to occur.

As used herein, the term "subject," "individual" or "patient," used interchangeably, means any animal, including mammals, such as mice, rats, other rodents, rabbits, dogs, cats, swine, cattle, sheep, horses, or primates, such as humans.

As used herein, the terms "a" or "an" means that "at least one" or "one or more" unless the context clearly indicates otherwise. It must also be noted that as used herein and in the appended claims, the singular forms "a", "an", and "the" include plural reference unless the context clearly dictates otherwise. Thus, for example, reference to "a cell" is a reference to one or more cells and equivalents thereof known to those skilled in the art, and so forth.

As used herein, the term "about" means that the numerical value is approximate and small variations would not significantly affect the practice of the disclosed embodiments. Where a numerical limitation is used, unless indicated otherwise by the context, "about" means the numerical value can vary by 10% and remain within the scope of the disclosed embodiments. Where a numerical value is used with the term "about" the numerical value without the term "about" is also disclosed and can be used without the term "about."

As used herein, the term "animal" includes, but is not limited to, humans and non-human vertebrates such as wild animals, rodents, such as rats, ferrets, and domesticated animals, and farm animals, such as horses, pigs, cows, sheep, goats. In some embodiments, the animal is a mammal. In some embodiments, the animal is a human. In some embodiments, the animal is a non-human mammal.

As used herein, the terms "comprising" (and any form of comprising, such as "comprise", "comprises", and "comprised"), "having" (and any form of having, such as "have" and "has"), "including" (and any form of including, such as "includes" and "include"), or "containing" (and any form of containing, such as "contains" and "contain"), are inclusive or open-ended and do not exclude additional, unrecited elements or method steps.

As used herein, the phrase "integer from X to Y" means any integer that includes the endpoints. That is, where a range is disclosed, each integer in the range including the endpoints is disclosed. For example, the phrase "integer from X to Y" discloses 1, 2, 3, 4, or 5 as well as the range 1 to 5.

As used herein, the term "mammal" means any animal in the class Mammalia such as rodent (i.e., a mouse, a rat, or a guinea pig), a monkey, a cat, a dog, a cow, a horse, a pig, or a human. In some embodiments, the mammal is a human.

As used herein, the phrase "therapeutically effective amount" means the amount of active compound or pharmaceutical agent that elicits the biological or medicinal response that is being sought in a tissue, system, animal, individual or human by a researcher, veterinarian, medical doctor or other clinician. The therapeutic effect is dependent upon the disorder being treated or the biological effect desired. As such, the therapeutic effect can be a decrease in the severity of symptoms associated with the disorder and/or inhibition (partial or complete) of progression of the disorder, or improved treatment, healing, prevention or elimination of a disorder, or side-effects. The amount needed to elicit the therapeutic response can be determined based on the age, health, size and sex of the subject. Optimal amounts can also be determined based on monitoring of the subject's response to treatment.

As used herein, the terms "treat," "treated," or "treating" can refer to therapeutic treatment wherein the object is to ameliorate or slow down (lessen) an undesired physiological condition, disorder or disease, or obtain beneficial or desired clinical results. For purposes of the embodiments described herein, beneficial or desired clinical results include, but are not limited to, alleviation of symptoms; diminishment of extent of condition, disorder or disease; stabilized (i.e., not worsening) state of condition, disorder or disease; delay in onset or slowing of condition, disorder or disease progression; amelioration of the condition, disorder or disease state or remission (whether partial or total), whether detectable or undetectable; an amelioration of at least one measurable physical parameter, not necessarily discernible by the patient; or enhancement or improvement of condition, disorder or disease. Treatment can also include eliciting a clinically significant response without excessive levels of side effects. Treatment also includes prolonging survival as compared to expected survival if not receiving treatment. For example, "treatment of a traumatic brain injury" means an activity that alleviates or ameliorates any of the primary phenomena or secondary symptoms associated with the traumatic brain injury.

This application describes compounds. Without being bound by any particular theory, the compounds described herein act as agonists of PIF-mediated signal transduction via the receptor or receptors of PIF. Thus, these compounds modulate signaling pathways that provide significant therapeutic benefit in the treatment of, but not limited to, traumatic brain injury, such as concussion, and BPD. The compounds of the present disclosure may exist in unsolvated forms as well as solvated forms, including hydrated forms. The compounds of the present disclosure also are capable of forming both pharmaceutically acceptable salts, including but not limited to acid addition and/or base addition salts. Furthermore, compounds of the present disclosure may exist in various solid states including an amorphous form (non-crystalline form), and in the form of clathrates, prodrugs, polymorphs, bio-hydrolyzable esters, racemic mixtures, non-racemic mixtures, or as purified stereoisomers including, but not limited to, optically pure enantiomers and diastereomers. In general, all of these forms can be used as an alternative form to the free base or free acid forms of the compounds, as described above and are intended to be encompassed within the scope of the present disclosure.

A "polymorph" refers to solid crystalline forms of a compound. Different polymorphs of the same compound can exhibit different physical, chemical and/or spectroscopic properties. Different physical properties include, but are not limited to stability (e.g., to heat or light), compressibility and density (important in formulation and product manufacturing), and dissolution rates (which can affect bioavailability). Different physical properties of polymorphs can affect their processing.

As noted above, the compounds of the present disclosure can be administered, inter alia, as pharmaceutically acceptable salts, esters, amides or prodrugs. The term "salts" refers to inorganic and organic salts of compounds of the present disclosure. The salts can be prepared in situ during the final isolation and purification of a compound, or by separately reacting a purified compound in its free base or acid form with a suitable organic or inorganic base or acid and isolating the salt thus formed. Representative salts include the hydrobromide, hydrochloride, sulfate, bisulfate, nitrate, acetate, oxalate, palmitinate, stearate, laurate, borate, benzoate, lactate, phosphate, tosylate, citrate, maleate, fumarate, succinate, tartrate, naphthylate, mesylate, glucoheptonate, lactobionate, and laurylsulphonate salts, and the like. The salts may include cations based on the alkali and alkaline earth metals, such as sodium, lithium, potassium, calcium, magnesium, and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. See, for example, S. M. Berge, et al., "Pharmaceutical Salts," J Pharm Sci, 66: 1-19 (1977). The term "salt" refers to acidic salts formed with inorganic and/or organic acids, as well as basic salts formed with inorganic and/or organic bases. Examples of these acids and bases are well known to those of ordinary skill in the art. Such acid addition salts will normally be pharmaceutically acceptable although salts of non-pharmaceutically acceptable acids may be of utility in the preparation and purification of the compound in question. Salts include those formed from hydrochloric, hydrobromic, sulphuric, phosphoric, citric, tartaric, lactic, pyruvic, acetic, succinic, fumaric, maleic, methanesulphonic and benzenesulphonic acids.

In some embodiments, salts of the compositions comprising either a PIF or PIF analog or PIF mutant may be formed by reacting the free base, or a salt, enantiomer or racemate thereof, with one or more equivalents of the appropriate acid. In some embodiments, pharmaceutical acceptable salts of the present disclosure refer to analogs having at least one basic group or at least one basic radical. In some embodiments, pharmaceutical acceptable salts of the present disclosure comprise a free amino group, a free guanidino group, a pyrazinyl radical, or a pyridyl radical that forms acid addition salts. In some embodiments, the pharmaceutical acceptable salts of the present disclosure refer to analogs that are acid addition salts of the subject compounds with (for example) inorganic acids, such as hydrochloric acid, sulfuric acid or a phosphoric acid, or with suitable organic carboxylic or sulfonic acids, for example aliphatic mono- or di-carboxylic acids, such as trifluoroacetic acid, acetic acid, propionic acid, glycolic acid, succinic acid, maleic acid, fumaric acid, hydroxymaleic acid, malic acid, tartaric acid, citric acid or oxalic acid, or amino acids such as arginine or lysine, aromatic carboxylic acids, such as benzoic acid, 2-phenoxy-benzoic acid, 2-acetoxybenzoic acid, salicylic acid, 4-aminosalicylic acid, aromatic-aliphatic carboxylic acids, such as mandelic acid or cinnamic acid, heteroaromatic carboxylic acids, such as nicotinic acid or isonicotinic acid, aliphatic sulfonic acids, such as methane-, ethane- or 2-hydroxyethane-sulfonic acid, or aromatic sulfonic acids, for example benzene-, p-toluene- or naphthalene-2-sulfonic acid. When several basic groups are present mono- or poly-acid addition salts may be formed. The reaction may be carried out in a solvent or medium in which the salt is insoluble or in a solvent in which the salt is soluble, for example, water, dioxane, ethanol, tetrahydrofuran or diethyl ether, or a mixture of solvents, which may be removed in vacuo or by freeze drying. The reaction may also be a metathetical process or it may be carried out on an ion exchange resin. In some embodiments, the salts may be those that are physiologically tolerated by a patient. Salts according to the present disclosure may be found in their anhydrous form or as in hydrated crystalline form (i.e., complexed or crystallized with one or more molecules of water).

"Administering" when used in conjunction with a therapeutic means to administer a therapeutic directly into or onto a target tissue or to administer a therapeutic to a patient. Thus, as used herein, the term "administering", when used in conjunction with PIF, can include, but is not limited to, providing PIF peptide into or onto the target tissue; providing PIF peptide systemically to a patient by, e.g., intravenous or subcutaneous injection; providing PIF peptide in the form of a nucleic acid molecule sequence that encodes PIF (e.g., by so-called gene-therapy techniques). "Administering" a composition may be accomplished by parenteral, oral or topical administration or any other suitable route.

As used herein, the terms "pharmaceutically acceptable", "physiologically tolerable" and grammatical variations thereof, as they refer to compositions, carriers, diluents and reagents, are used interchangeably and represent that the materials are capable of administration upon a mammal without the production of undesirable physiological effects such as nausea, dizziness, rash, or gastric upset. In a some embodiments, the therapeutic composition is not immunogenic when administered to a subject for therapeutic purposes. "Not immunogenic" refers to the composition not inducing an immune response against the therapeutic composition. The composition itself may impact the immune system or response of the subject that is being treated.

As used herein, the term "therapeutic" means an agent utilized to treat, combat, ameliorate, prevent or improve an unwanted condition or disease of a subject. In part, embodiments of the present disclosure are directed to treating, ameliorating, preventing or improving traumatic brain injury, such as a concussion, and other conditions as described herein.

A "therapeutically effective amount" or "effective amount" or "physiologically relevant amount" of a composition is an amount calculated to achieve a desired effect, i.e., to effectively inhibit or reduce symptoms and/or complications associated with traumatic brain injury or other conditions described herein. Effective amounts of compounds of the present disclosure can objectively or subjectively reduce or decrease the severity or frequency of symptoms associated with traumatic brain injury, such as concussion, or other conditions described herein. The specific dose of a compound administered according to this disclosure to obtain therapeutic and/or prophylactic effects will, of course, be determined by the particular circumstances surrounding the case, including, for example, the compound administered, the route of administration, and the condition being treated. The compounds are effective over a wide dosage range and, for example, dosages per day will normally fall within the range of from about 0.01 mg/kg to about 10 mg/kg, about 0.1 mg/kg to about 1 mg/kg. In some embodiments, the therapeutically effective dose of PIF or PIF analog or peptide is about 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, and 1 mg/kg.

It will be understood that the effective amount administered can also be determined by the physician in the light of the relevant circumstances including the condition to be treated, the choice of compound to be administered, and the chosen route of administration, and therefore the above dosage ranges are not intended to limit the scope of the disclosure in any way. A therapeutically effective amount of compound of this disclosure is typically an amount such that when it is administered in a physiologically tolerable excipient composition, it is sufficient to achieve an effective systemic concentration or local concentration in the tissue. In some embodiments, the term "therapeutically effective amount" as used herein, refers to that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated. In one aspect, the therapeutically effective amount is that which may treat or alleviate the disease or symptoms of the disease at a reasonable benefit/risk ratio applicable to any medical treatment. However, it is to be understood that the total daily usage of the compounds and compositions described herein may be decided by the attending physician within the scope of sound medical judgment. The specific therapeutically-effective dose level for any particular patient will depend upon a variety of factors, including the disorder being treated and the severity of the disorder; activity of the specific compound employed; the specific composition employed; the age, body weight, general health, gender and diet of the patient: the time of administration, route of administration, and rate of excretion of the specific compound employed, the duration of the treatment; drugs used in combination or coincidentally with the specific compound employed; and like factors well known to the researcher, veterinarian, medical doctor or other clinician of ordinary skill.

It is also appreciated that the therapeutically effective amount, whether referring to monotherapy or combination therapy, is advantageously selected with reference to any toxicity, or other undesirable side effect, that might occur during administration of one or more of the compounds described herein. Further, it is appreciated that the co-therapies described herein may allow for the administration of lower doses of compounds that show such toxicity, or other undesirable side effect, where those lower doses are below thresholds of toxicity or lower in the therapeutic window than would otherwise be administered in the absence of a co-therapy.

As used herein, "central nervous system" or CNS refers to the part of the nervous system containing the brain and the spinal cord. The CNS can also be said to encompass the retina, the optic nerve, the olfactory epithelium, and the olfactory nerves as they synapse directly on to brain tissue without intermediate ganglia. In contrast, the "peripheral nervous system" or PNS is the part of the nervous system that consists of the nerves and ganglia outside the brain spinal cord. The PNS connects the CNS to the limbs and organs of the body, serving as a communication relay. Unlike the CNS, the PNS is not protected by the bones of the vertebra or skull, which leaves it exposed to toxins and mechanical injuries.

As used herein, the term "composition" generally refers to any product comprising a specified component and, optionally, in a specified amounts, as well as any product which results, directly or indirectly, from combinations of any specified ingredients in any specified amounts, if recited. It is to be understood that the compositions described herein may be prepared from isolated compounds described herein or from salts, solutions, hydrates, solvates, and other forms of the compounds described herein. It is also to be understood that the compositions may be prepared from various amorphous, non-amorphous, partially crystalline, crystalline, and/or other morphological forms of the compounds described herein. It is also to be understood that the compositions may be prepared from various hydrates and/or solvates of the compounds described herein. Accordingly, such pharmaceutical compositions that recite compounds described herein are to be understood to include each of, or any combination of, the various morphological forms and/or solvate or hydrate forms of the compounds described herein.

Illustratively, compositions may include one or more carriers, diluents, and/or excipients. The compounds described herein, or compositions containing them, may be formulated in a therapeutically effective amount in any conventional dosage forms appropriate for the methods described herein. The compounds described herein, or compositions containing them, including such formulations, may be administered by a wide variety of conventional routes for the methods described herein, and in a wide variety of dosage formats, utilizing known procedures (see generally, Remington: The Science and Practice of Pharmacy, (21st ed., 2005)).

"Traumatic Brain Injury", also known as the acronym TBI or intracranial injury, refers to a traumatic injury to the brain from an external force. TBI can be classified based on severity, mechanism (i.e. closed or penetrating), or location. TBI is a major cause of death and disability, especially in children and young adults. Causes of TBI include, but are not limited to, falls, vehicle accidence, and violence. Brain trauma can occur as a consequence of a focal impact upon the cranium, by a sudden acceleration/deceleration within the cranium, or by a complex combination of both movement and sudden impact. Damage caused by TBI includes primary injury (damaged cause at the moment of injury) and secondary injury (a variety of events that take place in the time following the injury). Secondary injury process include, but are not limited to, alterations in cerebral blood flow and pressure within the skull. TBI can cause a host of physical, cognitive, social, emotional, and behavioral effects. TBI outcome can range from complete recovery to permanent disability or death. The force may be internal or external. For example, a traumatic brain injury can result when the head suddenly and violently hits an object, or when an object pierces the skull and enters brain tissue. Symptoms of a traumatic brain injury can be mild, moderate, or severe, depending on the extent of the damage to the brain.

"Spinal Cord Injury", also known as the acronym SCI, refers to an injury to the spinal cord resulting in a change, either temporary or permanent, in the cord's normal motor, sensory, or autonomic function. Common causes of damage are trauma (car accident, gunshot, falls, sports injuries, etc.) or disease (transverse myelitis, polio, spina bifida, Friedreich's ataxia, etc.). The spinal cord does not have to be severed in order for a loss of function to occur. Depending on where the spinal cord and nerve roots are damaged, the symptoms can vary widely, from pain to paralysis to incontinence. Spinal cord injuries are described at various levels of "incomplete", which can vary from having no effect on the patient to a "complete" injury which means a total loss of function. Treatment of spinal cord injuries starts with restraining the spine and controlling inflammation to prevent further damage. The actual treatment can vary widely depending on the location and extent of the injury. In many cases, spinal cord injuries require substantial physical therapy and rehabilitation, especially if the patient's injury interferes with activities of daily life. Research into treatments for spinal cord injuries includes controlled hypothermia and stem cells, though many treatments have not been studied thoroughly and very little new research has been implemented in standard care.

The term "concussion" as used herein refers to a type of traumatic brain injury that is caused by a direct or indirect mechanism, for example a direct blow to the head, face or neck or a blow elsewhere on the body with an "impulsive" force transmitted to the head. A concussion is characterized by an immediate and transient alteration in brain function, including alteration of mental status and level of consciousness. Diagnosis of concussion includes one or more of the following clinical domains. Symptoms include (a) somatic (e.g. Headache), cognitive (e.g. Feeling like in a fog, dullness) and/or emotional symptoms (e.g. lability, depression) (b) physical signs (e.g. loss of consciousness, amnesia, convulsions), (c) behavioural changes (e.g. irritability), (d) cognitive impairment (e.g. slowed reaction times), (e) sleep disturbance (e.g. drowsiness). Sequelae of concussion include recurrent concussion, migraine headaches, depression, Parkinson's disease, Alzheimer's disease, attention deficit hyperactivity disorder, learning disability, sleep disorders, neurotransmitter production disturbance (e.g. dopamine, serotonin, acetylcholine, GABA).

"Disease" or "disorder" refers to an impairment of the normal function of an organism. As used herein, a disease may be characterized by the levels of primary or secondary injury causing the impairment of normal function.

"Immune-modulating" refers to the ability of a compound of the present disclosure to alter (modulate) one or more aspects of the immune system. The immune system functions to protect the organism from infection and from foreign antigens by cellular and humoral mechanisms involving lymphocytes, macrophages, and other antigen-presenting cells that regulate each other by means of multiple cell-cell interactions and by elaborating soluble factors, including lymphokines and antibodies, that have autocrine, paracrine, and endocrine effects on immune cells.

"Auto-immune disease" refers to various diseases that arise from an abnormal immune response of the body against substances and tissues normally present in the body. This may be restricted to certain organs or involve a particular tissue in different places. A large number of auto-immune diseases are recognized, including, but not limited to, Hashimoto's thyroiditis, pernicious anemia, Addison's disease, type I (insulin dependent) diabetes, rheumatoid arthritis, systemic lupus erythematosus, dermatomyositis, Sjogren's syndrome, lupus erythematosus, multiple sclerosis, myasthenia gravis, Reiter's syndrome, and Grave's disease, alopecia greata, anklosing spondylitis, antiphospholipid syndrome, auto-immune hemolytic anemia, auto-immune hepatitis, auto-immune inner ear disease, auto-immune lymphoproliferative syndrome (ALPS), auto-immune thrombocytopenic purpura (ATP), Behcet's disease, bullous pemphigoid, cardiomyopathy, celiac sprue-dermatitis, chronic fatigue syndrome immune deficiency syndrome (CFIDS), chronic inflammatory demyelinating polyneuropathy, cicatricial pemphigoid, cold agglutinin disease, CREST syndrome, Crohn's disease, Dego's disease, dermatomyositis, dermatomyositis, discoid lupus, essential mixed cryoglobulinemia, fibromyalgia-fibromyositis, Guillain-Barre syndrome, idiopathic pulmonary fibrosis, idiopathic thrombocytopenia purpura (ITP), IgA nephropathy, juvenile arthritis, Meniere's disease, mixed connective tissue disease, pemphigus vulgaris, polyarteritis nodosa, polychondritis, polyglancular syndromes, polymyalgia rheumatica, polymyositis, primary agammaglobulinemia, primary biliary cirrhosis, psoriasis, Raynaud's phenomenon, rheumatic fever, sarcoidosis, scleroderma, stiff-man syndrome, Takayasu arteritis, temporal arteritis/giant cell arteritis, ulcerative colitis, uveitis, vasculitis, vitiligo, and Wegener's granulomatosis.

"Collagen disease" or "connective tissue disease" refers to systemic diseases associated with defects in collagen, a major component of the connective tissue. In some embodiments, collagen diseases are forms of auto-immune diseases. Types of collagen diseases include, but are not limited to, lupus erythematosus, Sjogren's syndrome, scleroderma, dermatomyositis, and polyarteritis nodosa.

"Inflammatory response" or "inflammation" is a general term for the local accumulation of fluid, plasma proteins, and white blood cells initiated by physical injury, infection, or a local immune response. Inflammation is an aspect of many diseases and disorders, including but not limited to diseases related to immune disorders, viral infection, arthritis, autoimmune diseases, collagen diseases, allergy, asthma, pollinosis, and atopy. Inflammation is characterized by rubor (redness), dolor (pain), calor (heat) and tumor (swelling), reflecting changes in local blood vessels leading to increased local blood flow which causes heat and redness, migration of leukocytes into surrounding tissues (extravasation), and the exit of fluid and proteins from the blood and their local accumulation in the inflamed tissue, which results in swelling and pain, as well as the accumulation of plasma proteins that aid in host defense. These changes are initiated by cytokines produced by activated macrophages. Inflammation is often accompanied by loss of function due to replacement of parenchymal tissue with damaged tissue (e.g., in damaged myocardium), reflexive disuse due to pain, and mechanical constraints on function, e.g., when a joint swells during acute inflammation, or when scar tissue bridging an inflamed joint contracts as it matures into a chronic inflammatory lesion. In some embodiments, inflammation is caused or induced by pathogens, either directly or due to a local immune response. In the central nervous system, pathogens and pathogen induced inflammation is believed to be an underlying cause of many brain and spinal cord disorders. Pathogen induced inflammation may be caused by both bacterial and viral pathogens.

"Anti-inflammatory" define Regulation of inflammation not only anti-inflammatory refers to the ability of a compound to prevent or reduce the inflammatory response, or to soothe inflammation by reducing the symptoms of inflammation such as redness, pain, heat, or swelling. Inflammatory responses can be triggered by injury, for example injury to skin, muscle, tendons, or nerves. Inflammatory responses can also be triggered as part of an immune response. Inflammatory responses can also be triggered by infection, where pathogen recognition and tissue damage can initiate an inflammatory response at the site of infection. Generally, infectious agents induce inflammatory responses by activating innate immunity. Inflammation combats infection by delivering additional effector molecules and cells to augment the killing of invading microorganisms by the frontline macrophages, by providing a physical barrier preventing the spread of infection, and by promoting repair of injured tissue. "Inflammatory disorder" is sometimes used to refer to chronic inflammation due to any cause.

Inflammation triggered by various kinds of injuries to muscles, tendons or nerves caused by repetitive movement of a part of the body are generally referred to as repetitive strain injury (RSI). Diseases characterized by inflammation triggered by RSI include, but are not limited to, bursitis, carpal tunnel syndrome, Dupuytren's contracture, epicondylitis (e.g. "tennis elbow"), "ganglion" (inflammation in a cyst that has formed in a tendon sheath, usually occurring on the wrist) rotator cuff syndrome, tendinitis (e.g., inflammation of the Achilles tendon), tenosynovitis, and "trigger finger" (inflammation of the tendon sheaths of fingers or thumb accompanied by tendon swelling).

"Bronchopulmonary dysplasia", also known as BPD or chronic lung disease of infancy, is a chronic lung disorder that develops in patients who receive prolonged mechanical ventilation of high oxygen delivery. Such prolonged delivery, especially in premature infants, causes necrotizing bronchiolitis and alveolar septal injury with inflammation and scarring. Mild cases of BPD can have uniformly dilated acini with thin alveolar septa and little or no interstitial fibrosis. BPD and other inflammation disorders of the lungs can afflict patient requiring ventilation and oxygen delivery for treatment of other disorders, for example, traumatic brain injury or spinal cord injuries.

"Gaucher's disease" is a genetic disease in which glucosylceramide accumulate in cells and certain organs. The disorder is characterized by bruising, fatigue, anemia, low blood platelets, and enlargement of the liver and spleen. Gaucher's disease is the most common lysosomal storage diseases, and is caused by a hereditary deficiency of the enzyme glucorcerebrosidase. This enzyme acts on the glucolipid glucocerebroside. When the enzyme is defective, glucosylceramide accumulates, particularly in white blood cells. Manifestations may include enlarged spleen and liver, liver malfunction, skeletal disorders and bone lesions that may be painful, severe neurologic complications, swelling of lymph nodes and adjacent joints, distended abdomen, a brownish tint to the skin, anemia, low blood platelets, and yellow fatty deposits on the white of the eyes. The disease is caused by a recessive nutation in a gene located on chromosome 1 and affects both males and females.

As used herein, "conservative" amino acid substitutions may be defined as set out in Tables A, B, or C below. The PIF compounds of the disclosure include those wherein conservative substitutions (from either nucleic acid or amino acid sequences) have been introduced by modification of polynucleotides encoding polypeptides of the disclosure. Amino acids can be classified according to physical properties and contribution to secondary and tertiary protein structure. A conservative substitution is recognized in the art as a substitution of one amino acid for another amino acid that has similar properties. In some embodiments, the conservative substitution is recognized in the art as a substitution of one nucleic acid for another nucleic acid that leads to a conservative amino acid substitution. Exemplary conservative substitutions are set out in Table A.

TABLE A

Conservative Substitutions I

| Side Chain Characteristics | Amino Acid |
|---|---|
| Aliphatic | |
| Non-polar | G, A, P, I, L, V, F |
| Polar - uncharged | C, S, T, M, N, Q |
| Polar - charged | D, E, K, R |
| Aromatic | H, F, W, Y |
| Other | N, Q, D, E |

Alternately, conservative amino acids can be grouped as described in Lehninger, (Biochemistry, Second Edition; Worth Publishers, Inc. NY, N.Y. (1975), pp. 71-77) as set forth in Table B.

TABLE B

Conservative Substitutions II

| Side Chain Characteristic | Amino Acid |
|---|---|
| Non-polar (hydrophobic) | |
| Aliphatic: | A, L, I, V, P |
| Aromatic: | F, W, Y |
| Sulfur-containing: | M |
| Borderline: | G, Y |

TABLE B-continued

Conservative Substitutions II

| Side Chain Characteristic | Amino Acid |
|---|---|
| Uncharged-polar | |
| Hydroxyl: | S, T, Y |
| Amides: | N, Q |
| Sulfhydryl: | C |
| Borderline: | G, Y |
| Positively Charged (Basic): | K, R, H |
| Negatively Charged (Acidic): | D, E |

Alternately, exemplary conservative substitutions are set out in Table C.

TABLE C

Conservative Substitutions III

| Original Residue | Exemplary Substitution |
|---|---|
| Ala (A) | Val, Leu, Ile, Met |
| Arg (R) | Lys, His |
| Asn (N) | Gln |
| Asp (D) | Glu |
| Cys (C) | Ser, Thr |
| Gln (Q) | Asn |
| Glu (E) | Asp |
| Gly (G) | Ala, Val, Leu, Pro |
| His (H) | Lys, Arg |
| Ile (I) | Leu, Val, Met, Ala, Phe |
| Leu (L) | Ile, Val, Met, Ala, Phe |
| Lys (K) | Arg, His |
| Met (M) | Leu, Ile, Val, Ala |
| Phe (F) | Trp, Tyr, Ile |
| Pro (P) | Gly, Ala, Val, Leu, Ile |
| Ser (S) | Thr |
| Thr (T) | Ser |
| Trp (W) | Tyr, Phe, Ile |
| Tyr (Y) | Trp, Phe, Thr, Ser |
| Val (V) | Ile, Leu, Met, Ala |

As used herein, the terms "peptide," "polypeptide" and "protein" are used interchangeably and refer to two or more amino acids covalently linked by an amide bond or non-amide equivalent. The peptides of the disclosure can be of any length. For example, the peptides can have from about two to about 100 or more residues, such as, 5 to 12, 12 to 15, 15 to 18, 18 to 25, 25 to 50, 50 to 75, 75 to 100, or more in length. Preferably, peptides are from about 2 to about 18 residues in length. The peptides of the disclosure also include l- and d-isomers, and combinations of l- and d-isomers. The peptides can include modifications typically associated with posttranslational processing of proteins, for example, cyclization (e.g., disulfide or amide bond), phosphorylation, glycosylation, carboxylation, ubiquitination, myristylation, or lipidation. In some embodiments, the compositions or pharmaceutical compositions of the disclosure relate to analogs of any PIF sequence set forth in Table 1 that share no less than about 70%, about 75%, about 79%, about 80%, about 85%, about 86%, about 87%, about 90%, about 93%, about 94% about 95%, about 96%, about 97%, about 98%, about 99% homology with any one or combination of PIF sequences set forth in Table 1. In some embodiments, PIF may refer to an amino acid sequence selected from SEQ ID NOs: 1, 2, 3, 4, 5, 6, 7, 8, 9, 10, 11, 12, 13, 14, 15, 16, 17, 18, 19, or 20, or a functional fragment thereof that is about 70%, 75%, 80%, 85%, 90%, 91%, 92%, 93%, 94%, 95%, 96%, 97%, 98%, or 99% homologous to any such amino acid sequence. In some embodiments, PIF may refer to an amino acid sequence comprising, consisting essentially of, or consisting of a sequence that is at least 70%, 75%, 80%, 85%, 86%, 87%, 90%, 91%, 92%, 93%, 94%, 95%, 96%, 97%, 98%, or 99% homologous to SEQ ID. NO: 20. In some embodiments, the PIF mutant comprises a sequence selected from: XVZIKPGSANKPSD (SEQ ID NO: 21), XVZIKPGSANKPS (SEQ ID NO: 22), XVZIKPGSANKP (SEQ ID NO: 23), XVZIKPGSANK (SEQ ID NO: 24), XVZIKPGSAN (SEQ ID NO: 25), XVZIKPGSA (SEQ ID NO: 26), XVZIKPGS (SEQ ID NO: 27), XVZIKPG (SEQ ID NO: 28), XVZIKP (SEQ ID NO: 29), XVZIK (SEQ ID NO: 30), XVZI (SEQ ID NO: 31), or XVZ wherein X is a non-natural amino acid or a naturally occurring amino acid. In some embodiments, the PIF mutant comprises a sequence selected from: XVZIKPGSANKPSD (SEQ ID NO: 21), XVZIKPGSANKPS (SEQ ID NO: 22), XVZIKPGSANKP (SEQ ID NO: 23), XVZIKPGSANK (SEQ ID NO: 24), XVZIKPGSAN (SEQ ID NO: 25), XVZIKPGSA (SEQ ID NO: 26), XVZIKPGS (SEQ ID NO: 27), XVZIKPG (SEQ ID NO: 28), XVZIKP (SEQ ID NO: 29), XVZIK (SEQ ID NO: 30), XVZI (SEQ ID NO: 31), or XVZ wherein X is a non-natural amino acid or a naturally occurring amino acid except that X is not methionine if Z is arginine, and Z is not arginine if X is methionine. In some embodiments, the PIF analog or mutant is synthetic or synthetically made.

Peptides disclosed herein further include compounds having amino acid structural and functional analogs, for example, peptidomimetics having synthetic or non-natural amino acids (such as a norleucine) or amino acid analogues or non-natural side chains, so long as the mimetic shares one or more functions or activities of compounds of the disclosure. The compounds of the disclosure therefore include "mimetic" and "peptidomimetic" forms. As used herein, a "non-natural side chain" is a modified or synthetic chain of atoms joined by covalent bond to the α-carbon atom, β-carbon atom, or γ-carbon atom which does not make up the backbone of the polypeptide chain of amino acids. The peptide analogs may comprise one or a combination of non-natural amino-acids chosen from: norvaline, tert-butylglycine, phenylglycine, He, 7-azatryptophan, 4-fluoro-phenylalanine, N-methyl-methionine, N-methyl-valine, N-methyl-alanine, sarcosine, N-methyl-tert-butylglycine, N-methyl-leucine, N-methyl-phenylglycine, N-methyl-iso-leucine, N-methyl-tryptophan, N-methyl-7-azatryptophan, N-methyl-phenylalanine, N-methyl-4-fluorophenylalanine, N-methyl-threonine, N-methyl-tyrosine, N-methyl-valine, N-methyl-lysine, homocysteine. Non-natural side chains are disclosed in the art in the following publications: WO/2013/172954, WO2013123267, WO/2014/071241, WO/2014/138429, WO/2013/050615, WO/2013/050616, WO/2012/166559, US Application No. 20150094457, Ma, Z., and Hartman, M. C. (2012). In Vitro Selection of Unnatural Cyclic Peptide Libraries via mRNA Display. In J. A. Douthwaite & R. H. Jackson (Eds.), *Ribosome Display and Related Technologies: Methods and Protocols* (pp. 367-390). Springer New York., all of which are incorporated by reference in their entireties.

The terms "mimetic," "peptide mimetic" and "peptidomimetic" are used interchangeably herein, and generally refer to a peptide, partial peptide or non-peptide molecule that mimics the tertiary binding structure or activity of a selected native peptide or protein functional domain (e.g., binding motif or active site). These peptide mimetics include recombinantly or chemically modified peptides, as well as non-peptide agents such as small molecule drug mimetics, as further described below. The term "analog" refers to any polypeptide comprising at least one α-amino acid and at least one non-native amino acid residue, wherein the polypeptide is structurally similar to a naturally occurring full-length PIF protein and shares the biochemical or biological activity of the naturally occurring full-length protein upon which the analog is based. In some embodiments, the compositions, pharmaceutical compositions and kits comprise a peptide or peptidomimetic sharing share no less than about 70%, about 75%, about 79%, about 80%, about 85%, about 86%, about 87%, about 90%, about 93%, about 94% about 95%, about 96%, about 97%, about 98%, about 99% homology with any one or combination of PIF sequences set forth in Table 1; and wherein one or a plurality of amino acid residues is a non-natural amino acid residue or an amino acid residue with a non-natural sidechain. In some embodiments, peptide or peptide mimetics are provided, wherein a loop is formed between two cysteine residues. In some embodiments, the peptidomimetic may have many similarities to natural peptides, such as: amino acid side chains that are not found among the known 20 proteinogenic amino acids, non-peptide-based linkers used to effect cyclization between the ends or internal portions of the molecule, substitutions of the amide bond hydrogen moiety by methyl groups (N-methylation) or other alkyl groups, replacement of a peptide bond with a chemical group or bond that is resistant to chemical or enzymatic treatments, N- and C-terminal modifications, and conjugation with a non-peptidic extension (such as polyethylene glycol, lipids, carbohydrates, nucleosides, nucleotides, nucleoside bases, various small molecules, or phosphate or sulfate groups). As used herein, the term "cyclic peptide mimetic" or "cyclic polypeptide mimetic" refers to a peptide mimetic that has as part of its structure one or more cyclic features such as a loop, bridging moiety, and/or an internal linkage.

In some embodiments, peptide or peptide mimetics are provided, wherein the loop comprises a bridging moiety selected from the group consisting of:

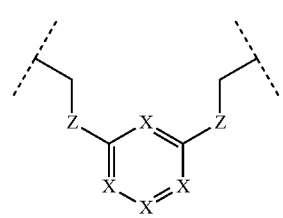

I

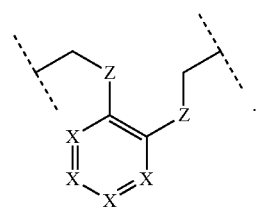

II

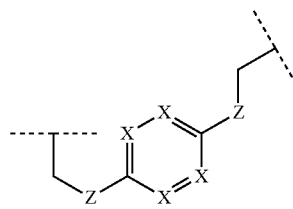

III

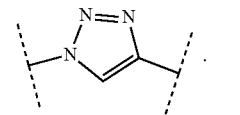

IV

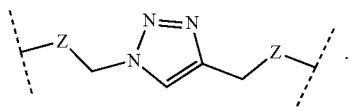

V

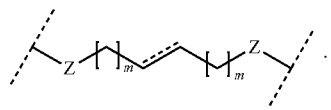

VI

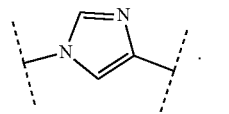

VII

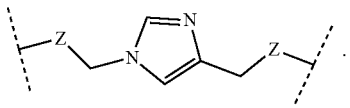

VIII

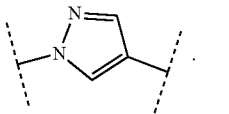

IX

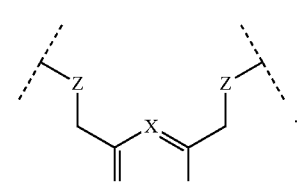

X

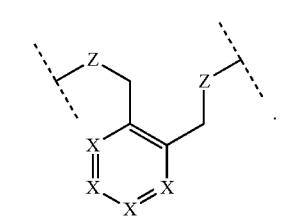

XI

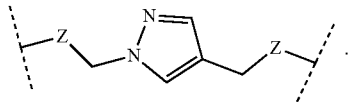

XII

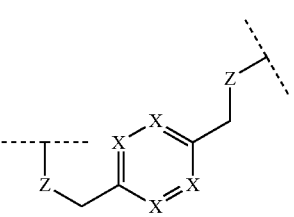

XIII

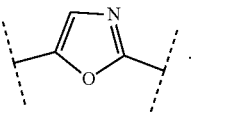

XIV

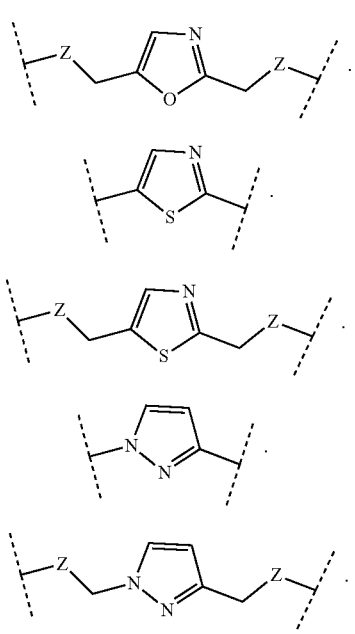

wherein each X is independently N or CH, such that no ring contains more than 2 N; each Z is independently a bond, NR, O, S, CH2, C(O)NR, NRC(O), S(O)vNR, NRS(O)v; each m is independently selected from 0, 1, 2, and 3; each v is independently selected from 1 and 2; each R is independently selected from H and $C_1$-$C_6$; and each bridging moiety is connected to the peptide by independently selected $C_0$-$C_6$ spacers.

In some embodiments, the PIF peptides of the disclosure are modified to produce peptide mimetics by replacement of one or more naturally occurring side chains of the 20 genetically encoded amino acids (or D amino acids) with other side chains, for instance with groups such as alkyl, lower alkyl, cyclic 4-, 5-, 6-, to 7 membered alkyl, amide, amide lower alkyl, amide di (lower alkyl), lower alkoxy, hydroxy, carboxy and the lower ester derivatives thereof, and with 4-, 5-, 6-, to 7 membered heterocyclics. For example, proline analogs can be made in which the ring size of the proline residue is changed from 5 members to 4, 6, or 7 members. Cyclic groups can be saturated or unsaturated, and if unsaturated, can be aromatic or nonaromatic. Heterocyclic groups can contain one or more nitrogen, oxygen, and/or sulphur heteroatoms. Examples of such groups include the furazanyl, furyl, imidazolidinyl, imidazolyl, imidazolinyl, isothiazolyl, isoxazolyl, morpholinyl (e.g. morpholino), oxazolyl, piperazinyl (e.g. 1-piperazinyl), piperidyl (e.g. 1-piperidyl, piperidino), pyranyl, pyrazinyl, pyrazolidinyl, pyrazolinyl, pyrazolyl, pyridazinyl, pyridyl, pyrimidinyl, pyrrolidinyl (e.g. 1-pyrrolidinyl), pyrrolinyl, pyrrolyl, thiadiazolyl, thiazolyl, thienyl, thiomorpholinyl (e.g. thiomorpholino), and triazolyl. These heterocyclic groups can be substituted or unsubstituted. Where a group is substituted, the substituent can be alkyl, alkoxy, halogen, oxygen, or substituted or unsubstituted phenyl. Peptidomimetics may also have amino acid residues that have been chemically modified by phosphorylation, sulfonation, biotinylation, or the addition or removal of other moieties.

In a further embodiment a compound of the formula $R_1$—$R_2$—$R_3$—$R_4$—$R_5$—$R_6$—$R_7$—$R_8$—$R_9$—$R_{10}$—$R_{11}$—$R_{12}$—$R_{13}$—$R_{14}$—$R_{15}$, wherein $R_1$ is Met or a mimetic of Met, $R_2$ is Val or a mimetic of Val, $R_3$ is Arg or a mimetic of Arg, or any amino acid, $R_4$ is Ile or a mimetic of Ile, $R_5$ is Lys or a mimetic of Lys, $R_6$ is Pro or a mimetic of Pro, $R_7$ is Gly or a mimetic of Gly, $R_8$ is Ser or a mimetic of Ser, $R_9$ is Ala or a mimetic of Ala, $R_{10}$ is Asn or a mimetic of Asn, $R_{11}$ is Lys or a mimetic of Lys, $R_{12}$ is Pro or a mimetic of Pro, $R_{13}$ is Ser or a mimetic of Ser, $R_{14}$ is Asp or a mimetic of Asp and $R_{15}$ is Asp or a mimetic of Asp is provided. In a further embodiment, a compound comprising the formula $R_1$—$R_2$—$R_3$—$R_4$—$R_5$—$R_6$—$R_7$—$R_8$—$R_9$—$R_{10}$, wherein $R_1$ is Ser or a mimetic of Ser, $R_2$ is Gln or a mimetic of Gln, $R_3$ is Ala or a mimetic of Ala, $R_4$ is Val or a mimetic of Val, $R_5$ is Gln or a mimetic of Gln, $R_6$ is Glu or a mimetic of Glu, $R_7$ is His or a mimetic of His, R is Ala or a mimetic of Ala, $R_9$ is Ser or a mimetic of Ser, and $R_{10}$ is Thr or a mimetic of Thr; a compound comprising the formula $R_1$—$R_2$—$R_3$—$R_4$—$R_5$—$R_6$—$R_7$—$R_8$—$R_9$—$R_{10}$—$R_{11}$—$R_{12}$—$R_{13}$—$R_{14}$—$R_{15}$—$R_{16}$—$R_{17}$—$R_{18}$, wherein $R_1$ is Ser or a mimetic of Ser, $R_2$ is Gly or a mimetic of Gly, $R_3$ is Ile or a mimetic of Ile, $R_4$ is Val or a mimetic of Val, $R_5$ is Ile or a mimetic of Ile, $R_6$ is Tyr or a mimetic of Tyr, $R_7$ is Gln or a mimetic of Gln, $R_8$ is Tyr or a mimetic of Tyr, $R_9$ is Met or a mimetic of Met, $R_{10}$ is Asp or a mimetic of Asp, $R_{11}$ is Asp or a mimetic of Asp, $R_{12}$ is Arg or a mimetic of Arg, $R_{13}$ is Tyr or a mimetic of Tyr, $R_{14}$ is Val or a mimetic of Val, $R_{15}$ is Gly or a mimetic of Gly, $R_{16}$ is Ser or a mimetic of Ser, $R_{17}$ is Asp or a mimetic of Asp and $R_{18}$ is Leu or a mimetic of Leu; and a compound comprising the formula $R_1$—$R_2$—$R_3$—$R_4$—$R_5$—$R_6$—$R_7$—$R_8$—$R_9$, wherein $R_1$ is Val or a mimetic of Val, $R_2$ is Ile or a mimetic of Ile, $R_3$ is Ile or a mimetic of Ile, $R_4$ is Ile or a mimetic of Ile, $R_5$ is Ala or a mimetic of Ala, $R_6$ is Gln or a mimetic of Gln, $R_7$ is Tyr or a mimetic of Tyr, $R_8$ is Met or a mimetic of Met, and $R_9$ is Asp or a mimetic of Asp is provided. In some embodiments, $R_3$ is not Arg or a mimetic of Arg.

A variety of techniques are available for constructing peptide mimetics with the same or similar desired biological activity as the corresponding native but with more favorable activity than the peptide with respect to solubility, stability, and/or susceptibility to hydrolysis or proteolysis (see, e.g., Morgan & Gainor, Ann. Rep. Med. Chem. 24, 243-252, 1989). Certain peptidomimetic compounds are based upon the amino acid sequence of the peptides of the disclosure. Often, peptidomimetic compounds are synthetic compounds having a three dimensional structure (i.e. a "peptide motif") based upon the three-dimensional structure of a selected peptide. The peptide motif provides the peptidomimetic compound with the desired biological activity, i.e., binding to PIF receptors, wherein the binding activity of the mimetic compound is not substantially reduced, and is often the same as or greater than the activity of the native peptide on which the mimetic is modeled. Peptidomimetic compounds can have additional characteristics that enhance their therapeutic application, such as increased cell permeability, greater affinity and/or avidity and prolonged biological half-life.

Peptidomimetic design strategies are readily available in the art (see, e.g., Ripka & Rich, Curr. Op. Chern. Bioi. 2, 441-452, 1998; Hruby et al., Curr. Op. Chem. Bioi. 1, 114-119, 1997; Hruby & Baise, Curr. Med. Chern. 9, 945-970, 2000). One class of peptidomimetics a backbone that is partially or completely non-peptide, but mimics the peptide backbone atom—for atom and comprises side groups that likewise mimic the functionality of the side groups of the native amino acid residues. Several types of chemical bonds, e.g., ester, thioester, thioamide, retroamide, reduced carbonyl, dimethylene and ketomethylene bonds, are known in the art to be generally useful substitutes for peptide bonds in the construction of protease-resistant peptidomimetics. Another class of peptidomimetics comprises a small non-peptide molecule that binds to another peptide or protein, but which is not necessarily a structural mimetic of the native peptide. Yet another class of peptidomimetics has arisen from combinatorial chemistry and the generation of massive chemical libraries. These generally comprise novel templates which, though structurally unrelated to the native peptide, possess necessary functional groups positioned on a nonpeptide scaffold to serve as "topographical" mimetics of the original peptide (Ripka & Rich, 1998, supra).

The first natural PIF compound identified, termed nPIF (SEQ ID NO: 1), is a 15 amino acid peptide. A synthetic version of this peptide, sPIF (SEQ ID NO:13), showed activity that was similar to the native peptide, nPIF (SEQ ID NO: I). This peptide is homologous to a small region of the Circumsporozoite protein, a malaria parasite. The second PIF peptide (SEQ ID NO:7), includes 13 amino acids and shares homology with a short portion of a large protein named thyroid and retinoic acid transcription co-repressor, which is identified as a receptor-interacting factor, (SMRT); the synthetic version is sPIF-2 (SEQ ID NO:14). The third distinct peptide, nPIF-3 (SEQ ID NO:10), consists of 18 amino acids and matches a small portion of reverse transcriptase; the synthetic version of this peptide sPIF-3 is (SEQ ID NO:15). nPIF-4 (SEQ ID NO: 12) shares homology with a small portion of reverse transcriptase.

A list of PIF peptides, both natural and synthetic, are provided below in Table 1. Antibodies to various PIF peptides and scrambled PIF peptides are also provided.

TABLE 1

PIF Peptides

| (SEQ ID NO) | Peptide | Amino Acid Sequence |
|---|---|---|
| SEQ ID NO: 1<br>isolated native, matches region of<br>Circumsporozoite protein (Malaria) | nPIF-1$_{15}$ | MVRIKPGSANKPSDD |
| SEQ ID NO: 2<br>isolated native, matches region of<br>Circumsporozoite protein (Malaria) | nPIF-1$_{(15\text{-}alter)}$ | MVRIKYGSYNNKPSD |
| SEQ ID NO: 3<br>isolated native, matches region of<br>Circumsporozoite protein (Malaria) | nPIF-1$_{(13)}$ | MVRIKPGSANKPS |
| SEQ ID NO: 4<br>isolated native, matches region of<br>Circumsporozoite protein (Malaria) | nPIF-1$_{(9)}$ | MVRIKPGSA |
| SEQ ID NO: 5<br>synthetic, scrambled amino acid sequence from<br>region of Circumsporozoite protein Malaria | scrPIF-1$_{15}$ | GRVDPSNKSMPKDIA |
| SEQ ID NO: 6<br>isolated native, matches region of human<br>retinoid and thyroid hormone receptor-SMRT | nPIF-2$_{(10)}$ | SQAVQEHAST |
| SEQ ID NO: 7<br>isolated native, matches region of human<br>retinoid and thyroid hormone receptor (SMRT) | nPIF-2$_{(13)}$ | SQAVQEHASTNMG |
| SEQ ID NO: 8<br>synthetic, scrambled amino acid sequence from<br>region of human retinoid and thyroid hormone<br>receptor SMRT | scrPIF-2$_{(13)}$ | EVAQHSQASTMNG |
| SEQ ID NO: 9 | scrPIF-2$_{(14)}$ | GQASSAQMNSTGVH |
| SEQ ID NO: 10<br>isolated native, matches region of Rev Trans | nPIF-3$_{(18)}$ | SGIVIYQYMDDRYVGSDL |
| SEQ ID NO: 11<br>synthetic, scrambled amino acid sequence from<br>region of Circumsporozoite protein Malaria | Neg control for<br>negPIF-1$_{(15)}$ | GMRELQRSANK |
| SEQ ID NO: 12<br>isolated native, matches region of Rev Trans | nPIF-4$_{(9)}$ | SEQ |
| antibody of native isolated nPIF-1$_{15}$ | AbPIF-1$_{(15)}$ | |
| (SEQ ID NO: 13)<br>synthetic, amino acid sequence from region of<br>Circumsporozoite protein Malaria | sPIF-1$_{(15)}$ | MVRIKPGSANKPSDD |
| (SEQ ID NO: 14)<br>synthetic, amino acid sequence from of human<br>retinoid and thyroid hormone receptor SMRT | sPIF-2$_{(13)}$ | SQAVQEHASTNMG |

TABLE 1-continued

PIF Peptides

| (SEQ ID NO) | Peptide | Amino Acid Sequence |
|---|---|---|
| (SEQ ID NO: 15) synthetic, amino acid sequence from region of Circumsporozoite protein Malaria | sPIF-3 (18) | SGIVIYQYMDDRYVGSDL |
| (SEQ ID NO: 16) synthetic, amino acid sequence from region of Circumsporozoite protein Malaria | sPIF-1 (9) | MVRIKPGSA |
| antibody of native isolated nPIF-2 (13) | AbPIF-2 (13) | |
| antibody of native isolated nPIF-3 (18) | AbPIF-3 (18) | |
| (SEQ ID NO: 17) Synthetic | sP1F-4 (9) | VIIIAQYMD |
| SEQ ID NO: 18 Synthetic | sP1F-1 (5) | MVRIK |
| SEQ ID NO: 19 Synthetic | sP1F-1 (4) | PGSA |
| SEQ ID NO: 20 | PIF (-3) | MVXIKPGSANKPSDD | n = native, s = synthetic, scr = scrambled, same AA, ( ) = number of AA, Ab = antibody, X = any amino acid, except arginine In some embodiments of the present disclosure, a PIF peptide is provided. Such PIF peptides may be useful for treating traumatic injury to the central nervous system, including the spinal cord and brain or for any other condition described herein. In some embodiments, the PIF peptides can be used to treat the autoimmune conditions described herein. In some embodiments, the PIF peptides can be used to treat paralysis, such as what is seen in multiple sclerosis ("MS"). Accordingly, in some embodiments, methods of treating MS induced paralysis are provided, wherein the method comprises administering a PIF peptide, such as SEQ ID NO: 13 to the subject with MS induced In some embodiments, the PIF peptides can be used to treat the autoimmune conditions described herein. In some embodiments, the paralysis is inflammation induced paralysis. In some embodiments, the inflammation is localized to the CNS or peripheral nervous system.

In another embodiment, a pharmaceutical composition comprising a PIF peptide is provided. In some embodiments, the pharmaceutical composition comprises a therapeutically effective amount of a PIF peptide or a pharmaceutically acceptable salt thereof.

In some embodiments, a method of treating TBI is provided. In some embodiments, the method comprises administering an effective amount of a PIF peptide to a subject in need thereof.

In some embodiments, a method for treating TBI comprising administering an effective amount of a PIF peptide in combination with one or more immunotherapeutic, anti-epileptic, diuretic, or blood pressure controlling drugs or compounds to a subject in need thereof is provided. Such a combination may enhance the effectiveness of the treatment of either component alone, or may provide less side effects and/or enable a lower dose of either component.

Ultimately, a novel embryo-derived peptide, PIF, creates a tolerogenic state at low doses following short-term treatment leading to long-term protection in several distinct severe autoimmune models. This effect is exerted without apparent toxicity.

For therapeutic treatment of the specified indications, a PIF peptide may be administered as such, or can be compounded and formulated into pharmaceutical compositions in unit dosage form for parenteral, transdermal, rectal, nasal, local intravenous administration, or oral administration. In some embodiments, it is administered subcutaneously. Such pharmaceutical compositions are prepared in a manner well known in the art and comprise at least one active PIF peptide associated with a pharmaceutically carrier. The term "active compound", as used throughout this specification, refers to at least one compound selected from compounds of the formulas or pharmaceutically acceptable salts thereof.

In such a composition, the active compound is known as "active ingredient." In making the compositions, the active ingredient can be mixed with a carrier, or diluted by a carrier, or enclosed within a carrier that may be in the form of a capsule, sachet, paper or other container. When the carrier serves as a diluent, it may be a solid, semisolid, or liquid material that acts as a vehicle, excipient of medium for the active ingredient. Thus, the composition can be in the form of tablets, pills, powders, lozenges, sachets, cachets, elixirs, emulsion, solutions, syrups, suspensions, soft and hard gelatin capsules, sterile injectable solutions, and sterile packaged powders.

The terms "pharmaceutical preparation" or "pharmaceutical composition" includes preparations suitable for administration to mammals, e.g., humans. When the compounds of the present disclosure are administered as pharmaceuticals to mammals, e.g., humans, they can be given per se or as a pharmaceutical composition containing, for example, from about 0.1 to about 99.5% of active ingredient in combination with a pharmaceutically acceptable carrier.

The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans.

The phrase "pharmaceutically acceptable carrier" is art recognized and includes a pharmaceutically acceptable material, composition or vehicle, suitable for administering compounds of the present disclosure to mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar, buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. Suitable pharmaceutical carriers are described in "Remington's Pharmaceutical Sciences" by E. W. Martin, which is incorporated herein by reference in its entirety. In some embodiments, the pharmaceutically acceptable carrier is sterile and pyrogen-free water. In some embodiments, the pharmaceutically acceptable carrier is Ringer's Lactate, sometimes known as lactated Ringer's solution.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, .alpha.-tocopherol, and the like; and metal chelating agents, such as citric acid, ethylenediamine tetraacetic acid (EDTA), sorbitol, tartaric acid, phosphoric acid, and the like.

Formulations of the present disclosure include those suitable for oral, nasal, topical, buccal, sublingual, rectal, vaginal and/or parenteral administration. The formulations may conveniently be presented in unit dosage form and may be prepared by any methods well known in the art of pharmacy. The amount of active ingredient that can be combined with a carrier material to produce a single dosage form will generally be that amount of the compound that produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Some examples of suitable carriers, excipients, and diluents include lactose, dextrose, sucrose, sorbitol, mannitol, starches, gum acacia, calcium phosphate alginates, calcium salicate, microcrystalline cellulose, polyvinylpyrrolidone, cellulose, tragacanth, gelatin, syrup, methyl cellulose, methyl- and propylhydroxybenzoates, talc, magnesium stearate, water, and mineral oil. The formulations can additionally include lubricating agents, wetting agents, emulsifying and suspending agents, preserving agents, sweetening agents or flavoring agents. The compositions may be formulated so as to provide quick, sustained, or delayed release of the active ingredient after administration to the patient by employing procedures well known in the art.

For oral administration, a compound can be admixed with carriers and diluents, molded into tablets, or enclosed in gelatin capsules. The mixtures can alternatively be dissolved in liquids such as 10% aqueous glucose solution, isotonic saline, sterile water, or the like, and administered intravenously or by injection.

The local delivery of inhibitory amounts of active compound for the treatment of immune disorders can be by a variety of techniques that administer the compound at or near the targeted site. Examples of local delivery techniques are not intended to be limiting but to be illustrative of the techniques available. Examples include local delivery catheters, site specific carriers, implants, direct injection, or direct applications, such as topical application.

Local delivery by an implant describes the surgical placement of a matrix that contains the pharmaceutical agent into the affected site. The implanted matrix releases the pharmaceutical agent by diffusion, chemical reaction, or solvent activators.

For example, in some aspects, the disclosure is directed to a pharmaceutical composition comprising a PIF peptide, and a pharmaceutically acceptable carrier or diluent, or an effective amount of pharmaceutical composition comprising a PIF peptide.

The compounds of the present disclosure can be administered in the conventional manner by any route where they are active. Administration can be systemic, topical, or oral. For example, administration can be, but is not limited to, parenteral, subcutaneous, intravenous, intramuscular, intraperitoneal, transdermal, oral, buccal, ocular routes, intravaginally, by inhalation, by depot injections, or by implants. Thus, modes of administration for the compounds of the present disclosure (either alone or in combination with other pharmaceuticals) can be, but are not limited to, sublingual, injectable (including short-acting, depot, implant and pellet forms injected subcutaneously or intramuscularly), or by use of vaginal creams, suppositories, pessaries, vaginal rings, rectal suppositories, intrauterine devices, and transdermal forms such as patches and creams.

Specific modes of administration will depend on the indication. The selection of the specific route of administration and the dose regimen is to be adjusted or titrated by the clinician according to methods known to the clinician in order to obtain the optimal clinical response. The amount of compound to be administered is that amount which is therapeutically effective. The dosage to be administered will depend on the characteristics of the subject being treated, e.g., the particular mammal or human treated, age, weight, health, types of concurrent treatment, if any, and frequency of treatments, and can be easily determined by one of skill in the art (e.g., by the clinician).

Pharmaceutical formulations containing the compounds of the present disclosure and a suitable carrier can be solid dosage forms which include, but are not limited to, tablets, capsules, cachets, pellets, pills, powders and granules; topical dosage forms which include, but are not limned to, solutions, powders, fluid emulsions, fluid suspensions, semi-solids, ointments, pastes, creams, gels and jellies, and foams; and parenteral dosage forms which include, but are not limited to, solutions, suspensions, emulsions, and dry powder; comprising an effective amount of a polymer or copolymer of the present disclosure. It is also known in the art that the active ingredients can be contained in such formulations with pharmaceutically acceptable diluents, fillers, disintegrants, binders, lubricants, surfactants, hydrophobic vehicles, water soluble vehicles, emulsifiers, buffers, humectants, moisturizers, solubilizers, preservatives and the like. The means and methods for administration are known in the art and an artisan can refer to various pharmacologic references for guidance. For example, *Modern Pharmaceutics*, Banker & Rhodes, Marcel Dekker, Inc. (1979); and *Goodman & Gilman's The Pharmaceutical Basis of Therapeutics,* 6th Edition, MacMillan Publishing Co., New York (1980) can be consulted.

The compounds of the present disclosure can be formulated for parenteral administration by injection, e.g., by bolus injection or continuous infusion. The compounds can be administered by continuous infusion subcutaneously over a predetermined period of time. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents.

For oral administration, the compounds can be formulated readily by combining these compounds with pharmaceutically acceptable carriers well known in the art. Such carriers enable the compounds of the disclosure to be formulated as tablets, pills, dragees, capsules, liquids, gels, syrups, slurries, suspensions and the like, for oral ingestion by a patient to be treated. Pharmaceutical preparations for oral use can be obtained by adding a solid excipient, optionally grinding the resulting mixture, and processing the mixture of granules, alter adding suitable auxiliaries, if desired, to obtain tablets or dragee cores. Suitable excipients include, but are not limited to, fillers such as sugars, including, but not limited to, lactose, sucrose, mannitol, and sorbitol; cellulose preparations such as, but not limited to, maize starch, wheat starch, rice starch, potato starch, gelatin, gum tragecanth, methyl cellulose, hydroxypropylmethyl-cellulose, sodium carboxymethylcellulose, and polyvinylpyrrolidone (PVP). If desired, disintegrating agents can be added, such as, but not limited to, the cross-linked polyvinyl pyrrolidone, agar, or alginic acid or a salt thereof such as sodium alginate.

Dragee cores can be provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

Pharmaceutical preparations which can be used orally include, but are not limited to, push-fit capsules made of gelatin, as well as soft, scaled capsules made of gelatin and a plasticizer, such as glycerol or sorbitol. The push-fit capsules can contain the active ingredients in admixture with filler such as, e.g., lactose, binders such as, e.g., starches, and/or lubricants such as, e.g., talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. All formulations for oral administration should be in dosages suitable for such administration.

For buccal administration, the compositions can take the form of, e.g., tablets or lozenges formulated in a conventional manner.

For administration by inhalation, the compounds for use according to the present disclosure are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

The compounds of the present disclosure can also be formulated in rectal compositions such as suppositories or retention enemas, e.g., containing conventional suppository bases such as cocoa butter or other glycerides.

In addition to the formulations described previously, the compounds of the present disclosure can also be formulated as a depot preparation. Such long acting formulations can be administered by implantation (for example subcutaneously or intramuscularly) or by intramuscular injection.

Depot injections can be administered at about 1 to about 6 months or longer intervals. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

In transdermal administration, the compounds of the present disclosure, for example, can be applied to a plaster, or can be applied by transdermal, therapeutic systems that are consequently supplied to the organism.

Pharmaceutical compositions of the compounds also can comprise suitable solid or gel phase carriers or excipients. Examples of such carriers or excipients include but are not limited to calcium carbonate, calcium phosphate, various sugars, starches, cellulose derivates, gelatin, and polymers such as, e.g., polyethylene glycols.

For parenteral administration, analog can be, for example, formulated as a solution, suspension, emulsion or lyophilized powder in association with a pharmaceutically acceptable parenteral vehicle. Examples of such vehicles are water, saline, Ringer's solution, dextrose solution, and 5% human serum albumin. Liposomes and nonaqueous vehicles such as fixed oils may also be used. The vehicle or lyophilized powder may contain additives that maintain isotonicity (e.g., sodium chloride, mannitol) and chemical stability (e.g., buffers and preservatives). The formulation is sterilized by commonly used techniques. For example, a parenteral composition suitable for administration by injection is prepared by dissolving 1.5% by weight of analog in 0.9% sodium chloride solution.

The present invention relates to routes of administration include intramuscular, sublingual, intravenous, intraperitoneal, intrathecal, intravaginal, intraurethral, intradermal, intrabuccal, via inhalation, via nebulizer and via subcutaneous injection. Alternatively, the pharmaceutical composition may be introduced by various means into cells that are removed from the individual. Such means include, for example, microprojectile bombardment and liposome or other nanoparticle device.

Solid dosage forms for oral administration include capsules, tablets, pills, powders and granules. In solid dosage forms, the analogs are generally admixed with at least one inert pharmaceutically acceptable carrier such as sucrose, lactose, starch, or other generally regarded as safe (GRAS) additives. Such dosage forms can also comprise, as is normal practice, an additional substance other than an inert diluent, e.g., lubricating agent such as magnesium state. With capsules, tablets, and pills, the dosage forms may also comprise a buffering agent. Tablets and pills can additionally be prepared with enteric coatings, or in a controlled release form, using techniques know in the art.

Liquid dosage forms for oral administration include pharmaceutically acceptable emulsions, solutions, suspensions and syrups, with the elixirs containing an inert diluent commonly used in the art, such as water. These compositions can also include one or more adjuvants, such as wetting agent, an emulsifying agent, a suspending agent, a sweetening agent, a flavoring agent or a perfuming agent.

In another embodiment of the invention the composition of the invention is used to treat a patient suffering from, or susceptible to Type I adult or juvenile diabetes, multiple sclerosis, Crohn's, or autoimmune hepatitis.

One of skill in the art will recognize that the appropriate dosage of the compositions and pharmaceutical compositions may vary depending on the individual being treated and the purpose. For example, the age, body weight, and medical history of the individual patient may affect the therapeutic efficacy of the therapy. Further, a lower dosage of the composition may be needed to produce a transient cessation of symptoms, while a larger dose may be needed to produce a complete cessation of symptoms associated with the disease, disorder, or indication. A competent physician can consider these factors and adjust the dosing regimen to ensure the dose is achieving the desired therapeutic outcome without undue experimentation. It is also noted that the clinician and/or treating physician will know how and when to interrupt, adjust, and/or terminate therapy in conjunction with individual patient response. Dosages may also depend on the strength of the particular analog chosen for the pharmaceutical composition.

The dose of the composition or pharmaceutical compositions may vary. The dose of the composition may be once per day. In some embodiments, multiple doses may be administered to the subject per day. In some embodiments, the total dosage is administered in at least two application periods. In some embodiments, the period can be an hour, a day, a month, a year, a week, or a two-week period. In an additional embodiment of the invention, the total dosage is administered in two or more separate application periods, or separate doses over the course of an hour, a day, a month, a year, a week, or a two-week period.

In some embodiments, subjects can be administered the composition in which the composition is provided in a daily dose range of about 0.0001 mg/kg to about 5000 mg/kg of the weight of the subject. The dose administered to the subject can also be measured in terms of total amount of PIF peptide or PIF analog or pharmaceutically acceptable salt thereof administered per day. In some embodiments, a subject is administered from about 0.001 to about 3000 milligrams of PIF peptide or PIF analog or pharmaceutically acceptable salt thereof per day. In some embodiments, a subject is administered up to about 2000 milligrams of PIF peptide or PIF analog or pharmaceutically acceptable salt thereof per day. In some embodiments, a subject is administered up to about 1800 milligrams of PIF peptide or PIF analog or pharmaceutically acceptable salt thereof per day.

In some embodiments, a subject is administered up to about 1600 milligrams of PIF peptide or PIF analog or pharmaceutically acceptable salt thereof per day. In some embodiments, a subject is administered up to about 1400 milligrams of PIF peptide or PIF analog or pharmaceutically acceptable salt thereof per day. In some embodiments, a subject is administered up to about 1200 milligrams of PIF peptide or PIF analog or pharmaceutically acceptable salt thereof per day. In some embodiments, a subject is administered up to about 1000 milligrams of PIF peptide or PIF analog or pharmaceutically acceptable salt thereof per day. In some embodiments, a subject is administered up to about 800 milligrams of PIF peptide or PIF analog or pharmaceutically acceptable salt thereof per day. In some embodiments, a subject is administered from about 0.001 milligrams to about 700 milligrams of PIF peptide or PIF analog or pharmaceutically acceptable salt thereof per dose. In some embodiments, a subject is administered up to about 700 milligrams of PIF peptide or PIF analog per dose. In some embodiments, a subject is administered up to about 600 milligrams of PIF peptide or PIF analog or pharmaceutically acceptable salt thereof per dose. In some embodiments, a subject is administered up to about 500 milligrams of PIF peptide or PIF analog or pharmaceutically acceptable salt thereof per dose. In some embodiments, a subject is administered up to about 400 milligrams of PIF peptide or PIF analog or pharmaceutically acceptable salt thereof per dose. In some embodiments, a subject is administered up to about 300 milligrams of PIF peptide or PIF analog or pharmaceutically acceptable salt thereof per dose. In some embodiments, a subject is administered up to about 200 milligrams of PIF peptide or PIF analog or pharmaceutically acceptable salt thereof per dose. In some embodiments, a subject is administered up to about 100 milligrams of PIF peptide or PIF analog or pharmaceutically acceptable salt thereof per dose. In some embodiments, a subject is administered up to about 50 milligrams of PIF peptide or PIF analog or pharmaceutically acceptable salt thereof per dose.

In some embodiments, subjects can be administered the composition in which the composition comprising a PIF peptide or PIF analog or pharmaceutically acceptable salt thereof is administered in a daily dose range of about 0.0001 mg/kg to about 5000 mg/kg of the weight of the subject. In some embodiments, the composition comprising a PIF analog or pharmaceutically acceptable salt thereof is administered in a daily dosage of up to about 450 mg/kg of the weight of the subject. In some embodiments, the composition comprising a PIF peptide or PIF analog or pharmaceutically acceptable salt thereof is administered in a daily dosage of up to about 400 mg/kg of the weight of the subject. In some embodiments, the composition comprising a PIF peptide or PIF analog or pharmaceutically acceptable salt thereof is administered in a daily dosage of up to about 350 mg/kg of the weight of the subject. In some embodiments, the composition comprising a PIF peptide or PIF analog or pharmaceutically acceptable salt thereof is administered in a daily dosage of up to about 300 mg/kg of the weight of the subject. In some embodiments, the composition comprising a PIF peptide or PIF analog or pharmaceutically acceptable salt thereof is administered in a daily dosage of up to about 250 mg/kg of the weight of the subject. In some embodiments, the composition comprising PIF peptide or a PIF analog or pharmaceutically acceptable salt thereof is administered in a daily dosage of up to about 200 mg/kg of the weight of the subject. In some embodiments, the composition comprising PIF peptide or a PIF analog or pharmaceutically acceptable salt thereof is administered in a daily dosage of up to about 150 mg/kg of the weight of the subject. In some embodiments, the composition comprising a PIF peptide or a PIF analog or pharmaceutically acceptable salt thereof is administered in a daily dosage of up to about 100 mg/kg of the weight of the subject. In some embodiments, the composition comprising a PIF peptide or a PIF analog or pharmaceutically acceptable salt thereof is administered in a daily dosage of up to about 50 mg/kg of the weight of the subject. In some embodiments, the composition comprising PIF peptide or a PIF analog or pharmaceutically acceptable salt thereof is administered in a daily dosage of up to about 25 mg/kg of the weight of the subject.

In some embodiments, the composition comprising a PIF peptide or a PIF analog or pharmaceutically acceptable salt thereof is administered in a daily dosage of up to about 10 mg/kg of the weight of the subject. In some embodiments, the composition comprising PIF peptide or a PIF analog or pharmaceutically acceptable salt thereof is administered in a daily dosage of up to about 5 mg/kg of the weight of the subject. In some embodiments, the composition comprising PIF peptide or a PIF analog or pharmaceutically acceptable salt thereof is administered in a daily dosage of up to about 1 mg/kg of the weight of the subject. In some embodiments, the composition comprising a PIF peptide or a PIF analog or pharmaceutically acceptable salt thereof is administered in a daily dosage of up to about 0.1 mg/kg of the weight of the subject. In some embodiments, the composition comprising a PIF analog or pharmaceutically acceptable salt thereof is administered in a daily dosage of up to about 0.01 mg/kg of the weight of the subject. In some embodiments, the composition comprising a PIF analog or pharmaceutically acceptable salt thereof is administered in a daily dosage of up to about 0.001 mg/kg of the weight of the subject. The dose administered to the subject can also be measured in terms of total amount of a PIF peptide or PIF analog administered per day.

In some embodiments, a subject in need thereof is administered from about 1 ng to about 500 µg of analog or pharmaceutically salt thereof per day. In some embodiments, a subject in need thereof is administered from about 1 ng to about 10 ng of analog or pharmaceutically salt thereof per day. In some embodiments, a subject in need thereof is administered from about 10 ng to about 20 ng of analog or pharmaceutically salt thereof per day. In some embodiments, a subject in need thereof is administered from about 10 ng to about 100 ng of analog or pharmaceutically salt thereof per day. In some embodiments, a subject in need thereof is administered from about 100 ng to about 200 ng of analog or pharmaceutically salt thereof per day. In some embodiments, a subject in need thereof is administered from about 200 ng to about 300 ng of analog or pharmaceutically salt thereof per day. In some embodiments, a subject in need thereof is administered from about 300 ng to about 400 ng of analog or pharmaceutically salt thereof per day. In some embodiments, a subject in need thereof is administered from about 400 ng to about 500 ng of analog or pharmaceutically salt thereof per day. In some embodiments, a subject in need thereof is administered from about 500 ng to about 600 ng of analog or pharmaceutically salt thereof per day. In some embodiments, a subject in need thereof is administered from about 600 ng to about 700 ng of analog or pharmaceutically salt thereof per day. In some embodiments, a subject in need thereof is administered from about 800 ng to about 900 ng of analog or pharmaceutically salt thereof per day. In some embodiments, a subject in need thereof is administered from about 900 ng to about 1 µg of analog or pharmaceutically salt thereof per day. In some embodiments, a subject in need thereof is administered from about 1 µg to about 100 µg of analog or pharmaceutically salt thereof per day. In some embodiments, a subject in need thereof is administered from about 100 µg to about 200 µg of analog or pharmaceutically salt thereof per day. In some embodiments, a subject in need thereof is administered from about 200 µg to about 300 µg of analog or pharmaceutically salt thereof per day. In some embodiments, a subject in need thereof is administered from about 300 µg to about 400 µg of analog or pharmaceutically salt thereof per day. In some embodiments, a subject in need thereof is administered from about 400 µg to about 500 µg of analog or pharmaceutically salt thereof per day. In some embodiments, a subject in need thereof is administered from about 500 µg to about 600 µg of analog or pharmaceutically salt thereof per day. In some embodiments, a subject in need thereof is administered from about 600 µg to about 700 µg of analog or pharmaceutically salt thereof per day. In some embodiments, a subject in need thereof is administered from about 800 µg to about 900 µg of analog or pharmaceutically salt thereof per day. In some embodiments, a subject in need thereof is administered from about 900 µg to about 1 mg of analog or pharmaceutically salt thereof per day.

In some embodiments, a subject in need thereof is administered from about 0.0001 to about 3000 milligrams of a PIF peptide or PIF analog or pharmaceutically salt thereof per day. In some embodiments, a subject is administered up to about 2000 milligrams of a PIF peptide or PIF analog or pharmaceutically salt thereof day. In some embodiments, a subject is administered up to about 1800 milligrams of a PIF peptide or PIF analog or pharmaceutically salt thereof per day. In some embodiments, a subject is administered up to about 1600 milligrams of a PIF peptide or PIF analog or pharmaceutically salt thereof per day. In some embodiments, a subject is administered up to about 1400 milligrams of a PIF peptide or PIF analog or pharmaceutically salt thereof per day. In some embodiments, a subject is administered up to about 1200 milligrams of a PIF peptide or PIF analog or pharmaceutically salt thereof per day. In some embodiments, a subject is administered up to about 1000 milligrams of a PIF peptide or PIF analog or pharmaceutically salt thereof per day. In some embodiments, a subject is administered up to about 800 milligrams of a PIF peptide or PIF analog or pharmaceutically salt thereof per day. In some embodiments, a subject is administered from about 0.0001 milligrams to about 700 milligrams of a PIF peptide or PIF analog or pharmaceutically salt thereof per dose. In some embodiments, a subject is administered up to about 700 milligrams of a PIF peptide or PIF analog or pharmaceutically salt thereof per dose. In some embodiments, a subject is administered up to about 600 milligrams of a PIF peptide or PIF analog or pharmaceutically salt thereof per dose. In some embodiments, a subject is administered up to about 500 milligrams of a PIF peptide or PIF analog or pharmaceutically salt thereof per dose. In some embodiments, a subject is administered up to about 400 milligrams of a PIF peptide or PIF analog or pharmaceutically salt thereof per dose. In some embodiments, a subject is administered up to about 300 milligrams of a PIF peptide or PIF analog or pharmaceutically salt thereof per dose. In some embodiments, a subject is administered up to about 200 milligrams of a PIF peptide or PIF analog or pharmaceutically salt thereof per dose. In some embodiments, a subject is administered up to about 100 milligrams of a PIF peptide or PIF analog or pharmaceutically salt thereof per dose. In some embodiments, a subject is administered up to about 50 milligrams of a PIF peptide or PIF analog or pharmaceutically salt thereof per dose. In some embodiments, a subject is administered up to about 25 milligrams of a PIF peptide or PIF analog or pharmaceutically salt thereof per dose. In some embodiments, a subject is administered up to about 15 milligrams of a PIF peptide or PIF analog or pharmaceutically salt thereof per dose.

In some embodiments, a subject is administered up to about 10 milligrams of a PIF peptide or PIF analog or pharmaceutically salt thereof per dose. In some embodiments, a subject is administered up to about 5 milligrams of a PIF peptide or PIF analog or pharmaceutically salt thereof per dose. In some embodiments, a subject is administered up to about 1 milligram of a PIF peptide or PIF analog or pharmaceutically salt thereof per dose. In some embodiments, a subject is administered up to about 0.1 milligrams of a PIF peptide or PIF analog or pharmaceutically salt thereof per dose. In some embodiments, a subject is administered up to about 0.001 milligrams of a PIF peptide or PIF analog or pharmaceutically salt thereof per dose.

The dose administered to the subject can also be measured in terms of total amount of a PIF peptide or PIF analog or pharmaceutically salt thereof administered per ounce of liquid prepared. In some embodiments, the PIF peptide or PIF analog or pharmaceutically salt thereof is at a concentration of about 2.5 grams per ounce of solution. In some embodiments, the PIF peptide or PIF analog or pharmaceutically salt thereof is at a concentration of about 2.25 grams per ounce of solution. In some embodiments, the PIF peptide or PIF analog or pharmaceutically salt thereof is at a concentration of about 2.25 grams per ounce of solution. In some embodiments, the PIF peptide or PIF analog or pharmaceutically salt thereof is at a concentration of about 2.0 grams per ounce of solution. In some embodiments, the PIF peptide or PIF analog or pharmaceutically salt thereof is at a concentration of about 1.9 grams per ounce of solution. In some embodiments, the PIF peptide or PIF analog or pharmaceutically salt thereof is at a concentration of about 1.8 grams per ounce of solution. In some embodiments, the PIF analog or pharmaceutically salt thereof is at a concentration of about 1.7 grams per ounce of solution. In some embodiments, the PIF peptide or PIF analog or pharmaceutically salt thereof is at a concentration of about 1.6 grams per ounce of solution. In some embodiments, the PIF peptide or PIF analog or pharmaceutically salt thereof is at a concentration of about 1.5 grams per ounce of solution. In some embodiments, the PIF peptide or PIF analog or pharmaceutically salt thereof is at a concentration of about 1.4 grams per ounce of solution. In some embodiments, the PIF peptide or PIF analog or pharmaceutically salt thereof is at a concentration of about 1.3 grams per ounce of solution. In some embodiments, the PIF peptide or PIF analog or pharmaceutically salt thereof is at a concentration of about 1.2 grams per ounce of solution. In some embodiments, the PIF peptide or PIF analog or pharmaceutically salt thereof is at a concentration of about 1.1 grams per ounce of solution. In some embodiments, the PIF peptide or PIF analog or pharmaceutically salt thereof is at a concentration of about 1.0 grams per ounce of solution. In some embodiments, the PIF peptide or PIF analog or pharmaceutically salt thereof is at a concentration of about 0.9 grams per ounce of solution. In some embodiments, the PIF peptide or PIF analog or pharmaceutically salt thereof is at a concentration of about 0.8 grams per ounce of solution. In some embodiments, the PIF peptide or PIF analog or pharmaceutically salt thereof is at a concentration of about 0.7 grams per ounce of solution. In some embodiments, the PIF peptide or PIF analog or pharmaceutically salt thereof is at a concentration of about 0.6 grams per ounce of solution. In some embodiments, the PIF peptide or PIF analog or pharmaceutically salt thereof is at a concentration of about 0.5 grams per ounce of solution. In some embodiments, the PIF peptide or PIF analog or pharmaceutically salt thereof is at a concentration of about 0.4 grams per ounce of solution. In some embodiments, the PIF peptide or PIF analog or pharmaceutically salt thereof is at a concentration of about 0.3 grams per ounce of solution. In some embodiments, the PIF peptide or PIF analog or pharmaceutically salt thereof is at a concentration of about 0.2 grams per ounce of solution. In some embodiments, the PIF peptide or PIF analog or pharmaceutically salt thereof is at a concentration of about 0.1 grams per ounce of solution. In some embodiments, the PIF peptide or PIF analog or pharmaceutically salt thereof is at a concentration of about 0.01 grams per ounce of solution. In some embodiments, the PIF peptide or PIF analog or pharmaceutically salt thereof is at a concentration of about 0.001 grams per ounce of solution prepared. In some embodiments, the PIF peptide or PIF analog or pharmaceutically salt thereof is at a concentration of about 0.0001 grams per ounce of solution prepared. In some embodiments, the PIF peptide or PIF analog or pharmaceutically salt thereof is at a concentration of about 0.00001 grams per ounce of solution prepared. In some embodiments, the PIF peptide or PIF analog or pharmaceutically salt thereof is at a concentration of about 0.000001 grams per ounce of solution prepared.

Dosage may be measured in terms of mass amount of analog per liter of liquid formulation prepared. One skilled in the art can increase or decrease the concentration of the analog in the dose depending upon the strength of biological activity desired to treat or prevent any above-mentioned disorders associated with the treatment of subjects in need thereof. For instance, some embodiments of the invention can include up to 0.00001 grams of analog per 5 mL of liquid formulation and up to about 10 grams of analog per 5 mL of liquid formulation.

In some embodiments the pharmaceutical compositions of the claimed invention comprises at least one or a plurality of active agents other than the PIF peptide, analog of pharmaceutically acceptable salt thereof. In some embodiments the active agent is covalently linked to the PIF peptide or PIF analog disclosed herein optionally by a protease cleavable linker (including by not limited to Pro-Pro or Cituline-Valine di-α-amino acid linkers). In some embodiments, the one or plurality of active agents is one or a combination of compounds chosen from: an anti-inflammatory compound, alpha-adrenergic agonist, antiarrhythmic compound, analgesic compound, and an anesthetic compound.

TABLE Y

Examples of anti-inflammatory compounds include:

aspirin
celecoxib
diclofenac
diflunisal
etodolac
ibuprofen
indomethacin
ketoprofen
ketorolac nabumetone
naproxen
oxaprozin
piroxicam
salsalate
sulindac
tolmetin TABLE Y-continued Examples of alpha-adrenergic agonists include:

Methoxamine
Methylnorepinephrine
Midodrine
Oxymetazoline
Metaraminol
Phenylephrine
Clonidine (mixed alpha2-adrenergic and imidazoline-I1 receptor agonist)
Guanfacine, (preference for alpha2A-subtype of adrenoceptor)
Guanabenz (most selective agonist for alpha2-adrenergic as opposed to imidazoline-I1)
Guanoxabenz (metabolite of guanabenz)
Guanethidine (peripheral alpha2-receptor agonist)
Xylazine,
Tizanidine
Medetomidine
Methyldopa
Fadolmidine
Dexmedetomidine Examples of antiarrhythmic compound include:

Amiodarone (Cordarone, Pacerone)
Bepridil Hydrochloride (Vascor)
Disopyramide (Norpace)
Dofetilide (Tikosyn)
Dronedarone (Multaq)
Flecainide (Tambocor)
Ibutilide (Corvert)
Lidocaine (Xylocaine)
Procainamide (Procan, Procanbid)
Propafenone (Rythmol)
Propranolol (Inderal)
Quinidine (many trade names)
Sotalol (Betapace)
Tocainide (Tonocarid)

Examples of analgesic compound include:

codeine
hydrocodone (Zohydro ER),
oxycodone (OxyContin, Roxicodone),
methadone
hydromorphone (Dilaudid, Exalgo),
morphine (Avinza, Kadian, MSIR, MS Contin), and
fentanyl (Actiq, Duragesic)

Examples of anesthetic compounds include:

Desflurane
Isoflurane
Nitrous oxide
Sevoflurane
Xenon

The compounds of the present disclosure can also be administered in combination with other active ingredients, such as, for example, adjuvants, or other compatible drugs or compounds where such combination is seen to be desirable or advantageous in achieving the desired effects of the methods described herein.

Methods

The methods disclosed herein can be used with any of the compounds, compositions, preparations, and kits disclosed herein.

The disclosure relates to methods for treating a bronchopulmonary dysplasia trauma comprising administering an effective amount of the compositions described herein to a subject in need thereof. The disclosure also includes the use of the compositions described here for simultaneously treating a subject who has suffered a neurodamage, for instance a traumatic neural damage and bronchopulmonary dysplasia.

The disclosure relates to methods for treating a CNS trauma comprising administering an effective amount of the compositions described herein to a subject in need thereof. The disclosure also includes the use of the compositions described here for treating a subject who has suffered a CNS trauma. In some embodiments, the CNS trauma is traumatic brain injury (TBI). In some embodiments, the CNS trauma is spinal cord injury (SCI).

In some embodiments, the CNS trauma is a concussion. Accordingly, the disclosure also relates to methods for treating a concussion comprising administering an effective amount of the compositions described herein to a subject in need thereof. The disclosure also relates to the use of the compositions described here for treating a subject who has suffered a concussion. In some embodiments, the present methods are used for treating a subject who has at least 1, 2, 3, 4 or 5 concussion symptoms. Concussion symptoms include, but are not limited to, headache, pressure in head, neck pain, nausea or vomiting, dizziness, blurred vision, sensitivity to light, sensitivity to noise, feeling slowed down, feeling "in a fog", "not feeling right", difficulty concentrating, difficulty remembering, fatigue or low energy, confusion, drowsiness, trouble falling asleep, increased emotions, irritability sadness and nervousness or anxiety. Optionally, the present methods are used for treating a subject who has been diagnosed with a traumatic brain injury or a concussion.

In some embodiments, the present methods are used for treating a post-concussive syndrome. Post-concussive syndromes include, but are not limited to, post-concussion disease, prolonged post-concussion disease, mild cognitive impairment, chronic traumatic encephalopathy and dementia pugilistica. In further embodiments the present methods are used for treating long-term complications of concussion such as post-concussive depression.

In some embodiments, the composition is administered once a day to a subject in need thereof. In another embodiment, the composition is administered every other day, every third day or once a week. In another embodiment, the composition is administered twice a day. In still another embodiment, the composition is administered three times a day or four times a day. In a further embodiment, the composition is administered at least once a day for at least 1, 2, 3, 4, 5, 6, 7, 8, 9, 10, 11 or 12 weeks. In still a further embodiment, the composition is administered at least once a day for a longer term such as at least 4, 6, 8, 10, 12 or 24 months. Administration in some embodiments includes but is not limited to a dosage of 10-50 mg of composition at a frequency of minimum 1, 2, 3 or 4 times per day. Optionally, administration continues until all symptoms are resolved and cleared by medical personnel via standardized testing such as SCAT 2.

In some embodiments, the composition is administered within 1, 2, 3, 5 or 7 days of the CNS trauma. In other embodiments, the composition is administered within 1, 2, 3, 5 or 7 days of the appearance of symptoms of a CNS trauma.

In some embodiments, the composition is administered at least once a day until the condition has ameliorated to where further treatment is not necessary. In another embodiment, the composition is administered until all symptoms of the traumatic brain injury are resolved. In another embodiment, the composition is administered until the subject is able to return to physical activity or "cleared to play" in a particular sport.

In some embodiments, the composition is administered for at least 1, 2, 3, 6, 8, 10 or 12 or 24 months after the subject is asymptomatic. Optionally, the composition is administered for at least 1, 2, 3, 6, 8, 10 or 12 or 24 months after the subject is able to return to physical activity or "cleared to play" in a particular sport.

The compositions of the present disclosure are useful and effective when administered to treat a CNS trauma such as, TBI, SCI, cerebral herniation or a concussion. The amount of each component present in the composition will be the amount that is therapeutically effective, i.e., an amount that will result in the effective treatment of the condition (e.g., traumatic brain injury) when administered. The therapeutically effective amount will vary depending on the subject and the severity and nature of the injury and can be determined routinely by one of ordinary skill in the art.

In some embodiments, the disclosure relates to a method of treating or preventing any of the indications as described herein and as set forth in U.S. Pat. Nos. 8,222,211, 7,723,289, 7,723,290, 8,454,967, 9,097,725, (each of which are incorporated by reference in their entireties) comprising administering compositions or pharmaceutical compositions comprising any one or plurality of PIF peptides, analogs, or pharmaceutically acceptable salts thereof disclosed herein.

In some methods, the disclosure relates to a method of stimulating the differentiation and/or proliferation of stem cells in a subject in need thereof comprising administering compositions or pharmaceutical compositions comprising any one or plurality of PIF peptides, analogs, or pharmaceutically acceptable salts thereof disclosed herein.

In some embodiments, the disclosure relates to any of the methods disclosed in U.S. Pat. Nos. 7,273,708, 7,695,977, 7,670,852, 7,670,851, 7,678,582, 7,670,850, 8,012,700 (each of which are incorporated by reference in their entireties) comprising administering compositions or pharmaceutical compositions comprising any one or plurality of PIF peptides, analogs, or pharmaceutically acceptable salts thereof disclosed herein.

This disclosure also incorporates by reference in their entireties U.S. Pat. Nos. 7,789,289, 7,723,290, 8,222,211, and 8,454,967.

In some embodiments, the disclosure relates to a method of treating traumatic injury of the central nervous system by administering at least one or a plurality of compositions disclosed herein comprising PIF peptide, an analog thereof, or a pharmaceutically acceptable salt thereof.

In some embodiments, the disclosure relates to a method of treating traumatic injury of the central nervous system by administering a therapeutically effective amount or dose of one or a plurality of compositions disclosed herein comprising at least one PIF peptide, an analog thereof, or a pharmaceutically acceptable salt thereof.

In some embodiments, the disclosure relates to a method of treating traumatic injury of the central nervous system by administration of a pharmaceutical composition comprising a therapeutically effective amount or dose of at least one PIF peptide, an analog thereof, or a pharmaceutically acceptable salt thereof, and a pharmaceutically acceptable carrier.

In some embodiments, the disclosure relates to a pharmaceutical composition comprising a therapeutically effective amount or dose of at least one PIF peptide, an analog thereof, or a pharmaceutically acceptable salt thereof, and a pharmaceutically acceptable carrier for the treatment of traumatic injury of the central nervous system.

In some embodiments, the disclosure relates to the use of a therapeutically effective amount or dose of any one or plurality of compositions disclosed herein comprising at least one PIF peptide, an analog thereof, or a pharmaceutically acceptable salt thereof, and a pharmaceutically acceptable carrier in the manufacture of a medicament for the treatment of traumatic injury of the central nervous system.

In some embodiments, the disclosure relates to the use of a pharmaceutical composition comprising a therapeutically effective amount or dose at least one PIF peptide, an analog thereof, or a pharmaceutically acceptable salt thereof, and a pharmaceutically acceptable carrier in the manufacture of a medicament for the treatment of traumatic injury of the central nervous system.

In some embodiments, the disclosure relates to a method of inducing an immunomodulation effect in a subject in need thereof, when subject has been or is suspect of having traumatic injury of the central nervous system.

In some embodiments, the disclosure relates to a method of treating traumatic brain injury by administering at least one or a plurality of compositions disclosed herein comprising PIF peptide, an analog thereof, or a pharmaceutically acceptable salt thereof.

In some embodiments, the disclosure relates to a method of treating traumatic brain injury by administering a therapeutically effective amount or dose of one or a plurality of compositions disclosed herein comprising at least one PIF peptide, an analog thereof, or a pharmaceutically acceptable salt thereof.

In some embodiments, the disclosure relates to a method of treating traumatic brain injury by administration of a pharmaceutical composition comprising a therapeutically effective amount or dose of at least one PIF peptide, an analog thereof, or a pharmaceutically acceptable salt thereof, and a pharmaceutically acceptable carrier.

In some embodiments, the disclosure relates to a pharmaceutical composition comprising a therapeutically effective amount or dose of at least one PIF peptide, an analog thereof, or a pharmaceutically acceptable salt thereof, and a pharmaceutically acceptable carrier for the treatment of traumatic brain injury.

In some embodiments, the disclosure relates to the use of a therapeutically effective amount or dose of any one or plurality of compositions disclosed herein comprising at least one PIF peptide, an analog thereof, or a pharmaceutically acceptable salt thereof, and a pharmaceutically acceptable carrier in the manufacture of a medicament for the treatment of traumatic brain injury.

In some embodiments, the disclosure relates to the use of a pharmaceutical composition comprising a therapeutically effective amount or dose at least one PIF peptide, an analog thereof, or a pharmaceutically acceptable salt thereof, and a pharmaceutically acceptable carrier in the manufacture of a medicament for the treatment of traumatic brain injury.

In some embodiments, the disclosure relates to a method of inducing an immunomodulation effect in a subject in need thereof, when subject has been or is suspect of having traumatic brain injury by administering at least one or a plurality of compositions disclosed herein comprising PIF peptide, an analog thereof, or a pharmaceutically acceptable salt thereof.

In some embodiments, the disclosure relates to a method of treating auto-immune hepatitis by administering at least one or a plurality of compositions disclosed herein comprising PIF peptide, an analog thereof, or a pharmaceutically acceptable salt thereof.

In some embodiments, the disclosure relates to a method of treating auto-immune hepatitis by administering a therapeutically effective amount or dose of one or a plurality of compositions disclosed herein comprising at least one PIF peptide, an analog thereof, or a pharmaceutically acceptable salt thereof.

In some embodiments, the disclosure relates to a method of treating auto-immune hepatitis by administration of a pharmaceutical composition comprising a therapeutically effective amount or dose of at least one PIF peptide, an analog thereof, or a pharmaceutically acceptable salt thereof, and a pharmaceutically acceptable carrier.

In some embodiments, the disclosure relates to a pharmaceutical composition comprising a therapeutically effective amount or dose of at least one PIF peptide, an analog thereof, or a pharmaceutically acceptable salt thereof, and a pharmaceutically acceptable carrier for the treatment of auto-immune hepatitis.

In some embodiments, the disclosure relates to the use of a therapeutically effective amount or dose of any one or plurality of compositions disclosed herein comprising at least one PIF peptide, an analog thereof, or a pharmaceutically acceptable salt thereof, and a pharmaceutically acceptable carrier in the manufacture of a medicament for the treatment of auto-immune hepatitis.

In some embodiments, the disclosure relates to the use of a pharmaceutical composition comprising a therapeutically effective amount or dose at least one PIF peptide, an analog thereof, or a pharmaceutically acceptable salt thereof, and a pharmaceutically acceptable carrier in the manufacture of a medicament for the treatment of auto-immune hepatitis.

In some embodiments, the disclosure relates to a method of inducing an immunomodulation effect in a subject in need thereof, when subject has been or is suspect of having auto-immune hepatitis.

In some embodiments, the disclosure relates to a method of treating graft-versus-host disease by administering at least one or a plurality of compositions disclosed herein comprising PIF peptide, an analog thereof, or a pharmaceutically acceptable salt thereof.

In some embodiments, the disclosure relates to a method of treating graft-versus-host disease by administering a therapeutically effective amount or dose of one or a plurality of compositions disclosed herein comprising at least one PIF peptide, an analog thereof, or a pharmaceutically acceptable salt thereof.

In some embodiments, the disclosure relates to a method of treating graft-versus-host disease by administration of a pharmaceutical composition comprising a therapeutically effective amount or dose of at least one PIF peptide, an analog thereof, or a pharmaceutically acceptable salt thereof, and a pharmaceutically acceptable carrier.

In some embodiments, the disclosure relates to a pharmaceutical composition comprising a therapeutically effective amount or dose of at least one PIF peptide, an analog thereof, or a pharmaceutically acceptable salt thereof, and a pharmaceutically acceptable carrier for the treatment of graft-versus-host disease.

In some embodiments, the disclosure relates to the use of a therapeutically effective amount or dose of any one or plurality of compositions disclosed herein comprising at least one PIF peptide, an analog thereof, or a pharmaceutically acceptable salt thereof, and a pharmaceutically acceptable carrier in the manufacture of a medicament for the treatment of graft-versus-host disease.

In some embodiments, the disclosure relates to the use of a pharmaceutical composition comprising a therapeutically effective amount or dose at least one PIF peptide, an analog thereof, or a pharmaceutically acceptable salt thereof, and a pharmaceutically acceptable carrier in the manufacture of a medicament for the treatment of graft-versus-host disease.

In some embodiments, the disclosure relates to a method of inducing an immunomodulation effect in a subject in need thereof, when subject has been or is suspect of having graft-versus-host disease.

In some embodiments, the disclosure relates to a method of treating type I diabetes by administering at least one or a plurality of compositions disclosed herein comprising PIF peptide, an analog thereof, or a pharmaceutically acceptable salt thereof.

In some embodiments, the disclosure relates to a method of treating type I diabetes by administering a therapeutically effective amount or dose of one or a plurality of compositions disclosed herein comprising at least one PIF peptide, an analog thereof, or a pharmaceutically acceptable salt thereof.

In some embodiments, the disclosure relates to a method of treating type I diabetes by administration of a pharmaceutical composition comprising a therapeutically effective amount or dose of at least one PIF peptide, an analog thereof, or a pharmaceutically acceptable salt thereof, and a pharmaceutically acceptable carrier.

In some embodiments, the disclosure relates to a pharmaceutical composition comprising a therapeutically effective amount or dose of at least one PIF peptide, an analog thereof, or a pharmaceutically acceptable salt thereof, and a pharmaceutically acceptable carrier for the treatment of type I diabetes.

In some embodiments, the disclosure relates to the use of a therapeutically effective amount or dose of any one or plurality of compositions disclosed herein comprising at least one PIF peptide, an analog thereof, or a pharmaceutically acceptable salt thereof, and a pharmaceutically acceptable carrier in the manufacture of a medicament for the treatment of type I diabetes.

In some embodiments, the disclosure relates to the use of a pharmaceutical composition comprising a therapeutically effective amount or dose at least one PIF peptide, an analog thereof, or a pharmaceutically acceptable salt thereof, and a pharmaceutically acceptable carrier in the manufacture of a medicament for the treatment of type I diabetes.

In some embodiments, the disclosure relates to a method of inducing an immunomodulation effect in a subject in need thereof, when subject has been or is suspect of having type I diabetes.

In some embodiments, the disclosure relates to a method of treating multiple sclerosis, including but not limited to MS induced paralysis, by administering at least one or a plurality of compositions disclosed herein comprising PIF peptide, an analog thereof, or a pharmaceutically acceptable salt thereof.

In some embodiments, the disclosure relates to a method of treating multiple sclerosis, including but not limited to MS induced paralysis, by administering a therapeutically effective amount or dose of one or a plurality of compositions disclosed herein comprising at least one PIF peptide, an analog thereof, or a pharmaceutically acceptable salt thereof.

In some embodiments, the disclosure relates to a method of treating multiple sclerosis, including but not limited to MS induced paralysis, by administration of a pharmaceutical composition comprising a therapeutically effective amount or dose of at least one PIF peptide, an analog thereof, or a pharmaceutically acceptable salt thereof, and a pharmaceutically acceptable carrier.

In some embodiments, the disclosure relates to a pharmaceutical composition comprising a therapeutically effective amount or dose of at least one PIF peptide, an analog thereof, or a pharmaceutically acceptable salt thereof, and a pharmaceutically acceptable carrier for the treatment of multiple sclerosis, including but not limited to MS induced paralysis.

In some embodiments, the disclosure relates to the use of a therapeutically effective amount or dose of any one or plurality of compositions disclosed herein comprising at least one PIF peptide, an analog thereof, or a pharmaceutically acceptable salt thereof, and a pharmaceutically acceptable carrier in the manufacture of a medicament for the treatment of multiple sclerosis, including but not limited to MS induced paralysis.

In some embodiments, the disclosure relates to the use of a pharmaceutical composition comprising a therapeutically effective amount or dose at least one PIF peptide, an analog thereof, or a pharmaceutically acceptable salt thereof, and a pharmaceutically acceptable carrier in the manufacture of a medicament for the treatment of multiple sclerosis, including but not limited to MS induced paralysis.

In some embodiments, the disclosure relates to a method of inducing an immunomodulation effect in a subject in need thereof, when subject has been or is suspect of having multiple sclerosis, including but not limited to MS induced paralysis.

In some embodiments, the disclosure relates to a method of treating ulcerative colitis by administering at least one or a plurality of compositions disclosed herein comprising PIF peptide, an analog thereof, or a pharmaceutically acceptable salt thereof.

In some embodiments, the disclosure relates to a method of treating ulcerative colitis by administering a therapeutically effective amount or dose of one or a plurality of compositions disclosed herein comprising at least one PIF peptide, an analog thereof, or a pharmaceutically acceptable salt thereof.

In some embodiments, the disclosure relates to a method of treating ulcerative colitis by administration of a pharmaceutical composition comprising a therapeutically effective amount or dose of at least one PIF peptide, an analog thereof, or a pharmaceutically acceptable salt thereof, and a pharmaceutically acceptable carrier.

In some embodiments, the disclosure relates to a pharmaceutical composition comprising a therapeutically effective amount or dose of at least one PIF peptide, an analog thereof, or a pharmaceutically acceptable salt thereof, and a pharmaceutically acceptable carrier for the treatment of ulcerative colitis.

In some embodiments, the disclosure relates to the use of a therapeutically effective amount or dose of any one or plurality of compositions disclosed herein comprising at least one PIF peptide, an analog thereof, or a pharmaceutically acceptable salt thereof, and a pharmaceutically acceptable carrier in the manufacture of a medicament for the treatment of ulcerative colitis.

In some embodiments, the disclosure relates to the use of a pharmaceutical composition comprising a therapeutically effective amount or dose at least one PIF peptide, an analog thereof, or a pharmaceutically acceptable salt thereof, and a pharmaceutically acceptable carrier in the manufacture of a medicament for the treatment of ulcerative colitis.

In some embodiments, the disclosure relates to a method of inducing an immunomodulation effect in a subject in need thereof, when subject has been or is suspect of having ulcerative colitis.

In some embodiments, the disclosure relates to a method of treating Crohn's disease by administering at least one or a plurality of compositions disclosed herein comprising PIF peptide, an analog thereof, or a pharmaceutically acceptable salt thereof.

In some embodiments, the disclosure relates to a method of treating Crohn's disease by administering a therapeutically effective amount or dose of one or a plurality of compositions disclosed herein comprising at least one PIF peptide, an analog thereof, or a pharmaceutically acceptable salt thereof.

In some embodiments, the disclosure relates to a method of treating Crohn's disease by administration of a pharmaceutical composition comprising a therapeutically effective amount or dose of at least one PIF peptide, an analog thereof, or a pharmaceutically acceptable salt thereof, and a pharmaceutically acceptable carrier.

In some embodiments, the disclosure relates to a pharmaceutical composition comprising a therapeutically effective amount or dose of at least one PIF peptide, an analog thereof, or a pharmaceutically acceptable salt thereof, and a pharmaceutically acceptable carrier for the treatment of Crohn's disease.

In some embodiments, the disclosure relates to the use of a therapeutically effective amount or dose of any one or plurality of compositions disclosed herein comprising at least one PIF peptide, an analog thereof, or a pharmaceutically acceptable salt thereof, and a pharmaceutically acceptable carrier in the manufacture of a medicament for the treatment of Crohn's disease.

In some embodiments, the disclosure relates to the use of a pharmaceutical composition comprising a therapeutically effective amount or dose at least one PIF peptide, an analog thereof, or a pharmaceutically acceptable salt thereof, and a pharmaceutically acceptable carrier in the manufacture of a medicament for the treatment of Crohn's disease.

In some embodiments, the disclosure relates to a method of inducing an immunomodulation effect in a subject in need thereof, when subject has been or is suspect of having Crohn's disease.

In some embodiments, the disclosure relates to a method of treating inflammatory bowel disease by administering at least one or a plurality of compositions disclosed herein comprising PIF peptide, an analog thereof, or a pharmaceutically acceptable salt thereof.

In some embodiments, the disclosure relates to a method of treating inflammatory bowel disease by administering a therapeutically effective amount or dose of one or a plurality of compositions disclosed herein comprising at least one PIF peptide, an analog thereof, or a pharmaceutically acceptable salt thereof.

In some embodiments, the disclosure relates to a method of treating inflammatory bowel disease by administration of a pharmaceutical composition comprising a therapeutically effective amount or dose of at least one PIF peptide, an analog thereof, or a pharmaceutically acceptable salt thereof, and a pharmaceutically acceptable carrier.

In some embodiments, the disclosure relates to a pharmaceutical composition comprising a therapeutically effective amount or dose of at least one PIF peptide, an analog thereof, or a pharmaceutically acceptable salt thereof, and a pharmaceutically acceptable carrier for the treatment of inflammatory bowel disease.

In some embodiments, the disclosure relates to the use of a therapeutically effective amount or dose of any one or plurality of compositions disclosed herein comprising at least one PIF peptide, an analog thereof, or a pharmaceutically acceptable salt thereof, and a pharmaceutically acceptable carrier in the manufacture of a medicament for the treatment of inflammatory bowel disease.

In some embodiments, the disclosure relates to the use of a pharmaceutical composition comprising a therapeutically effective amount or dose at least one PIF peptide, an analog thereof, or a pharmaceutically acceptable salt thereof, and a pharmaceutically acceptable carrier in the manufacture of a medicament for the treatment of inflammatory bowel disease.

In some embodiments, the disclosure relates to a method of inducing an immunomodulation effect in a subject in need thereof, when subject has been or is suspect of having inflammatory bowel disease.

In some embodiments, the disclosure relates to a method of treating inflammation by administering at least one or a plurality of compositions disclosed herein comprising PIF peptide, an analog thereof, or a pharmaceutically acceptable salt thereof.

In some embodiments, the disclosure relates to a method of treating inflammation by administering a therapeutically effective amount or dose of one or a plurality of compositions disclosed herein comprising at least one PIF peptide, an analog thereof, or a pharmaceutically acceptable salt thereof.

In some embodiments, the disclosure relates to a method of treating inflammation by administration of a pharmaceutical composition comprising a therapeutically effective amount or dose of at least one PIF peptide, an analog thereof, or a pharmaceutically acceptable salt thereof, and a pharmaceutically acceptable carrier.

In some embodiments, the disclosure relates to a pharmaceutical composition comprising a therapeutically effective amount or dose of at least one PIF peptide, an analog thereof, or a pharmaceutically acceptable salt thereof, and a pharmaceutically acceptable carrier for the treatment of inflammation.

In some embodiments, the disclosure relates to the use of a therapeutically effective amount or dose of any one or plurality of compositions disclosed herein comprising at least one PIF peptide, an analog thereof, or a pharmaceutically acceptable salt thereof, and a pharmaceutically acceptable carrier in the manufacture of a medicament for the treatment of inflammation.

In some embodiments, the disclosure relates to the use of a pharmaceutical composition comprising a therapeutically effective amount or dose at least one PIF peptide, an analog thereof, or a pharmaceutically acceptable salt thereof, and a pharmaceutically acceptable carrier in the manufacture of a medicament for the treatment of inflammation.

In some embodiments, the disclosure relates to a method of inducing an immunomodulation effect in a subject in need thereof, when subject has been or is suspect of having inflammation.

In some embodiments, the disclosure relates to a method of treating arthritis by administering at least one or a plurality of compositions disclosed herein comprising PIF peptide, an analog thereof, or a pharmaceutically acceptable salt thereof.

In some embodiments, the disclosure relates to a method of treating arthritis by administering a therapeutically effective amount or dose of one or a plurality of compositions disclosed herein comprising at least one PIF peptide, an analog thereof, or a pharmaceutically acceptable salt thereof.

In some embodiments, the disclosure relates to a method of treating arthritis by administration of a pharmaceutical composition comprising a therapeutically effective amount or dose of at least one PIF peptide, an analog thereof, or a pharmaceutically acceptable salt thereof, and a pharmaceutically acceptable carrier.

In some embodiments, the disclosure relates to a pharmaceutical composition comprising a therapeutically effective amount or dose of at least one PIF peptide, an analog thereof, or a pharmaceutically acceptable salt thereof, and a pharmaceutically acceptable carrier for the treatment of arthritis.

In some embodiments, the disclosure relates to the use of a therapeutically effective amount or dose of any one or plurality of compositions disclosed herein comprising at least one PIF peptide, an analog thereof, or a pharmaceutically acceptable salt thereof, and a pharmaceutically acceptable carrier in the manufacture of a medicament for the treatment of arthritis.

In some embodiments, the disclosure relates to the use of a pharmaceutical composition comprising a therapeutically effective amount or dose at least one PIF peptide, an analog thereof, or a pharmaceutically acceptable salt thereof, and a pharmaceutically acceptable carrier in the manufacture of a medicament for the treatment of arthritis.

In some embodiments, the disclosure relates to a method of inducing an immunomodulation effect in a subject in need thereof, when subject has been or is suspect of having arthritis.

In some embodiments, the disclosure relates to a method of treating allergies by administering at least one or a plurality of compositions disclosed herein comprising PIF peptide, an analog thereof, or a pharmaceutically acceptable salt thereof.

In some embodiments, the disclosure relates to a method of treating allergies by administering a therapeutically effective amount or dose of one or a plurality of compositions disclosed herein comprising at least one PIF peptide, an analog thereof, or a pharmaceutically acceptable salt thereof.

In some embodiments, the disclosure relates to a method of treating allergies by administration of a pharmaceutical composition comprising a therapeutically effective amount or dose of at least one PIF peptide, an analog thereof, or a pharmaceutically acceptable salt thereof, and a pharmaceutically acceptable carrier.

In some embodiments, the disclosure relates to a pharmaceutical composition comprising a therapeutically effective amount or dose of at least one PIF peptide, an analog thereof, or a pharmaceutically acceptable salt thereof, and a pharmaceutically acceptable carrier for the treatment of allergies.

In some embodiments, the disclosure relates to the use of a therapeutically effective amount or dose of any one or plurality of compositions disclosed herein comprising at least one PIF peptide, an analog thereof, or a pharmaceutically acceptable salt thereof, and a pharmaceutically acceptable carrier in the manufacture of a medicament for the treatment of allergies.

In some embodiments, the disclosure relates to the use of a pharmaceutical composition comprising a therapeutically effective amount or dose at least one PIF peptide, an analog thereof, or a pharmaceutically acceptable salt thereof, and a pharmaceutically acceptable carrier in the manufacture of a medicament for the treatment of allergies.

In some embodiments, the disclosure relates to a method of inducing an immunomodulation effect in a subject in need thereof, when subject has been or is suspect of having allergies.

In some embodiments, the disclosure relates to a method of treating asthma by administering at least one or a plurality of compositions disclosed herein comprising PIF peptide, an analog thereof, or a pharmaceutically acceptable salt thereof.

In some embodiments, the disclosure relates to a method of treating asthma by administering a therapeutically effective amount or dose of one or a plurality of compositions disclosed herein comprising at least one PIF peptide, an analog thereof, or a pharmaceutically acceptable salt thereof.

In some embodiments, the disclosure relates to a method of treating asthma by administration of a pharmaceutical composition comprising a therapeutically effective amount or dose of at least one PIF peptide, an analog thereof, or a pharmaceutically acceptable salt thereof, and a pharmaceutically acceptable carrier.

In some embodiments, the disclosure relates to a pharmaceutical composition comprising a therapeutically effective amount or dose of at least one PIF peptide, an analog thereof, or a pharmaceutically acceptable salt thereof, and a pharmaceutically acceptable carrier for the treatment of asthma.

In some embodiments, the disclosure relates to the use of a therapeutically effective amount or dose of any one or plurality of compositions disclosed herein comprising at least one PIF peptide, an analog thereof, or a pharmaceutically acceptable salt thereof, and a pharmaceutically acceptable carrier in the manufacture of a medicament for the treatment of asthma.

In some embodiments, the disclosure relates to the use of a pharmaceutical composition comprising a therapeutically effective amount or dose at least one PIF peptide, an analog thereof, or a pharmaceutically acceptable salt thereof, and a pharmaceutically acceptable carrier in the manufacture of a medicament for the treatment of asthma.

In some embodiments, the disclosure relates to a method of inducing an immunomodulation effect in a subject in need thereof, when subject has been or is suspect of having asthma.

In some embodiments, the disclosure relates to a method of treating eczema by administering at least one or a plurality of compositions disclosed herein comprising PIF peptide, an analog thereof, or a pharmaceutically acceptable salt thereof.

In some embodiments, the disclosure relates to a method of treating eczema by administering a therapeutically effective amount or dose of one or a plurality of compositions disclosed herein comprising at least one PIF peptide, an analog thereof, or a pharmaceutically acceptable salt thereof.

In some embodiments, the disclosure relates to a method of treating eczema by administration of a pharmaceutical composition comprising a therapeutically effective amount or dose of at least one PIF peptide, an analog thereof, or a pharmaceutically acceptable salt thereof, and a pharmaceutically acceptable carrier.

In some embodiments, the disclosure relates to a pharmaceutical composition comprising a therapeutically effective amount or dose of at least one PIF peptide, an analog thereof, or a pharmaceutically acceptable salt thereof, and a pharmaceutically acceptable carrier for the treatment of eczema.

In some embodiments, the disclosure relates to the use of a therapeutically effective amount or dose of any one or plurality of compositions disclosed herein comprising at least one PIF peptide, an analog thereof, or a pharmaceutically acceptable salt thereof, and a pharmaceutically acceptable carrier in the manufacture of a medicament for the treatment of eczema.

In some embodiments, the disclosure relates to the use of a pharmaceutical composition comprising a therapeutically effective amount or dose at least one PIF peptide, an analog thereof, or a pharmaceutically acceptable salt thereof, and a pharmaceutically acceptable carrier in the manufacture of a medicament for the treatment of eczema.

In some embodiments, the disclosure relates to a method of inducing an immunomodulation effect in a subject in need thereof, when subject has been or is suspect of having eczema.

In some embodiments, the disclosure relates to a method of treating urticaria by administering at least one or a plurality of compositions disclosed herein comprising PIF peptide, an analog thereof, or a pharmaceutically acceptable salt thereof.

In some embodiments, the disclosure relates to a method of treating urticaria by administering a therapeutically effective amount or dose of one or a plurality of compositions disclosed herein comprising at least one PIF peptide, an analog thereof, or a pharmaceutically acceptable salt thereof.

In some embodiments, the disclosure relates to a method of treating urticaria by administration of a pharmaceutical composition comprising a therapeutically effective amount or dose of at least one PIF peptide, an analog thereof, or a pharmaceutically acceptable salt thereof, and a pharmaceutically acceptable carrier.

In some embodiments, the disclosure relates to a pharmaceutical composition comprising a therapeutically effective amount or dose of at least one PIF peptide, an analog thereof, or a pharmaceutically acceptable salt thereof, and a pharmaceutically acceptable carrier for the treatment of urticaria.

In some embodiments, the disclosure relates to the use of a therapeutically effective amount or dose of any one or plurality of compositions disclosed herein comprising at least one PIF peptide, an analog thereof, or a pharmaceutically acceptable salt thereof, and a pharmaceutically acceptable carrier in the manufacture of a medicament for the treatment of urticaria.

In some embodiments, the disclosure relates to the use of a pharmaceutical composition comprising a therapeutically effective amount or dose at least one PIF peptide, an analog thereof, or a pharmaceutically acceptable salt thereof, and a pharmaceutically acceptable carrier in the manufacture of a medicament for the treatment of urticaria.

In some embodiments, the disclosure relates to a method of inducing an immunomodulation effect in a subject in need thereof, when subject has been or is suspect of having urticaria.

In some embodiments, the disclosure relates to a method of treating atopic dermatitis by administering at least one or a plurality of compositions disclosed herein comprising PIF peptide, an analog thereof, or a pharmaceutically acceptable salt thereof.

In some embodiments, the disclosure relates to a method of treating atopic dermatitis by administering a therapeutically effective amount or dose of one or a plurality of compositions disclosed herein comprising at least one PIF peptide, an analog thereof, or a pharmaceutically acceptable salt thereof.

In some embodiments, the disclosure relates to a method of treating atopic dermatitis by administration of a pharmaceutical composition comprising a therapeutically effective amount or dose of at least one PIF peptide, an analog thereof, or a pharmaceutically acceptable salt thereof, and a pharmaceutically acceptable carrier.

In some embodiments, the disclosure relates to a pharmaceutical composition comprising a therapeutically effective amount or dose of at least one PIF peptide, an analog thereof, or a pharmaceutically acceptable salt thereof, and a pharmaceutically acceptable carrier for the treatment of atopic dermatitis.

In some embodiments, the disclosure relates to the use of a therapeutically effective amount or dose of any one or plurality of compositions disclosed herein comprising at least one PIF peptide, an analog thereof, or a pharmaceutically acceptable salt thereof, and a pharmaceutically acceptable carrier in the manufacture of a medicament for the treatment of atopic dermatitis.

In some embodiments, the disclosure relates to the use of a pharmaceutical composition comprising a therapeutically effective amount or dose at least one PIF peptide, an analog thereof, or a pharmaceutically acceptable salt thereof, and a pharmaceutically acceptable carrier in the manufacture of a medicament for the treatment of atopic dermatitis.

In some embodiments, the disclosure relates to a method of inducing an immunomodulation effect in a subject in need thereof, when subject has been or is suspect of having atopic dermatitis.

In some embodiments, the disclosure relates to a method of treating bronchopulminary dysplasia by administering at least one or a plurality of compositions disclosed herein comprising PIF peptide, an analog thereof, or a pharmaceutically acceptable salt thereof.

In some embodiments, the disclosure relates to a method of treating bronchopulminary dysplasia by administering a therapeutically effective amount or dose of one or a plurality of compositions disclosed herein comprising at least one PIF peptide, an analog thereof, or a pharmaceutically acceptable salt thereof.

In some embodiments, the disclosure relates to a method of treating bronchopulminary dysplasia by administration of a pharmaceutical composition comprising a therapeutically effective amount or dose of at least one PIF peptide, an analog thereof, or a pharmaceutically acceptable salt thereof, and a pharmaceutically acceptable carrier.

In some embodiments, the disclosure relates to a pharmaceutical composition comprising a therapeutically effective amount or dose of at least one PIF peptide, an analog thereof, or a pharmaceutically acceptable salt thereof, and a pharmaceutically acceptable carrier for the treatment of bronchopulmonary dysplasia.

In some embodiments, the disclosure relates to the use of a therapeutically effective amount or dose of any one or plurality of compositions disclosed herein comprising at least one PIF peptide, an analog thereof, or a pharmaceutically acceptable salt thereof, and a pharmaceutically acceptable carrier in the manufacture of a medicament for the treatment of bronchopulmonary dysplasia.

In some embodiments, the disclosure relates to the use of a pharmaceutical composition comprising a therapeutically effective amount or dose at least one PIF peptide, an analog thereof, or a pharmaceutically acceptable salt thereof, and a pharmaceutically acceptable carrier in the manufacture of a medicament for the treatment of bronchopulminary dysplasia.

In some embodiments, the disclosure relates to a method of inducing an immunomodulation effect in a subject in need thereof, when subject has been or is suspect of having bronchopulminary dysplasia.

In some embodiments, the disclosure relates to a method of treating Gaucher's disease by administering at least one or a plurality of compositions disclosed herein comprising PIF peptide, an analog thereof, or a pharmaceutically acceptable salt thereof.

In some embodiments, the disclosure relates to a method of treating Gaucher's disease by administering a therapeutically effective amount or dose of one or a plurality of compositions disclosed herein comprising at least one PIF peptide, an analog thereof, or a pharmaceutically acceptable salt thereof.

In some embodiments, the disclosure relates to a method of treating Gaucher's disease by administration of a pharmaceutical composition comprising a therapeutically effective amount or dose of at least one PIF peptide, an analog thereof, or a pharmaceutically acceptable salt thereof, and a pharmaceutically acceptable carrier.

In some embodiments, the disclosure relates to a pharmaceutical composition comprising a therapeutically effective amount or dose of at least one PIF peptide, an analog thereof, or a pharmaceutically acceptable salt thereof, and a pharmaceutically acceptable carrier for the treatment of Gaucher's disease.

In some embodiments, the disclosure relates to the use of a therapeutically effective amount or dose of any one or plurality of compositions disclosed herein comprising at least one PIF peptide, an analog thereof, or a pharmaceutically acceptable salt thereof, and a pharmaceutically acceptable carrier in the manufacture of a medicament for the treatment of Gaucher's disease.

In some embodiments, the disclosure relates to the use of a pharmaceutical composition comprising a therapeutically effective amount or dose at least one PIF peptide, an analog thereof, or a pharmaceutically acceptable salt thereof, and a pharmaceutically acceptable carrier in the manufacture of a medicament for the treatment of Gaucher's disease.

In some embodiments, the disclosure relates to a method of inducing an immunomodulation effect in a subject in need thereof, when subject has been or is suspect of having Gaucher's disease.

In some embodiments, the disclosure relates to a method of treating auto-immune disease by administering at least one or a plurality of compositions disclosed herein comprising PIF peptide, an analog thereof, or a pharmaceutically acceptable salt thereof.

In some embodiments, the disclosure relates to a method of treating auto-immune disease by administering a therapeutically effective amount or dose of one or a plurality of compositions disclosed herein comprising at least one PIF peptide, an analog thereof, or a pharmaceutically acceptable salt thereof.

In some embodiments, the disclosure relates to a method of treating auto-immune disease by administration of a pharmaceutical composition comprising a therapeutically effective amount or dose of at least one PIF peptide, an analog thereof, or a pharmaceutically acceptable salt thereof, and a pharmaceutically acceptable carrier.

In some embodiments, the disclosure relates to a pharmaceutical composition comprising a therapeutically effective amount or dose of at least one PIF peptide, an analog thereof, or a pharmaceutically acceptable salt thereof, and a pharmaceutically acceptable carrier for the treatment of auto-immune disease.

In some embodiments, the disclosure relates to the use of a therapeutically effective amount or dose of any one or plurality of compositions disclosed herein comprising at least one PIF peptide, an analog thereof, or a pharmaceutically acceptable salt thereof, and a pharmaceutically acceptable carrier in the manufacture of a medicament for the treatment of auto-immune disease.

In some embodiments, the disclosure relates to the use of a pharmaceutical composition comprising a therapeutically effective amount or dose at least one PIF peptide, an analog thereof, or a pharmaceutically acceptable salt thereof, and a pharmaceutically acceptable carrier in the manufacture of a medicament for the treatment of auto-immune disease.

In some embodiments, the disclosure relates to a method of inducing an immunomodulation effect in a subject in need thereof, when subject has been or is suspect of having auto-immune disease.

In some embodiments, the disclosure relates to a method of treating collagen disease by administering at least one or a plurality of compositions disclosed herein comprising PIF peptide, an analog thereof, or a pharmaceutically acceptable salt thereof.

In some embodiments, the disclosure relates to a method of treating collagen disease by administering a therapeutically effective amount or dose of one or a plurality of compositions disclosed herein comprising at least one PIF peptide, an analog thereof, or a pharmaceutically acceptable salt thereof.

In some embodiments, the disclosure relates to a method of treating collagen disease by administration of a pharmaceutical composition comprising a therapeutically effective amount or dose of at least one PIF peptide, an analog thereof, or a pharmaceutically acceptable salt thereof, and a pharmaceutically acceptable carrier.

In some embodiments, the disclosure relates to a pharmaceutical composition comprising a therapeutically effective amount or dose of at least one PIF peptide, an analog thereof, or a pharmaceutically acceptable salt thereof, and a pharmaceutically acceptable carrier for the treatment of collagen disease.

In some embodiments, the disclosure relates to the use of a therapeutically effective amount or dose of any one or plurality of compositions disclosed herein comprising at least one PIF peptide, an analog thereof, or a pharmaceutically acceptable salt thereof, and a pharmaceutically acceptable carrier in the manufacture of a medicament for the treatment of collagen disease.

In some embodiments, the disclosure relates to the use of a pharmaceutical composition comprising a therapeutically effective amount or dose at least one PIF peptide, an analog thereof, or a pharmaceutically acceptable salt thereof, and a pharmaceutically acceptable carrier in the manufacture of a medicament for the treatment of collagen disease.

In some embodiments, the disclosure relates to a method of inducing an immunomodulation effect in a subject in need thereof, when subject has been or is suspect of having collagen disease.

In some embodiments, the disclosure relates to a method of treating connective tissue disease by administering at least one or a plurality of compositions disclosed herein comprising PIF peptide, an analog thereof, or a pharmaceutically acceptable salt thereof.

In some embodiments, the disclosure relates to a method of treating connective tissue disease by administering a therapeutically effective amount or dose of one or a plurality of compositions disclosed herein comprising at least one PIF peptide, an analog thereof, or a pharmaceutically acceptable salt thereof.

In some embodiments, the disclosure relates to a method of treating connective tissue disease by administration of a pharmaceutical composition comprising a therapeutically effective amount or dose of at least one PIF peptide, an analog thereof, or a pharmaceutically acceptable salt thereof, and a pharmaceutically acceptable carrier.

In some embodiments, the disclosure relates to a pharmaceutical composition comprising a therapeutically effective amount or dose of at least one PIF peptide, an analog thereof, or a pharmaceutically acceptable salt thereof, and a pharmaceutically acceptable carrier for the treatment of connective tissue disease.

In some embodiments, the disclosure relates to the use of a therapeutically effective amount or dose of any one or plurality of compositions disclosed herein comprising at least one PIF peptide, an analog thereof, or a pharmaceutically acceptable salt thereof, and a pharmaceutically acceptable carrier in the manufacture of a medicament for the treatment of connective tissue disease.

In some embodiments, the disclosure relates to the use of a pharmaceutical composition comprising a therapeutically effective amount or dose at least one PIF peptide, an analog thereof, or a pharmaceutically acceptable salt thereof, and a pharmaceutically acceptable carrier in the manufacture of a medicament for the treatment of connective tissue disease.

In some embodiments, the disclosure relates to a method of inducing an immunomodulation effect in a subject in need thereof, when subject has been or is suspect of having connective tissue disease.

In some embodiments, the disclosure relates to a method of treating inflammation disorders by administering at least one or a plurality of compositions disclosed herein comprising PIF peptide, an analog thereof, or a pharmaceutically acceptable salt thereof.

In some embodiments, the disclosure relates to a method of treating inflammation disorders by administering a therapeutically effective amount or dose of one or a plurality of compositions disclosed herein comprising at least one PIF peptide, an analog thereof, or a pharmaceutically acceptable salt thereof.

In some embodiments, the disclosure relates to a method of treating inflammation disorders by administration of a pharmaceutical composition comprising a therapeutically effective amount or dose of at least one PIF peptide, an analog thereof, or a pharmaceutically acceptable salt thereof, and a pharmaceutically acceptable carrier.

In some embodiments, the disclosure relates to a pharmaceutical composition comprising a therapeutically effective amount or dose of at least one PIF peptide, an analog thereof, or a pharmaceutically acceptable salt thereof, and a pharmaceutically acceptable carrier for the treatment of inflammation disorders.

In some embodiments, the disclosure relates to the use of a therapeutically effective amount or dose of any one or plurality of compositions disclosed herein comprising at least one PIF peptide, an analog thereof, or a pharmaceutically acceptable salt thereof, and a pharmaceutically acceptable carrier in the manufacture of a medicament for the treatment of inflammation disorders.

In some embodiments, the disclosure relates to the use of a pharmaceutical composition comprising a therapeutically effective amount or dose at least one PIF peptide, an analog thereof, or a pharmaceutically acceptable salt thereof, and a pharmaceutically acceptable carrier in the manufacture of a medicament for the treatment of inflammation disorders.

In some embodiments, the disclosure relates to a method of inducing an immunomodulation effect in a subject in need thereof, when subject has been or is suspect of having inflammation disorders.

In some embodiments, the disclosure relates to a method of treating repetitive strain injuries by administering at least one or a plurality of compositions disclosed herein comprising PIF peptide, an analog thereof, or a pharmaceutically acceptable salt thereof.

In some embodiments, the disclosure relates to a method of treating repetitive strain injuries by administering a therapeutically effective amount or dose of one or a plurality of compositions disclosed herein comprising at least one PIF peptide, an analog thereof, or a pharmaceutically acceptable salt thereof.

In some embodiments, the disclosure relates to a method of treating repetitive strain injuries by administration of a pharmaceutical composition comprising a therapeutically effective amount or dose of at least one PIF peptide, an analog thereof, or a pharmaceutically acceptable salt thereof, and a pharmaceutically acceptable carrier.

In some embodiments, the disclosure relates to a pharmaceutical composition comprising a therapeutically effective amount or dose of at least one PIF peptide, an analog thereof, or a pharmaceutically acceptable salt thereof, and a pharmaceutically acceptable carrier for the treatment of repetitive strain injuries.

In some embodiments, the disclosure relates to the use of a therapeutically effective amount or dose of any one or plurality of compositions disclosed herein comprising at least one PIF peptide, an analog thereof, or a pharmaceutically acceptable salt thereof, and a pharmaceutically acceptable carrier in the manufacture of a medicament for the treatment of repetitive strain injuries.

In some embodiments, the disclosure relates to the use of a pharmaceutical composition comprising a therapeutically effective amount or dose at least one PIF peptide, an analog thereof, or a pharmaceutically acceptable salt thereof, and a pharmaceutically acceptable carrier in the manufacture of a medicament for the treatment of repetitive strain injuries.

In some embodiments, the disclosure relates to a method of inducing an immunomodulation effect in a subject in need thereof, when subject has been or is suspect of having repetitive strain injuries.

In some embodiments, the disclosure relates to methods of treating or preventing pathogen induced inflammation in the brain or CNS by administering at least one or a plurality of compositions disclosed herein comprising PIF peptide, an analog thereof, or a pharmaceutically acceptable salt thereof.

In some embodiments, the disclosure relates to a methods of treating or preventing pathogen induced inflammation in the brain or CNS by administering a therapeutically effective amount or dose of one or a plurality of compositions disclosed herein comprising at least one PIF peptide, an analog thereof, or a pharmaceutically acceptable salt thereof.

In some embodiments, the disclosure relates to a methods of treating or preventing pathogen induced inflammation in the brain or CNS by administration of a pharmaceutical composition comprising a therapeutically effective amount or dose of at least one PIF peptide, an analog thereof, or a pharmaceutically acceptable salt thereof, and a pharmaceutically acceptable carrier.

In some embodiments, the disclosure relates to a pharmaceutical composition comprising a therapeutically effective amount or dose of at least one PIF peptide, an analog thereof, or a pharmaceutically acceptable salt thereof, and a pharmaceutically acceptable carrier for the treatment of pathogen induced inflammation in the brain or CNS.

In some embodiments, the disclosure relates to the use of a therapeutically effective amount or dose of any one or plurality of compositions disclosed herein comprising at least one PIF peptide, an analog thereof, or a pharmaceutically acceptable salt thereof, and a pharmaceutically acceptable carrier in the manufacture of a medicament for the treatment of pathogen induced inflammation in the brain or CNS.

In some embodiments, the disclosure relates to the use of a pharmaceutical composition comprising a therapeutically effective amount or dose at least one PIF peptide, an analog thereof, or a pharmaceutically acceptable salt thereof, and a pharmaceutically acceptable carrier in the manufacture of a medicament for the treatment of pathogen induced inflammation in the brain or CNS.

In some embodiments, the disclosure relates to a methods of treating or preventing pathogen induced inflammation in the brain or CNS in a subject in need thereof, when subject has been or is suspect of having pathogen induced inflammation in the brain or CNS.

In some embodiments, the disclosure relates to methods of increasing myelination in the brain or CNS comprising by administering at least one or a plurality of compositions disclosed herein comprising PIF peptide, an analog thereof, or a pharmaceutically acceptable salt thereof.

In some embodiments, the disclosure relates to methods of increasing myelination in the brain or CNS comprising by administering a therapeutically effective amount or dose of one or a plurality of compositions disclosed herein comprising at least one PIF peptide, an analog thereof, or a pharmaceutically acceptable salt thereof.

In some embodiments, the disclosure relates to methods of increasing myelination in the brain or CNS comprising by administration of a pharmaceutical composition comprising a therapeutically effective amount or dose of at least one PIF peptide, an analog thereof, or a pharmaceutically acceptable salt thereof, and a pharmaceutically acceptable carrier.

In some embodiments, the disclosure relates to a pharmaceutical composition comprising a therapeutically effective amount or dose of at least one PIF peptide, an analog thereof, or a pharmaceutically acceptable salt thereof, and a pharmaceutically acceptable carrier for the increase myelination in the brain or CNS.

In some embodiments, the disclosure relates to the use of a therapeutically effective amount or dose of any one or plurality of compositions disclosed herein comprising at least one PIF peptide, an analog thereof, or a pharmaceutically acceptable salt thereof, and a pharmaceutically acceptable carrier in the manufacture of a medicament for the increase myelination in the brain or CNS.

In some embodiments, the disclosure relates to the use of a pharmaceutical composition comprising a therapeutically effective amount or dose at least one PIF peptide, an analog thereof, or a pharmaceutically acceptable salt thereof, and a pharmaceutically acceptable carrier in the manufacture of a medicament for the increase myelination in the brain or CNS.

In some embodiments, the disclosure relates to methods increasing myelination in the brain or CNS in a subject in need thereof, when subject has been or is suspect of having a condition that requires increasing myelination in the brain or CNS. Such conditions include, but are not limited to those described herein, including MS.

In some embodiments, the disclosure relates to methods of preventing the decrease of myelination in the brain of CNS comprising by administering at least one or a plurality of compositions disclosed herein comprising PIF peptide, an analog thereof, or a pharmaceutically acceptable salt thereof.

In some embodiments, the disclosure relates to methods of preventing the decrease of myelination in the brain of CNS comprising by administering a therapeutically effective amount or dose of one or a plurality of compositions disclosed herein comprising at least one PIF peptide, an analog thereof, or a pharmaceutically acceptable salt thereof.

In some embodiments, the disclosure relates to methods of preventing the decrease of myelination in the brain of CNS comprising by administration of a pharmaceutical composition comprising a therapeutically effective amount or dose of at least one PIF peptide, an analog thereof, or a pharmaceutically acceptable salt thereof, and a pharmaceutically acceptable carrier.

In some embodiments, the disclosure relates to a pharmaceutical composition comprising a therapeutically effective amount or dose of at least one PIF peptide, an analog thereof, or a pharmaceutically acceptable salt thereof, and a pharmaceutically acceptable carrier for preventing the decrease of myelination in the brain of CNS.

In some embodiments, the disclosure relates to the use of a therapeutically effective amount or dose of any one or plurality of compositions disclosed herein comprising at least one PIF peptide, an analog thereof, or a pharmaceutically acceptable salt thereof, and a pharmaceutically acceptable carrier in the manufacture of a medicament for preventing the decrease of myelination in the brain of CNS.

In some embodiments, the disclosure relates to the use of a pharmaceutical composition comprising a therapeutically effective amount or dose at least one PIF peptide, an analog thereof, or a pharmaceutically acceptable salt thereof, and a pharmaceutically acceptable carrier in the manufacture of a medicament for preventing the decrease of myelination in the brain of CNS.

In some embodiments, the disclosure relates to methods preventing a decrease in myelination in the brain or CNS in a subject in need thereof, when subject has been or is suspect of having a condition that requires the prevention of decreasing myelination in the brain or CNS. Such conditions include, but are not limited to those described herein, including MS.

Kits

According to some embodiments of the invention, the formulation may be supplied as part of a kit. In some embodiments, the kit comprises comprising a PIF peptide and/or a PIF analog or pharmaceutically acceptable salt thereof, the PIF peptide and/or a PIF analog or pharmaceutically acceptable salt thereof comprises a non-natural amino acid or is at least 70% homologous to SEQ ID NO:20. In some embodiments, the PIF peptide is a peptide comprising an amino acid sequence as described herein, such as but not limited to SEQ ID NO: 13. In another embodiment, the kit comprises a pharmaceutically acceptable salt of an analog with a rehydration mixture. In another embodiment, the pharmaceutically acceptable salt of an analog are in one container while the rehydration mixture is in a second container. The rehydration mixture may be supplied in dry form, to which water or other liquid solvent may be added to form a suspension or solution prior to administration. Rehydration mixtures are mixtures designed to solubilize a lyophilized, insoluble salt of the invention prior to administration of the composition to a subject takes at least one dose of a purgative. In another embodiment, the kit comprises a pharmaceutically acceptable salt in orally available pill form.

The kit may contain two or more containers, packs, or dispensers together with instructions for preparation and administration. In some embodiments, the kit comprises at least one container comprising the pharmaceutical composition or compositions described herein and a second container comprising a means for delivery of the compositions such as a syringe. In some embodiments, the kit comprises a composition comprising an analog in solution or lyophilized or dried and accompanied by a rehydration mixture. In some embodiments, the analog and rehydration mixture may be in one or more additional containers.

The compositions included in the kit may be supplied in containers of any sort such that the shelf-life of the different components are preserved, and are not adsorbed or altered by the materials of the container. For example, suitable containers include simple bottles that may be fabricated from glass, organic polymers, such as polycarbonate, polystyrene, polypropylene, polyethylene, ceramic, metal or any other material typically employed to hold reagents or food; envelopes, that may consist of foil-lined interiors, such as aluminum or an alloy. Other containers include test tubes, vials, flasks, and syringes. The containers may have two compartments that are separated by a readily removable membrane that upon removal permits the components of the compositions to mix. Removable membranes may be glass, plastic, rubber, or other inert material.

Kits may also be supplied with instructional materials. Instructions may be printed on paper or other substrates, and/or may be supplied as an electronic-readable medium, such as a floppy disc, CD-ROM, DVD-ROM, zip disc, videotape, audio tape, or other readable memory storage device. Detailed instructions may not be physically associated with the kit; instead, a user may be directed to an internet web site specified by the manufacturer or distributor of the kit, or supplied as electronic mail.

In another embodiment, a packaged kit is provided that contains the pharmaceutical formulation to be administered, i.e., a pharmaceutical formulation containing PIF peptide and/or a PIF analog or pharmaceutically acceptable salt thereof, a container (e.g., a vial, a bottle, a pouch, an envelope, a can, a tube, an atomizer, an aerosol can, etc.), optionally sealed, for housing the formulation during storage and prior to use, and instructions for carrying out drug administration in a manner effective to treat any one or more of the indications disclosed herein. The instructions will typically be written instructions on a package insert, a label, and/or on other components of the kit.

Depending on the type of formulation and the intended mode of administration, the kit may also include a device for administering the formulation (e.g., a transdermal delivery device). The administration device may be a dropper, a swab, a stick, or the nozzle or outlet of an atomizer or aerosol can. The formulation may be any suitable formulation as described herein. For example, the formulation may be an oral dosage form containing a unit dosage of the active agent, or a gel or ointment contained within a tube. The kit may contain multiple formulations of different dosages of the same agent. The kit may also contain multiple formulations of different active agents.

The present kits will also typically include means for packaging the individual kit components, i.e., the pharmaceutical dosage forms, the administration device (if included), and the written instructions for use. Such packaging means may take the form of a cardboard or paper box, a plastic or foil pouch, etc.

This disclosure and embodiments illustrating the method and materials used may be further understood by reference to the following non-limiting examples. Examples are intended to create a context to present neurotrauma as an integrated multiprong disease and PIF's ability to address the disease locally and systemically addressing its cause not only consequences as they were to become apparent.

The following examples are merely illustrative and should not be construed as limiting the scope of the embodiments in any way as many variations and equivalents that are encompassed by these embodiments will become apparent to those skilled in the art upon reading the present disclosure.

Example 1: sPIF Therapy to Arrest and/or Reverse Both Acute and Chronic Neurotrauma PreImplantation Factor (PIF) is a 15 amino-acid peptide produced by solid phase synthesis at human grade quality (sPIF). [3-6] Following severe neurotrauma, sPIF reduces inflammation, while promoting myelin repair and nerve regeneration, also reverses advanced paralysis and severe neurologic injury through local and systemic protection. PIF targets directly the CNS and promotes endogenous stems cells proliferation and differentiation. Accordingly, PIF can be a safe and effective drug to address acute and long-term neurotrauma sequela. Due to its high safety profile and comprehensive preclinical results, [7-14] sPIF is currently FAST-TRACK awarded, FDA approved University-sponsored clinical trial for autoimmune disorder. (ClinicalTrials.gov NCT02239562). Thus, PIF can be a safe and effective drug to address acute and long-term neurotrauma sequela. Overall, PIF is a novel approach for the comprehensive management of neurotrauma from acute to the chronic phase integrating both local and systemic protection.

Pregnancy perspective: PIF exerts broad neurotrophic and neuroprotective effects. Native PIF is endogenously expressed by the embryo/fetus and placenta and its presence in circulation is associated with favorable pregnancy outcome (absence in non-viable embryos). Starting post fertilization PIF plays a determining role to create maternal tolerance without immune suppression, regulating immunity, inflammation and transplant acceptance. In short, PIF comprehensively regulates inflammation, immunity and transplant acceptance. PIF specifically promotes neural development and protects against maternal adverse environment. PIF targets the embryo to reduce oxidative stress and protein misfolding, both critical elements of neurotrauma. In vivo PIF reduces spontaneous and LPS induced pregnancy loss decreasing placental inflammation. Synthetic PIF (sPIF) successfully translates pregnancy-induced native's peptide effect, including its beneficial neuroprotective properties to clinically relevant models outside pregnancy. As such PIF presents qualities for a comprehensive neurotrauma preventative and therapeutic. PIF-based therapy is a paradigm-shift approach regulating inflammation locally and systemically, early or later, and in acute or chronic neurotrauma. The data comprehensively address the unmet need. Therefore herein, the following examples are representative of a comprehensive, synergizing therapeutic platform.

Results

PIF Targets and Regulates Human Immune Cells to Create Th2/Th1 Bias—In Vivo PIF Reduces Activated Macrophages/Neutrophil Extravasation Systemically.

The resulting systemic inflammatory response is a key for both short and long term neurotrauma. sPIF orchestrates global anti-inflammatory effects in human mononuclear cells (PBMCs) (Barnea, et al. 2012, Roussev et al. 2013, Barnea et al. 2015). Preserving basal immunity sPIF blocks mixed lymphocyte reaction (MLR) and activated PBMCs proliferation. By increasing IL-10 (rather than IFN-γ expression) sPIF may counteract several pro-inflammatory (TNF-α, IFN-γ IL-12B) macrophage activators (Barnea, et al. 2012). sPIF also reduces NK cells cytotoxicity by inhibiting pro-inflammatory CD69 expression. PIF targets systemic immunity independent of early Ca++ mobilization hallmark of immune suppressive drugs.

sPIF direct anti-inflammatory effect was tested in vivo. In a murine model following LPS-induced peritonitis sPIF injection reduced macrophage migration. Neutrophil extravasation was reduced in post-chemically induced peritonitis. (Karl-Heintz et al. 2015). In addition in a cremasteric muscle induced inflammation model, PIF reduces neutrophils rolling and extravasdation post TNF-induced inflammation. sPIF targets Kv1.3b the K+ alpha pore acts as competitive inhibitor of cortisone. sPIF acts as cortisone to reduce K+ flux which was confirmed in vivo (Karl-Heintz et al. 2015). The Kv1.3 is critical for neurotransmission. sPIF regulates Ca+ flux through the K+ flux, thereby not acting as an immune suppressor as cortisone does. Due to peptide's small size and its high flexibility sPIF through its core R-I-K-P sequence targets multiple proteins. This is complemented by changes in protein targets folding structure which can affect sPIF binding. Among them, sPIF targets insulin degrading enzyme when protein is attached to insulin thereby regulates the growth factor function. IDE is critical for Alzheimer's disease—prevents b-amyloid accumulation. PIF reduces oxidative stress and protein misfolding by targeting protein-disulfide isomerase and heat shock protein 70 (Barnea et al. 2104, Barnea et al. 2015, Almogi-Hazan et al. 2014). Thus sPIF acts to regulate systemic immunity restoring homeostasis. As such sPIF has a critical integrating anti-inflammatory role.

sPIF: A Single Aminoacid Mutation Leads to Loss of Activity in Both Neural Cells and Systemic Immune Cells—Relevance of sPIF for Neuroprotection.

Figure 2:
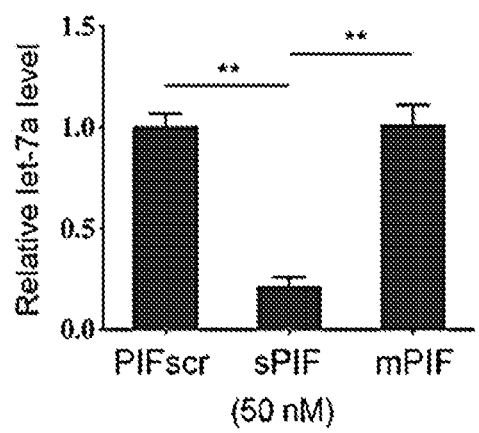
FIG. 2 depicts a measurement of let-7a levels in two identified cell lines after exposure of the cells to a scrambled PIF sequence (PIFscr), a synthetic PIF sequence (sPIF), and a mutated PIF sequence (m3PIF).
Figure 2:
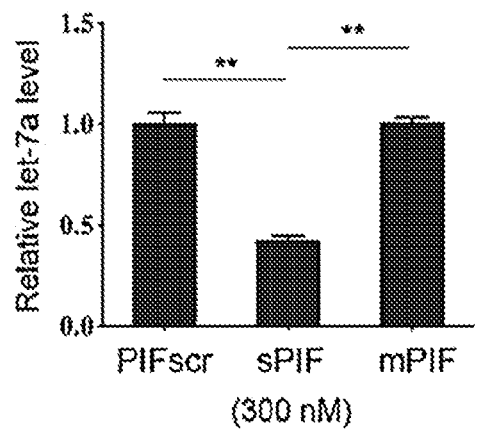
Figure 3:
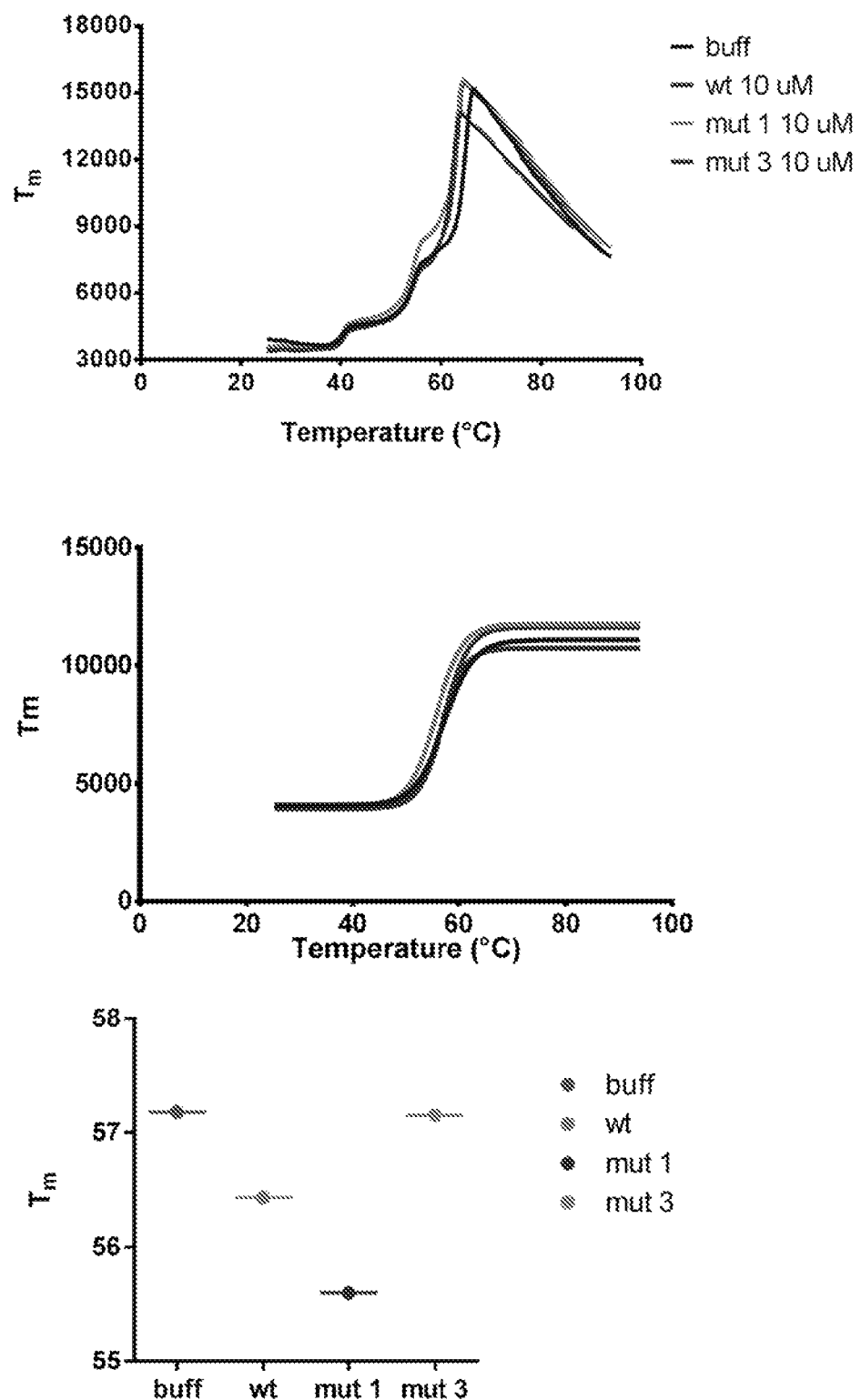
FIG. 3 depicts a fluorescent based thermal shift assay, showing the binding of two PIF mutants to the insulin degrading enzyme (IDE). Concentrations of the ligands 10 uM and 1 uM of the receptor, buffer consisting of 10 mM HEPES-HCL, 150 mM MaCl, and protein folding sensitive dye SyO 1:1000. The PIF(mutant-1) had a decreased Tm compared to the PIF(wt), suggesting higher affinity of binding to the receptor, while PIF(mutant-3) had an actually increased Tm, compared to the PIF(wt), suggesting decreased binding affinity of this mutant to the IDE.
Figure 4:
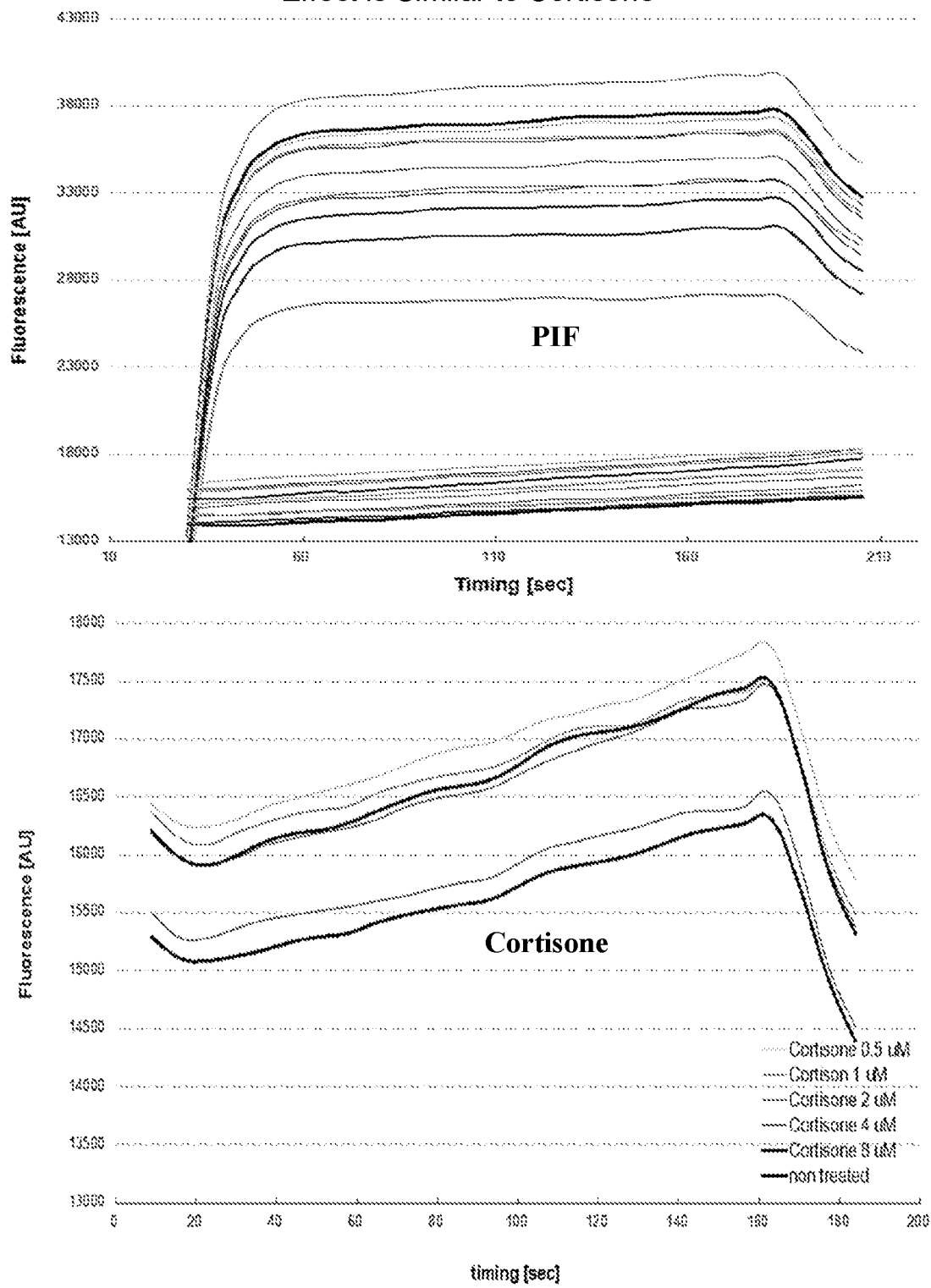
FIG. 4 depicts a comparison of fluorescence measurements correlating the effect of PIF, PIF mutants (1 or 3) or cortisone on K+ flux inhibition in Jurkat T-cells.

Modifications of the sPIF sequence lead to altered biological activity. sPIF binding to PDI was compared to scrambled PIF (the same amino acid in random sequence). Due to the modified peptide structure rigidity, its interaction with PDI target was greatly reduced. (FIG. 2). Using Kv1.3b (potassium channel beta) as a binding target, the modifications of a single amino acid of sPIF were assessed. The data showed that most the changes at the 4 and 6 positions may be relevant for biologic activity. (FIG. 3). Thermal shift assay for IDE demonstrated that mut-1 likely increases the biologic activity since it has a reduced thermal shift when compared with the wild type PIF. On the other hand, the mut-3 PIF activity was decreased which was also confirmed in lack of effect on let-7 micrtoRNA in both microglia as well as neural cell lines Consequently sPIF effect was examined in cell based systems. Using the Jurkat cells line the effect of sPIF was compared to the mutated sPIF (Mut-3 and Mut 1) as it reflected on K+ flux. Data demonstrated that the effect was significant reducing the K+ flux as compared with control. Both mutated sPIF at high doses (control) had no effect. (FIG. 4). In addition when compared to cortisone, sPIF had a similar inhibitory effect on K+ flux. Thus dependent on the target Kv1.3 or IDE the mutated PIF-1 can have a target-specific effect which can also translate to diverse biological activity.

sPIF Reduces Gaucher, and Gaucher-Like Disease—Mucopolysaccharidosis Induced Systemic Inflammation In Vitro.

Figure 23:
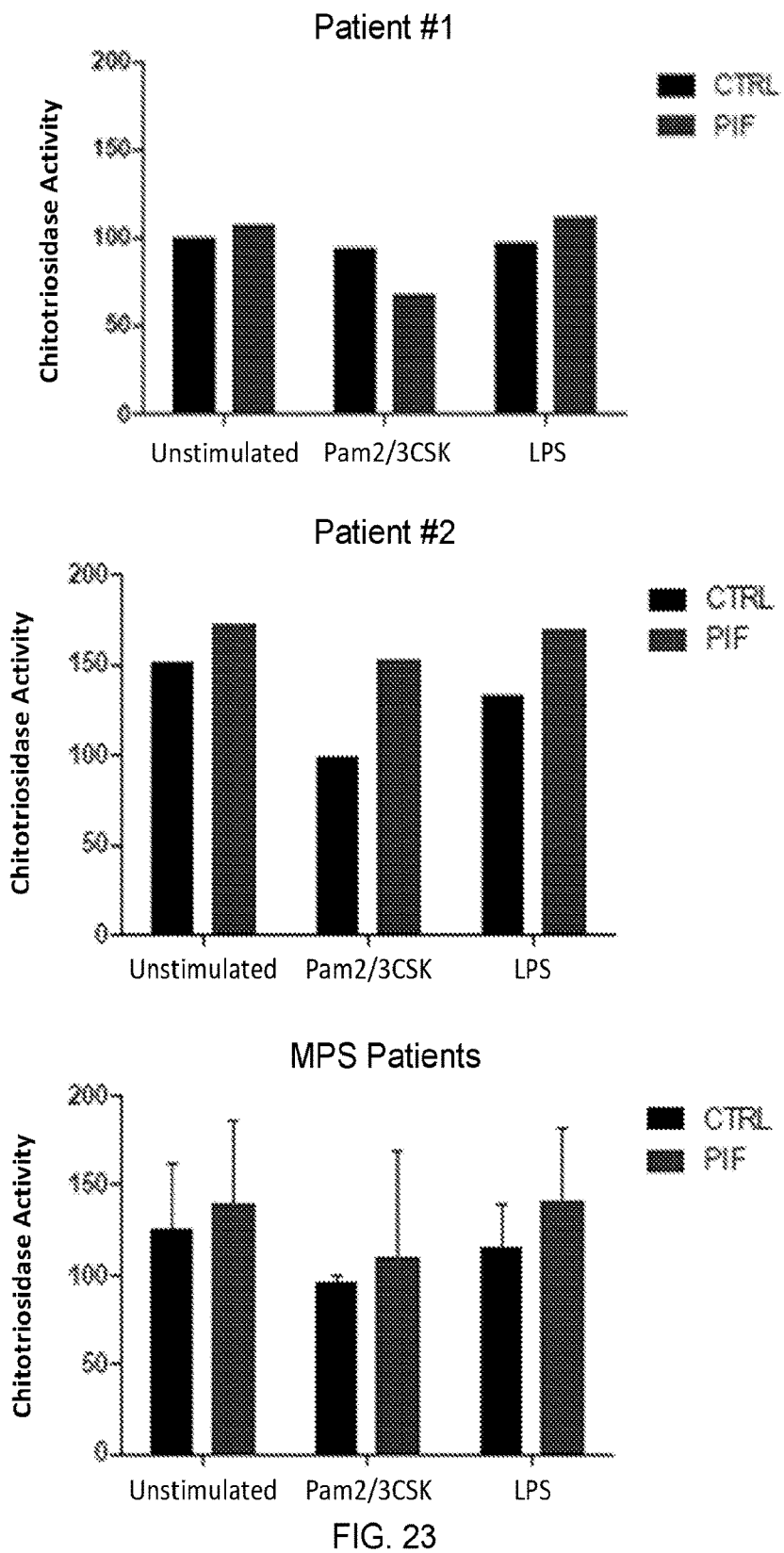
FIG. 23 depicts a measurement of enzymatic activity in a Gaucher's disease model. PIF was able to increase the enzymatic defect of mucopolysaccharidosis.

Gaucher Disease (typically diagnosed in childhood) is defined as a rare hereditary disorder of lipid metabolism caused by an enzyme deficiency and characterized by enlargement of the spleen and liver, bone lesions, and neurological impairment. Beyond the potential neural dysfunction (local), patients with the disease can also have systemic inflammation. Whether PIF can alter immune response in children with Gaucher disease was examined. Blood collected from two children PBMCs were separated and the effect of PIF also or following activation by LPS was determined. PIF increased chitotriosidase levels as compared to unstimulated, Pam2/3csk (marker inducer) and LPS-treated PBMC. (FIG. 23). PIF reduced LPS-induced chitotriosidase activity reflecting an anti-inflammatory response. This data substantiates that sPIF may control systemic manifestations of central neuroinflammatory disease thereby reducing the resulting central inflammatory response.

sPIF Reverses Brain Injury HIE Model: Acute-Neurotrauma Intervention.

Acute injury blunt/blast/penetrating injury of the brain and spinal cord can create a compromised blood supply, strong inflammatory response (activated microglia, oligodendrocytes) and decreased oxygen supply. In addition the CNS may initiate an infectious process, if the wound is severe. Following acute-neurotrauma, immediate specialized care is frequently not available in military setting. In civilian cases rapid evacuation to a hospital can take place. Once the patient is in the hospital, if the neuroinjury is severe, neurosurgery has to be involved. However mostly supportive measures are initiated which are followed by long-term rehabilitation. Thus, an acute intervention to mitigate initiation and uncontrolled progression of inflammation caused by neurotrauma would be a major breakthrough.

For effective immediate intervention sPIF is readily available, stable in harsh environment (RT) and has rapid and sustained action. The hypoxic ischemic (HIE) model provides a clinically relevant model to examine sPIF efficacy in acute neurotrauma setting. The HIE model is associated with high morbidity and mortality. The HIE clinically-relevant model is three-prong: 1. ligation of the carotid artery in one side, 2. exposure to low oxygen for several minutes and 3. LPS-induced inflammation. Thus, HIE closely represents an acute/severe CNS injury.

Figure 5A:
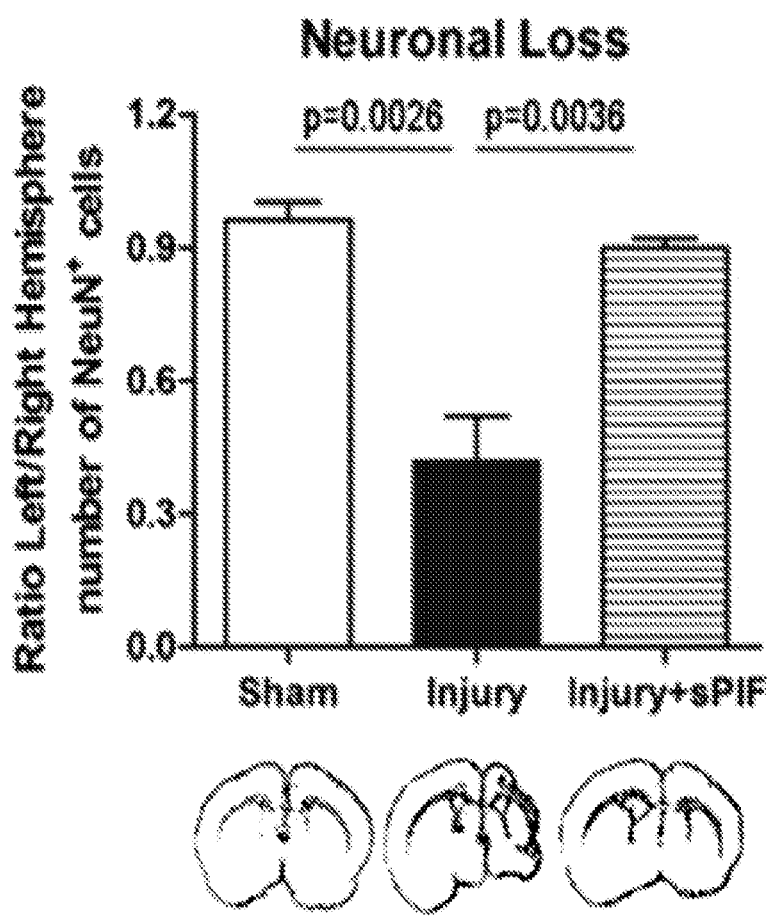
FIGS. 5A-5G depict sPIF treatment results and proposed molecular pathways.
Figure 5B:
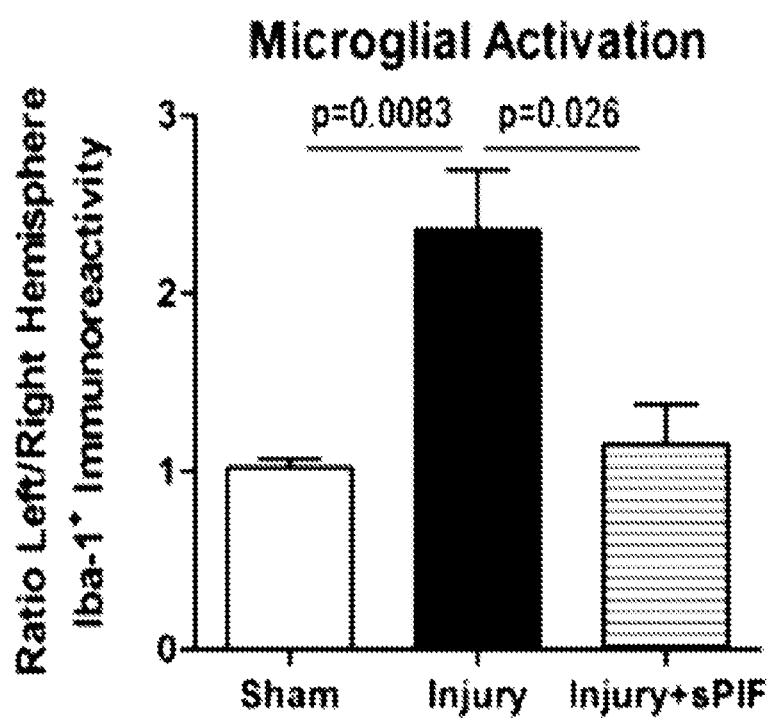

To mimic clinical scenarios seen frequently in the battlefield and sometimes with civilians if rapid intervention is not available subcutaneous sPIF therapy was started only 3 days post-injury and has lasted only for 6 days. sPIF led to significant neuroprotection assessed clinically and revealing effect on pathways relevant for neurologic disorders and specific to CNS injury. Remarkably, sPIF reduces brain cells death, reverses neuronal loss and restores proper cortical architecture and reduced microglial activation (FIGS. 5A, 5B) The effect of sPIF was direct (or local) targeting both microglia (macrophages) and neural cells. It is important to remark that in order for sPIF to act since one carotid artery was obstructed therefore to reverse neuronal injury sPIF had to pass from the apparently healthy to the injured hemisphere. Thus sPIF was observed to traverse the BBB intact.

Figure 5C:
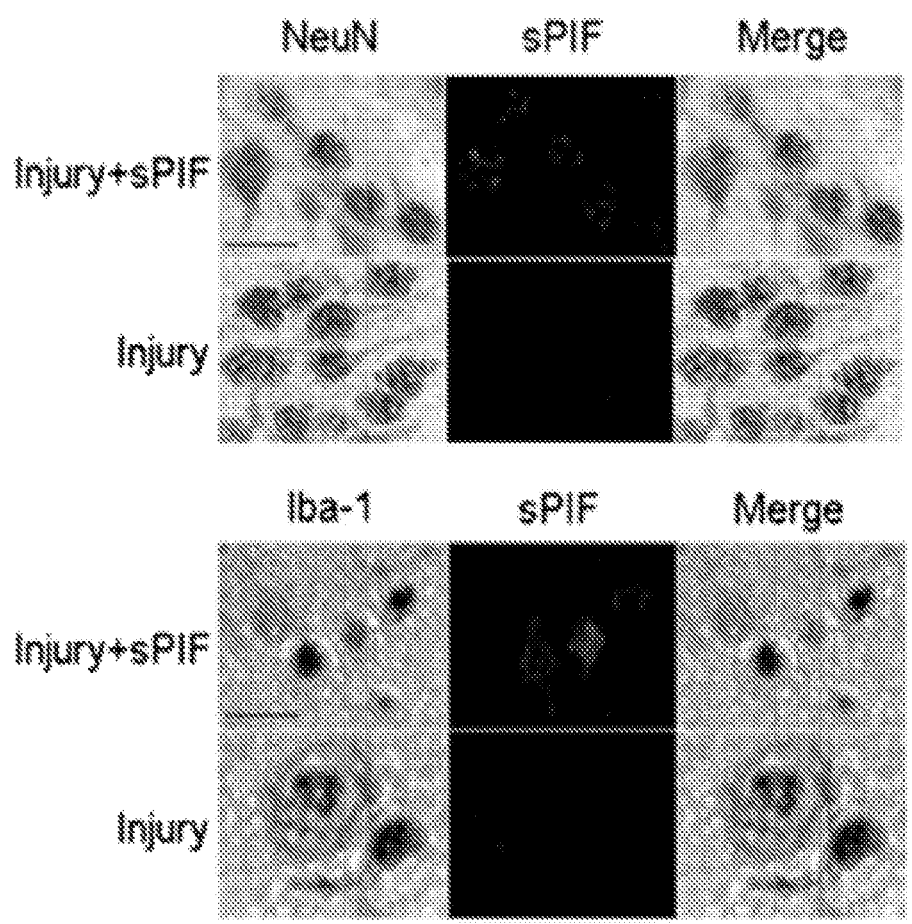
Figure 5D:
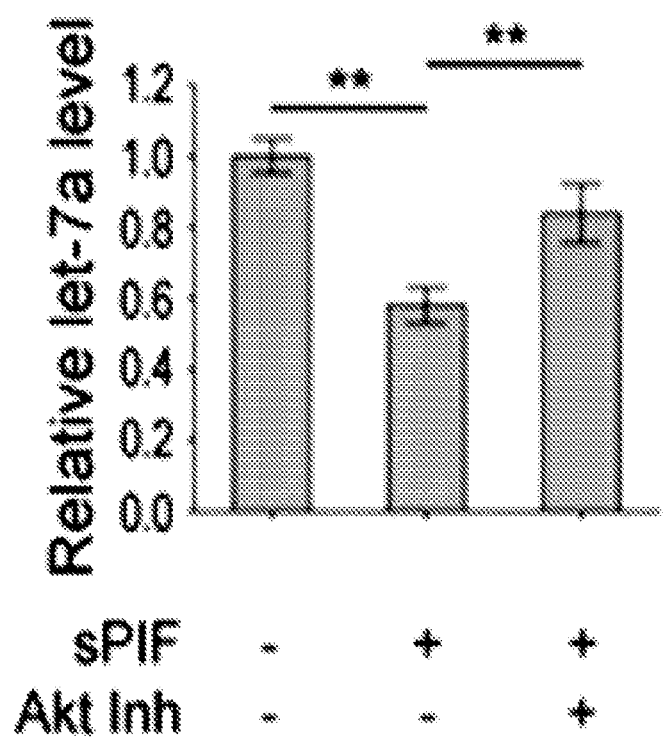
Figure 5E:
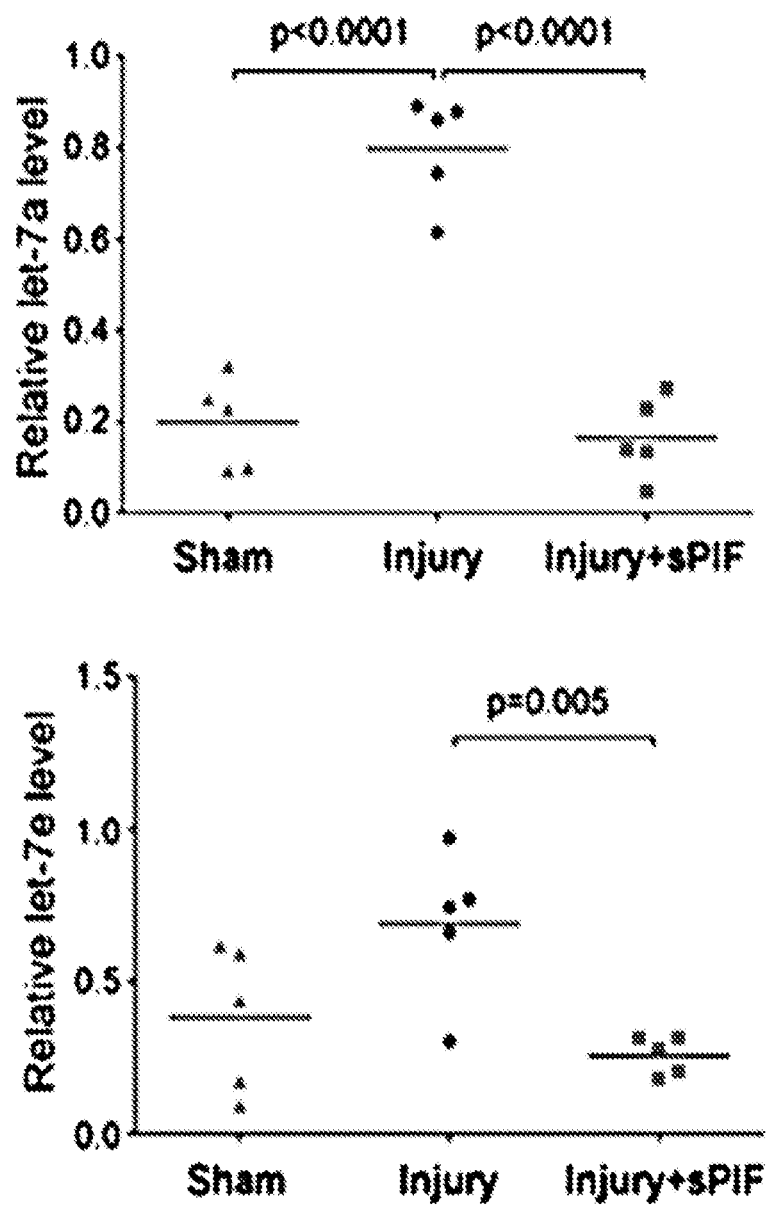
Figure 5F:
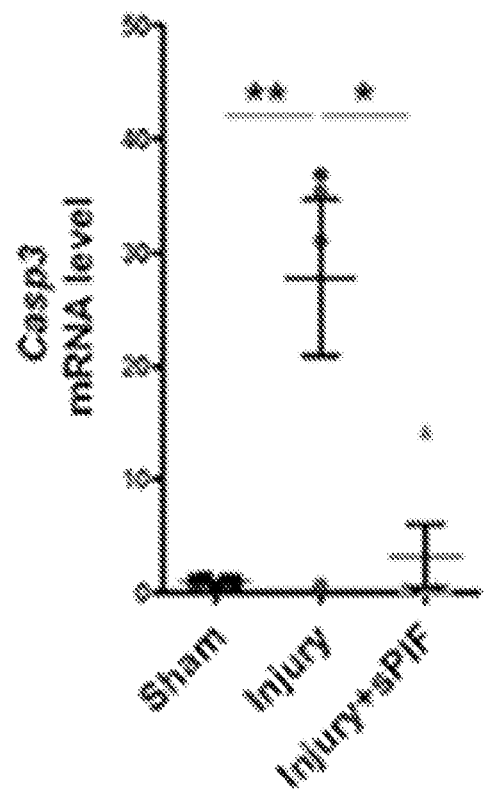
Figure 5F:
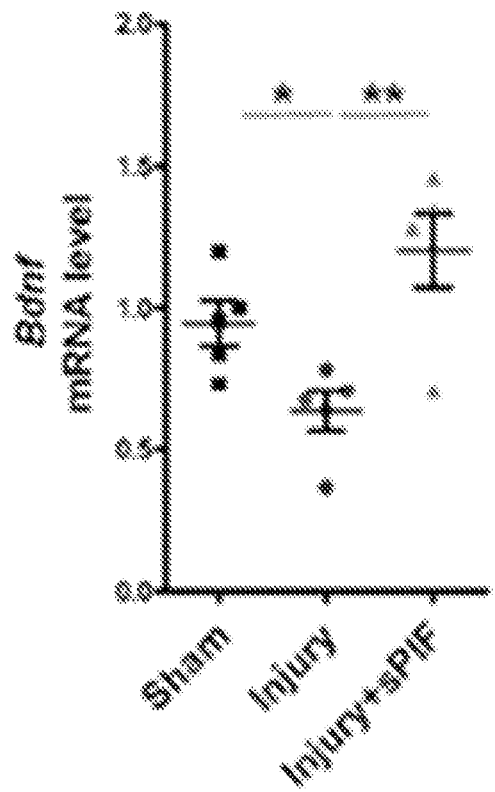
Figure 5G:
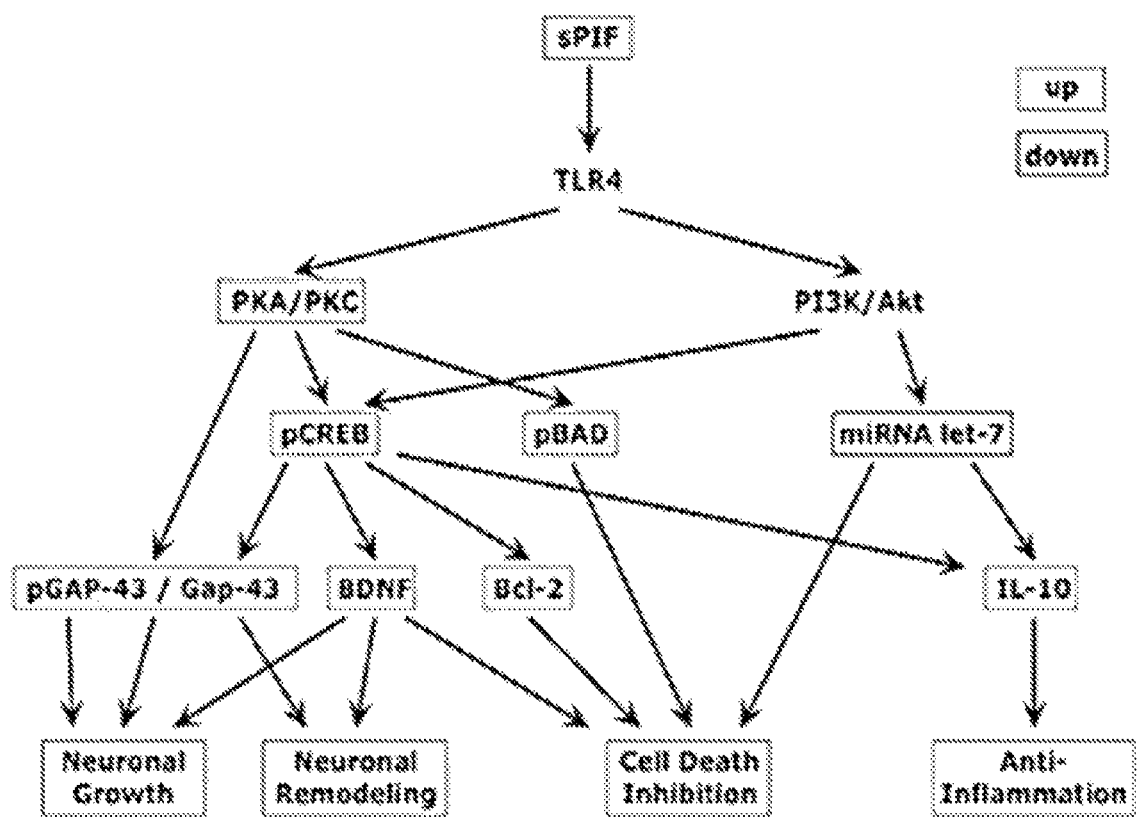

This direct effect on target cells was confirmed by targeting microglia and neuron cell line (Neu) in vitro (FIGS. 5C, D). Two major complementary mechanisms of clear relevance support sPIF induced neuroprotection; namely reduced pro-apoptotic let-7microRNA coupled with regulation of phosphorylated PKC/PKA pathways. sPIF reduced let-7 while increasing IL-10 expression—effects were TLR4/PI3-AKT dependent (FIGS. 5C-5E). sPIF activates (PKA)/(PKC) signaling, leading to increased phosphorylation of major neuroprotective substrates (GAP-43, BAD, and CREB). Phosphorylated CREB in turn facilitates expression of (Gap43, Bdnf and Bcl2) (FIG. 5F) that play important role regulating neuronal growth, survival, which is dependent on TLR4 signaling (FIG. 5G). PKA/PKC was reported to impart TBI (Lucke-Wold, Logsdon et al. 2014; Zohar, Lavy et al. 2011; Titus 2013). Overall, despite delayed intervention (3 days) sPIF reversed advanced brain injury—reflecting strong applicability to emergency scenario where immediate advanced intervention is not available. For currently used neuroprotective drugs ability to reach the brain in both intact and damaged settings is difficult. Therefore frequently drugs in order to pass the BBB they have to be very small, or have to be added to agents that would favor passage.

Figure 6:
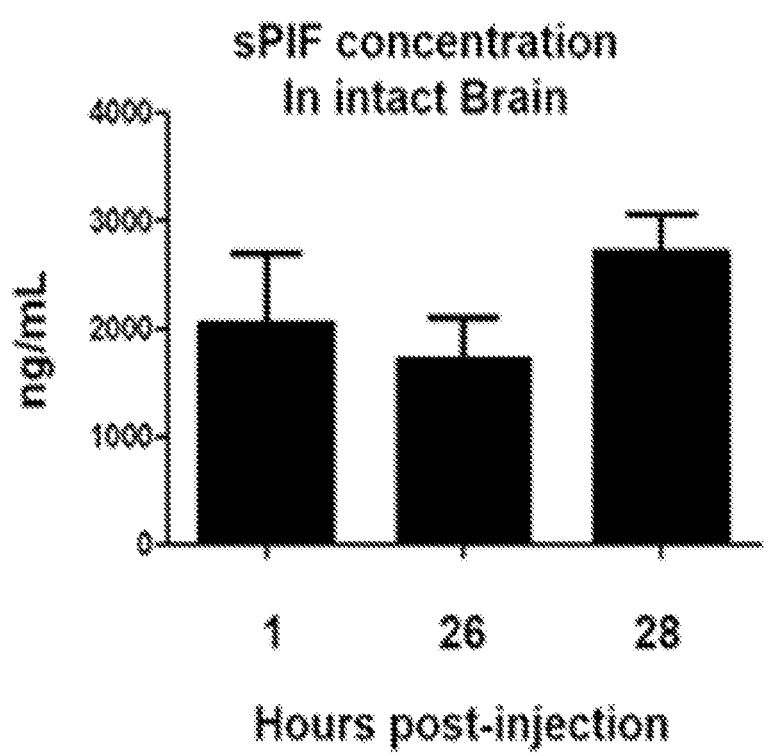
FIG. 6 depicts sPIF concentration in adult intact brains. Healthy adult CD-1 mice were injected with sPIF (0.75 mg/kg body weight) subcutaneously every 12 hours (n=3 each time point). sPIF was detected using liquid chromatography with tandem mass spectrometric detection. sPIF can be detected 1 hours after injection in brain tissue and the concentration does not change significantly after 26 (3 injections) and 28 hours (3 injections).
Figure 7:
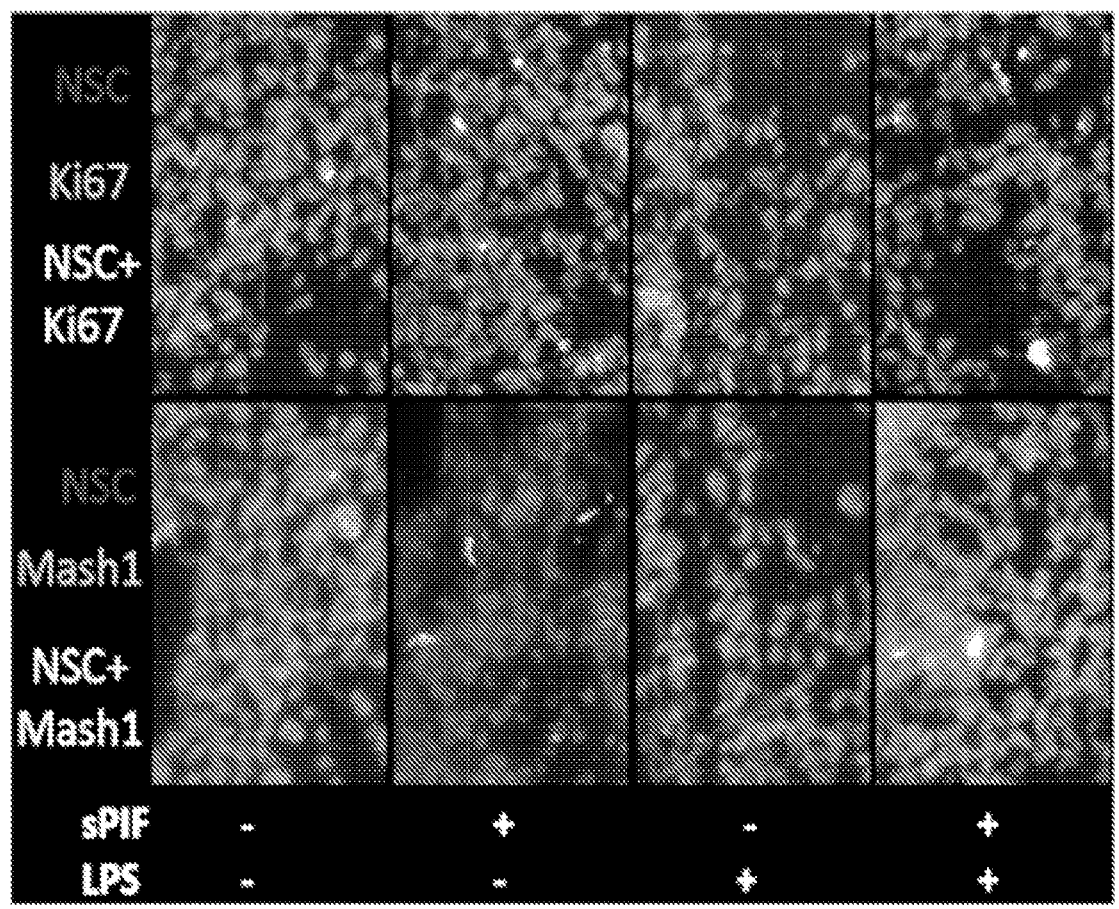
FIGS. 7 and 8 depicts images of PIF effect on neural stem cell proliferation and differentiation. Animals were treated with LPS or NaCl on postnatal day 1. On the following day the sPIF treatment (0.75 mg/kg b.w. twice daily) was started for 5 days. LPS induces NPCs proliferation and differentiation (compared to healthy animals). sPIF induces increased NPCs proliferation and differentiation compared to NaCl or LPS treated animals. Brains were removed following mice sacrifice and placed in MRI machine observing brain architecture comparing LPS with PIF+LPS and sham control. Expression of H19 was also examined.
Figure 8:
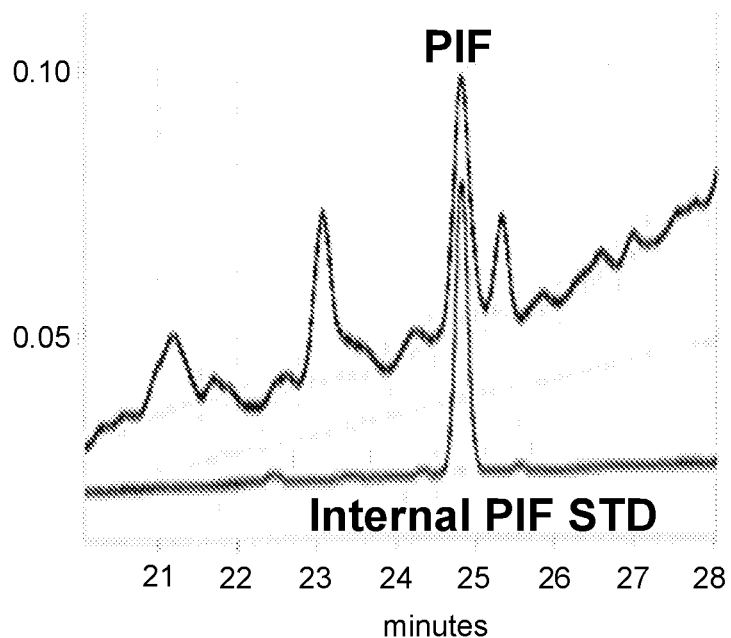
Figure 8:
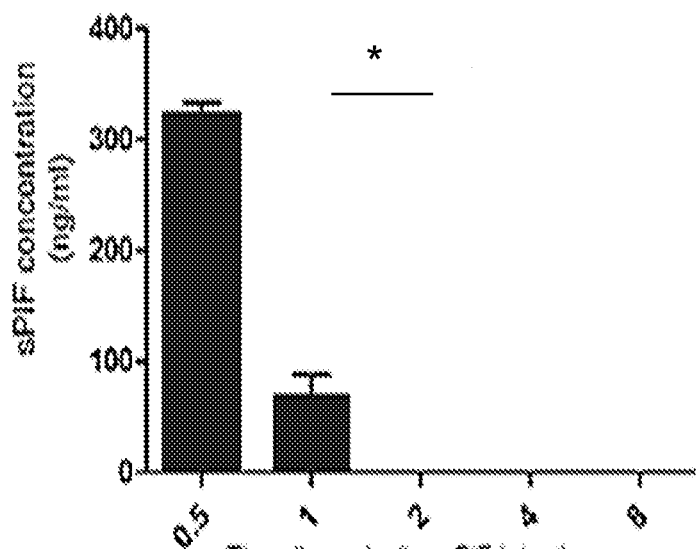
Figure 9:
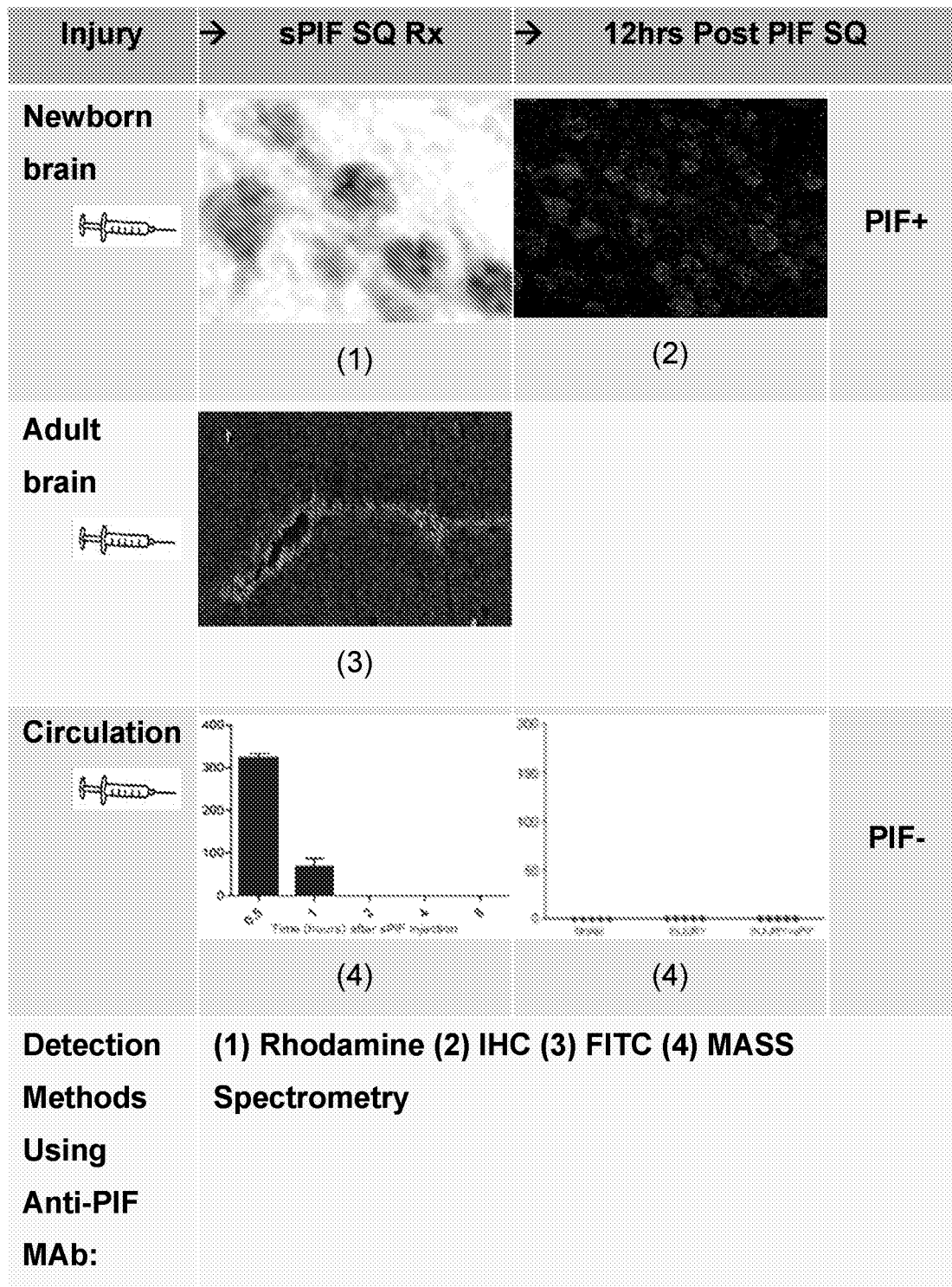
FIGS. 9 and 10 depict PIF presence in the brain targeting microglia and neurons as demonstrated by anti-PIF monoclonal antibody staining. Also injected Rhodamine-PIF crosses the BBB reaching the brain. In contrast, at the same time point 12 h post-injection in the HIE model PIF is not found in the serum.

Highly critical for sPIF use for neurotrauma management is that it traverses BBB rapidly, intact that means it is not degraded. sPIF was injected into adult mice subcutaneously and at different time points brain tissue harvested was extracted using HPLC/mass-spectrometry using sPIF as internal standard. sPIF was found intact in the brain after 12-26 hrs after injection thus making the drug an attractive as a long-term neuroprotectant. (FIG. 6). Within 30 min reaches a peak after subcutaneous injection while at the same time point it also targets the systemic immunity. FIG. 7 shows the detection of PIF by mass spectrometry using an internal PIF-8 dalton larger standard. The clearance of PIF from mice circulation following high dose PIF administration is also shown. (HPLC/Masspectrometry method. FIG. 8 shows that while PIF reaches the brain detected by antiPIF monoclonal antibody documenting a target effect on both microglia and neurons. at the same it has already been cleared from the circulation (FIG. 8). It further demonstrates that Rhodamine-PIF crosses the BBB to target the brain. Simultaneous local (brain) and systemic (immune) targeting reflect an integrated sPIF induced protection. This shows that sPIF can be easily and efficiently deployed and rapidly utilized post-acute neurotrauma.

sPIF Promotes Endogenous Stems Cells Proliferation/Differentiation: Chronic Neurotrauma Therapy.

Neuronal loss frequently occurs post-CNS injury, due to the progressive uncontrolled inflammation. To restore neurotrauma disease, the challenge remains to repair or replace those cells and restore their communication with other cells to integrate function. sPIF has the potential to be effective in that respect. In the developing brain, radial glia act as neural stem cells (NSCs) and is located in the subventricular zone (SVZ). NSCs generate oligodendrocytes and restricted populations of neurons and importantly represent a large reservoir of cells for repair post-injury. However, NSCs progressively become quiescent post-natally. During self-renewal NSCs divide symmetrically into two NSCs or asymmetrically into one NSC and one transit amplifying cell (TAC). Electroporation in neonates is able to selectively target and manipulate radial glia-NSCs enabling accurate assessment of proliferative cells transfected (fluorescently labelled) NSCs examining their fate by TACs measurements (Mash1 positive cells). Activated dormant NSCs induce de novo gliogenesis and neurogenesis for endogenous repair following injury (FIG. 7) NSCs in the SVZ are resistant to hypoxia-ischemia while TACs, oligodendrocyte progenitors, and newborn neurons are vulnerable contributing to oligodendrocyte and neuron depletion. Thus, targeting NPCs and increasing TACs is an attractive repair strategy.

sPIF may activate NPCs via PI3/AKT-mTOR signaling. sPIF treatment (0.75 mg/kg twice daily s.c.) NPCs in healthy and LPS-pretreated animals (sham controlled design, n=8 each group) was examined. After 5 days brains were probed with Ki67 (proliferation marker) and Mash1 (TAC marker). Indeed sPIF treatment results in NSCs activation (both proliferation and differentiation into TACs) in healthy or LPS pretreated brains. (FIG. 7). Collectively sPIF has strong potential to activate NSCs and may impart neuroregeneration post-TBI. The observations in this model were also translated to imaging using advanced MRI (FIG. 7). Results showed that sPIF following exposure to LPS treatment has led to restored brain architecture as compared to (normal) LPS-treated animal. When the data on sPIF was compared to sham treated animal no significant differences were noted.

This documents that sPIF induced protection is translated to significant brain repair. Mechanistically based on the data the effect may be due to the activation of the H19-related pathway.

sPIF Directly Targets Specific Proteins in the Brain. (HIE Model).

Figure 10:
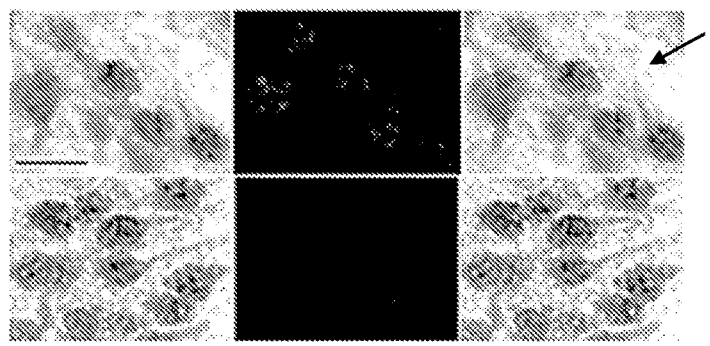
Figure 10:
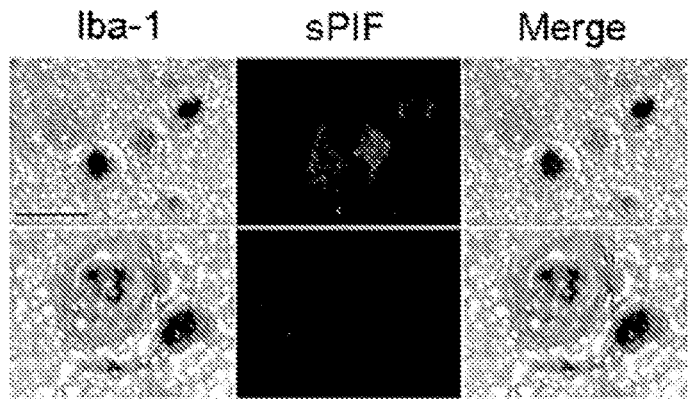
Figure 10:
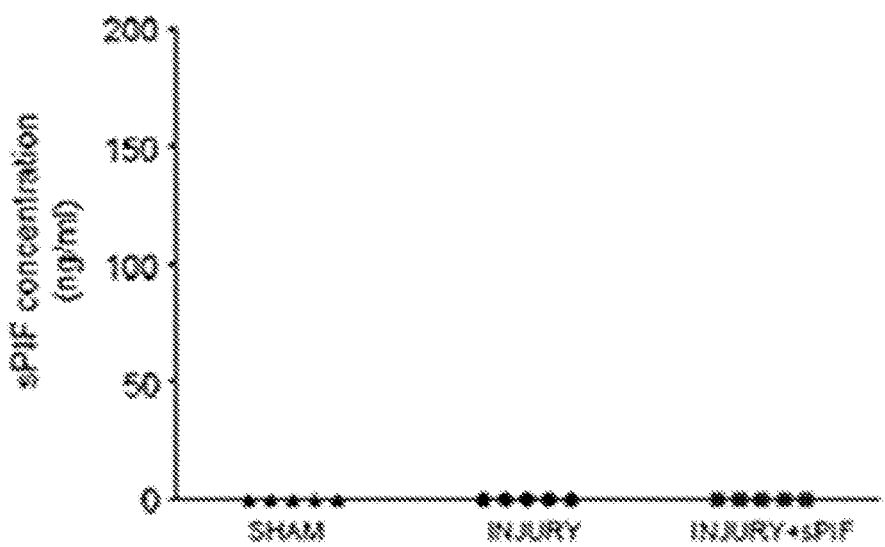
Figure 11:
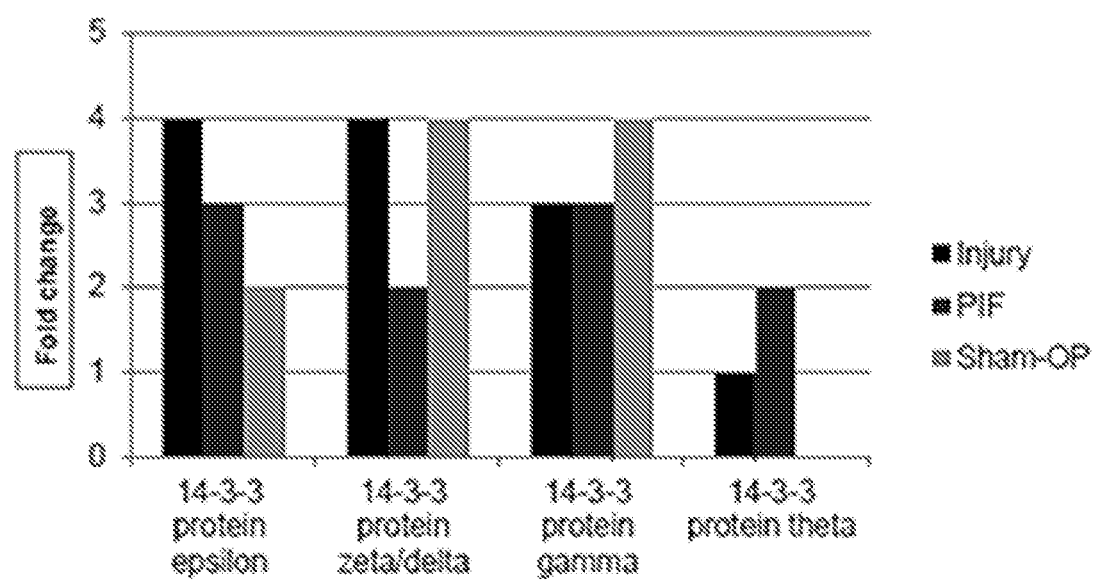
FIGS. 11 and 12 depict how PIF functions locally in the brain by regulating the phosphorylated 14-3-3 and PKA/PKC inflammatory pathways. Identifies specific PIF binding targets in the brain and the effect of PIF on their regulation comparing injured vs intact hemisphere in the HIE model.
Figure 12:
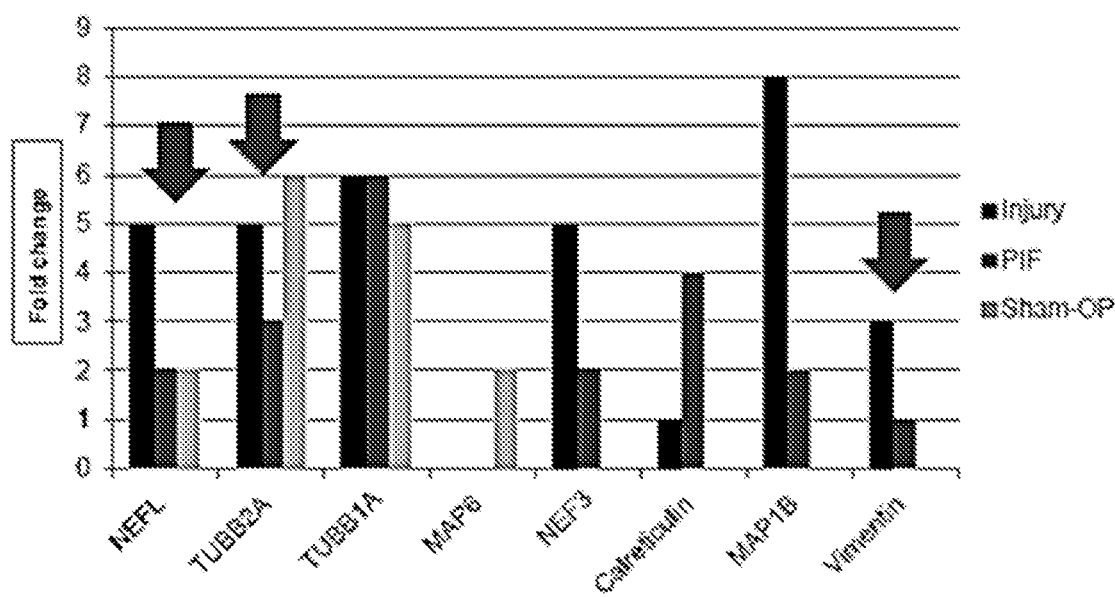

PIF modifies the brain protein ratio when comparing the intact to the injured part of the brain. Following harvesting, the brain was divided onto two hemispheres (injured and intact). PBS-treated and sham-operated rats were used as controls. The published method where sPIF was shown using an sPIF-affinity column which identifies specific targets binding to the peptide was utilized (Barnea 2014, PloS One). In this study, following extraction of the brain samples (treated and different controls) were passed through the PIF affinity column collecting different fractions. The fractions were passed through HPLC followed by mass spectrometry analysis. As figures show, sPIF has exerted its protective effects by affecting a specific limited number of signaling pathways. The main pathway is the 14-3-3 and PKC/PKA signaling. Pathways (FIGS. 10,11) The data generated provided important mechanistic insight into sPIF specific protein targets that affect the PKC/PKA pathway. Specifically sPIF reduced NEFL, NEF3, MAP1b, vimentin. In contrast, sPIF increased calreticulin concentration. The effect on this pathway leads to increase in brain maturation coupled with reduced neural death. In addition sPIF also affected the 14-3-3 pathway regulating several members of the group further reducing apoptosis. The change in the folding structure of a target protein may have a major contributing effect on sPIF activity. The inflammatory condition may affect the protein structure which could increase or decrease the ability for sPIF to bind to the target. Data substantiates the protective effect that sPIF exerts by directly targeting specific proteins.

sPIF Reverses HIE Induced Injury.

Figure 13:
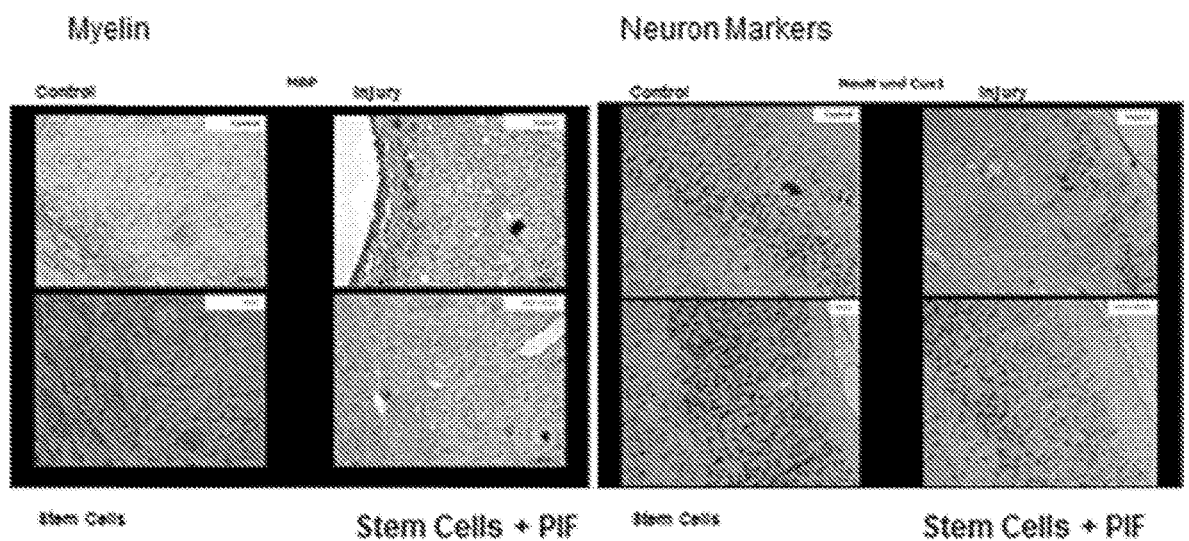
FIGS. 13 and 14 depict a comparison of treatment in rodents following brain injury where stem cells are provided as a control and stem cells with PIF as therapy. Brain cells were stained with a marker for viability and inflammatory elements.
Figure 14:
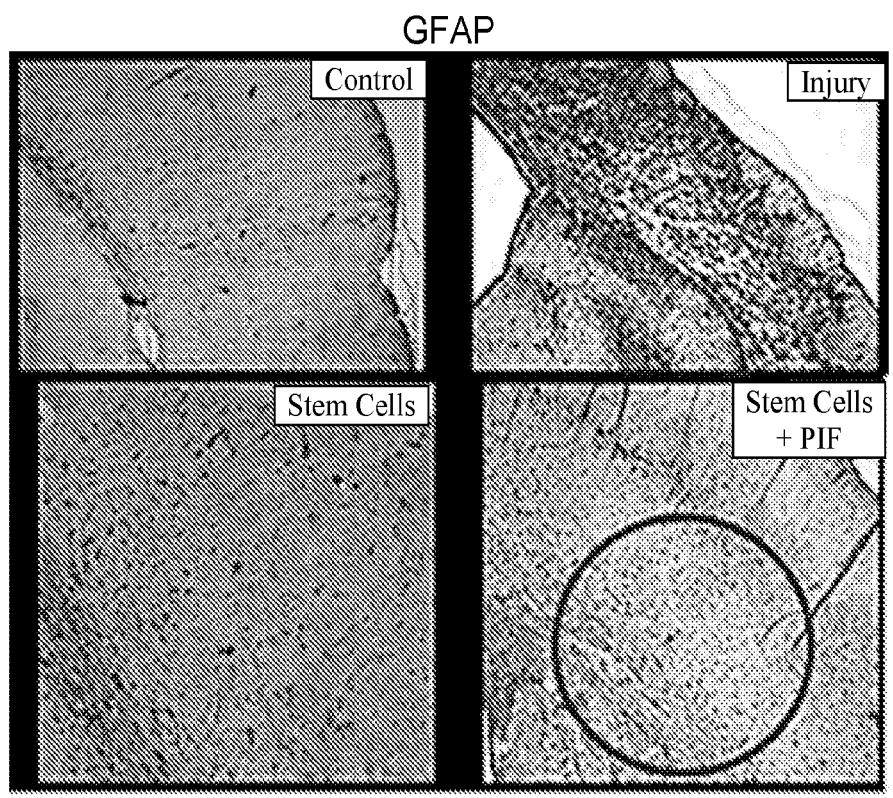

Subcutaneously injected sPIF is superior to intracranially injected stem cells—Chronic neurotrauma therapy. Stem cells use for treating neurotrauma has been advocated and has been used successfully in a limited number of well controlled clinical studies. To determine how sPIF is compared with stems cells, the HIE model was utilized. sPIF alone versus intracranially injected stem cells were compared. As shown, sPIF alone led to significant neural protection. sPIF was injected together with intracranially administered stem cells, starting therapy 3 days post-injury. Data showed that sPIF potentiated the stem cells effect as evidenced by increasing myelinization as well the Neun and Cux1 neuronal markers expression (IHC). (FIG. 13) In addition, by increasing the glial fibrillary acid protein sPIF promotes neuro-regeneration as compared to stems cells alone. (FIG. 14) Collectively, it indicated that a minimally invasive subcutaneous sPIF injection is more effective that the highly invasive stem cells injection. As such it makes sPIF an attractive drug for acute and chronic neurotrauma management since as shown above that the endogenous stems cells are being effectively activated by sPIF alone.

PIF Reduces/Regulates Inflammation to Promote Neural Repair—Chronic Neurotrauma—Therapy.

Figure 15:
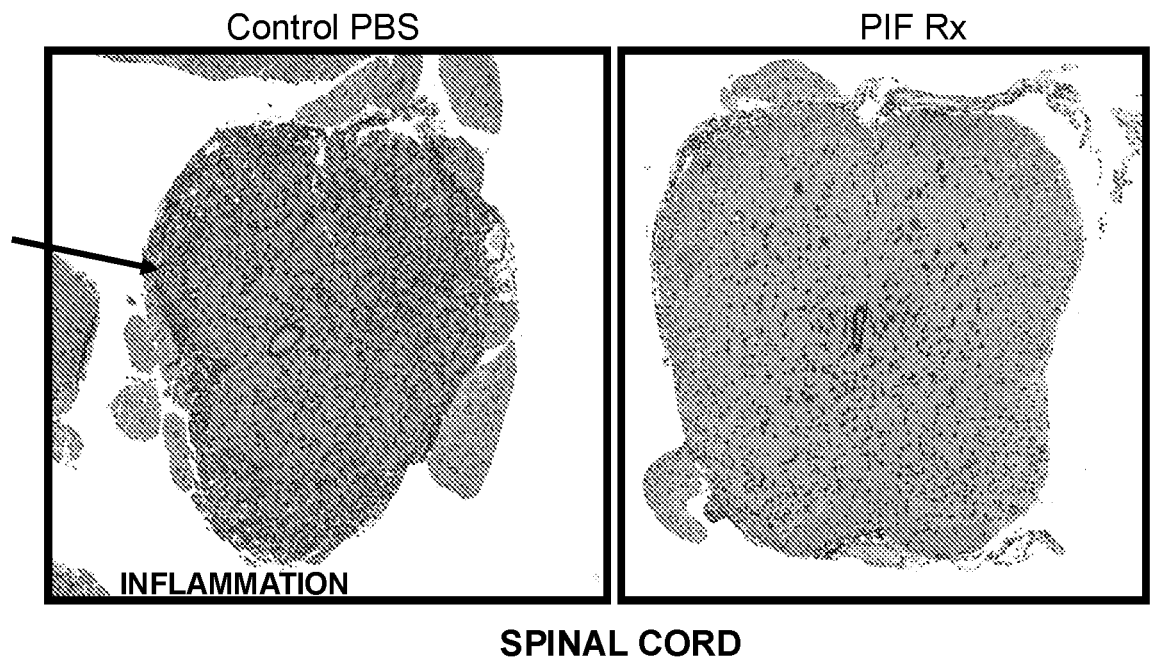
FIG. 15 depicts how PIF administration to animals prevents immune cell infiltration into the spinal cord in the EAE model (Weiss et al. 2012).
Figure 15:
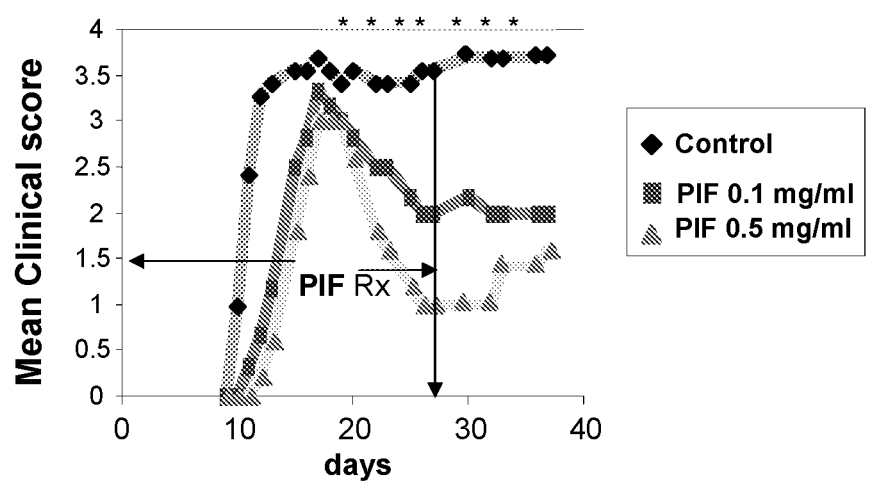

Based on current data post-acute neurotrauma if the subject survives is based on the extent of the trauma, it can remain conscious; can enter later in to a vegetative state, or vegetative state with minimal consciousness. Otherwise the long-term resulting motor, sensory and emotional state cannot be predicted in early stages of neurotrauma. Thus, a continuum occurs where it is not possible to predict prognosis whether partial or total recovery will ensue long-term following neurotrauma. Beyond the severe CNS (mentioned above) mild to moderate trauma can also have long-term sequela where the critical acute brain and spinal cord inflammation becomes progressive leading to and being associated with neurodegeneration. There is evidence that the resulting systemic inflammation causes or at least further compounds the destructive CNS process. The inflammatory cells activated perpetuate the damage by penetrating the CNS. Current measures to reverse this relentless course are widely ineffective beyond physical therapy and neuroleptic drugs as needed. The neuroinflammatory clinically relevant models used in the adult both antigen driven and infective which document for first time efficacy in this type of model aimed to address chronic the chronic consequences of CNS related disorders. (Weiss et al. 2012, Shainer et al. 2015, Paidas, et al. 2012 PIF reverses chronic paralysis, including severe paralysis, and protects both brain and spinal cord—Chronic neurotrauma management. This set of studies aimed to address early, mid and chronic phases of inflammation/neurodegeneration seen frequently post-acute neurotrauma initiating shortly after and lasting long-term. The combination of PLP-neurotropic antigen, with pertussis, and tuberculin inoculum creates a particularly harsh neuroinflammation milieu evidenced both in the brain and the spinal cord. Unless treated, if inflammation is severe high mortality ensues. FIG. 15 shows that sPIF reduces access of inflammatory cells to the spinal cord and reduces the clinical score in a dose-dependent manner. The effect persists up to 12 days post-therapy without added therapy. Mechanistically, sPIF protected against proteins involved in oxidative phosphorylation thereby reducing oxidative stress and protein misfolding—similar to the HIE model. Increased MTAP protein promotes free tubulins-neuron backbone assembly to neurons. Increase in proteins involved in neural synaptic transmission was noted as well. PIF reduced circulating pro-inflammatory IL12—a macrophage marker and PLP activated-splenocytes (IL6, IL17) secretion also at 2 weeks post-therapy. Thus sPIF represents effective treatment regimen to reverse chronic consequences of CNS injury, including paralysis, where inflammation plays a critical role. Further data showing both local and systemic effects demonstrate a global (comprehensive) protective action.

sPIF Prevents and Reduces Mortality Long-Term.

Figure 16:
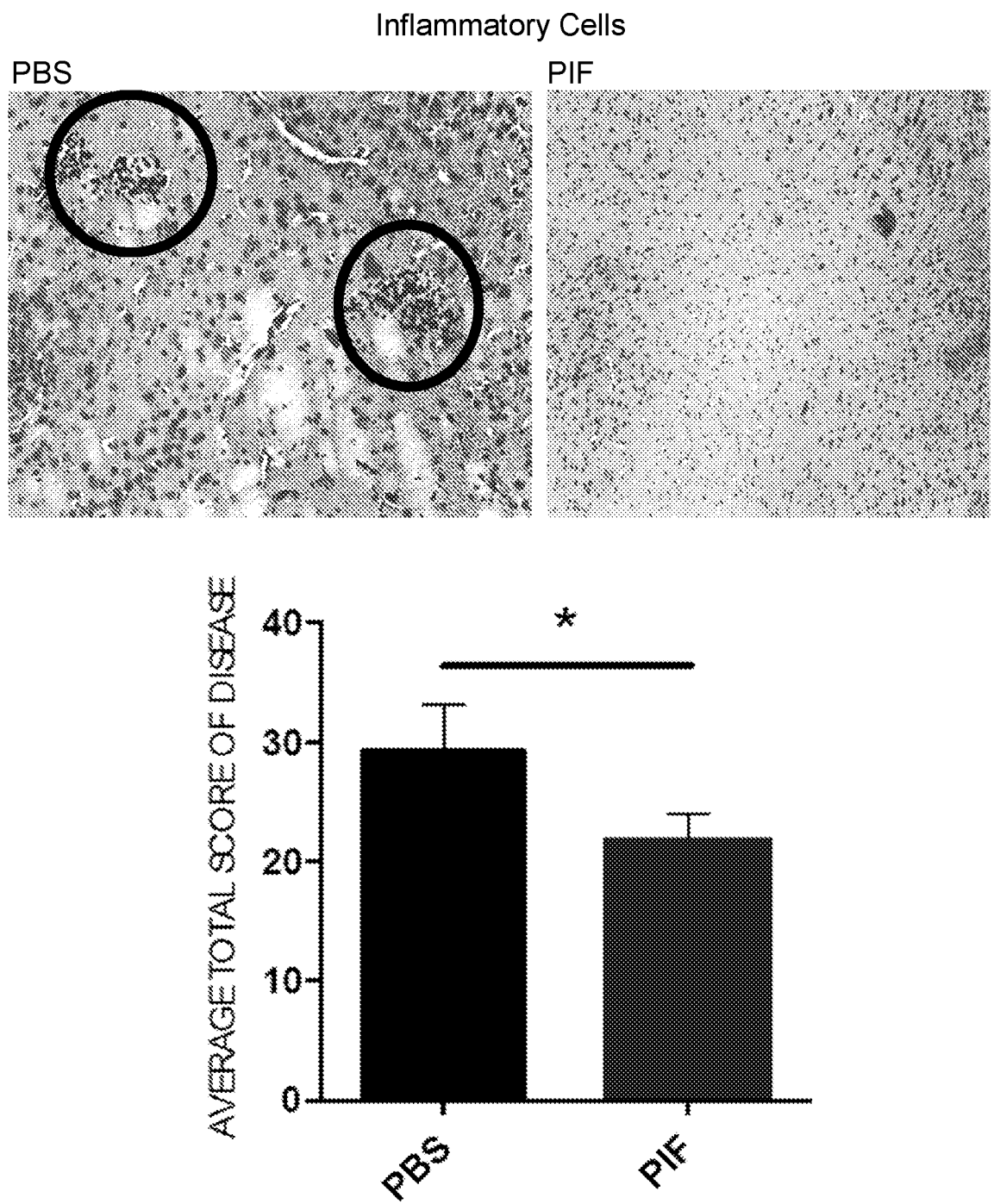
FIG. 16 depicts how PIF can reverse chronic paralysis over time in comparison to subcutaneous injection of Copaxone®. Effect on the clinical score.
Figure 17:
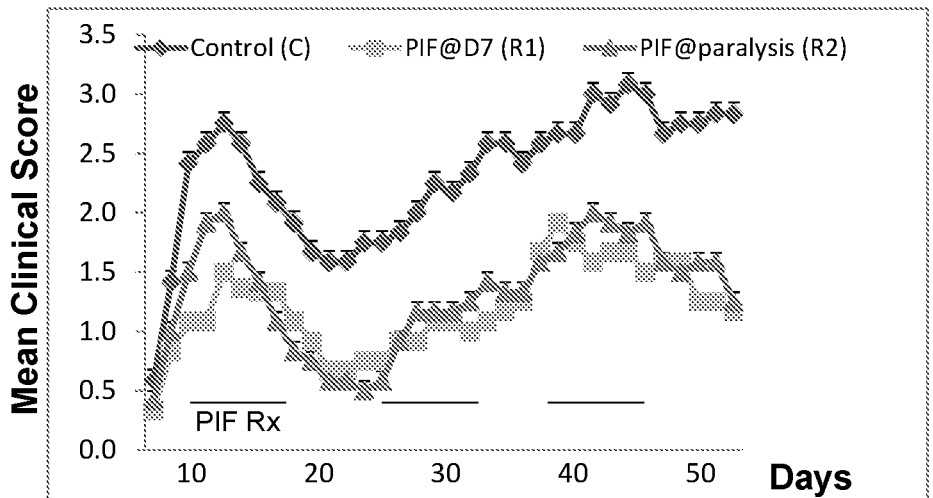
FIG. 17 depicts how PIF was successful at treating chronic brain inflammation in an experimental allergic encephalomyelitis (EAE) animal model.
Figure 17:
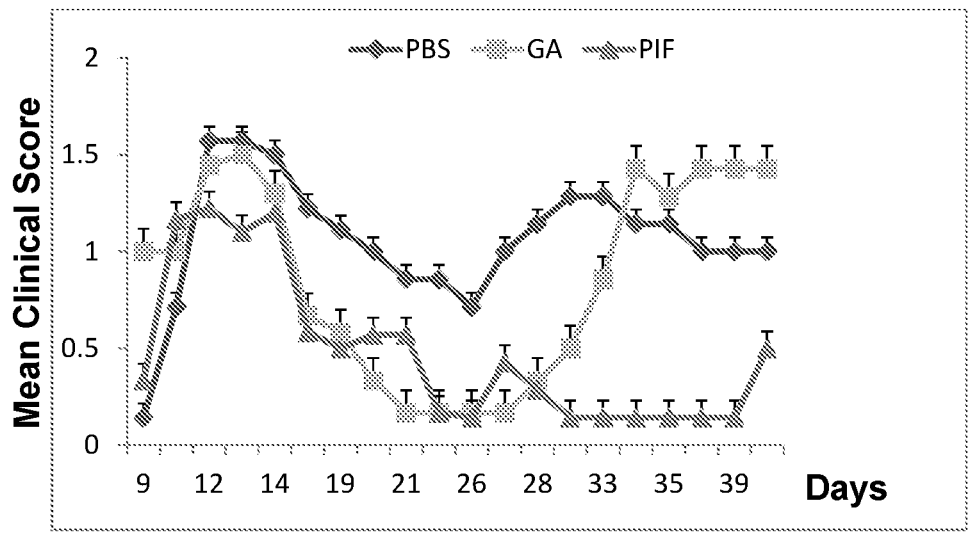

Episodic (short-term sPIF subcutaneous injections) completely reversed paralysis remarkably from paraplegia (stage 4/5) in 68% of cases vs. Copaxone (GA) and PBS used as controls (12.5%), P<0.007. (FIG. 16). An integrated local (brain and spinal cord) decrease in inflammation and inflammatory cells access was also noted. The brain was analyzed using global phosphorylated proteins analysis comparing sPIF to PBS treatment as well non-treated controls. In addition PIF also reduced the access of inflammatory cells into the brain (FIG. 17)

sPIF Reverses Paralysis and Reduces Brain Inflammation Post-Infection: Chronic CNS Neuro Injury Management.

Figure 18:
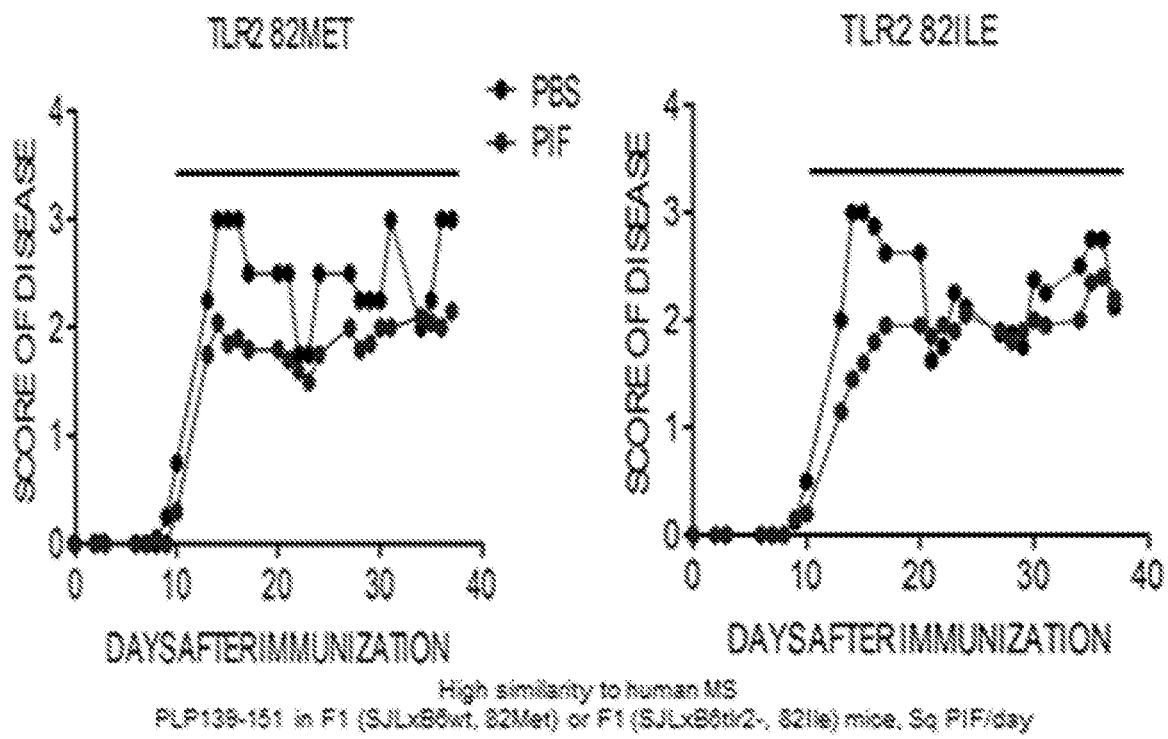
FIGS. 18 and 19 depict how in an infectious—Smegamtis EAE model PIF administration to animals prevents pro-inflammatory immune cells infiltration into the brain. Also shows that FITC-PIF directly targets the brain and the spinal cord.
Figure 19:
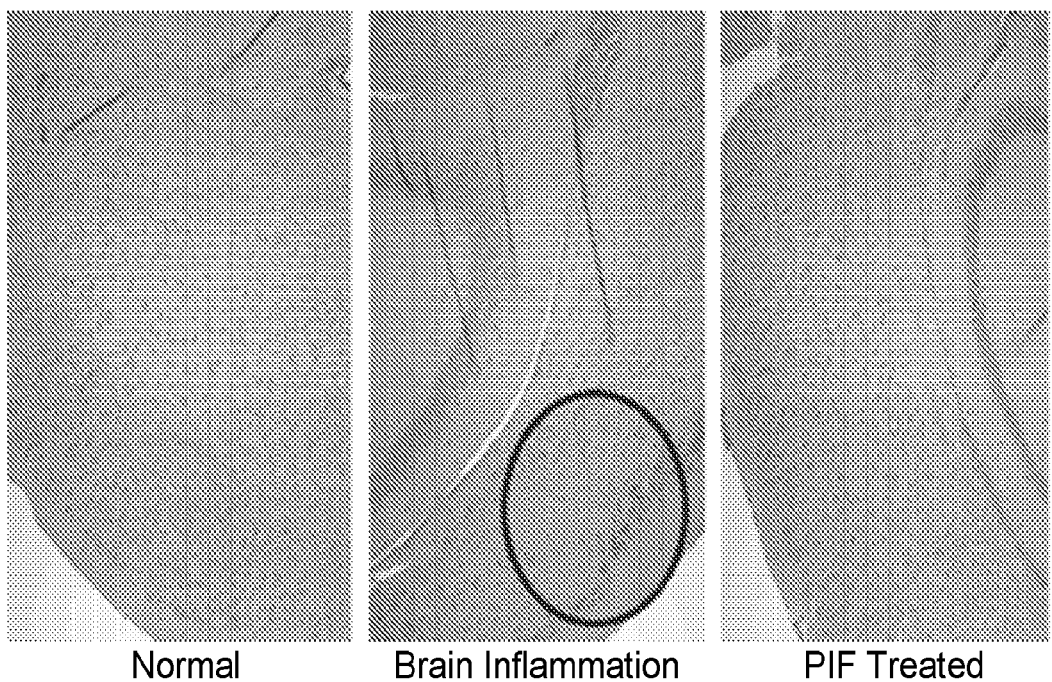
Figure 20:
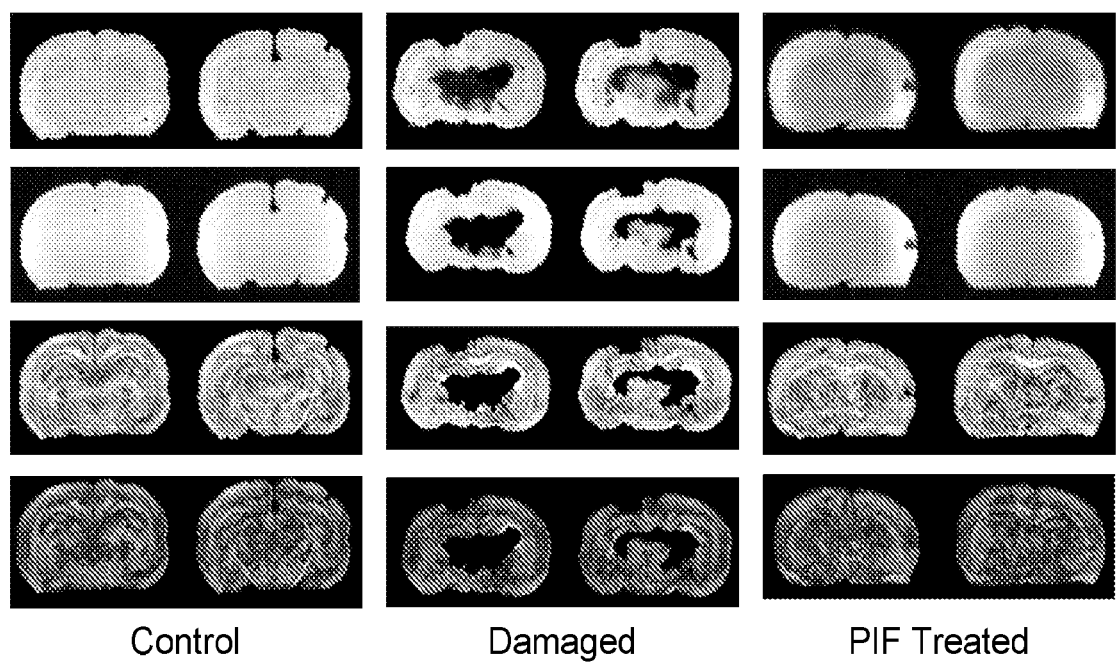
FIG. 20 depicts how two different mouse strains with a mutated TLR2 gene known to develop paralysis have reduced disease score when treated with PIF.
Figure 21:
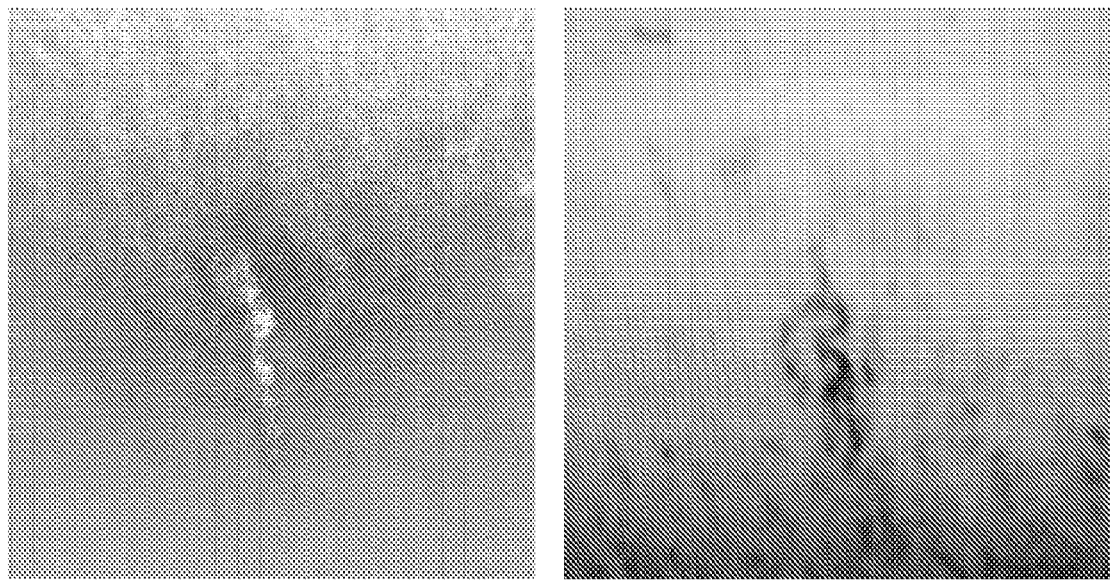
FIG. 21 depicts how PIF targets both the brain and the spinal cord in a *smegmatis* bacteria model.

Based on current evidence, environmental factors (bacteria, virus) may cause progressive neurodegenerative diseases in the CNS. The *Smegmatis* bacteria model in an important prototype where an innocuous bacterium activates the immune system and then the bacteria is subsequently eliminated while neurodegeneration continues to progress long-term. This clinically-relevant model could replicate also a neurodegenerative chronic neurotrauma including and multiple sclerosis—(MS) shown by (Nicollo, Ria J of immunology 2102). sPIF reversed brain infection, inflammation and paralysis post-inoculation with *Mycobacterium Smegmatis* (MPT64-PLP139-151). Brain IHC analysis showed that sPIF reduced the access of inflammatory cells into the brain. (FIGS. 18-19) Beyond the long-term reduction in paralysis observed, global brain gene analysis demonstrated reduced oxidative stress as well as up-regulated additional protective pathways. (FIGS TO ADD Systemically, PIF down-regulates the pro-inflammatory IL23 and IL17 expression in draining lymph nodes. Thus PIF has both a local (brain and spinal cord) and systemic neuroprotective effect.

Whether sPIF penetrates the brain (BBB) following chronic inflammation was furthermore studied. FITC-sPIF was injected IP and subsequently the brain was imaged. Imaging demonstrated that sPIF enters the brain, and very importantly it targets the CNS vasculature. This is highly relevant since sPIF was shown to prevent vascular inflammation. Thus, in addition to targeting the microglia and neurons, sPIF also protects against the ensuing vascular inflammation—offering an integrated protection against chronic neurotrauma.

sPIF Reverses Chronic Neuroinflammation in TLR-2 Mutated Mice—Chronic Neurotrauma Therapy.

Figure 22:
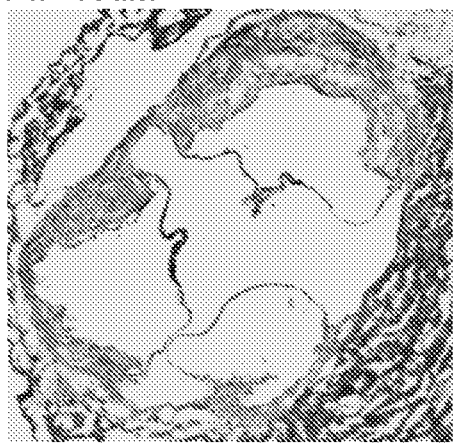
FIG. 22 depicts a 0.3-3 mg/kg dose of PIF in a murine model for vascular disease. The data demonstrate that PIF is successful in reducing the volume of plaques in aortic roots of animals with a high fat diet.
Figure 22:
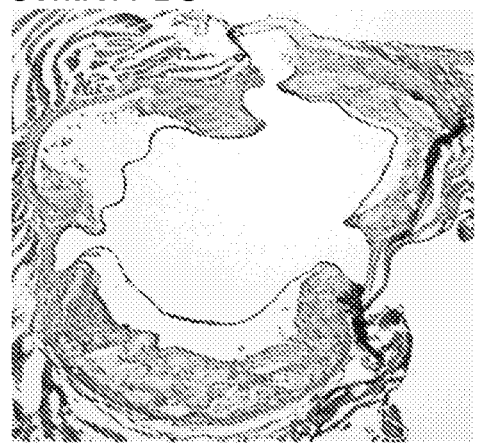
Figure 22:
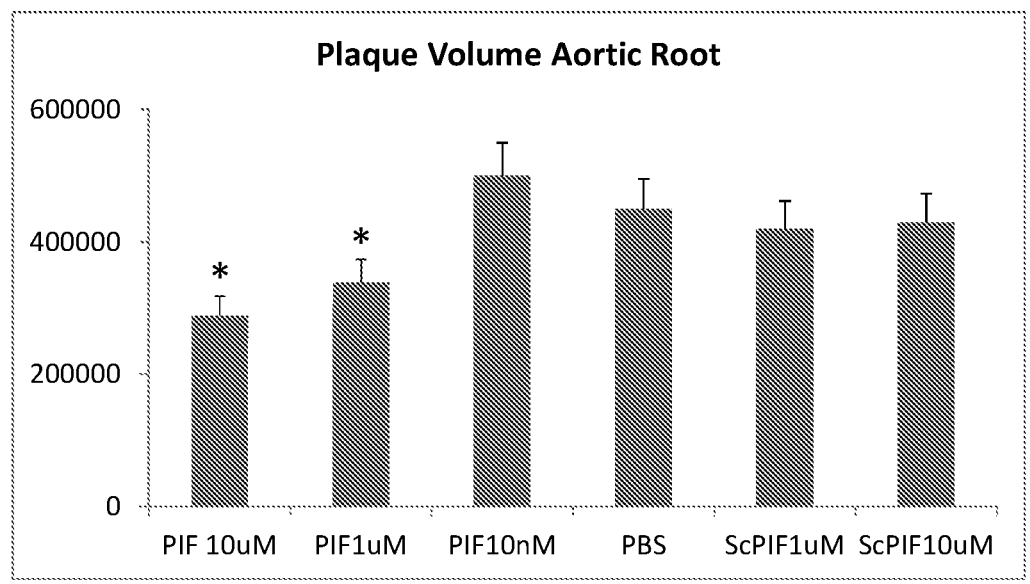
Figure 24:
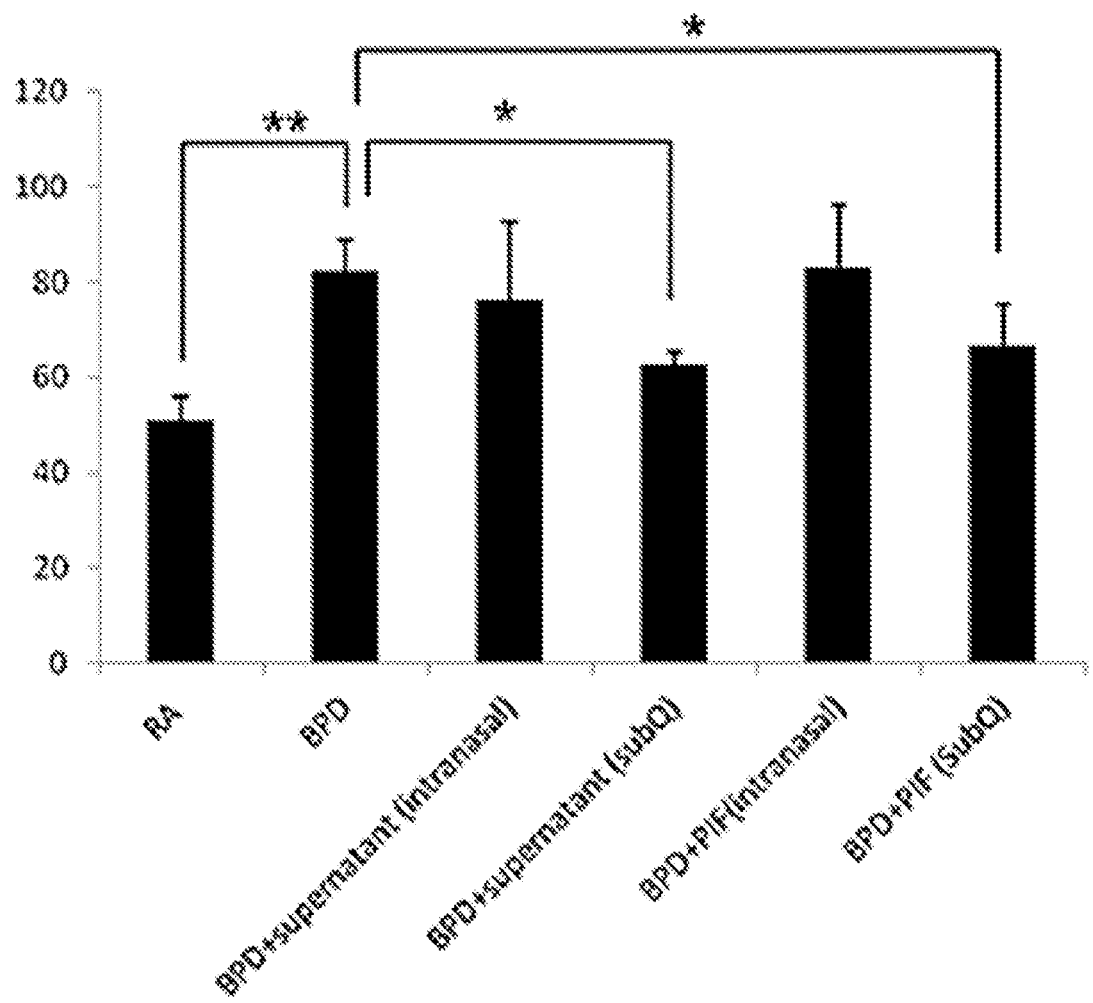
FIG. 24 depicts the effect of PIF on hyperoxigenation (following neurotrauma) induced broncho-pulmonary dysplasia. The Mean pulmonary cord length (in µm) was reduced using PIF. *Significant to 0.005 **significant to 0.01. This indicates that PIF cannot only reverse neurotrauma but also negates the damage caused by the obligatory exposure to high intensity oxygenation.

Based on current evidence, modification of the TLR locus in mice followed by injection of PLP 139-151 in the SJL/B6wt model leads to severe paralysis. Initiation of subcutaneous sPIF treated after 10 day post-induction has led to a therapeutic effect as shown by the decrease in the score of the disease (decrease of paralysis score). Irrespective of the two different TLR-2 mutations, sPIF decreased the clinical score. (FIG. 22). This data further substantiates that sPIF is an effective agent that could reverse chronic neuroinflammation irrespective of the underlying cause, inflammation, infection or pro-inflammatory cytokine mutation.

sPIF Reduces Bronchopulmonary Dysplasia Following Hyper-Oxygenation.

sPIF Reduces acute neurotrauma associated therapy side effects. Post-neurotrauma frequently there is a phase of significant apnea requiring exposure to high oxygen concentration. This standard of care aims to increase the oxygenated blood flow to the injured tissues assisting in the healing process. Due to the severity of the injury, the exposure to such high and prolonged levels of oxygen can lead to long-term damage including bronchopulmonary dysplasia (BPD).

sPIF's protective effect against BPD development was compared to conditioned media derived from MSC isolated from Wharton's Jelly (WJMSC). WJMSC were grown in DMEM+10% FBS until 70% confluency then washed and grown in DMEM without FBS for 24 hrs, and supernatant was concentrated. Newborn WT mice were exposed to hyperoxia from post-natal day 1-4 (saccular stage of murine lung development) and allowed to recover in room air for 10 days. Mice were sacrificed on post-natal day 14. Newborn mice were injected subcutaneously or intranasally daily with the supernatant (10 ul/day), or sPIF (1 mg/k/d) for 4 consecutive days during hyperoxia. Alveolar size was estimated from the mean+/−SD chord length of the airspace (N=4 for each group) analyzed Student two-tailed unpaired t-test, $P<0.05$ considered statistically significant. Chord length is a morphometric estimate of alveolar size (shorter is better) known to be increased in BPD. Average cord length was 50.97 μm in control animals and 82.54 j m in BPD animals. Subcutaneous injection of sPIF and conditioned media significantly reduced alveolar space as demonstrated by shorter cord length of 66.81 μm (sPIF) and 62.80 μm (conditioned media; $p<0.05$) and improved alveolar architecture (FIG. 24). Intranasal injection of sPIF and conditioned media showed no benefit. sPIF and conditioned media from WJMSC delivered subcutaneously are effective in treating alveolar damage 30 secondary to BPD. Data shows that sPIF presents a beneficial effect in addition to neurodamage protection reducing the possible lung injury that is associated with hyper-oxygenation. Such beneficial effect provides further evidence that sPIF can be an effective drug for neurotrauma and/or BPD.

Summary

As recent data emerged that the central and leading consequence of neurotrauma is the progressive and not fully timed, predictable and or quantifiable inflammatory response to injury. This response is recognized as being both local (brain and spinal cord) and systemic (lymph nodes and circulatory elements). Even a mild trauma can lead to long-term impairment. Due to PIF's endogenous (embryonic origin) and inherent regulatory function, in particular its comprehensive neuroprotective properties and effect on systemic circulation, shows that it can be an effective drug to treat both local and systemic neurotrauma manifestations. This stems from the following observations and support data generated.

First, PIF's protective effect on the embryo translates to adult clinically relevant preclinical models. The observed protective effect is due to sPIF targeting proteins which reduce oxidative stress and associated protein misfolding. Such pathways are critical for protecting against neurotrauma. Inflammation is the primary response of the CNS/neurotrauma and current therapy following injury results in progressive neurodegeneration in the long-term. Paradoxically, the aim to self-repair actually perpetuates the ensuing inflammation. Second, in acute and chronic settings, sPIF is effective in reversing brain injury, brain inflammation and spinal cord inflammation. Thus long-term effect of sPIF in the treatment of neurotrauma is evidenced by the reduced mortality and resolution of high grade paralysis.

The ability of sPIF to exert these beneficial effects stems from the fact that PIF has a unique integrated mechanistic effect targeting specific proteins in the brain (FIGS. 6-10). The ratio of proteins from the intact to injured site is clearly evident. These proteins are involved in protecting against oxidative stress and neurodegeneration. In order for sPIF to exert such an effect first it has to be able to penetrate the BBB both in the injured and healthy brain. As demonstrated following PIF administration, it was found within the brain in an intact form—not degraded (sequence documented). In the brain in order to exert the reparative effect.

sPIF targets microglia to reduce inflammation as well neural cells to promote neuroprotection. This neuroprotection is due to activation the endogenous stems cells to proliferate and differentiate. Further PIF also protects against the neurodegenerative effect of LPS by imparting neuroprotection thereby almost doubling the brain size as compared to controls. PIF targets the vascular system within the brain. Such a direct effect on the vascular system was demonstrated to protect against inflammation reducing platelet and macrophage attachment as shown in the APoE-E model of atherosclerosis. Thus through local action in the brain and spinal cord following injury, sPIF has a direct effect on inflammatory elements, nerve cells, and vascularity. As such sPIF offers an integrated effect on CNS damage.

Systemic immune response is usually a delayed reaction to the CNS/neurotrauma) injury. PIF prevents the access of inflammatory cells both to the brain and the spinal cord. Thereby CNS inflammation is not further amplified which would perpetuate damage. Systemic reduction in response to CNS damage is evidenced both at the cellular level where sPIF reduces draining lymph nodes prime pro-inflammatory IL-17 and IL-23 cytokines. This reduction is coupled by the decrease noted in circulating and spleen-secreted splenocytes as well pro-inflammatory cytokine secretion. Such cell and circulating elements together with reduced access to the brain and spinal cord constitute an integral systemic protection against neurotrauma.

REFERENCES

1. Schoenfeld, A. J., M. D. Laughlin, B. J. McCriskin, J. O. Bader, B. R. Waterman, and P. J. Belmont, Jr., Spinal injuries in United States military personnel deployed to Iraq and Afghanistan: an epidemiological investigation involving 7877 combat casualties from 2005 to 2009. Spine (Phila Pa. 1976), 2013. 38(20): p. 1770-8.
2. Bell, R. S., A. H. Vo, C. J. Neal, J. Tigno, R. Roberts, C. Mossop, J. R. Dunne, and R. A. Armonda, Military traumatic brain and spinal column injury: a 5-year study of the impact blast and other military grade weaponry on the central nervous system. J Trauma, 2009. 66(4 Suppl): p. S104-11.
3. Barnea, E. R., Insight into early pregnancy events: the emerging role of the embryo. Am J Reprod Immunol, 2004. 51(5): p. 319-22.
4. Stamatkin, C. W., R. G. Roussev, M. Stout, C. B. Coulam, E. Triche, R. A. Godke, and E. R. Barnea, Preimplantation factor negates embryo toxicity and promotes embryo development in culture. Reprod Biomed Online, 2011. 23(4): p. 517-24.
5. Stamatkin, C. W., R. G. Roussev, M. Stout, V. Absalon-Medina, S. Ramu, C. Goodman, C. B. Coulam, R. O. Gilbert, R. A. Godke, and E. R. Barnea, PreImplantation Factor (PIF) correlates with early mammalian embryo development-bovine and murine models. Reprod Biol Endocrinol, 2011. 9: p. 63.
6. Barnea, E. R., Applying embryo-derived immune tolerance to the treatment of immune disorders. Ann NY Acad Sci, 2007. 1110: p. 602-18.
7. Weiss, L., S. Bernstein, R. Jones, R Amunugama, D. Krizman, L. Jebailey, O. Almogi-Hazan, Z. Yekhtin, R. Shiner, I. Reibstein, E. Triche, S. Slavin, R. Or, and E. R. Barnea, Preimplantation factor (PIF) analog prevents type I diabetes mellitus (TIDM) development by preserving pancreatic function in NOD mice. Endocrine, 2011. 40(1): p. 41-54.
8. Weiss, L., R. Or, R. C. Jones, R. Amunugama, L. JeBailey, S. Ramu, S. A. Bernstein, Z. Yekhtin, O. Almogi-Hazan, R. Shainer, I. Reibstein, A. O. Vortmeyer, M. J. Paidas, M. Zeira, S. Slavin, and E. R. Barnea, Preimplantation factor (PIF*) reverses neuroinflammation while promoting neural repair in EAE model. J Neurol Sci, 2012. 312(1-2): p. 146-57.
9. Azar, Y., R. Shainer, O. Almogi-Hazan, R. Bringer, S. R. Compton, M. J. Paidas, E. R. Barnea, and R. Or, PreImplantation Factor Reduces Graft-versus-Host Disease by Regulating Immune Response and Lowering Oxidative Stress (Murine Model). Biology of Blood and Marrow Transplantation, 2013. 19: p. 519-528.
10. Shainer, R., Y. Azar, O. Almogi-Hazan, R. Bringer, S. R. Compton, M. J. Paidas, E. R. Barnea, and R. Or, Immune Regulation and Oxidative Stress Reduction by Preimplantation Factor following Syngeneic or Allogeneic Bone Marrow Transplantation. Conference Papers in Medicine, 2013. 2013(Article ID 718031): p. 1-8.
11. Mueller, M., J. Zhou, L. Yang, Y. Gao, F. Wu, A. Schoeberlein, D. Surbek, E. R. Barnea, M. Paidas, and Y. Huang, PreImplantation factor promotes neuroprotection by targeting microRNA let-7. Proc Natl Acad Sci USA, 2014. 111(38): p. 13882-7.
12. Mueller, M., A. Schoeberlein, A. Zhou, M. Joerger-Messerli, B. Oppliger, U. Reinhart, A. Bordey, D. Surbek, E. R. Barnea, Y. Huang, and M. Paidas, PreImplantation Factor Bolsters Neuroprotection via Modulating Q10 Protein Kinase A and Protein Kinase C Signaling. Cell Death Differ, 2015. DOI: 10.1038/cdd.2015.55.
13. Chen, Y. C., J. Rivera, M. Fitzgerald, C. Hausding, X. Wang, K. Todorova, S. Hayrabedyan, E. R. Barnea, and P. Karlheinz, PreImplantation Factor Prevents Atherosclerosis via it Anti-inflammatory Effects without Affecting Serum Lipids. 2015. (submitted).
14. Migliara, G., M. Mueller, M. J. Paidas, E. R. Barnea, and F. Ria, PIF Ameliorates Clinically Relevant *B. Smegmatis* Induced Brain Infection by Reducing Oxidative Stress and Protein Misfolding. 2015. (submitted).
15. Barnea, E. R., J. Simon, S. P. Levine, C. B. Coulam, G. S. Taliadouros, and P. C. Leavis, Progress in characterization of pre-implantation factor in embryo cultures and in vivo. Am J Reprod Immunol, 1999. 42(2): p. 95-9.
16. Barnea, E. R., Applying Embryo-Derived Immune Tolerance to the Treatment of Immune Disorders. Annals of the New York Academy of Sciences, 2007. 1110: p. 602-618.
17. Than, N. G., M. J. Paidas, S. Mizutani, S. Sharma, J. Padbury, and E. R. Barnea, Embryo-placento-maternal interaction and biomarkers: from diagnosis to therapy—a workshop report. Placenta, 2007. 28 Suppl A: p. S107-10.
18. Barnea, E. R., D. Kirk, S. Ramu, B. Rivnay, R. Roussev, and M. J. Paidas, PreImplantation Factor (PIF) orchestrates systemic antiinflammatory response by immune cells: effect on peripheral blood mononuclear cells. Am J Obstet Gynecol, 2012. 207(4): p. 313 e1-11.
19. Moindjie, H., E. D. Santos, L. Loeuillet, H. Gronier, P. de Mazancourt, E. R. Barnea, F. Vialard, and M. N. Dieudonne, Preimplantation factor (PIF) promotes human trophoblast invasion. Biol Reprod, 2014. 91(5): p. 118.
20. Paidas, M. J., G. Krikun, S. J. Huang, R. Jones, M. Romano, J. Annunziato, and E. R. Barnea, A genomic and proteomic investigation of the impact of preimplantation factor on human decidual cells. Am J Obstet Gynecol, 2010. 202(5): p. 459 e1-8.
21. Duzyj, C. M., E. R. Barnea, M. Li, S. J. Huang, G. Krikun, and M. J. Paidas, Preimplantation factor promotes first trimester trophoblast invasion. Am J Obstet Gynecol, 2010. 203(4): p. 402 e1-4.
22. Duzyj, C. M., M. J. Paidas, L. Jebailey, J. S. Huang, and E. R. Barnea, PreImplantation Factor (PIF*) promotes embryotrophic and neuroprotective decidual genes: effect negated by epidermal growth factor. Journal of Neurodevelopmental Disorders, 2014. 6(1): p. 36.
23. Shainer, R., Z. Yekhtin, L. Weiss, O. Almogi-Hazan, M. Mueller, M. J. Paidas, R. Or, and E. R. Barnea, Episodic PreImplantation Factor (PIF*) Administration Reverses Chronic Paralysis by Reducing Brain PKA/PKC Phosphorylation 2015. (in preparation).
24. Roussev, R. G., B. V. Dons'koi, C. Stamatkin, S. Ramu, V. P. Chernyshov, C. B. Coulam, and E. R. Barnea, Preimplantation factor inhibits circulating natural killer cell cytotoxicity and reduces CD69 expression: implications for recurrent pregnancy loss therapy. Reprod Biomed Online, 2013. 26(1): p. 79-87.
25. Barnea, E. R., D. Kirk, K. Todorova, J. McElhinney, S. Hayrabedyan, and N. Fernandez, PIF direct immune regulation: Blocks mitogen-activated PBMCs proliferation, promotes T2/T1 bias, independent of Ca. Immunobiology, 2015. DOI:10.1016/j.imbio.2015.01.010.
26. Barnea, E. R., D. M. Lubman, Y. H. Liu, V. Absalon-Medina, S. Hayrabedyan, K. Todorova, R. O. Gilbert, J. Guingab, and T. J. Barder, Insight into PreImplantation Factor (PIF*) mechanism for embryo protection and development: target oxidative stress and protein misfolding (PDI and HSP) through essential RIPK binding site. PLoS One, 2014. 9(7): p. e100263.
27. Almogi-Hazan, O., R. Shainer, E. R. Barnea, and R. Or, The Role of Nitric Oxide Toxicity and Oxidative Stress in Graft vs Host Disease, in Oxidative Stress: Causes, Role in Diseases and Biological Effects. 2014, Nova Science Publishers, Inc.
28. Barnea, E. R., S. Hayrabedyan, K. Todorova, O. Almogi-Hazan, R. Or, J. Guingab, J. McElhinney, N. Fernandez, and T. J. Barder, PIF Regulates Systemic Immunity and Targets Protective Regulatory and Cytoskeleton Proteins. Scientific Reports, Nature, 2015. (under revision).
29. Kuluz, J., A. Samdani, D. Benglis, M. Gonzalez-Brito, J. P. Solano, M. A. Ramirez, A. Luqman, R. De los Santos, D. Hutchinson, M. Nares, K. Padgett, D. He, T. Huang, A. Levi, R. Betz, and D. Dietrich, Pediatric spinal cord injury in infant piglets: description of a new large animal model and review of the literature. J Spinal Cord Med, 2010. 33(1): p. 43-57.
30. Cheriyan, T., D. J. Ryan, J. H. Weinreb, J. Cheriyan, J. C. Paul, V. Lafage, T. Kirsch, and T. J. Errico, Spinal cord injury models: a review. Spinal Cord, 2014. 52(8): p. 588-95.
32. Abou-Donia, M. B., M. M. Abou-Donia, E. M. ElMasry, J. A. Monro, and M. F. Mulder, Autoantibodies to nervous system-specific proteins are elevated in sera of flight crew members: biomarkers for nervous system injury. J Toxicol Environ Health A, 2013. 76(6): p. 363-80.

Example 2: sPIF Promotes Brain Re-Myelination while Regulating Systemic Inflammation Neurologic disease diagnosis and treatment is challenging. Multiple Sclerosis (MS) is likely caused by brain infection triggering systemic immune response. *Mycobacterium Smegmatis* (MyS), a tuberculosis-like bacteria, can provide antigen- and non-antigen-related signals involved in driving effective autoimmunity for the CNS. *M. Smegmatis* was confirmed as MS causing candidate using a clinically realistic Relapsing Remitting-EAE model (RR-EAE). PIF, secreted by viable embryos, has a determining role in pregnancy, regulating local and systemic immunity. Synthetic PIF (PIF) transposes endogenous peptide protective effect in preclinical autoimmune and transplantation models. PIF protects against brain ischemia by directly targeting microglia and neurons promoting neuroprotection. In chronic EAE model PIF reverses paralysis while promoting neural repair. It is reported that PIF directly promotes brain re-myelination and reverses paralysis 20 days post-therapy in clinically relevant MyS-induced RR-EAE model. PIF crosses the blood brain barrier to target microglia and the vascular system. Systemically PIF decreased pro-inflammatory IL23 and IL17 cytokines, while preserving CNS-specific T-cell repertoire. Global brain gene analysis revealed that PIF regulates critical Na+/K+/Ca++ ions, amino acids and glucose genes expression. The reduced oxidative stress, DNA methylation and cell cycle regulation, EF2 improved proteins stability and prevented degradation through ubiquitination. PIF upregulated StAR, spermine oxidase and arrestin beta genes promoting neurons, glia development, axonal transport and neurotransmission. PIF-induced upstream regulation involves both MYCN (ERK/MAPK signalling) through let-7 microRNA, a PIF target, and the cortisol binding site (NR3C1). In primary cultured astrocytes PIF promoted BDNF-myelin synthesis promoter and SLC2A1 (glucose transport) while reducing deleterious E2F5, and HSP90ab1 (oxidative stress) genes expression. By targeting primary cultured microglia, PIF promotes anti-inflammatory IL10 while reducing pro-inflammatory INFγ secretion. Collectively PIF promotes myelination and neuroprotection in RR-EAE clinically-realistic paralysis model. Together with ongoing, FAST-TRACK FDA approved clinical trial NCT #02239562 (immune disorder), current data support PIF translation for treatment of neurodegenerative disorders.

Materials and Methods

Mice, Peptides and *Mycobacterium* Strain: Eight week-old SJL female mice were purchased from Charles River (Calco, Italy) and kept in a conventional facility at "Universitià Cattolica del Sacro Cuore" in Rome. All experimental procedures involving animals were approved by the internal Ethical Committee and by the Italian Ministry for Health. Peptide 139-151 of proteolipid protein (p139, HSLGKWLGHPDKF) was purchased from PRIMM (Milan, Italy) and was >95% pure by HPLC, as determined by mass spectroscopy. *Mycobacterium Smegmatis* Bacteria expressing the chimeric protein containing the p139 fused with MPT64 (rMSp139) was obtained as previously described. [45]

Synthetic PIF (PIF). PIF, MVRIKPGSANKPSDD, and fluorescein isothiocyanate labelled PIF (FITC-PIF) was provided by Bio-Synthesis, Inc. (Lewisville, Tex.). Peptide identity was verified by matrix-assisted laser desorption/ionization time-of-flight (MALDI-TOF) mass spectrometry and amino-acid analysis, and the peptides were purified to >95% by HPLC, as documented by mass spectrometry. [29, 37, 38]

RR-EAE Induction and Clinical Evaluation: SJL female mice, 8-10 weeks old, were infected s.c. in the back with 4×106 CFU of rMSp139 in PBS 100 μl/mouse. Clinical signs of EAE were evaluated daily and in a blinded fashion according to the following scale 0-5: 0, no clinical score; 1, loss of tail tone; 2, weak hind leg paresis; 3, hind leg paresis; 4, complete paraplegia; and 5, death or moribund. Intermediate values were assigned for incomplete symptoms. Average total score of disease (ATSD) was calculated as the average of the sum of daily scores of each mouse. Area under the curve (AUC) at the peak was calculated using a score of 0.5 as baseline in composite experiments. [29]

PIF Treatment: To test PIF effects two different treatment regimens were used. First continuous administration was tested: Mice were injected intraperitoneally (i.p.) with PIF (0.75 mg/kg or 1.5 mg/kg in PBS 100 μl daily) starting on day 3 after infection with rMSp139 until the end of the experiment. Control group received vehicle only. Further intermittent administration was tested: Mice were injected i.p. with PIF (0.75 mg/kg in PBS 100 μl daily) starting on symptoms onset and until remission of the symptoms. Administration at subsequent relapse was resumed. Control group received PBS vehicle only.

FITC-PIF Administration to Observe Uptake in the Brain (Cross Intact BBB): Mice, previously treated with continuous daily administration for 3 weeks with PIF 0.75 mg/kg, or PBS were tested. By day 62 after infection mice were treated with an injection of FITC-PIF 0.75 mg/kg in 100 μl of PBS or with vehicle only. At 3 hours after injection mice were sacrificed and the brain and spinal cord were analyzed for uptake.

Tissue Harvesting and Brain Evaluation: At day 28-30 after EAE induction, mice under deep anaesthesia (Ketamine 75 µg/Kg, Medetomidine 1 µg/Kg i.p.) were perfused with 50 ml of PBS and sacrificed. Spleen and brain tissue was collected. Tissue was placed in nitrogen in cryovials for 10 min and stored at −80 C. Given that myelin loss is a prominent event in MS myelin staining was evaluated [47, 48]. Briefly, fixed brains were embedded in paraffin and sectioned into 7 µm slices. Slides were rinsed in ddH2O, counterstained in Cresyl violet (Nissl body staining for neuronal structure and gross brain morphology) and Luxol Fast Blue (to reveal areas of myelination in the subcortical white matter), dehydrated in a series of ethanol baths (95%>100%) and xylene, and mounted with Eukitt (Sigma-Aldrich, St. Louis, Mo.). For FITC-PIF localization in the CNS, mice were perfused under deep anaesthesia (Ketamine 75 mg/Kg, Medetomidine 1 mg/Kg i.p.) through the aorta with 50 ml of PBS, followed by 50 ml of 4% paraformaldehyde (VWR international). Brain and spinal cord were removed and immersed in the same fixative for 24 hrs. Tissue blocks were routinely embedded in paraffin and 10 µm thick slice were prepared. Localization of FITC-PIF was assessed using an inverted confocal microscope (DMIRE2, Leica Microsystems, Wetzlar, Germany) with a 20× oil immersion objective (NA 0.5). Ar/Ak laser at 488 nm excited FITC. Fluorescent and bright field images were acquired.

Cytokine Production and Transcription Factors mRNA Expression: Following immunization and PIF administration or vehicle at day 10 of the experiment mice were sacrificed draining popliteal lymph nodes (LNs) were collected and 5×10^6 cells LN cells/well were cultured for 3 hrs in RPMI-1640 medium (Sigma-Aldrich, St Louis, Mo., USA) supplemented with 2 mM L-glutamine, 50 µM 2-ME, 50 µg/ml gentamicin (Sigma-Aldrich, St Louis, Mo., USA) and 0.2% mouse serum. LN cells were re-suspended in RLT buffer for RNA extraction. Total mRNA was isolated using RNeasy Mini Kit (Qiagen, Valencia, Calif.) and cDNA was synthesized using qScript™ cDNA SuperMix (Quanta BioSciences, Inc., Gaithersburg) according to the manufacture instructions. Quantification of mRNA was performed at 260 nm using NanoDrop 1000 (Thermo Scientific, Waltham, Mass.).

Quantitative mRNA expression: qRT-PCRs were performed using iQ SYBR® Green Supermix and an iQ5 Real-Time PCR Detection System (Bio-Rad, Hercules, Calif.). Relative expression levels of cytokine and transcription factors mRNAs were normalized using 18S as housekeeping gene and calculated with the 2−ΔΔCt method. Samples were loaded in triplicate. qRT-PCR was followed by a melting curve to assess presence of a specific replicons and primer dimers. The following primers (Invitrogen™ Life Technologies, Paisley, UK) were used: mouse IFN-γ, forward 5'-CAG CAA CAG CAA GGC GAA AAA GG-3' and reverse 5'-TTT CCG CTT CCT GAG GCT GGA T-3'; mouse FoxP3, forward 5'-CCT GGT TGT GAG AAG GTC TTC G-3' and reverse 5'-TGC TCC AGA GAC TGC ACC ACT T-3'; mouse IL-6, forward 5'-ACA CAT GTT CTC TGG GAA ATC GT-3' and reverse 5'-AAG TGC ATC ATC GTT GTT CAT ACA-3'; mouse IL-12b, forward 5'-GAA GCA CGG CAG CAG AAT-3' and reverse 5'-AGC CAA CCA AGC AGA AGA CA-3'; mouse IL-13, forward 5'-AAC GGC AGC ATG GTA TGG AGT G-3' and reverse 5'-TGG GTC CTG TAG ATG GCA TTG C-3', mouse IL-17, forward 5'-CAG ACT ACC TCA ACC GTT CCA C-3' and reverse 5'-TCC AGC TTT CCC TCC GCA TTG A-3', mouse IL-23, forward 5'-CAT GGG CTA TCA GGG AGT A-3' and reverse 5'-AAT AAT GTG CCC CGT ATC CA-3', mouse TGF-b, forward 5'-ACC CCC ACT GAT ACG CCT GA-3' and reverse 5'-AGC AGT GAG CGC TGA ATC GAA-3', mouse 18S, forward 5'-CTG CCC TAT CAA CTT TCG ATG G-3' and reverse 5'-CCG TTT CTC AGG CTC CCT CTC-3', mouse IL-10, forward 5'-GCT CCT AGA GCT GCG GAC T-3' and reverse 5'-TGT TGT CCA GCT GGT CCT TT-3', mouse IL-5, forward 5'-CTC TGT TGA CAA GCA ATG AGA CG T-3' and reverse 5'-TCT TCA GTA TGT CTA GCC CCT G-3', mouse t-bet (tbx21) forward 5'-AGC AAG GAC GGC GAA TGT T-3' and reverse 5'-GGG TGG ACA TAT AAG CGG TTC-3', mouse RORγ-t forward 5'-CTA CTG AGG AGG ACA GGG AG-3' and reverse 5'-AGT AGG CCA CAT TAC ACT GCT-3', mouse GATA-3 forward 5'-CTC GGC CAT TCG TAC ATG GAA-3' and reverse 5'-GGA TAC CTC TGC ACC GTA GC-3'.

TCR spleen repertoire analysis: Repertoire analysis was performed using a modification of a described protocol. [49]. For the TCR spleen repertoire analysis, 107/well splenocytes were cultured on 24-well plates in RPMI-1640 medium (Sigma-Aldrich, St Louis, Mo.) supplemented with 2 mM L-glutamine, 50 µM 2-ME, 50 µg/ml gentamicin (Sigma-Aldrich, St Louis, Mo., USA) and 0.2% mouse serum in presence or absence of 10 µg/ml p139. After 72 hrs splenocytes were re-suspended in RLT buffer for RNA extraction. Total mRNA was isolated using RNeasy Mini Kit (Qiagen, Hilden, Germany) and cDNA was synthesized using qScript™ cDNA SuperMix (Quanta BioSciences, Inc., Gaithersburg, Md.) according to the manufacturer's instructions. Quantification of mRNA was performed at 260 nm using NanoDrop 1000 (Thermo Scientific, Waltham, Mass.). For the immunoscope analysis, cDNA was subjected to PCR amplification using a common constant β primer (Cβ 5'-CAC TGA TGT TCT GTG TGA CAG-3') in combination with the variable β (Vβ) primer previously described.[50] Using 2 µl of this product as a template, run-off reactions were performed with a single internal fluorescent primer for each Jβ tested.[50] The products were then denatured in formalin and analysed on a 3130 Genetic Analyzer using Gene Mapper 4.0 (Applied Biosystem Foster City, Calif., US). Results are reported as relative stimulation index,[51] (RSI), obtained from the ratio between the normalized peak area of cells stimulated with p139 and the normalized peak area of non-stimulated cells. T cells carrying a TCR rearrangement are considered expanded in a peptide-driven manner when RSI is >2.

Global gene expression: To detect the global gene changes in the brain a gene array was performed. Briefly, 30 mg of brain tissue (n=3 PIF versus PBS) was excised and homogenized in a Fastprep 120 tissue homogenizer (30 s at 4.0 m/sec) in cell lysis buffer (Qiagen, Hombrechtikon, Switzerland). Total RNAs were extracted from cells using PureLink RNA Mini Kit (Ambion, catalog number 12183018A). Total RNA (250 ng) was amplified into cRNA using TotalPrep RNA amplification kit (AMIL1791, Ambion) following manufacture's instruction. After amplification, 1.5 µg of cRNA was mixed with the hybridization controls and it was hybridized to MouseRef-8 array (BD-202-0202, Illumina, USA). The array was hybridized for 16 hrs in a hybridization oven with a rocking platform at 58° C. The array chip then went through a series of washes before it was stained with streptavidin-Cy3. After the staining, it went through a final wash and drying. The array was scanned using the Illumina HiScan Scanner.

Preparation and testing PIF effect on of primary mouse astrocytes: Gene array validation. PIF targeting microglia cell line and neurons both in vitro and in vivo was demonstrated [27, 28] however whether PIF targets astrocytes which emerged as an important cell type in neurodegenerative diseases such as MS has not been tested. [52] Astrocyte cultures were prepared from 2-day C57BL/6 mouse neonates. Cortices were isolated, stripped of their meninges and mechanically dissociated in ice-cold HBSS. The cell suspension was then incubated with 0.05% trypsin for 25 min at 37° C. followed by rinsing and filtration through a nylon mesh (70-µm pore size). Cells were plated on collagen coated plates and were maintained in astrocyte medium (ThermoFisher Scientific). Cells were used after 2 weeks in culture. The effect of PIF 100 or 200 nM on BDNF—recognized as key for MS therapy was tested after culture for 48 hours. [52] In addition three genes identified in the brain array were also validated using qRT-PCR namely SLC2A1 (glucose transporter) and HSP90ab1, and E2f5 related to oxidative stress and protein folding. At the end of the experiments cells were rinsed RNA was extracted and processed for qRT-PCR. Fold change was determined and compared to control. Data was generated in triplicate in three different experiments setting significance at P<0.05.

PIF effect on cytokine expression by primary microglia. Primary microglia were obtained from (StemCells, Newark, Ca). Cells were isolated from neonate day two C57BL/6 mouse brain tissues and placed in culture. The effect of PIF 0 to 200 nM on INFγ and IL10 expression was examined after 48 hours in culture. At the end of the experiments cells were rinsed RNA was extracted and processed for qRT-PCR. Fold change was determined and compared to control. Data was generated in triplicate in 3 independent experiments. Setting significance at P<0.05.

Real-time quantitative PCR analysis of astrocytes and microglia. Total RNA was isolated from cultured astrocytes using QIAzol reagent (Qiagen, Valencia, Calif.) according to the manufacturer's protocol. 0.5 µg of RNA was employed to synthesize cDNA by Thermoscript (Invitrogen, Carlsbad, Calif.) with oligodT primers. A primer optimization step was performed for each set of primers to determine the optimal primer concentrations. Primers, 25 µL of 2×SYBR Green Master Mix (Invitrogen), and 30 to 100 ng cDNA samples were re-suspended in a total volume of 50 µL PCR amplification solution. Reactions were run on an ABI Prism 7000 Sequence Detection System (Applied Biosystems, Foster City, Calif.). Cycle threshold (Ct) values were obtained from the ABI 7000 software. S12 or β-actin levels were also determined for each RNA sample as controls.

Statistical Analysis: Statistical analysis of the results was performed when appropriate with two-tailed Wilcoxon-Mann-Whitney test for non-parametric values or with chi squared tests, using GraphPad Prism 5.03 (GraphPad Software, Inc. La Jolla, USA). p<0.05 was considered significant. The output of the limma analysis was used to perform gene set enrichment analysis (GSEA) using the SetRank method. The key principle of this algorithm is that it discards gene sets that have initially been flagged as significant, if their significance is only due to the overlap with another gene set. It calculates the p-value of a gene set using the ranking of its genes in the ordered list of p-values as calculated by limma. The following databases were searched for significant gene sets: BIOCYC [53], Gene Ontology [54], ITFP 5 [55], KEGG [56], LIPID MAPS [57], PhosphoSitePlus [58], REACTOME [59], and WikiPathways [60].

Pathway Ingenuity Analysis: Genes found to be significantly different between PIF and control (P<0.05, two-tail Student's t test, n=168) were analysed. First a Z score was determined to identify the highest association within the pathways. Further using pathway analysis ranking gene clusters and their association was examined by determining the statistical value of a pathway and whether the interaction led to up or down-regulation of a given gene cluster.

Results

Continuous and Intermittent PIF Administration Consistently Ameliorates RR-EAE

Figure 25A:
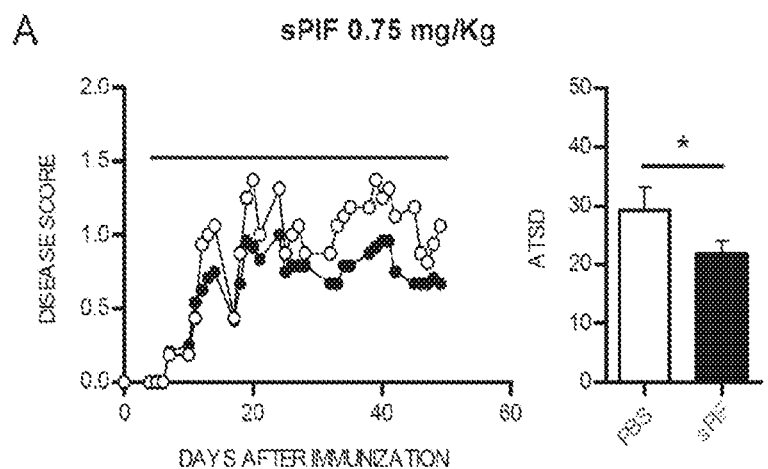
FIGS. 25A-25C depict that continuous and intermittent administration PIF lowers clinical score (RR-EAE model). SJL mice (4-7 per group) were infected sc with 4×106 CFU of live recombinant *M Smegmatis* expressing a recombinant chimeric protein MPT64-PLP139-151 (rMSp139), as previously published. Starting on day 3 after infection, mice were treated daily with PIF (closed symbols and bars) or vehicle only (PBS, open symbols and bars), i.p.

Given that early MS can directly start as acute paralytic attack and PIF was shown to prevent and reverse paralysis of the spinal cord [29], continuous PIF administration was tested using a RR-EAE model (FIG. 25A). The RR-EAE model is utilitarian for anti-anti-MS drugs development. Notably although *M. Smegmatis* bacteria is rapidly cleared, neuroinflammation becomes progressive—reflecting early disease. [45] To mimic clinical approach mice were treated with PIF (PIF 0.75 mg/kg i.p daily) or PBS [29]. Expectantly, starting PIF on third day post-inoculation significantly decreased the clinical score (FIG. 25A) of injured animals. Maximal decrease was present already at the acute disease phase. Mean clinical score and average total disease score (ATDS) were significantly lower compared to control group (closed symbols and bars as compared with open symbols and bars). The maximal decrease was already noted after a couple of days of PIF administration at the acute phase. Practically until the end and throughout the experiment, mean clinical score was lower than in vehicle treated controls. The ATDS significantly decreased by PIF (PBS 29.25 vs PIF 21.75; p=0.01, Wilcoxon-Mann-Whitney test). Hence continuous PIF administration can consistently ameliorate post-infective acute paralysis.

Figure 25B:
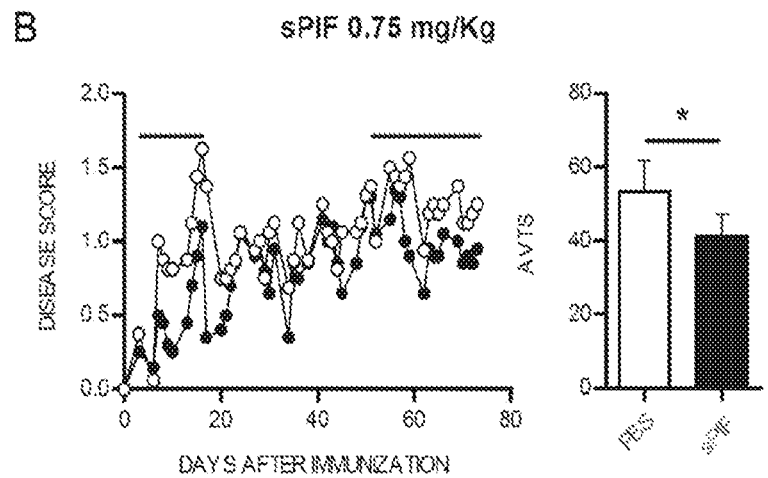

Again, aiming to mimic human acute MS therapy, which has a RR course, next it was examined whether intermittent PIF administration as needed when symptomatic is also effective. (FIG. 25B) Female SJL mice, 8-10 weeks old were infected as above and treated only during acute disease phase, interrupting treatment during the remission period. Similar to previously described experiment, PIF decreased significantly the clinical score compared with controls (ATDS PBS 53.31 vs PIF 41.05; p=0.032, Wilcoxon-Mann-Whitney test). The improved clinical score persisted for 20 days post-therapy and remarkably even after >70 days from inoculation the protective effect of PIF remained significant.

Figure 25C:
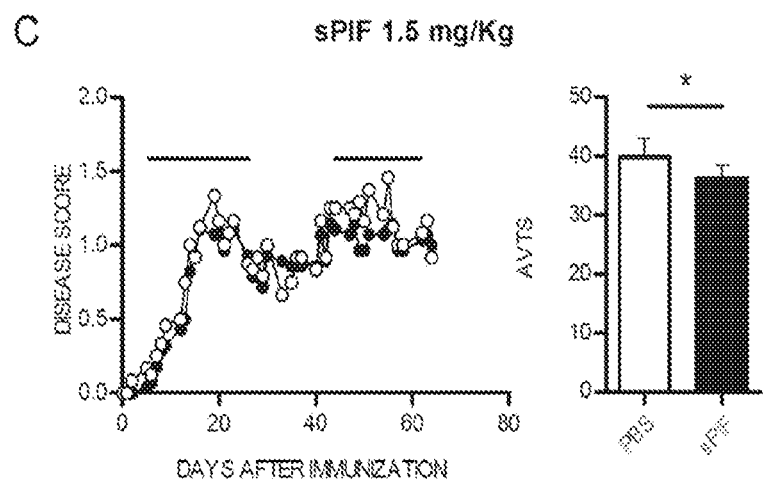

In order to determine whether a higher single PIF dose would further ameliorate disease course, mice were treated intermittently on days 5-27 and then on days 44-62 with PIF (1.5 mg/Kg) or with vehicle only monitoring the EAE course. (FIG. 25C) The PIF treated mice had a significantly milder disease score (ATSD PBS 39.79 vs PIF 34.92; p=0.026) than control mice. However, the increased PIF dose did not further improve ATDS versus the lower dose confirming that optimal effects are obtained in physiological range of concentration. [1] The composite effect of PIF on AUC of the different RR-EAE experiments are shown. (Supplement I) Overall data reveals that PIF is effective in reducing paralysis in a clinically realistic acute MS model long-term.

PIF Promotes Brain Myelination.

Figure 26A:
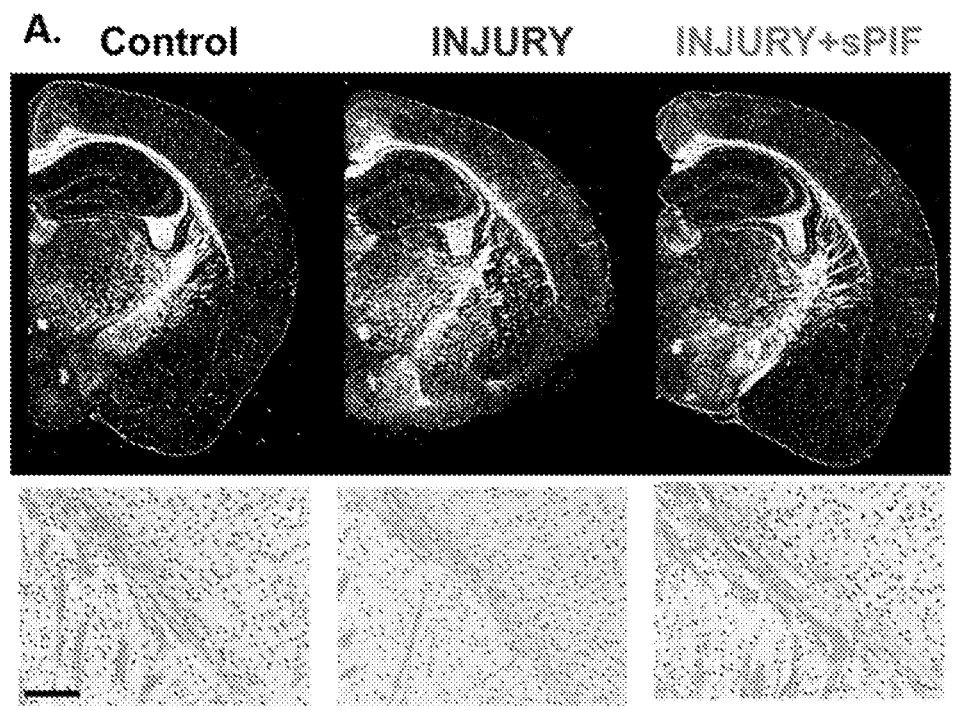
FIGS. 26A and 26B depict that PIF promotes brain re-mieylination. PIF effect on myelin expression was compared to vehicle treated control and naïve SJL mice.
Figure 26B:
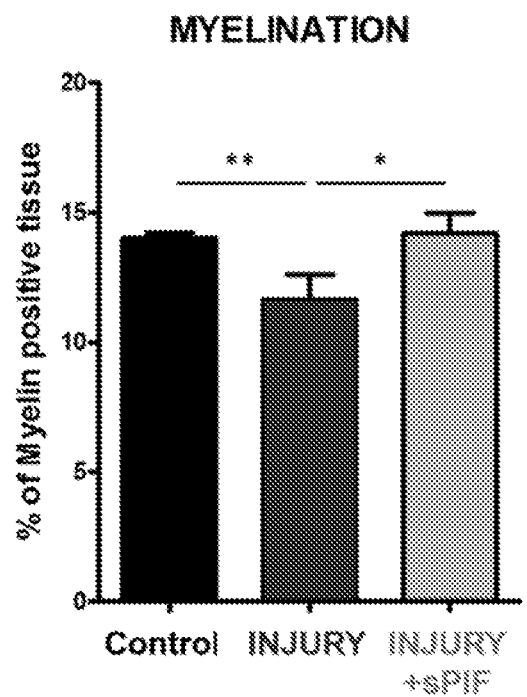

Given that PIF ameliorates RR-EAE (FIGS. 25A-25C) and myelination deficit are a hallmark of MS, next PIF effect was tested on myelin expression. Indeed, the exposure to *Smegmatis* challenge (injury) resulted in significant reduction of myelin positive cells (FIG. 26A compare injury versus control). Importantly, PIF treatment resulted in significant amelioration of the induced myelination loss (see FIG. 26B compare injury+PIF versus Injury). The results in the PIF treatment group are similar to that observed in naïve controls. (see Compare Injury+PIF to normal control) Without being bound to any particular theory, it is hypothesize that observed effect on brain myelination and previously reported effect on the spine [29] are mainly due to modulation of the inflammatory response. Whether PIF effect is direct on the brain was tested next.

PIF Crosses the BBB Intact Targeting Brain and Spinal Cord Vessel Walls and Microglia.

Figure 27A:
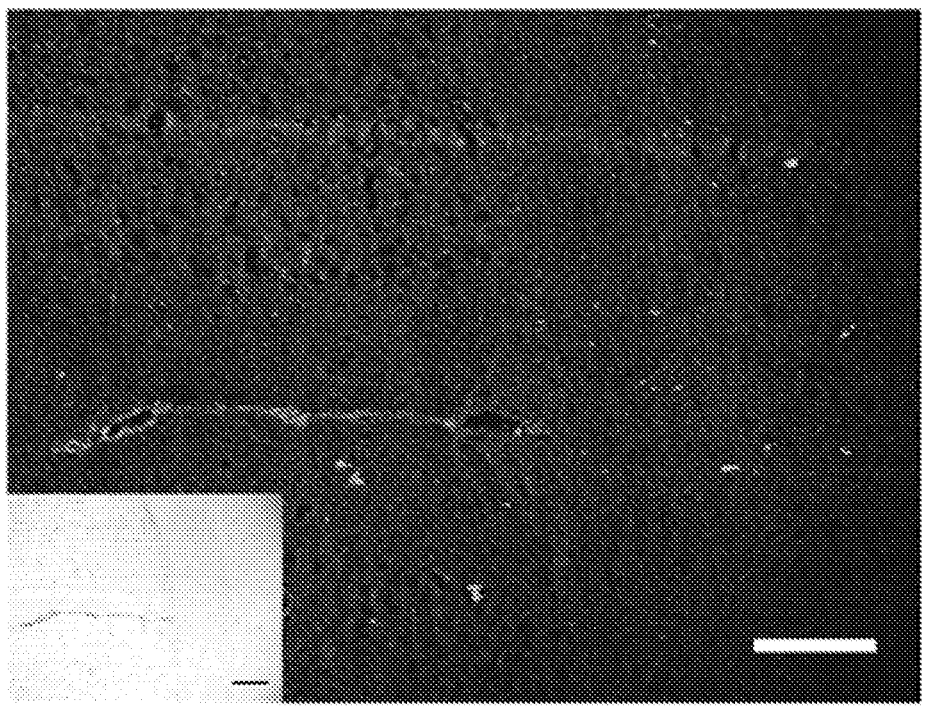
FIGS. 27A-27D depict FITC-PIF targets both brain and spinal cord. SJL mice previously infected with rMSp139 and in late phase of chronic disease (>60 days after infection) treated with PIF or PBS for 3 weeks were injected with a single FITC-PIF or PBS dose and sacrificed 3 hours later. CNS was prepared for histology. Samples were embedded in formalin, cut in 10 µm slice that were directly observed at confocal microscopy.
Figure 27B:
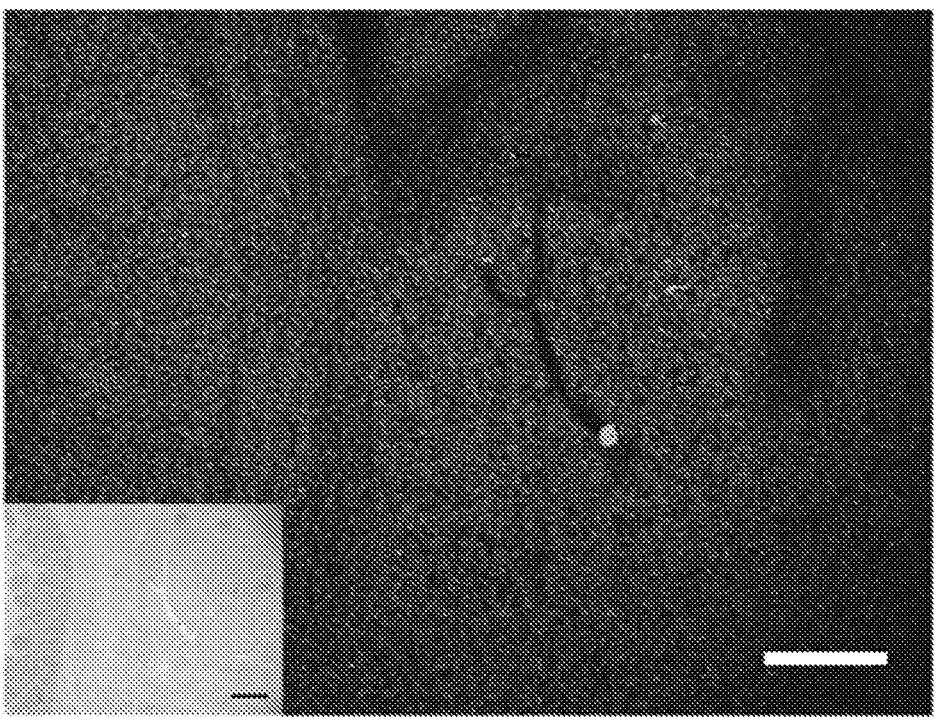
Figure 27C:
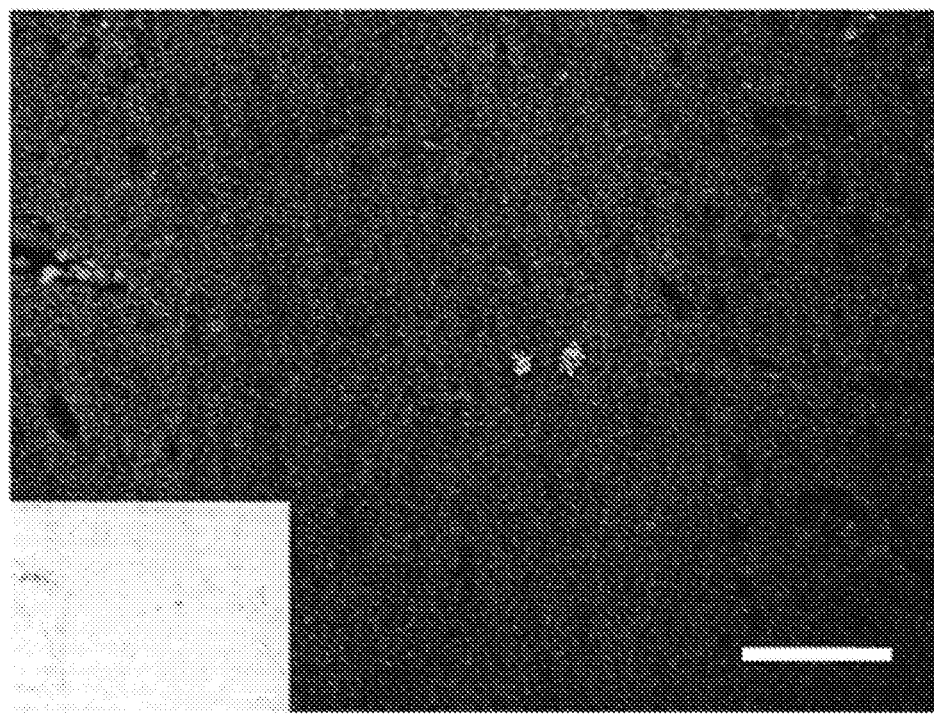
Figure 27D:
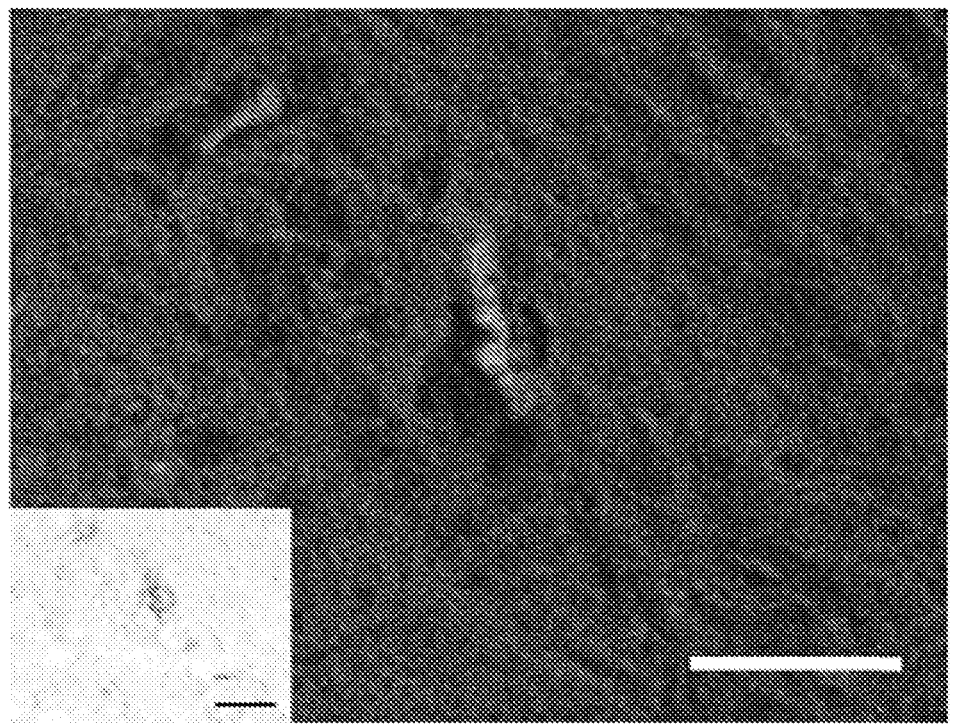

It was previously shown that PIF reaches the brain intact, traversing the BBB barrier following brain trauma. [27] Herein PIF was shown to improve RR-EAE. To assess whether in chronic RR-EAE intact PIF can cross the BBB to reach CNS was determined. Three 11 week old female SJL mice previously infected with rMSp139 at chronic phase of disease (>62 days after infection) were injected with single dose of FITC-PIF or PBS. After sacrifice, the brain and spinal cord samples were flushed and prepared for histology and observed by using confocal microscopy. (FIG. 27A) In the FITC-PIF injected mice the vessel wall and immediate surrounding cells were neatly stained and some of the microglia cells as well. In contrast, in controls no staining was noted (FIG. 27B). FITC-PIF also targeted the microglia cells in clusters (FIG. 27C). The spinal cord vasculature, similar to that in the brain, and the immediate cells lining the vessels were also targeted. (FIG. 27D). Thus PIF crosses the BBB intact targeting brain and spinal cord during chronic inflammation phase supporting targeted therapy.

PIF Reduces Pro-Inflammatory Cytokines in Lymph Node while not Altering T-Cells Recruitment.

Figure 28:
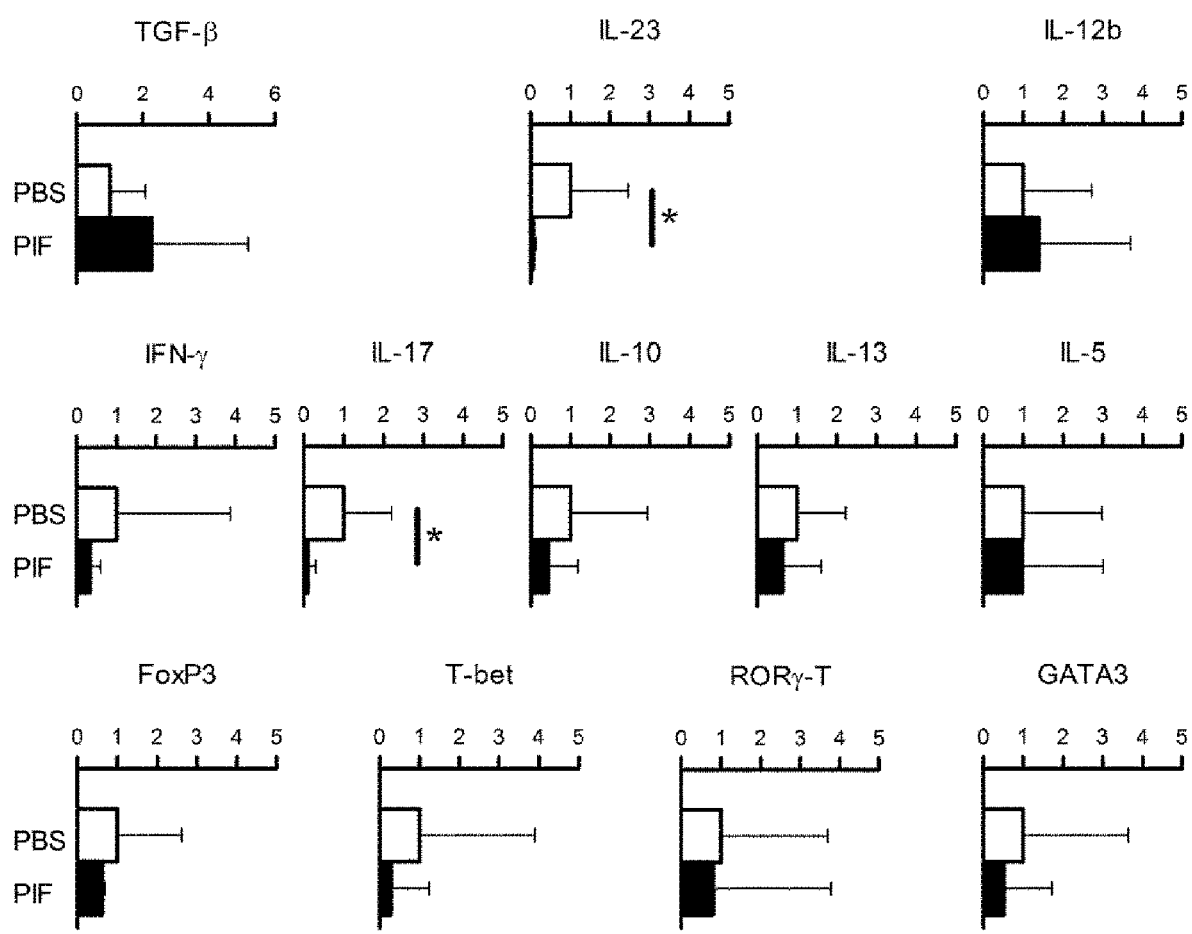
FIG. 28 depicts PIF effect on cytokine expression in draining lymph nodes. Five SJL mice per group were infected sc with rMSp139 and treated daily with 0.75 mg/Kg of PIF (Black bars) or vehicle only (white bars). Ten days later, cells from draining lymph nodes were obtained and cultured for 3 hours. Levels of mRNA specific for the indicated cytokines and transcription factors were measured by Quantitative RT-PCR, using RNA specific for 18S as internal standard. Data report average and SD of values normalized to the average value obtained in untreated mice. PIF reduced significantly the expression of IL-17 and IL23. *p<0.05 (Mann-Whitney Test)

Neuroinflammation is a progressive disease where in early stages the innate immune system is the main participant however, as inflammation progresses the adaptive arm of immunity comes into play. Therefore, initially the effect of PIF was tested in early-stage disease where systemic cytokine profile may be affected. Given that PIF systemic effects are well described [26, 29], gene expression of crucial cytokines was tested (acute time point of the injury at day 10) (FIG. 28) detecting significantly reduced IL-23 and IL-17a cytokines expression in lymph nodes. Interestingly, IL-23 is part of the innate immunity (mainly dendritic cells and macrophages) and promotes the expansion of CD4+ T-cells secreting IL-17 (Th17) a potent pro-inflammatory cytokine. [61] IL-17 plays a dominant role in MS (and EAE) and in several autoimmune diseases. [62] Further the ability of PIF to modulate IL-23 while preserving IL-12B expression (which regulates polarization of T-cells to Th1 phenotype) may explain pregnancy-induced protection against autoimmunity with preserved anti-pathogenic response.

To further address the adaptive arm of immunity following PIF or PBS injections until 25 day 30 spleen cells were isolated and cultured in presence (activation) or absence of p139 (without PLP activation—control). The characterization of the immunization-induced T-cell repertoire was determined: 1. CD4+(Vb 4-Jb1.6; Vb10-Jb1.1) [51]. 2. CD8+(Vb17-Jb1.6; Vb20-Jb2.3), [45] specific for p139 and 3. T-cell repertoire specific for this epitope present in spontaneously activated naïve mice (Vb18-Jb1.2; Vb19-Jb1.2). [62] FIG. 29 shows that PIF did not modify T-cells recruitment. Without being bound to any particular theory, it is hypothesized that PIF does not affect the systemic T cell lineage to maintain anti-pathogen activity of cells not accessing the CNS.

PIF Regulates Genes Involved in Solute Transport, Oxidative Stress and Protein Misfolding in the Brain.

Figure 30:
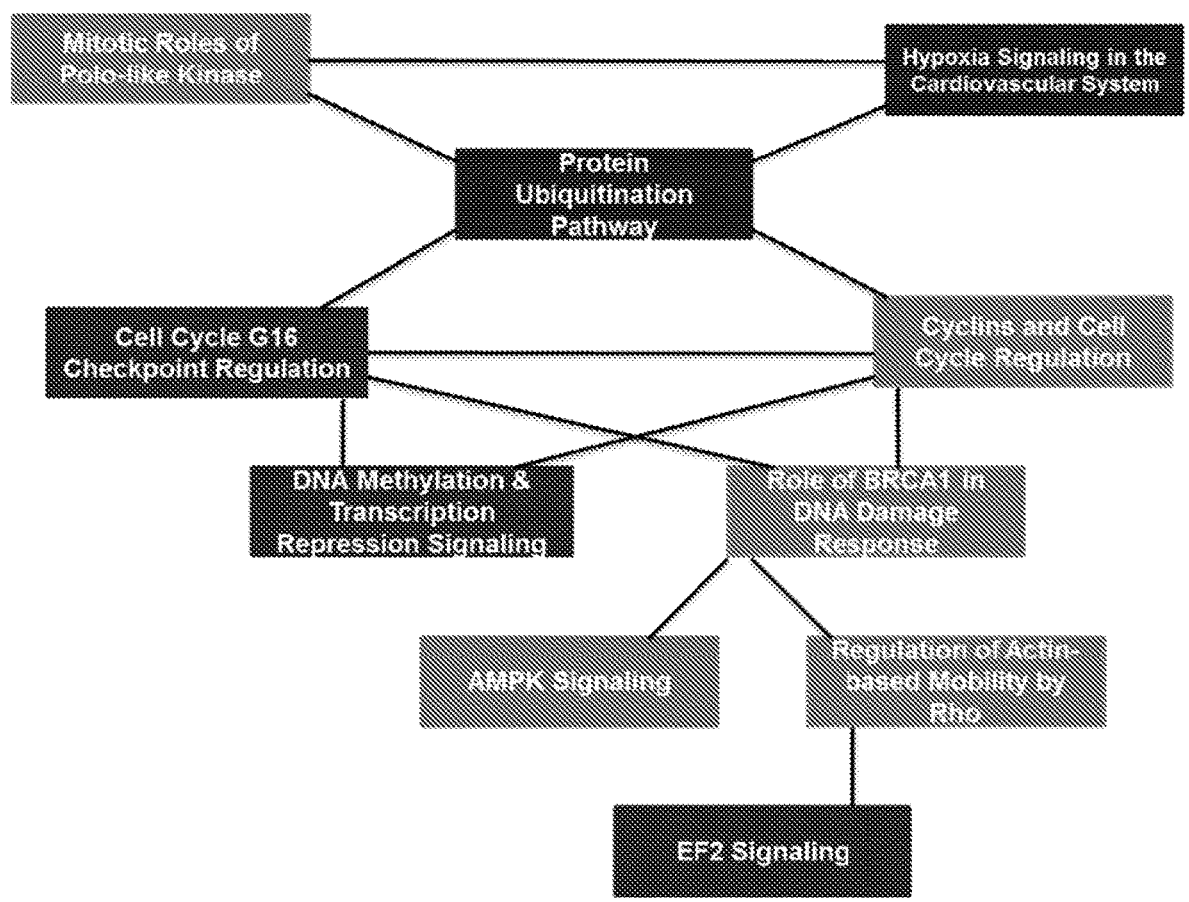
FIG. 30 depicts PIF effect of global brain genome pathways by Ingenuity analysis. Schematic pathways that are significantly affected by PIF and their interaction. Leading among them was the ubiquitin, oxidative stress and the EF2 signalling pathway.
Figure 31:
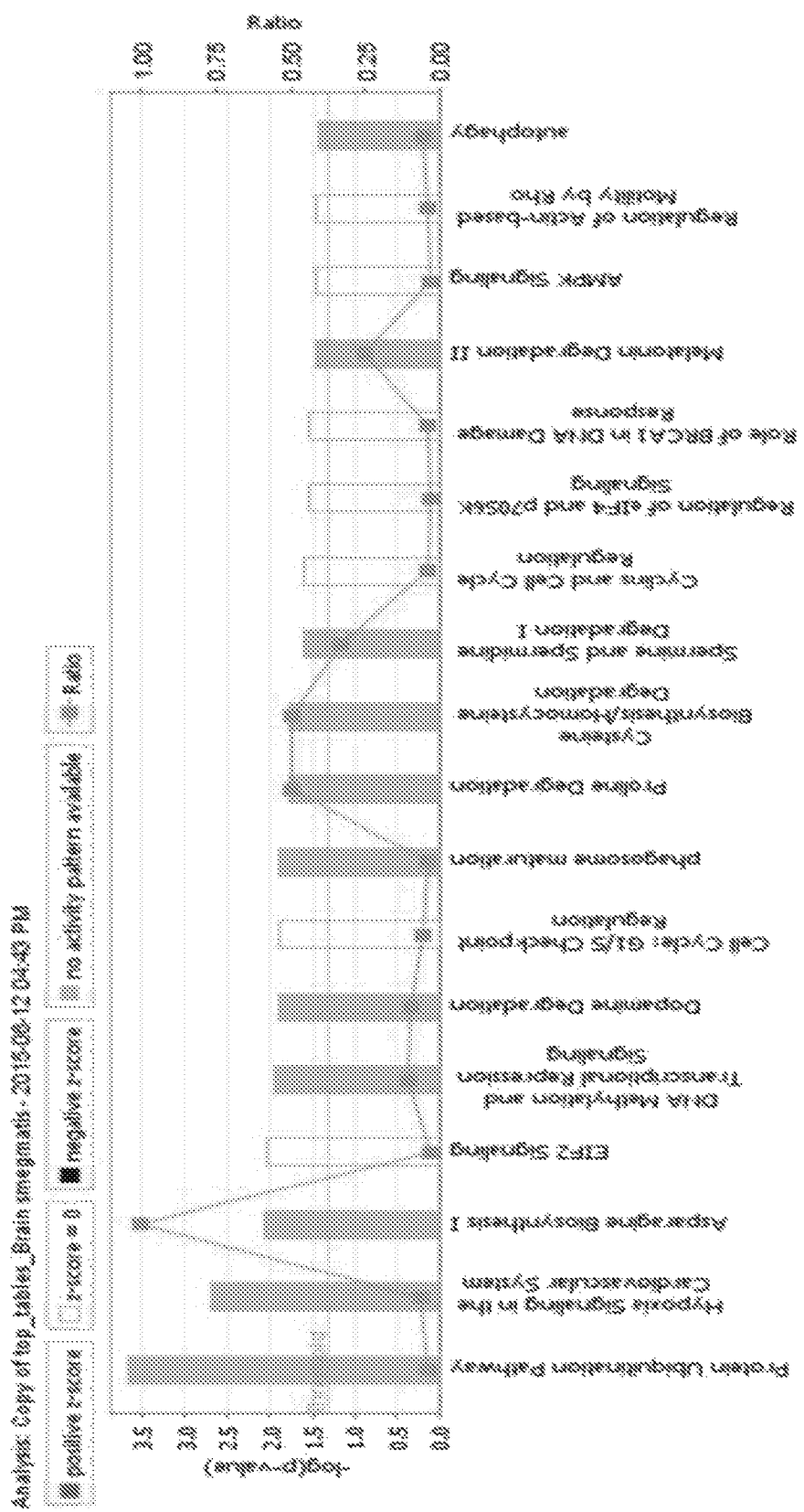
FIG. 31 depicts PIF effect on global genome—Ingenuity statistics. Evaluation of the pathways involved describing the effect PIF whether it is up or down regulated as well the associated level of significance.

Given that the immune response in the brain is much more complex that the peripheral response, a global gene array was used to determine the effect of PIF on the brain. (FIG. 30) Detected were a total of 168 genes increased/decreased regulated by PIF vs. the injury group (p<0.05). Ingenuity based pathway demonstrated that effect on neurovascular disease had the highest Z score followed by movement disorders—ie. paralysis. (Table 2 below) Further pathway analysis (FIGS. 30 and 31) showed that PIF protects against hypoxia and protein degradation induced by ubiquitination. To further visualize, heat map analysis. revealed that PIF affected pathways related to protein formation and degradation specifically involved in EF4A1-RNA binding and translation of proteins formed and ultimately their degradation by Rnf13 (E3 Ubiquitin-Protein Ligase) pathway, respectively. The largest group of genes identified critical for brain function are solute carriers (SLC7a10, SLC2a1, SLC25a11, SLC7a14, SLC24a3, and SLC2a1) involved in Na+/K+/Ca++ exchange, while others in glucose and amino acid transport.

TABLE 2

PIF protects against brain infection/inflammation: genome Z score analysis

| CONDITION | Z log |
| --- | --- |
| Neuromuscular disease | 3.209 |
| Movement disorders | 3.095 |
| Progressive motor Neuropathy | 3.02 |
| Disorders of basal ganglia | 2.62 |

PIF Protects Against Oxidative Stress and Protein Misfolding.

Oxidative stress and protein misfolding are hallmark of inflammatory disease. It was found that PIF protects against oxidative stress and protein misfolding by down-regulating (CUL1, UBE2E1, UBE2Q1, PSMD1, HSP40, HSP90AB1, SUMO1) while up-regulating (USP54 an ubiquitin peptidase) expression genes expression. [63] By affecting EIF2 eukaryotic initiation factor pathway genes (IF2B1, EIF3I, EIF4A1, PPP1CB, RPL22) beyond regulating cellular stress they are pivotal binding initiators of methionyl-tRNA and mRNA to the 40S ribosomal subunit forming the 48S initiation complex. [63] Notably, PIF also regulates asparagine biosynthesis pathway, which is altered in cases of microcephaly and is associated with progressive encephalopathy.[64] Among top ranking genes PIF promoted spermine oxidase expression, the encoded protein promotes neurotransmission via cell-surface receptor, amino acids and regulates reactive oxygen species. [58] PIF promoted StAR expression involved acute regulation of steroid hormone synthesis converting cholesterol to pregnenolone. In the brain StAR is restricted to specific neurons and astrocytes promote their development exerting neuroprotective effects. Finally, increased ARRB2, arrestin beta promotes synaptic receptors and MCF2L axonal transport in the brain. [65]

Supplement V shows a more comprehensive analysis of PIF induced action-Ingenuity analysis. As expected PIF top diseases examined by number of genes affected were neurologic where 40/168 genes significantly changed. This is closely followed by skeletal and muscular disorders. Overall pathway analysis is in line with PIF-induced protection against oxidative and protein misfolding in EAE model. [24, 25]

PIF-Induced Upstream Regulation Involves MYCN (ERK/MAPK Signalling) and Cortisol Binding Site (NR3C1).

MYCN-neuroblastoma homolog gene regulates cell proliferation, survival, and apoptosis: (Supplement V) This upstream regulator is involved in the myc signalling and regulated by let-7 microRNA. Let-7 is down-regulated in the brain by PIF, thereby protecting against hypoxic ischemic brain damage. [27] PIF increased both (RPL22, SLC2A1) genes expression. Since these genes are upregulated by MYCN, indicates that this pathway is also regulated by PIF. In contrast, PIF decreased the expression of (NCL, E2F5, HSPAB1, EIF4A1, RBBP7, TPI1, ACTB) genes. Since MYCN activates (NCL, E2F5, HSP90AB1, and EIF4A1) indicates that PIF down-regulates MYCN effect. Finally, in case of ACTB both MYCN and PIF act in a similar manner to down-regulate the same gene. Also MYCN targets NCL a gene which expression is decreased by PIF.

The second ranking upstream regulator is NR3C1 a glucocorticoid receptor that plays a major role in cell proliferation, remodelling and apoptosis: NR3C1 is a homodimer that interacts with HSP90, a PIF target. [24] PIF Increased the expression of: (USP54, BRD2, ARRB2) and decreased the expression of (WDR37, CUL1, SIAHA, HIC2. HSP90AB1, ATG12, PTP4A2, TM2D2, NMT1, ABI1, ACTB) genes. NR3C1 also interacts with SUMO1, an ubiquitin related gene which expression is decreased by PIF. Overall this data implies PIF involvement in MYC as well as glucocorticoid signalling reflecting regulation of inflammatory response in the brain.

PIF Promotes BDNF, SLC2a1, and Reduces HSP90ab1, and E2F5 Genes Expression in Primary Astrocytes.

Originally astrocytes were viewed as support system for the brain however as recently indicated they are involved in microarchitecture, support neural cells development and brain defence releasing cytokines and several neurotrophic factors among them BDNF. [52] Importantly, these cells through BDNF action lead to restored myelin in neuroinflammatory disease model. It was found that PIF unregulated the expression of BDNF in primary astrocytes. Thus the restored myelination seen in our study using astrocytes could also be due to BDNF's role in promoting myelin synthesis.

Figure 32A:
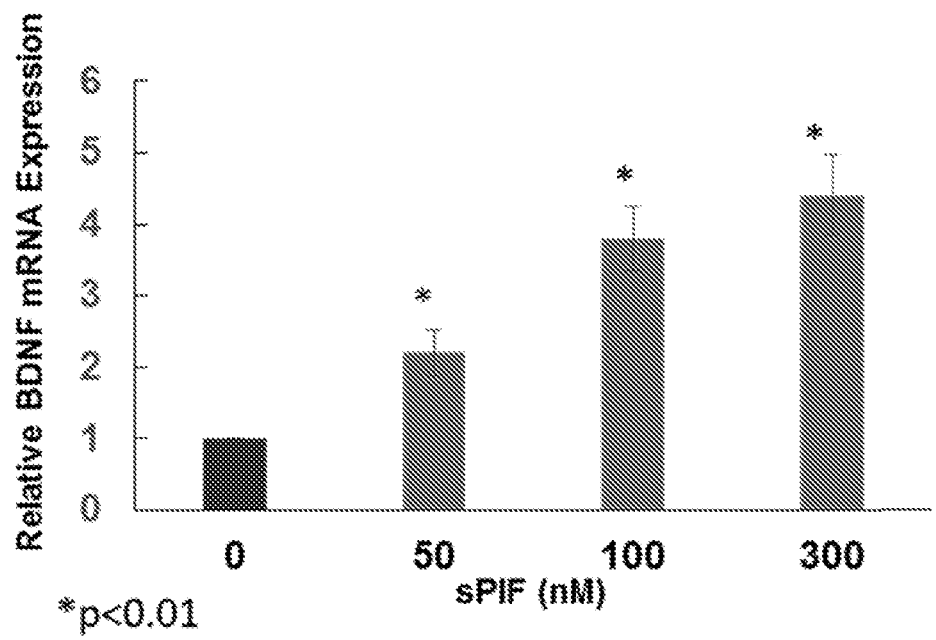
FIGS. 32A-32D depict that PIF promotes BDNF, SLC2a1, and reduces HSP90ab1, and E2F5 expression in astrocytes. Primary astrocytes were cultured with different PIF concentrations up to 48 hours. Effect was compared to control. Data on fold change was evaluated by RT-qPCR.
Figure 32B:
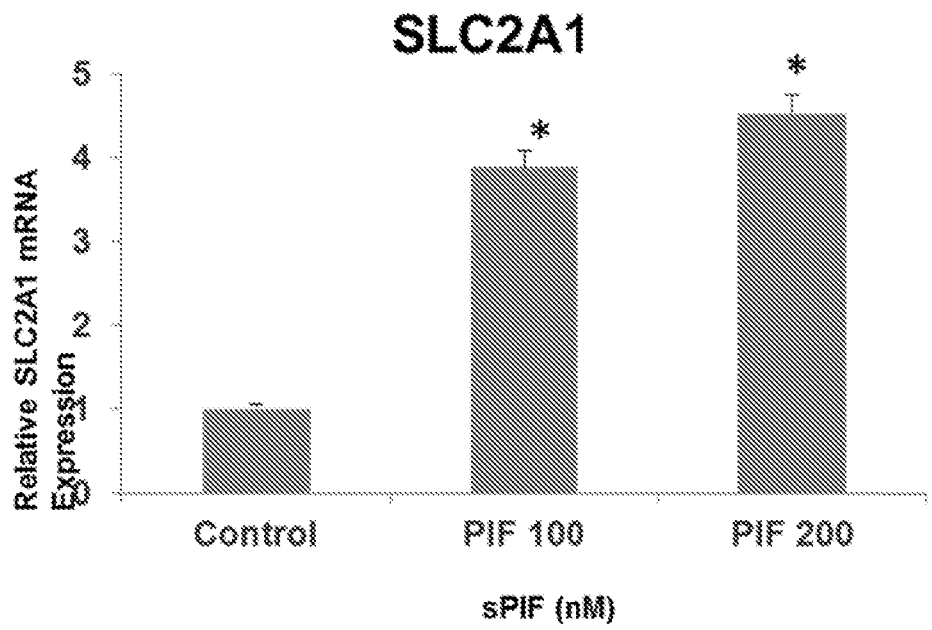
Figure 32C:
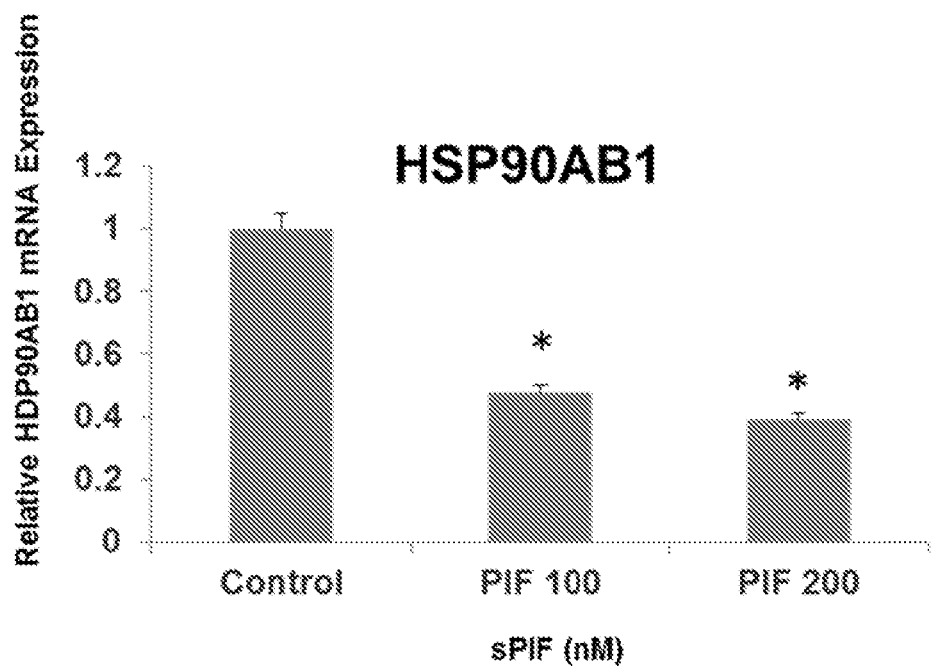
Figure 32D:
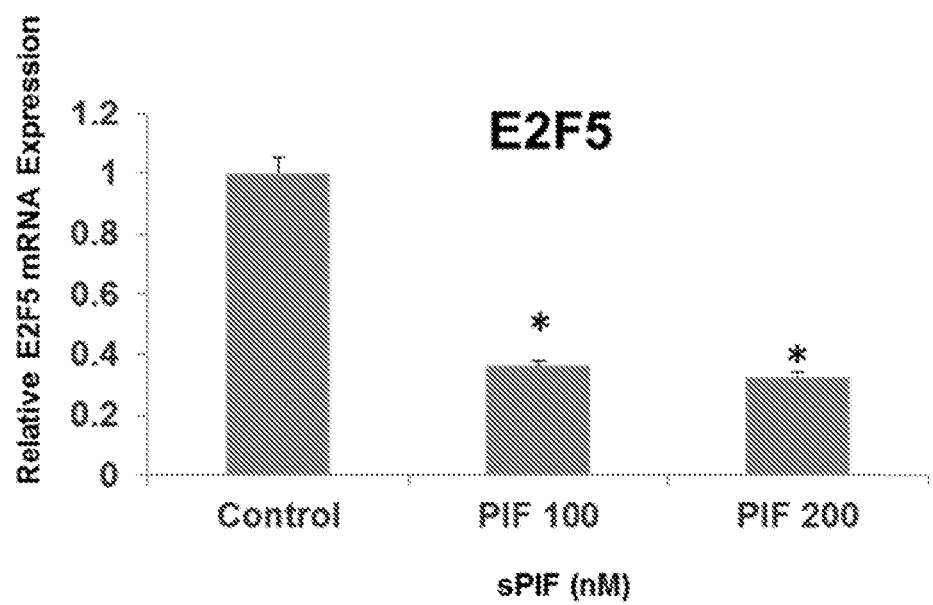

Whether PIF action on the brain gene array involves an effect on astrocytes was tested next. Gene array showed that PIF regulates several solute transporters. It was found that PIF promotes SLC2A1 expression in primary astrocyte culture thus confirming the gene expression data. (FIG. 32B) This gene is involved in glucose transport. In further validation study PIF in contrast reduced HSP90AB1 expression (FIG. 32C) thereby protects against protein degradation. Notably the protein product is a major PIF target. [22, 24] In addition, PIF also reduced E2F5 expression (a cell cycle protein). (FIG. 32D) This gene is expressed in post-traumatic injury in the spinal cord. [66] The present data reveal a direct regulatory role of PIF on primary astrocytes.

PIF Promotes IL10 and Reduces INFγ Expression by Primary Microglia Cultures.

Figure 33:
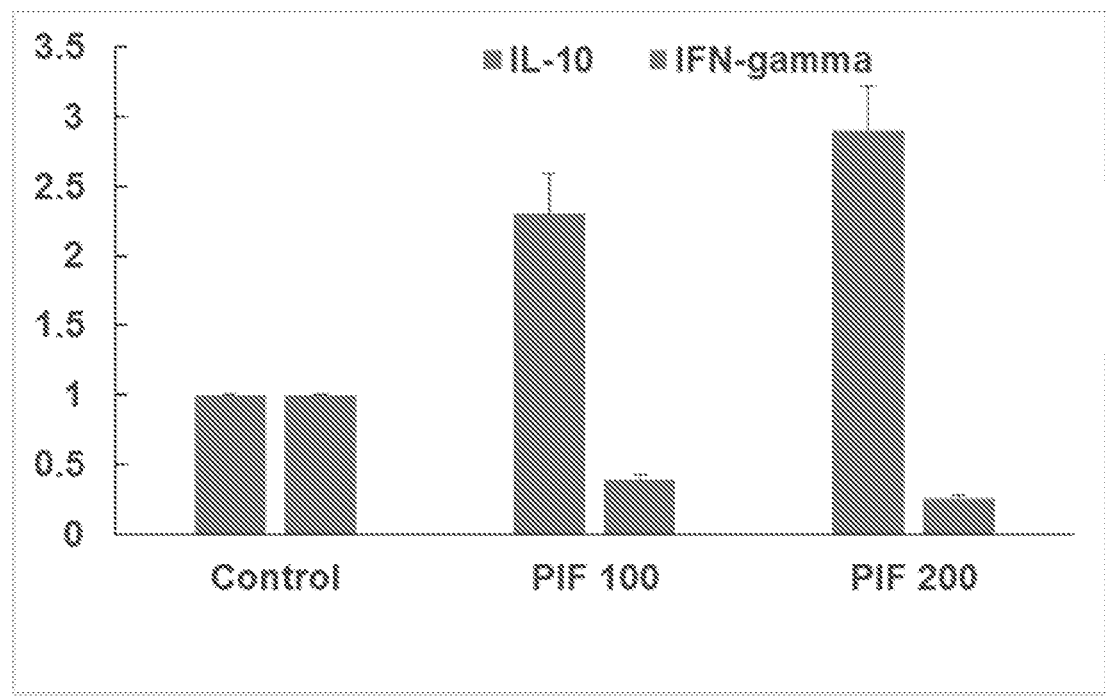
FIG. 33 depicts a graph showing that PIF promotes IL10 and reduces INFγ expression in microglia cultures. PIF at different concentrations were tested on two prime cytokine expression. After 48 hours of culture cells were extracted and analysed by RT-qPCR. PIF led to increased IL10 while the expression of INFγ decreased in a dose dependent manner. *p<0.001.

In the current study PIF was shown to directly target microglia when the BBB appear to be intact. (FIG. 33) Whether PIF also regulates these brain derived macrophages was tested next. In microglia cell lines PIF was shown to promote IL10 [27, 28] therefore herein the effect of PIF using primary cells was examined. In addition, it was determined whether this action is also associated with a decrease in INFγ—a prime pro-inflammatory cytokine secretion. Data showed the dual action increased the pro-tolerance while reducing the pro-inflammatory cytokine expression supporting the inflammation regulatory effect of PIF in the brain.

Summary

There is an urgent need to develop safe, easy to administer, and effective MS/neuroinflammation therapy. Due to sub-clinical and indolent nature of progressive neurologic disorders they are especially difficult to diagnose early and treat. In MS brain myelin loss is key evidence for disease progression therefore safe reversal would be a major feat. Our major finding is that PIF targets microglia and vascularity to promote re-myelination in post-infectious clinically realistic RR-EAE model. Addressing critical aspects of disease PIF through integrated action centrally mitigated paralysis while reducing systemic inflammation. Global brain gene analysis revealed that PIF promoted solute transporters, while reducing oxidative stress and protein degradation. In primary astrocytes PIF promotes BDNF expression—key for myelin synthesis. As PIF is in FAST-Track FDA Phase Ib clinical trial for autoimmune disease implementation for MS/Neuroflammation therapy may also be envisaged.

MS has chronic and variable clinical course and finding that PIF is effective long-term, by continuous or episodic administration point to clinical potential. Thus early or delayed drug administration may be envisaged. Since intermittent PIF efficacy lasted ~80 days—it may reflect years in human. In the classic EAE model a similar long term protection was noted. [29] PIF single daily and low physiologic dose was effective which increases compliance. Similarly, a single ascending daily dose was used on our Phase Ia clinical which was completed satisfactorily leading to the ongoing (5 days) daily dose trial (ClinicalTrial.gov NCT02239562). Upon completion of this Phase Ib trial implementation for MS/Neuroinflammation clinical testing is planned.

Infectious-EAE (RR-EAE) although less harsh reflect early stage MS however the observed demyelination is clinically significant. Remarkably PIF through direct action restored brain myelination to that seen in naïve mice in contrast to vehicle only treated control. This key finding addresses a pathology which is difficult to achieve by current therapy. Drugs used for neurologic diseases have to be small or lipid soluble to cross by transmembrane diffusion. The use of transporters may improve larger proteins and peptides access to the CNS. [67] In the HIE model PIF directly targets brain microglia and neurons although rapidly cleared from circulation-reflecting a pharmacodynamic and not kinetic effect. [27, 28] This may also explain the long term protective effect in the RR-EAE model and as seen by other preclinical models. [25, 26] In the RR-EAE model the focus was the brain. Therefore, PIF targeting of brain microglia and vascularity support a direct effect on myelin restoration.

Immune disorders, including neuroinflammation/MS have both local and systemic components- to prevent relapse both have to be addressed satisfactorily. PIF directly targets systemic immunity in vitro confirmed in vivo. [19, 21, 22, 25, 29] The decreased IL-23 and IL-17 cytokines expression observed in draining lymph nodes reflect systemic protection. Similar to the IL-23 homodimer circulating IL-12 levels were reduced by PIF in the classic EAE model reversing paralysis long-term. [29] PIF targets macrophages which secrete IL-23 and IL-12. [26, 68, 69] IL-17 plays key role in autoimmunity, and PIF reduced this ligand in PLP activated splenocytes. [29] In progressive neuroinflammation the T-cell repertoire was not affected by PIF thus only the innate (acute phase) and not the adaptive arm of immunity is regulated-maintaining beneficial anti-pathogen protection. Overall PIF's integrated local and central protection leads to amelioration of the clinical score.

In classic EAE contrary to current RR-EAE model the focus was the spinal cord while in MS the brain is the main target. Mechanistically in classic EAE PIF beyond reducing oxidative stress and inflammatory response promoted neural repair by reduced tubulin break-down and increased axon assembly. This was coupled with improved synaptic transmission. [29] For the first time brain global CNS gene expression and two independent complementary methods of analysis provide important insight into the protective effects of PIF. Herein damage is caused both by transient exposure to bacteria and ensuing inflammation—a highly complex model, while in classic EAE—is practically only antigen driven. It was found that PIF regulates both infection and inflammation driven genes expression. Irrespective whether Smegmatis bacteria is innocuous and is eliminated, its footprint persists >70 days—as chronic inflammation. PIF primarily affected oxidative stress, cell cycle check-point regulation and DNA methylation pathways—protective mechanisms. By regulating ubiquitination PIF prevents misfolded proteins degradation-key for neurodegenerative diseases—i.e. prions. Effect on EIF2 related genes reflect amino acids processed post-mRNA activation supporting protein neo-synthesis. The reduction in CD4 activation may further aid in the repair process. The highest ranking upstream regulator of PIF was MYCN—myc related transcription is let-7 microRNA down-regulated by PIF. [27] This reflect commonality between brain injury/inflammation and infection/inflammation protective mechanisms. [27-29, 37]

Notably PIF affected several genes associated with diverse neurologic disorders. For example, increased RPH3A, Ras-related protein Rab-3A promotes synaptic vesicle traffic and fusion while aberrant interaction with alpha-synuclein leads to aggregates found in Huntington chorea. [70] SFRS6 constitutively splice/missplice Tau exon-10 causing fronto-temporal dementia. [65] VARS is involved in brain malformation. [71] SPG7, ATP-dependent zinc metalloprotease is involved in spastic paraplegia. [72] BRD2 microdeletion contributes to juvenile myoclonic epilepsy. [24]

On the other hand, decreased (ATP6AP2, UBE2e1, and Ube2q1) genes to prevent mitochondrial oxidative stress leading to Parkinson's, Alzheimer's and X-linked mental retardation. FRMPd4 expression regulates excitatory synaptic transmission. [73] SPG21 a negative CD4 regulator involved in spastic paraplegia, PDCD10 aberration can cause cavernous cerebral malformation development. [74] ATAD1 regulates AMPA receptors involved in synaptic plasticity learning and memory. [75] Thus environmental influences induced by M. Smegmatis or similar pathogens could lead to diverse neurologic disorders beyond MS. Consequently, PIF could also protect other neurological disorders however—they are beyond the scope of the current paper.

The gene array data revealed a complex effect of PIF on diverse genes. Astrocytes recently have been implicated in MS pathology and play a key role myelin synthesis. [52] The finding that PIF promotes a key myelin synthesis inducer; BDNF in primary astrocytes support our in vivo observation which documented myelin restoration. Evidencing further astrocytes role in neural repair is shown by PIF promoting glucose transport (SLC2A1) while reducing oxidative stress related genes, confirming the gene array data. Injected PIF is detected robustly in brain blood vessels which are fully lined by astrocytes. This suggests PIF—astrocyte interaction in vivo- to be confirmed by further study. Astrocytes play an important role in blood flow regulation, and since PIF negatively regulates phospholipase A2, activating protein (Plaa) expression suggest involvement in this important process. Under basal O2 consumption PIF protects against oxidative stress [26] and phospholipase A2 promotes vasoconstriction. However as O2 consumption rises, vasodilation prevails and through Ca++ flux promotes arachidonic acid which via COX-1 action releases PGE2 [76] PIF targeting also the spinal cord vasculature enables a coordinated CNS protective action. This was confirmed since PIF protected against aortic vascular inflammation by preventing macrophage induced atherosclerotic plaque formation. [23] Microglia play key role in inflammatory response redirecting towards damage or repair depending on the activator. [77] In this study PIF targets microglia seen on cultured primary microglia cells. PIF promoted IL10 while reducing major pro-inflammatory INFγ expression supporting the protective effect. Similarly, in HIE model brain IL10 increased while microRNA let-7 expression decreased. [27] Overall intact PIF crosses BBB to reach the CNS targets microglia, vessels and importantly astrocytes to enable integrated protection against neurodegeneration.

Conclusion: continuous or intermittent PIF directly promotes re-myelination while reducing paralysis in clinically-realistic MS/neuroinflammation model. Promotion of BDNF by cultured astrocytes—support possible local myelin synthesis. Local CNS protection is coupled with reduced systemic inflammation. PIF induced brain Na+/K+/Ca++ ions, amino acid and glucose transport is coupled with reduced oxidative stress and protein degradation pathways. The physiological PIF dose used, is similar to endogenous maternal circulating levels where MS symptoms frequently improve. [4]

REFERENCES REFERRED TO IN EXAMPLE 2

[1] Barnea E R, Almogi-Hazan O, Or R, Mueller M, Ria F, Weiss L et al. Immune regulatory and neuroprotective properties of preimplantation factor: From newborn to adult. Pharmacol Ther, 2015; 156:10-25.
[2] de Man Y A, Dolhain R J E M, van de Geijn F E, Willemsen S P, Hazes J M W. Disease activity of rheumatoid arthritis during pregnancy: results from a nationwide prospective study. Arthritis and rheumatism, 2008; 59:1241-8.
[3] Barnea E R, Rambaldi M, Paidas M J, Mecacci F. Reproduction and autoimmune disease: important translational implications from embryo-maternal interaction. Immunotherapy, 2013; 5:769-80.
[4] Paidas M J, Annunziato J, Romano M, Weiss L, Or R, Barnea E R. Pregnancy and Multiple Sclerosis (MS): A Beneficial Association. Possible therapeutic application of embryo-specific Pre-implantation Factor (PIF*). Am J Reprod Immunol, 2012; 68:456-64.
[5] Waites G T, Whyte A. Effect of pregnancy on collagen-induced arthritis in mice. Clinical and experimental immunology, 1987; 67:467-76.
[6] Langer-Gould A, Garren H, Slansky A, Ruiz P J, Steinman L. Late pregnancy suppresses relapses in experimental autoimmune encephalomyelitis: evidence for a suppressive pregnancy-related serum factor. J Immunol, 2002; 169:1084-91.
[7] McClain M A, Gatson N N, Powell N D, Papenfuss T L, Gienapp I E, Song F et al. Pregnancy suppresses experimental autoimmune encephalomyelitis through immuno-

[8] López C, Comabella M, Tintore M, Sastre-Garriga J, Montalban X. Variations in chemokine receptor and cytokine expression during pregnancy in multiple sclerosis patients. Multiple sclerosis (Houndmills, Basingstoke, England), 2006; 12:421-7.

[9] Gilli F, Lindberg R L, Valentino P, Marnetto F, Malucchi S, Sala A et al. Learning from nature: pregnancy changes the expression of inflammation-related genes in patients with multiple sclerosis. PLoS One, 2010; 5:e8962.

[10] Roussev R G, Dons'koi B V, Stamatkin C, Ramu S, Chernyshov V P, Coulam C B et al. Preimplantation factor inhibits circulating natural killer cell cytotoxicity and reduces CD69 expression: implications for recurrent pregnancy loss therapy. Reprod Biomed Online, 2013; 26:79-87.

[11] Barnea E R. Applying Embryo-Derived Immune Tolerance to the Treatment of Immune Disorders. Annals of the New York Academy of Sciences, 2007; 1110:602-18.

[12] Ramu S, Stamatkin C, Timms L, Ruble M, Roussev R G, Barnea E R. PreImplantation factor (PIF) detection in maternal circulation in early pregnancy correlates with live birth (bovine model). Reprod Biol Endocrinol, 2013; 11:105.

[13] Moindjie H, Santos E D, Loeuillet L, Gronier H, de Mazancourt P, Barnea E R et al. Preimplantation factor (PIF) promotes human trophoblast invasion. Biol Reprod, 2014; 91:118.

[14] Barnea E, Coulam C B. Embryonic Signals. In: Jauniaux E, Barnea E, Edwards R G, editors. Embryonic Medicine and Therapy, New York: Oxford University Press; 1997, p. 63-75.

[15] Barnea E R, Simon J, Levine S P, Coulam C B, Taliadouros G S, Leavis P C. Progress in characterization of pre-implantation factor in embryo cultures and in vivo. Am J Reprod Immunol, 1999; 42:95-9.

[16] Stamatkin C W, Roussev R G, Stout M, Coulam C B, Triche E, Godke R A et al. Preimplantation factor negates embryo toxicity and promotes embryo development in culture. Reproductive biomedicine online, 2011; 23:517-24.

[17] Duzyj C M, Barnea E R, Li M, Huang S J, Krikun G, Paidas M J. Preimplantation factor promotes first trimester trophoblast invasion. Am J Obstet Gynecol, 2010; 203:402 e1-4.

[18] Paidas M J, Krikun G, Huang S J, Jones R, Romano M, Annunziato J et al. A genomic and proteomic investigation of the impact of preimplantation factor on human decidual cells. American journal of obstetrics and gynecology, 2010; 202:459. e1-8.

[19] Barnea E R, Kirk D, Ramu S, Rivnay B, Roussev R, Paidas M J. PreImplantation Factor (PIF) orchestrates systemic antiinflammatory response by immune cells: effect on peripheral blood mononuclear cells. Am J Obstet Gynecol, 2012; 207:313 e1-11.

[20] Duzyj C M, Paidas M J, Jebailey L, Huang J S, Barnea E R. PreImplantation Factor (PIF*) promotes embryotrophic and neuroprotective decidual genes: effect negated by epidermal growth factor. Journal of Neurodevelopmental Disorders, 2014; 6:36.

[21] Barnea E R, Kirk D, Todorova K, McElhinney J, Hayrabedyan S, Fernandez N. PIF direct immune regulation: Blocks mitogen-activated PBMCs proliferation, promotes TH2/TH1 bias, independent of Ca(2+). Immunobiology, 2015; 220:865-75.

[22] Barnea E R, Hayrabedyan S, Todorova K, Almogi-Hazan O, Or R, Guingab J et al. PreImplantation factor (PIF*) regulates systemic immunity and targets protective regulatory and cytoskeleton proteins. Immunobiology, 2016; 221:778-93.

[23] Chen Y C, Rivera J, Fitzgerald M, Hausding C, Ying Y L, Wang X et al. PreImplantation factor prevents atherosclerosis via its immunomodulatory effects without affecting serum lipids. Thromb Haemost, 2016; 115:1010-24.

[24] Barnea E R, Lubman D M, Liu Y H, Absalon-Medina V, Hayrabedyan S, Todorova K et al. Insight into PreImplantation Factor (PIF*) mechanism for embryo protection and development: target oxidative stress and protein misfolding (PDI and HSP) through essential RIPK binding site. PLoS One, 2014; 9:e100263.

[25] Weiss L, Bernstein S, Jones R, Amunugama R, Krizman D, Jebailey L et al. Preimplantation factor (PIF) analog prevents type I diabetes mellitus (TIDM) development by preserving pancreatic function in NOD mice. Endocrine, 2011; 40:41-54.

[26] Azar Y, Shainer R, Almogi-Hazan O, Bringer R, Compton S R, Paidas M J et al. Preimplantation factor reduces graft-versus-host disease by regulating immune response and lowering oxidative stress (murine model). Biol Blood Marrow Transplant, 2013; 19:519-28.

[27] Mueller M, Zhou J, Yang L, Gao Y, Wu F, Schoeberlein A et al. PreImplantation factor promotes neuroprotection by targeting microRNA let-7. Proc Natl Acad Sci USA, 2014; 111:13882-7.

[28] Mueller M, Schoeberlein A, Zhou J, Joerger-Messerli M, Oppliger B, Reinhart U et al. PreImplantation Factor bolsters neuroprotection via modulating Protein Kinase A and Protein Kinase C signaling. Cell death and differentiation, 2015; 22:2078-86.

[29] Weiss L, Or R, Jones R C, Amunugama R, JeBailey L, Ramu S et al. Preimplantation factor (PIF*) reverses neuroinflammation while promoting neural repair in EAE model. J Neurol Sci, 2012; 312:146-57.

[30] Sospedra M, Martin R. Immunology of multiple sclerosis. Annual review of immunology, 2005; 23:683-747.

[31] Karussis D M, Lehmann D, Slavin S, Vourka-Karussis U, Mizrachi-Koll R, Ovadia H et al. Inhibition of acute, experimental autoimmune encephalomyelitis by the synthetic immunomodulator linomide. Ann Neurol, 1993; 34:654-60.

[32] Sturzebecher S, Wandinger K P, Rosenwald A, Sathyamoorthy M, Tzou A, Mattar P et al. Expression profiling identifies responder and non-responder phenotypes to interferon-beta in multiple sclerosis. Brain, 2003; 126:1419-29.

[33] Johnson K P, Brooks B R, Cohen J A, Ford C C, Goldstein J, Lisak R P et al. Copolymer 1 reduces relapse rate and improves disability in relapsing-remitting multiple sclerosis: results of a phase III multicenter, double-blind placebo-controlled trial. The Copolymer 1 Multiple Sclerosis Study Group. Neurology, 1995; 45:1268-76.

[34] Fox R J, Miller D H, Phillips J T, Hutchinson M, Havrdova E, Kita M et al. Placebo-controlled phase 3 study of oral BG-12 or glatiramer in multiple sclerosis. N Engl J Med, 2012; 367:1087-97.

[35] Shirani A, Zhao Y, Karim M E, Evans C, Kingwell E, van der Kop M L et al. Association between use of interferon beta and progression of disability in patients with relapsing-remitting multiple sclerosis. JAMA, 2012; 308:247-56.

[36] Marriott J J, Miyasaki J M, Gronseth G, O'Connor P W, Therapeutics, Technology Assessment Subcommittee of

[36] the American Academy of N. Evidence Report: The efficacy and safety of mitoxantrone (Novantrone) in the treatment of multiple sclerosis: Report of the Therapeutics and Technology Assessment Subcommittee of the American Academy of Neurology. Neurology, 2010; 74:1463-70.

[37] Stromnes I M, Goverman J M. Active induction of experimental allergic encephalomyelitis. Nature Protocols, 2006; 1:1810-9.

[38] Stromnes I M, Goverman J M. Passive induction of experimental allergic encephalomyelitis. Nature Protocols, 2006; 1:1952-60.

[39] Baxter A G. The origin and application of experimental autoimmune encephalomyelitis. Nature reviews Immunology, 2007; 7:904-12.

[40] Simmons S B, Pierson E R, Lee S Y, Goverman J M. Modeling the heterogeneity of multiple sclerosis in animals. Trends in immunology, 2013; 34:410-22.

[41] Fernando M M A, Stevens C R, Walsh E C, De Jager P L, Goyette P, Plenge R M et al. Defining the Role of the MHC in Autoimmunity: A Review and Pooled Analysis. PLoS genetics, 2008; 4.

[42] Ramagopalan S V, Knight J C, Ebers G C. Multiple sclerosis and the major histocompatibility complex. Current opinion in neurology, 2009; 22:219-25.

[43] Oksenberg J R. Decoding multiple sclerosis: an update on genomics and future directions. Expert review of neurotherapeutics, 2013; 13:11-9.

[44] Nicolo C, Di Sante G, Orsini M, Rolla S, Columba-Cabezas S, Romano Spica V et al. *Mycobacterium tuberculosis* in the adjuvant modulates the balance of Th immune response to self-antigen of the CNS without influencing a "core" repertoire of specific T cells. Int Immunol, 2006; 18:363-74.

[45] Nicolo C, Sali M, Di Sante G, Geloso M C, Signori E, Penitente R et al. *Mycobacterium smegmatis* expressing a chimeric protein MPT64-proteolipid protein (PLP) 139-151 reorganizes the PLP-specific T cell repertoire favoring a CD8-mediated response and induces a relapsing experimental autoimmune encephalomyelitis. J Immunol, 2010; 184:222-35.

[46] Nicolo C, Di Sante G, Procoli A, Migliara G, Piermattei A, Valentini M et al. *M. tuberculosis* in the adjuvant modulates time of appearance of CNS-specific effector T cells in the spleen through a polymorphic site of TLR2. PLoS One, 2013; 8:e55819.

[47] Gregg C, Shikar V, Larsen P, Mak G, Chojnacki A, Yong V W et al. White matter plasticity and enhanced remyelination in the maternal CNS. The Journal of Neuroscience, 2007; 27:1812-23.

[48] Zeng X X, Tan K H, Yeo A, Sasajala P, Tan X, Xiao Z C et al. Pregnancy-associated progenitor cells differentiate and mature into neurons in the maternal brain. Stem cells and development, 2010; 19:1819-30.

[49] Ria F, Gallard A, Gabaglia C R, Guery J C, Sercarz E E, Adorini L. Selection of similar naive T cell repertoires but induction of distinct T cell responses by native and modified antigen. J Immunol, 2004; 172:3447-53.

[50] Rolla S, Nicolo C, Malinarich S, Orsini M, Forni G, Cavallo F et al. Distinct and non-overlapping T cell receptor repertoires expanded by DNA vaccination in wild-type and HER-2 transgenic BALB/c mice. J Immunol, 2006; 177:7626-33.

[51] Nicolò C, Sante G D, Orsini M, Rolla S, Columba-Cabezas S, Spica V R et al. *Mycobacterium tuberculosis* in the adjuvant modulates the balance of Th immune response to self-antigen of the CNS without influencing a "core" repertoire of specific T cells. International Immunology, 2006; 18:363-74.

[52] Fulmer C G, VonDran M W, Stillman A A, Huang Y, Hempstead B L, Dreyfus C F. Astrocyte-derived BDNF supports myelin protein synthesis after cuprizone-induced demyelination. J Neurosci, 2014; 34:8186-96.

[53] Karp P D, Ouzounis C A, Moore-Kochlacs C, Goldovsky L, Kaipa P, Ahren D et al. Expansion of the BioCyc collection of pathway/genome databases to 160 genomes. Nucleic acids research, 2005; 33:6083-9.

[54] Ashburner J, Friston K J. Voxel-based morphometry—the methods. NeuroImage, 2000; 11:805-21.

[55] Zheng G, Tu K, Yang Q, Xiong Y, Wei C, Xie L et al. ITFP: an integrated platform of mammalian transcription factors. Bioinformatics, 2008; 24:2416-7.

[56] Kanehisa M, Goto S, Sato Y, Kawashima M, Furumichi M, Tanabe M. Data, information, knowledge and principle: back to metabolism in KEGG. Nucleic acids research, 2014; 42:D199-205.

[57] Fahy E, Subramaniam S, Murphy R C, Nishijima M, Raetz C R, Shimizu T et al. Update of the LIPID MAPS comprehensive classification system for lipids. J Lipid Res, 2009; 50 Suppl:S9-14.

[58] Hornbeck P V, Kornhauser J M, Tkachev S, Zhang B, Skrzypek E, Murray B et al. PhosphoSitePlus: a comprehensive resource for investigating the structure and function of experimentally determined post-translational modifications in man and mouse. Nucleic acids research, 2012; 40:D261-70.

[59] Croft D, Mundo A F, Haw R, Milacic M, Weiser J, Wu G et al. The Reactome pathway knowledgebase. Nucleic acids research, 2014; 42:D472-7.

[60] Kelder T, van Iersel M P, Hanspers K, Kutmon M, Conklin B R, Evelo C T et al. WikiPathways: building research communities on biological pathways. Nucleic acids research, 2012; 40:D1301-7.

[61] Aggarwal S, Ghilardi N, Xie M H, de Sauvage F J, Gurney A L. Interleukin-23 promotes a distinct CD4 T cell activation state characterized by the production of interleukin-17. J Biol Chem, 2003; 278:1910-4.

[62] Penitente R, Nicolò C, Elzen P Vd, Sante G D, Agrati C, Aloisi F et al. Administration of PLP139-151 Primes T Cells Distinct from Those Spontaneously Responsive In Vitro to This Antigen. The Journal of Immunology, 2008; 180:6611-22.

[63] Fishman-Jacob T, Reznichenko L, Youdim M B, Mandel S A. A sporadic Parkinson disease model via silencing of the ubiquitin-proteasome/E3 ligase component SKP1A. J Biol Chem, 2009; 284:32835-45.

[64] Ruzzo E K, Capo-Chichi J M, Ben-Zeev B, Chitayat D, Mao H, Pappas A L et al. Deficiency of asparagine synthetase causes congenital microcephaly and a progressive form of encephalopathy. Neuron, 2013; 80:429-41.

[65] Sierra A, Lavaque E, Perez-Martin M, Azcoitia I, Hales D B, Garcia-Segura L M. Steroidogenic acute regulatory protein in the rat brain: cellular distribution, developmental regulation and overexpression after injury. Eur J Neurosci, 2003; 18:1458-67.

[66] Wu J, Pajoohesh-Ganji A, Stoica B A, Dinizo M, Guanciale K, Faden A I. Delayed expression of cell cycle proteins contributes to astroglial scar formation and chronic inflammation after rat spinal cord contusion. Journal of neuroinflammation, 2012; 9:169.

[67] Pardridge W M. Drug transport in brain via the cerebrospinal fluid. Fluids Barriers CNS, 2011; 8:7.

[68] Barnea E R, Kirk D, Paidas M J. Preimplantation factor (PIF) promoting role in embryo implantation: increases endometrial integrin-alpha2beta3, amphiregulin and epiregulin while reducing betacellulin expression via MAPK in decidua. Reprod Biol Endocrinol, 2012; 10:50.

[69] Shainer R, Azar Y, Almogi-Hazan O, Bringer R, Compton S R, Paidas M J et al. Immune Regulation and Oxidative Stress Reduction by Preimplantation Factor following Syngeneic or Allogeneic Bone Marrow Transplantation. Conference Papers in Medicine, 2013; 2013: 1-8.

[70] Dalfo E, Barrachina M, Rosa J L, Ambrosio S, Ferrer I. Abnormal alpha-synuclein interactions with rab3a and rabphilin in diffuse Lewy body disease. Neurobiol Dis, 2004; 16:92-7.

[71] Karaca E, Harel T, Pehlivan D, Jhangiani S N, Gambin T, Coban Akdemir Z et al. Genes that Affect Brain Structure and Function Identified by Rare Variant Analyses of Mendelian Neurologic Disease. Neuron, 2015; 88:499-513.

[72] Kara E, Tucci A, Manzoni C, Lynch D S, Elpidorou M, Bettencourt C et al. Genetic and phenotypic characterization of complex hereditary spastic paraplegia. Brain, 2016.

[73] Matosin N, Fernandez-Enright F, Fung S J, Lum J S, Engel M, Andrews J L et al. Alterations of mGluR5 and its endogenous regulators Norbin, Tamalin and Presol in schizophrenia: towards a model of mGluR5 dysregulation. Acta neuropathologica, 2015; 130:119-29.

[74] Komiyama M, Miyatake S, Terada A, Ishiguro T, Ichiba H, Matsumoto N. Vein of Galen Aneurysmal Malformation in Monozygotic Twin. World Neurosurg, 2016.

[75] Zhang J, Wang Y, Chi Z, Keuss M J, Pai Y M, Kang H C et al. The AAA+ ATPase Thorase regulates AMPA receptor-dependent synaptic plasticity and behavior. Cell, 2011; 145:284-99.

[76] Chuang D Y, Simonyi A, Kotzbauer P T, Gu Z, Sun G Y. Cytosolic phospholipase A2 plays a crucial role in ROS/NO signaling during microglial activation through the lipoxygenase pathway. Journal of neuroinflammation, 2015; 12:199.

[77] Aloisi F, Ria F, Adorini L. Regulation of T-cell responses by CNS antigen-presenting cells: different roles for microglia and astrocytes. Immunol Today, 2000; 21:141-7.

Example 3: PIF Reverse Neural Damage and Paralysis

The role of PIF in protecting neurons and reversing neuronal damage was studied. Data reveals that PIF directly targets the brain and exert major regulatory role on PKC/PKA phosphorylated proteins. Since PIF in clinical trials testing in patients with MS/neuroinflammation is warranted.

Episodic PIF Reverses Chronic Neuroinflammation:

MS is a relapsing remitting (RR) disease that currently is treated effectively. However, once MS is chronic it becomes progressively debilitating and current therapies are of limited efficacy. To assess PIF's translational value effect on harsh RR model SJL/J mice inoculated with PLP139-151 was studied. In this controlled study following induction of disease at clinical score one and above PIF, or controls (GA, or PBS) were administered until paralysis resolved. To establish PIF efficacy PIF was in short, medium and long term experiments with the aim to determine efficacy as it compares with controls.

In short term study EAE scores were significantly lower in PIF-treated mice than both PBS and GA treated control groups (data not shown). The mean clinical scores in PIF treated mice were lower both at day 13 (peak of the first relapse) and first wave of disease, day 15. The paralysis free mice percent was significantly lower at end of study day 19 versus controls. (P<0.005). At the end of the first remission, 12/18 PIF treated mice were free of paralysis in contrast to both control groups where none were paralysis free. The data are shown in the table below.

| PIF treated mice have low paralysis score at the end of the experiment - Short term experiments | | | |
| --- | --- | --- | --- |
| | MCS | PP | MCE |
| Experiment 1 | | | |
| PIF | 0.96 +/- 0.19** | 2.1 +/- 0.3 | 0.6 +/- 0.2* |
| GA | 1.58 +/- 0.15 | 2.4 +/- 0.4 | 1.3 +/- 0.4 |
| PBS | 1.51 +/- 0.18 | 2.5 +/- 0.3 | 1.6 +/- 0.4 |
| Experiment 2 | | | |
| PIF | 0.93 +/- 0.23** | 2.3 +/- 0.3 | 0.4 +/- 0.2* |
| GA | 1.4 +/- 0.27 | 2.5 +/- 0.4 | 0.8 +/- 0.2* |
| PBS | 1.53 +/- 0.17 | 2.4 +/- 0.3 | 1.5 +/- 0.4 |

Recognizing that MS tends to be chronic the effect of PIF was examined in medium term model as well. Both episodic PIF and GA reversed the first wave of paralysis however despite continued GA administration the clinical score was similar to PBS. PIF reduced MCE as compared with peak paralysis as compared with PBS while GA induced reduction was not significant. PIF reversed paralysis (4/7) vs. PBS 0/7 (×2; P=0.01). In contrast, in GA-treated mice, paralysis score increased, one mouse died and only 1/7 mice were disease free at day 41. Accordingly, PIF was superior than the PBS control and the GA-treated mice.

This long-term study—chronic disease was repeated by again using episodic PIF, GA, and PBS administration as above, and continued until day 50—reflecting advanced chronic model. All mice became severely paralyzed and three mice of GA and PBS and one PIF-treated mouse died. Despite the disease severity, PIF led to long-term paralysis resolution vs. GA and PBS. The PIF MCS and the MCE scores were lower than controls. Remarkably, at the end of the study 7/8 of PIF treated mice were disease free vs. 1/9 in GA group (P<0.007) and 2/9 in PBS group. This data confirms PIF ability to reverse advanced neuroinflammation.

PIF Totally Reverses Paralysis in >60% of Cases:

Overall, at the end of 4 independent experiments, 60.6% of PIF treated mice were paralysis free vs. 9.3% in PBS treated mice (×2, Df 17.6, p=0.000001). Episodic PIF reduced mortality and reversed paraplegia leading to total recovery in 68% as compared with episodic GA (12.5%) or PBS (12.5%), P<0.007.

PIF Attenuates Brain and Spinal Cord Inflammation:

The above results provided evidence that in a controlled study PIF is effective in chronic EAE model. It has been shown that PIF protected the spinal cord by reducing inflammatory cells access as well by lowered but not significantly local inflammation. The brain IHC also was examined which reduced access of inflammatory cells to the cortex but not reaching significance.

PIF Reverses EAE Induced Phosphoproteome Changes:

Despite the data generated on PIF efficacy in the chronic EAE paralysis reversal the brain histology results were not clearly informative in this respect. It has already reported that in the hypoxic ischemic encephalopathy (HIE) model PIF affects phosphorylated proteins expression in the brain. Therefore, to gain insight into mechanisms involved in PIF's protective role a similar approach was followed. Using phosphorylation peptides enrichment LTQ Orbitrap non-labeled quantitative proteomics approach the sample was able to be enriched for and detect EAE induced changes in global proteome with respect to pSer, pTyr and pThr phosphorylation and compare quantitatively these changes to PIF treated EAE mice as compared with PBS treated (control) and intact healthy mice as well (second control).

It was found that the EAE induced changes in phospho-proteins and their representative peptides in most cases were rescued by PIF treatment. PIF induced reversal of most proteins was equal or of higher amplitude, while a smaller set of proteins underwent lesser reversal changes. Other proteins were induced by PIF in EAE mice, but this effect was not attributable to EAE alone, since in PBS treated EAE mice no significant change in expression was noted (FIG. 3B. Only the expression of few proteins was not restored to levels observed in control.

From the pathways rescued Axon guidance, ErbB signaling pathway, Calcium signaling pathway, GnRH signaling pathway, Phosphatidylinositol signaling system, Regulation of actin cytoskeleton, Cytokine-cytokine receptor interaction, Chemokine signaling pathway, etc. were noted. The Reactome pathway database was used to assess affected pathways and also those rescued by PIF in EAE model or not rescued at all as compared using peptides differential expression clustering. The database produced an averaged expression estimate on our three experimental scenarios using global proteome changes. Thus it was found Axon guidance and L1CAM Interactions to be among the highly represented Reactome pathways.

It was then functionally classified proteins according their proteomics detected phosphorylation variants (phosphopeptides profile). It was found that most abundant of unique phosphorylation sites varying among different detected peptides were proteins being classified as Adaptor/scaffold, Adhesion or extracellular matrix protein, Apoptosis, Cell cycle regulation, Cytoskeletal protein, Protein kinase, Ser/Thr (non-receptor), Transcriptional regulator, and Vesicle proteins.

Using EGAN analysis hypergeometric graphs were built linking most significant high fold change proteins in kinase-substrate manner, annotating it with GO terms and Reactome pathways overrepresentation. The data clearly demonstrated proteins up- or down-regulated in EAE (PBS treated) to be reversely regulated, i.e. down- or up-regulated after PIF treatment of EAE accordingly. For example in EAE, Prkaca was down-regulated, while Src was up-regulated. In PIF treated EAE this phenomenon was reversed. Using Cell Signaling Technology (Boston, Mass., US) curated PhosphoKinome derived Kinase-Substrate data was used to explore by EGAN the PIF induced KINOME changes in EAE as compared with PBS treated mice and naïve untreated controls as annotated with GO terms and KEGG pathways. From the EAE perturbed phosphokinases, to mention a few were: Src and Prkacb—upregulated and Prkaca—downregulated along with Src substrate—the kinase Dlg4. With Prkca, several chemokines and cytokines related to inflammation were modulated in EAE and reversed back by PIF as shown by EGAN generated "Comparative Network of Protein-Protein Interaction and Kinase-Substrate Interaction focused on PRKACA." Thus, PIF was shown to reverse changes that were observed in PBS treated group. Moreover, in several instances following PIF treatment the brain protein expression pattern was the same as observed in intact mice. The proteins that were identified are important for inflammation control and synaptic function—Camk2b, Stat6, PTEN and Dlg4.

Since it was found Tyr and Ser kinases and other protein groups to be represented by proteins with higher ($6<m<27$) than the average ($1<n<3$) unique phosphorylation patterns additional correlation analysis of phospho-sites were conducted to extract kinase/phosphatase and phospho-peptide associations and link them to GO and pathway enrichment. It was found "protein phosphatase binding" to be most enriched among phosphopeptides in PIF treated EAE, while peptides in EAE alone have demonstrated a decreased enrichment for this term and an increased "actin binding" enrichment. Similarly, the terms "axon", "neuron projection", "synapse", "actin cytoskeleton" become enriched among peptides in PIF treated EAE. An overrepresented positive correlation between Ppm1g phosphatase and its corresponding substrates exemplified the above mentioned phosphatase enrichments. According to their potential phosphorylation sites peptides resembling the detected EAE/PIF treated proteome were divided into three sub-clusters and each cluster additionally subjected to GO terms enrichment. Phosphorylation ratio in distinct sub-clusters suggested that EAE induced decrease phosphorylation in part of the representative peptide pool, an action being reversed by PIF. In other cases EAE induced a significant increase in peptides phosphorylation ratio, but then, PIF treated EAE suggested a rescue action again, as PIF treatment resulted in reduced phosphorylation ratios. Of reduced phosphorylation forms, cluster 1 encompassed Sdc1, Krt1, Dsp, and Cep170, which were all rescued by PIF. Similarly, of over phosphorylated Cd2bp2, Tll2 and Sptbn2 (Q3UGZ4), the expression of all three was reduced down to control levels.

In conclusion, PIF rescues EAE effects by modulating the expression of variety of phosphatases and kinases, thus tuning the phosphoproteome to preserve homeostatic control.

PIF Regulates Key Brain Phosphoprotein Levels:

The analysis above provided a global view indicating that PIF exerted a major impact on the brain phosphoproteins. It was further found that on certain individual phosphoproteins PIF exerted a marked effect. Among them Spectrin beta chain, non-erythrocytic 2 (SPTBN2), decreased (−137 fold). This protein regulates glutamate signaling pathway and when mutated is involved in spinocerebellar ataxia protein 5-syndrome. This was followed by TLL2 (−80 fold). It is a metalloproteinase involved in degradation of extracellular matrix. This protein is involved in bipolar and avoidance behavior (de Mooij-van Malsen J G Genes Brain Behav. 2013 August; 12(6):653-7.)

On the other hand the highest increase in expression noted was with desmoplakin, (48 fold) this protein is involved in linking intermediate filaments with desmosomes. It is significantly downregulated following norbin-1 downregulation leading to defective neurogenesis. Wang H Proc Natl Acad Sci USA. 2015 Aug. 4; 112(31):9745-50. Titin increased (46.5 fold) it is a very large sarcomeric protein responsible for the elasticity of relaxed striated muscle. It has a protein serine/threonine kinase activity. The decreased expression of this protein is associated with a rapid decline in patients with ALS. Watanabe H. J Neurol Neurosurg Psychiatry. 2016 Jan. 8. pii: jnnp-2015-311541. Such data identified specific proteins that when their regulation is altered neurologic disease may ensue.

PIF Regulates Syndecan-1 and Calmodulin-2 Expression in Cultured Primary Microglia:

PIF increased the expression of syndecan-1 phosphoprotein in the brain (37 fold). This protein is a heparin sulfate fibroblast growth factor that has anti-inflammatory properties. It interacts with MAPK1,3, affecting down-stream ERK dependent signaling. It has three parts extra cellular where glycosylation takes place, intra membrane and intracellular domains. This protein is expressed in the choroid plexus. In sdc-1$^{-/-}$ mice its depletion led to a severe EAE induced disease due to increased immune cells recruitment to the brain. Zhang X, J Immunol. 2013 Nov. 1; 191(9):4551-61.

In view that microglia are drivers of the inflammatory response in the brain which PIF was shown to target in vivo, the effect of PIF on syndecan 1 expression in these cells was examined. Data showed that PIF led to a dose dependent increase in this protein expression confirming the observations made in the brain.

In contrast, it was found that PIF led to downregulation of calmodulin-2 phosphoprotein in the brain (−4.6 fold). This protein is a negative regulator of brain function as it promotes inflammation of brain blood vessels in culture. Waldsee R, J Neuroinflammation. 2014 May 16; 11:90. doi: 10.1186/1742-2094-11-90. Therefore, the effect of PIF on calmodulin 2 protein was examined by testing the effect on both the protein itself and its phosphorylated form. Data showed that PIF downregulated both forms. Data generated indicates that microglia play an important role on PIF's protective effect on the brain.

PIF Promotes Th2 Cytokine IL 10 and IL4 Secretion by Activated Splenocytes:

PIF was previously shown to act as a potent immune modulator and in PLP (proteolipid protein) activated splenocytes reduced the prominent pro-inflammatory $Th_1$ and $Th_{17}$ cytokines. It was recently shown that PIF neuroprotective effect is exerted by increased IL10 expression in the HIE brain LPS-induced microglia. Whether PIF action involves similar protective effects was subsequently examined. The effect of PIF on PLP-induced cultured splenocytes derived from EAE mice was evaluated after 72 h. PIF significantly increased both IL-10 and IL-4 cytokines secretion which is associated with a Th2 response as compared to PBS treated cultures. No changes in levels of Th1 associated cytokine IFN-γ secretion was observed. Negative control cells were cultured without PLP peptide, whereas positive control cells were cultured with ConA. Data indicates that PIF neuro protective action involves an increase in systemic Th2 cytokines.

Splenocyte Populations are Affected by PIF Based on Severity of EAE:

Although the etiology of MS is unknown, autoreactive $Th_1$ and $Th_{17}$ cells play an essential role in the pathogenesis of the disease. After observing differences in the cytokine secretion in the splenocytes culture, the studies proceeded to determine whether PIF administration can modulate spleen cells population. Both CD4+ and CD8+ cells take part in the pathophysiology of MS [24, 25]. In addition effect of PIF on CD11b+ monocytes and FoxP3+ expressing cells were examined. FoP3+ is a marker of active regulatory T cells ($T_{regs}$). Which was reported to be relevant for neuroprotection (REF) To determine whether PIF administration modulates splenocytes effect on CD8+, CD4+ and FoxP3+ T-cells and monocytes (11b) was examined using FACS analysis. Notably the severity of the disease dictated changes in percentage of CD4+ and CD8+ T cells. In the mild disease, PIF decreased %/CD4+ T cells vs. PBS (P<0.04). In contrast, in severe EAE PIF reduced % CD8+ cells vs. GA, while % CD4 and % monocytes remained unchanged. Regulatory T-cells (% FoxP3+) cells were not affected whether the paralysis was mild or severe. This data implies that PIF reverses paralysis by regulating systemic immune response dependent of the intensity of the disease.

Neuroinflammation that leads to MS development is the most frequent cause of non-traumatic paralysis. Prevention is not possible since there are no preclinical signs and when clinically manifested the disease is already in an advanced stage. Unfortunately, current therapeutic measures are limited; they reduce frequency of attacks but do not prevent progression to a chronic form of disease. PIF can reverse chronic paralysis due to a robust regulation of brain phosphorylated proteins. The main effect appears to be exerted through reduction in PKC/PKA phosphorylation pathways. Such data reveal a novel mechanism involved in PIF action. Remarkably up to 60% of PIF treated mice became paralysis free at the end of the study by day 50 as compared to only 10-15% in controls. The observed systemic Th2 cytokine bias is important for an integrated neuro protective effect. Unlike other drugs PIF crosses the BBB intact without degradation. Such data provides critical insight into a potential treatment of chronic MS and other neurodegenerative disorders.

EAE is a well-established model of MS where antigen presenting cells lead to T cell activation and differentiation into encephalitogenic Th1/Th17 cells. The EAE model has led to introduction of several drugs for the treatment of MS. Episodic PIF was effective long-term as compared with GA which was effective only short term, similar drug efficacy using GA was also observed in MS patients.

In the EAE prevention model PIF decreased spinal cord inflammation and preserved organ micro-architecture documented by H&E staining. In chronic EAE at day 82 of study PIF reversed paralysis, promoted neural repair coupled with improved spinal cord re-myelination. Without being bound to any particular theory, it is suggested that since MS/EAE is a relapsing/remitting disease, residual inflammatory cells may reach the brain/spinal cord to activate disease at every paralytic episode, cells which however, are not cleared away during the remission period. Consequently, most studies have focused on the spinal cord and not the brain. However MS is essentially a brain disease and therefore evidencing PIF action on this organ is critical for therapeutic targeting. PIF decreased brain inflammation which was coupled with reversal of chronic paralysis. Such protective effect is exerted by PIF binding and regulating local phosphorylated proteins. This data helps to reconcile the clinical and mechanistic effects of PIF—revealed for the first time. The global phosphoprotein analysis provided an important insight into PIF-induced neuroprotection. It was recognized that among various signaling pathways that could be involved in PIF action on the brain the PKC/PKA phosphorylation pathways are more likely to be prominent (Muller CDD 2015). Phosphorylation changes proteins conformation to activate, inactivate or alter their function. Based on that notion, the enriched phosphoproteome regulated by PIF was identified and quantified. By using a group of PIF treated, vehicle treated and naïve mice as control, enabled a three way comparison elucidating specific phosphoproteins, site of phosphorylation and whether or not they were affected by PIF. Due to the fact that analysis of phosphoproteins is complex, a multilevel analysis was carried out which identified the individual phosphoproteins and their involvement in a specific pathway. PIF restores phosphoproteins related to neuroprotection which are reduced by EAE. Phosphoproteomics data revealed that PIF is able to reverse several EAE induced kinase mediated signaling events. PIF-induced kinases rescued EAE-induced decrease in phosphorylation in part of the representative peptide pool, like in the case of Sdc1, Krt1, Dsp, and Cep170. PIF also reverses the effect on axon-genesis and cytoskeletal organization proteins. In terms of action on kinases and phosphatases it is dualistic, PIF acts on both groups depending on their biological function, rather than their enzyme activity. Interestingly, PIF action on the phosphoproteome was exerted through three distinct mechanisms. 1. PIF increased the phosphorylation of proteins that were dephosphorylated by EAE. 2. Through an opposite action, PIF reversed over-phosphorylated proteins enriched for synapse, neuronal morphogenesis and postsynaptic density. 3. The larger cluster is proteins which phosphorylation was not affected, reflect a decreased enrichment for actin cytoskeleton, neuronal morphogenesis among others. Overall, PIF action in the brain involved promotion of actin cytoskeleton, synapse and axon related proteins, through modulation either by expression or by regulating their phosphorylation state. EAE induced changes in several Ser-/Thr-phosphokinases lead to up-regulation of Prkacb and Srk, while down-regulating Prkaca and Srk substrate Dlg4. These changes are related to several chemokines and cytokines involved in inflammation and together with Srk, Dlg4 and PTEN were all rescued by exposure to PIF. Thus PIF resolved membrane-associated guanylate kinase Dlg4 that participates in K+ channel regulation and N-methyl-D-aspartate ion channel receptor (NMDAR) in the brain. This molecule is associated with a rare autoimmune disease, anti-NMDAR encephalitis. Notably, PIF regulates K+ flux by targeting the Kv1.3b channel, the cortisone binding site. (T&H) Another restored protein-calcium/calmodulin-dependent protein kinase, Camk2b acts downstream from NMDAR, and is involved in dendritic spine, synapse formation and neuronal plasticity. EAE-decreased STAT6,1 which expression was up-regulated by PIF. In the brain, astrocytes and but not the microglia are able to sense $H_2O_2$ induced active oxygen species to rapidly phosphorylate the transcription factor STAT6. This results in STAT6-dependent increase in cyclooxygenase-2 expression and subsequent release of PGE2 and prostacyclin. Prostaglandins that are released from $H_2O_2$-stimulated astrocytes inhibited the microglia derived TNF-α expression. This STAT6 phosphorylation is related to Src-JAK. Src up-regulation by EAE was also reduced by PIF treatment in both EAE model and in naïve controls. Generally, in intact mice, PIF up-regulated both Prkca and Prkcb, but did not affect Prkcd, linking to Leu induced endothelial migration, while reducing Src and Dlg4 expression. Another major regulatory loop regulated by PIF was PTEN, decreased in EAE and which following PIF treatment the protein level increased. Tyr-phosphatase, PTEN regulates mostly phosphatidylinositol-3,4,5-trisphosphate 3-phosphatase through phosphoinositide dephosphorylation, which led to blockade of the Akt/PKB pathway. The activation of PTEN by PIF would reduce Alt/mTORC1 and Akt/NF-kB/TNF-alpha pathways, thus enhancing anti-inflammatory signaling pathways.

Alternatively, PIF led to similar "switch" of EAE modulated molecules, but in reverse direction, activating phosphatases, again by reversing over-phosphorylation of Cd2bp2, Tll2 and Sptbn2 (Q3UGZ4). Phosphoproteomics also revealed that PIF rescued EAE-induced inflammation by several other pathways; regulating calcium signaling, cytokine-cytokine receptor and chemokines, phosphatidylinositol signaling, endocytosis, Fc epsilon RI and Fc gamma R-mediated phagocytosis, actin cytoskeleton and vascular smooth muscle contraction, Of note, some phosphoproteins were enriched also through 14-3-3, yet another important PIF binding target. The studies examining PIF effect on microglia cultures provided further supportive evidence confirming the effect on brain macrophages. PIF reduced the Calmodulin2 protein as well as its phosphorylation, seen also in vivo. One the other hand, the PIF induced increase in Syndecan-1 expression in microglia cultures validated the in vivo observations as well. Overall, data reveal that the major pathology of EAE and possibly MS involve changes in local phosphoprotein levels. Based on our data PIF restored several proteins affected by EAE up to those levels present in naïve mice brain. In certain cases this effect was magnified beyond that present in the normal brain a reflecting a compensatory protective mechanism.

Auto-reactive Th1 and Th17 cells and APCs play an essential role in MS pathogenesis. The IL-6 and TGF-β cytokines are responsible for the differentiation of Th17 cells which product. IL-17 leads to autoimmunity and is present in chronic MS brain lesions. The observed PIF induced increase in IL-10 and 1-4 expression is similar to that seen in the HIE model in the brain, cultured microglia and activated immune cells. Our current data demonstrate that PIF through a compensatory mechanism increases Th2 cytokines expression to further amplify the protective mechanism that was previously shown by the observed decrease in pro-inflammatory IL-6 and IL-17 cytokines in chronic EAE. IL-10 is secreted also by regulatory T cells, inhibits co-stimulatory molecules effect on APCs required for Th1 cells activation. IL-10 plays a critical role in EAE regulation by controlling auto-pathogenic Th1 responses. IL-4 is a Th2 cytokine which promote IL10 to blocks inflammatory cytokines (IL-1, IL-6) and down-regulate nitric oxide (NO*). IL-4 deficient EAE mice clinical symptoms are severe, promoting M1 macrophage activation and oxidative stress through nitric oxide synthase (iNOS) and NO*. Conversely 1-4 in EAE redirects macrophages from M1 to M2 type to promote neural repair. Also central administration of IL-4 shifts brain microglia to M2 type in healthy mice. Infiltration of iNOS expressing macrophages to the sciatic nerve promotes NO* secretion and oxidative stress. It was reported that PIF by shifting M1 to M2 macrophages reduces NO* secretion by down-regulating the iNOS pathway following LPS induction. Thus by promoting critical Th2 cytokines and ability to shift macrophages to M2 regulatory type PIF is effective in reversing chronic EAE.

Both CD4+ and CD8+ T cell populations have a well-documented role in MS as for CD8+ which plays a major role in EAE. CD4+ T cells are involved in axonal damage and paralysis. In MS patients brain tissue plaques with CD8+ infiltrates are prominent [48] 25. Therefore changes in systemic T cells populations are expected to vary since both cell type populations CD4+ and CD8+ may be affected. Interestinglym it was found that in mild EAE PIF reduced CD4+ while in a severe case of paralysis CD8+ cells percent decreased. Whether this is a reproducible finding also in the brain remains to be further examined. Since PIF did not affect Tregs (Foxp3+) cells implies that the observed protective action is likely independent of T-regulatory cells at least in the systemic immunity. Collectively, PIF regulates the T cells phenotype percent in tandem with severity of EAE.

The detection of intact PIF without degradation in the brain is of major importance. It supports the view that the observed beneficial effects herein are due to PIF direct and targeted action in the brain. This further confirmed that the observed IHC staining in microglia and neuron are likely due to presence of intact PIF locally. Overall such data support the clinical potential of PIF use in neurodegenerative diseases with a preserved BBB.

Without being bound to any particular theory, taken together, data herein indicates that PIF protective effects against neuro-inflammation are likely to be related to its inflammatory regulatory properties. The elucidation of PIF effect on the brain phosphoproteome through PKC/PKA signaling pathways support translation for treatment of progressive neurodegenerative diseases.

Materials and Methods

PIF Synthesis:

Synthetic PIF (PIF), a novel fifteen-amino-acid peptide (MVRIKPGSANKPSDD, SEQ ID NO: 1), was produced using solid-phase peptide synthesis (Peptide Synthesizer, Applied Biosystems, Foster City, Calif.) employing Fmoc (9-fluorenylmethoxycarbonyl) chemistry. Final purification was carried out by reversed-phase high-pressure liquid chromatography (HPLC), peptide identity was verified by matrix-assisted laser desorption/ionization time-of-flight (MALDI-TOF) mass spectrometry and amino acid analysis, and the peptide was purified to >95% by HPLC, as documented by mass spectrometry and fluorescein isothiocyanate labeled PIF (FITC-PIF) was generated. (Bio-Synthesis, Inc., Lewisville, Tex.). Clinical grade Glatiramer acetate (GA) (Teva Israel) was received as a gift from Dr. Karousis, Hadassah Medical Center, Department of Neurology.

Mice:

SJL mice (5-6 week old female) were obtained from Harlan Laboratories Ltd. (Israel). Mice were kept and monitored in SPF conditions with autoclaved cages. The study was conducted under appropriate conditions and approved by the Institutional Animal Welfare Committee of the Hebrew University of Jerusalem.

EAE Induction:

All procedures were conducted using facilities and protocols approved by the Animal Care and Use Committee of the Hadassah-Hebrew University School of Medicine. EAE was induced in mice as previously described (Weiss L, Or R, Jones R C et al. Preimplantation Factor (PIF*) reverses neuroinflammation while promoting neural repair in EAE model. J Neurol Sci, 312(1-2), 146-157 (2012)). Briefly, SJL females were immunized subcutaneously on day 0 with a 1:1 emulsion comprised of 100 μg proteolipid protein (PLP) (aa 139-151 peptide) and complete Freund's adjuvant (CFA) containing 100 μg of *Mycobacterium* H37R (BD Biosciences Clontech, Palo Alto, Calif.). On day 0 and day +2, pertussis toxin (Sigma Chemicals, St. Louis, Mo.) was administered (250 ng/mouse) intra-peritoneal (I.P.) injection. Animals were monitored daily, starting on day +6 until sacrifice.

Subacute EAE Models:

Episodic PIF vs. Episodic: Short Term GA.

(N=16-18/group in two independent experiments). PIF (0.75 mg/kg), Glatiramer acetate (GA) is a clinically used drug therefore served as positive control (Aharoni 2005) (5 mg/kg) or PBS was administered twice daily initiated when paralysis was documented (score 1 and up) and continued until paralysis regressed. Treatment was administered episodically again but only when a given mouse has started to develop signs of paralysis. Study continued until day 19.

Episodic PIF Vs. Continuous One-Course GA: Medium Term.

(N=18-20/group, in two independent experiments). PIF (0.75 mg/kg) was administered twice daily started when paralysis developed (score 1 and up) and continued until paralysis regressed. Treatment was administered episodically again but only when a given mouse has started to develop signs of paralysis. GA (5 mg/kg) was administered twice daily started when paralysis developed (score 1 and up) and carried out for six consecutive days. As an added control group, PBS was administered episodically as well. Study continued until day 23.

Episodic PIF vs. Episodic GA: Long Term.

(N=9-12/group two independent experiments). PIF (0.75 mg/kg twice daily), GA (5 mg/kg) or PBS administration was initiated when paralysis was documented and continued until paralysis regressed. Treatment was administered episodically again but only when a given mouse had started to develop signs of paralysis. Study was continued up to day 50.

Clinical Evaluation of Neuroinflammation:

In all experiments the separation of mice to groups was randomized. The first signs of paralysis appeared within a few days post-immunization which varied due to the intensity of the disease. In general the clinical signs started within 6-11 days (~9) from inoculation. Mice were monitored daily, starting on day 6 up to day 50 according to the specific experiment. The mice were scored daily using the standard EAE six-point scale: 0-normal behavior; 1-low tail tonus; 2-hind-leg weakness; 3-hind-leg paralysis; 4-full paralysis; and 5-death. In all cases, the following scores were calculated: mean clinical score (MCS) is the average of the daily scores of all mice within each group; mean peak paralysis scores (PP) is the average of individual scores of all mice in the group; mean clinical score at end (MCE) is the average score of all mice within each group on the last day of study at day 21-50 of the experiment.

Hematoxylin and Eosin (H&E) Staining:

Briefly, the H&E staining of the spinal cord was performed as previously described (Weiss L, Or R, Jones R C et al. Preimplantation Factor (PIF*) reverses neuroinflammation while promoting neural repair in EAE model. J Neurol Sci, 312(1-2), 146-157 (2012)). At the end of the experiment treated mice were sacrificed and the whole spinal cord was removed and fixed in blocks for analysis, results were compared with naïve mice processed in the same manner as well (control). Inflammation was graded as 1—Mild, 2—Moderate, 3—Prominent, 4—Severe.

Luxol Fast Blue (LFB) Staining:

Briefly, the LFB staining for myelin was performed as previously described (Weiss L, Or R, Jones R C et al. Preimplantation Factor (PIF*) reverses neuroinflammation while promoting neural repair in EAE model. J Neurol Sci, 312(1-2), 146-157 (2012)). At the end of the experiment treated mice were sacrificed and the whole spinal cord was removed and fixed in blocks for analysis, results were compared with naïve mice processed in the same manner (control). The myelin stained blue-green and the nissl substances stained purple-dark blue. Positive and negative controls were included in each staining protocol. LFB loss was graded as 1—Small, 2—Focal, 3—Multifocal.

Splenocyte Cultures:

Method of culture and cytokine testing were previously reported (Weiss L, Or R, Jones R C et al. Preimplantation Factor (PIF*) reverses neuroinflammation while promoting neural repair in EAE model. J Neurol Sci, 312(1-2), 146-157 (2012)). Briefly, spleens from sacrificed mice from PIF, GA, PBS treated or naïve mice groups were harvested and their splenocytes isolated. Cells were cultured in DMEM medium supplemented with 10% fetal bovine serum, 2 mM L-glutamine, 100 U/ml penicillin and 100 g/ml streptomycin. Cells were cultured in duplicate at $5\times10^6$ cells/well in 2 ml volume in presence of 4 mg/ml PLP peptides. Negative control wells were cultured without PLP peptides, whereas positive control wells were cultured with 2.5 µg/ml concanavalin A (ConA). All wells were incubated for 3 days. After the period of incubation the supernatant was collected and frozen at −80 C. Spleen supernatants cytokine levels were determined by using the FlowCytomix Mouse Th1/Th2 10plex testing 10 different cytokines according to the manufacturer recommendation, (Bender MedSystems GmbH, Vienna, Austria).

Flow Cytometry Analysis:

Splenocytes from experimental groups were incubated for 1 h with antibodies against markers for immune-cell populations: anti-CD4 Pacific Blue (BioLegend), anti-CD8 PE and anti-CD11b APC, FoxP3 (SouthernBiotech), FACS analysis was performed using the MACSQuant® analyzer (Miltenyi Biotech).

Histological Analysis:

Tissue samples of brain and spinal cord were obtained from sacrificed mice and fixed in 4% neutral-buffered formalin. Samples were embedded in paraffin, cut into 10-micron thick sections, and stained in Hematoxylin and Eosin (H&E) and Luxol Fast Blue (LFB). In the H&E staining, the inflammation was graded as 1—Mild, 2—Moderate, 3—Prominent, 4—Severe. In the LFB staining, the myelin stained blue-green and the nissl substances stained purple-dark blue. LFB loss was graded as 1—Small, 2—Focal, 3—Multifocal.

Detection of sPIF in Intact Brain:

Detection of sPIF concentration in mouse brains was performed as recently published (1). Adult (2 months old, male) CD-1 mice from Charles River Laboratories were injected subcutaneously with sPIF (0.75 mg/kg body weight every 12 hours). Animals were anesthetized by isoflurane, performed cardiac perfusion with PBS followed by immediate brain harvesting and freezing in liquid nitrogen. Brains were harvested 1 hour, 26, and 28 hours after sPIF treatment. Tissue was stored in an −80° C. freezer, and shipped to Biosynthesis, Tx for analysis of sPIF concentrations using liquid chromatography (LC) with tandem mass spectrometric detection (MS/MS) as recently reported (1).

Brain Sample Preparation:

Briefly, tissue sample were extracted in a total extraction solution of 550 µl using buffer A. The extraction mixture was homogenized, sonicated for 20 minutes and briefly vortexed vigorously. Next, perchloric acid (70%) was added to the extraction mixture to precipitate interfering proteins to a final percentage of 30%. The resulting mixture was centrifugated for 30 minutes at 4° C. in a speedvac at 14,000 rpm. An aliquot of 300 µl from the supernatant was used for the analysis by analytical HPLC. The aliquot was first concentrated in a speedvac to dryness and resuspended in 100 µl buffer A. An aliquot of 25 µl was injected into the HPLC after filtering through a 45 micron micro filter.

Analytical HPLC

HPLC based analyses was performed using a Beckman System Gold Liquid Chromatography system, equipped with a binary pump delivery system, an autosampler, a column thermostat, and a multi-wavelength detector (DAD). Chromatography method used were using standard conditions using a 5 min, 150×2.1 mm column (Phenomenx), at 20° C., with detection monitoring at λ=210 and 280 nm. Mobile phase A was 0.05% TFA, 0.02% formic acid in ultrapure water, while mobile phase B was neat acetonitrile. The separation was obtained at a flow rate of 0.2 mL/min using a linear gradient program.

Real-Time PCR

Total RNA was extracted using RNeasy midi kit according to the manufacturer's instructions (Qiagen). Reverse transcription reaction was carried out using 2 µg total RNA as described for the RT-PCR analysis. A primer optimization step was tested for each set of primers to determine the optimal primer concentrations. Primers, 25 µL of 2×SYBR Green Master Mix (Invitrogen), and 30 to 100 ng cDNA samples were resuspended in a total volume of 50 µL PCR amplification solution. The following primers were used:

```
S12-forward,
                                    (SEQ ID NO: 32)
TGCTGGAGGTGTAATGGACG, reverse
                                    (SEQ ID NO: 33)
CAAGCACACAAAGATGGGCT.
```

Reactions were run on an ABI Prism 7000 Sequence Detection System (Applied Biosystems, Foster City, Calif.). Cycle threshold (Ct) values were obtained from the ABI 7000 software. S12 or β-actin levels were also determined for each RNA sample as controls.

Statistical Analysis:

Non-parametric data were analyzed using the Mann-Whitney U test. Mouse survival and the disease-free ratio at the end of the study were determined by $\chi 2$ analysis. P<0.05 was considered statistically significant.

Unless context dictates a different definition, the list of Abbreviations Used for the Purpose of the Patent Disclosure is as follows:

BPD Bronchopulmonary Dysplasia
FDA Food & Drug Administration
NK Natural Killer
OEF Operation Enduring Freedom
OIF Operation Iraqi Freedom
OND Operation New Dawn
PBS Phosphate buffered saline
PIF PreImplantation Factor
sPIF Synthetic PreImplantation Factor
SC Spinal Cord
SCI Spinal Cord Injury
TI Traumatic Injury

The invention claimed is:

1. A method of improving the clinical outcome in a subject suffering with, diagnosed with, or suspected of having acute neurotrauma comprising administering to the subject a pharmaceutical composition comprising: (i) a therapeutically effective amount of preimplantation factor (PIF) peptide, an analog thereof, or a pharmaceutically acceptable salt thereof; and (ii) a pharmaceutically acceptable carrier, wherein the acute neurotrauma comprises acute traumatic brain injury (TBI), acute spinal cord injury (SCI) and/or acute peripheral nerve injury.

2. The method of claim 1, wherein the method further comprises administering to the subject one or a combination of additional active agents chosen from: an anti-inflammatory compound, an alpha-adrenergic agonist, an antiarrhythmic compound, an analgesic compound, or an anesthetic compound.

3. The method of claim 1, wherein the acute neurotrauma causes paralysis, and wherein administration of the PIF peptide to the subject reverses the paralysis.

4. The method of claim 1, wherein the PIF peptide, analog thereof, or a pharmaceutically acceptable salt thereof comprises an amino acid sequence comprising at least about 86% sequence identity to SEQ ID NO: 13.

5. The method of claim 1, wherein the PIF peptide, analog thereof, or a pharmaceutically acceptable salt thereof comprises an amino acid sequence comprising at least about 86% sequence identity to SEQ ID NO: 1, SEQ ID NO: 2, or SEQ ID NO: 3.

6. The method of claim 1, wherein the PIF peptide comprises an amino acid sequence comprising at least about 86% sequence identity to SEQ ID NO: 20.

7. The method of claim 1, wherein the pharmaceutical composition is administered via parenteral injection, via subcutaneous injection, via intravenous injection, via intramuscular injection, via intraperitoneal injection, transdermally, orally, buccally, ocular routes, intravaginally, by inhalation, by depot injection, or by implant.

8. The method of claim 1, wherein the acute neurotrauma is concussion.

9. The method of claim 1, wherein the subject develops or has bronchopulmonary dysplasia, and wherein administration of the PIF peptide treats the bronchopulmonary dysplasia in the subject.

10. A method of reducing microglial activation in a subject suffering with, diagnosed with, or suspected of having acute neurotrauma, the method comprising administering to the subject a pharmaceutical composition comprising: (i) a therapeutically effective amount of preimplantation factor (PIF) peptide, an analog thereof, or a pharmaceutically acceptable salt thereof; and (ii) a pharmaceutically acceptable carrier.

* * * * *